(12) United States Patent
Kim et al.

(10) Patent No.: US 7,438,920 B1
(45) Date of Patent: Oct. 21, 2008

(54) CRYSTALS OF HEPATITIS C VIRUS HELICASE OR FRAGMENTS THEREOF COMPRISING A HELICASE BINDING POCKET

(75) Inventors: Joseph L. Kim, Natick, MA (US); Kurt Morgenstern, Derry, NH (US); Paul Caron, Malden, MA (US); Chao Lin, Brookline, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 09/303,216

(22) Filed: Apr. 30, 1999

Related U.S. Application Data

(63) Continuation of application No. PCT/US98/16879, filed on Aug. 13, 1998.

(60) Provisional application No. 60/055,772, filed on Aug. 14, 1997.

(51) Int. Cl.
  *A61K 39/29*    (2006.01)
  *A61K 38/43*    (2006.01)
  *G01N 33/53*    (2006.01)
  *C12N 9/00*     (2006.01)

(52) U.S. Cl. .................. 424/228.1; 435/7.1; 435/183; 514/2; 514/12

(58) Field of Classification Search ............... 530/350; 514/12; 536/23.1; 435/6, 183
See application file for complete search history.

(56) References Cited

FOREIGN PATENT DOCUMENTS

WO    WO 97/12043    4/1997

OTHER PUBLICATIONS

D.G. Brown et al., "Crystallography in the Study of Protein-DNA Interactions", *Methods in Molecular Biology*, 56 pp. 293-318 (1996).
P.N. Bryan, "Protein Engineering", *Biotech Adv.*, 5, pp. 221-234 (1987).
I.D. Campbell et al., "Diffraction, in Biological Spectroscopy", *The Benjamin/Cummings Publishing Company, Inc.*, Menlo Park, CA, pp. 299-326 (1984).
J. Jancarik et al., "Sparse Matrix Sampling: A Screening Method for Crystallization of Proteins", *J. Appl. Cryst.*, 24, pp. 409-411, (1991).
A. Kajihara et al., "Protein Modelling Using a Chimera Reference Protein Derived From Exons", *Protein Eng'g*, 6, pp. 615-620 (1993).
K.A. Morgenstern et al., "Polynucleotide Modulation of the Protease, Nucleoside Triphosphatase, and Helicase Activities of a Hepatitis C Virus NS3-NS4A Complex Isolated from Transfected COS Cells", *J. of Virology*, 71, pp. 3767-3775 (1997).
A.J. Russell et al., "Rational Modification of Enzyme Catalysis by Engineering Surface Charge", *Nature*, 328, pp. 496-500 (1987).
U. Uhlin et al., "Crystallization and Crystallographic Investigations of Ribonucleotide Reductase Protein R1 From *Escherichia coli*", *FEBS*, 336(1), pp. 148-152 (1993).
N. Yao et al., "Structure of the Hepatitis C Virus RNA Helicase Domain", *Nature Structural Biology*, 4, pp. 463-467 (1997).

*Primary Examiner*—Marianne P Allen
(74) *Attorney, Agent, or Firm*—Ropes & Gray LLP; James F. Haley, Jr.

(57) ABSTRACT

The invention relates to the X-ray crystal structure of the hepatitis C virus helicase domain. More specifically, the invention relates to crystallized complexes of HCV helicase and an oligonucleotide, to crystallizable compositions of HCV helicase and an oligonucleotide and to methods of crystallizing an HCV helicase-oligonucleotide complex. The invention further relates to a computer programmed with the structure coordinates of the HCV helicase oligonucleotide binding pocket or the HCV helicase nucleotide triphosphate pocket wherein said computer is capable of displaying a three-dimensional representation of that binding pocket.

3 Claims, 84 Drawing Sheets

FIGURE 1

HCV NS3 HELICASE COORDINATES

|      | Atom Type | Resid | #  | X      | Y      | Z      | OCC  | B     |
|------|-----------|-------|----|--------|--------|--------|------|-------|
| ATOM | 1  | N   | PRO | 190 | -0.567 | 24.363 | 16.753 | 1.00 | 49.28 |
| ATOM | 2  | CD  | PRO | 190 | -0.755 | 25.375 | 17.807 | 1.00 | 48.44 |
| ATOM | 3  | CA  | PRO | 190 | -0.399 | 23.026 | 17.339 | 1.00 | 49.21 |
| ATOM | 4  | CB  | PRO | 190 | -0.793 | 23.252 | 18.793 | 1.00 | 48.67 |
| ATOM | 5  | CG  | PRO | 190 | -0.283 | 24.643 | 19.036 | 1.00 | 48.14 |
| ATOM | 6  | C   | PRO | 190 | -1.288 | 21.990 | 16.644 | 1.00 | 49.61 |
| ATOM | 7  | O   | PRO | 190 | -2.520 | 22.007 | 16.772 | 1.00 | 49.44 |
| ATOM | 8  | N   | PRO | 191 | -0.669 | 21.098 | 15.857 | 1.00 | 49.77 |
| ATOM | 9  | CD  | PRO | 191 | 0.761  | 21.088 | 15.505 | 1.00 | 50.59 |
| ATOM | 10 | CA  | PRO | 191 | -1.389 | 20.053 | 15.125 | 1.00 | 49.68 |
| ATOM | 11 | CB  | PRO | 191 | -0.296 | 19.432 | 14.245 | 1.00 | 49.43 |
| ATOM | 12 | CG  | PRO | 191 | 0.723  | 20.544 | 14.109 | 1.00 | 50.11 |
| ATOM | 13 | C   | PRO | 191 | -2.024 | 19.007 | 16.033 | 1.00 | 49.16 |
| ATOM | 14 | O   | PRO | 191 | -1.368 | 18.447 | 16.911 | 1.00 | 49.03 |
| ATOM | 15 | N   | ALA | 192 | -3.309 | 18.751 | 15.823 | 1.00 | 48.24 |
| ATOM | 16 | CA  | ALA | 192 | -4.000 | 17.745 | 16.616 | 1.00 | 47.12 |
| ATOM | 17 | CB  | ALA | 192 | -5.477 | 17.713 | 16.265 | 1.00 | 47.93 |
| ATOM | 18 | C   | ALA | 192 | -3.356 | 16.408 | 16.283 | 1.00 | 45.46 |
| ATOM | 19 | O   | ALA | 192 | -2.803 | 16.234 | 15.193 | 1.00 | 44.90 |
| ATOM | 20 | N   | VAL | 193 | -3.398 | 15.481 | 17.230 | 1.00 | 43.63 |
| ATOM | 21 | CA  | VAL | 193 | -2.823 | 14.164 | 17.009 | 1.00 | 42.13 |
| ATOM | 22 | CB  | VAL | 193 | -2.825 | 13.322 | 18.299 | 1.00 | 40.58 |
| ATOM | 23 | CG1 | VAL | 193 | -2.060 | 12.023 | 18.080 | 1.00 | 39.57 |
| ATOM | 24 | CG2 | VAL | 193 | -2.217 | 14.124 | 19.442 | 1.00 | 38.30 |
| ATOM | 25 | C   | VAL | 193 | -3.641 | 13.482 | 15.909 | 1.00 | 42.80 |
| ATOM | 26 | O   | VAL | 193 | -4.810 | 13.132 | 16.109 | 1.00 | 42.17 |
| ATOM | 27 | N   | PRO | 194 | -3.033 | 13.309 | 14.724 | 1.00 | 42.99 |
| ATOM | 28 | CD  | PRO | 194 | -1.601 | 13.536 | 14.488 | 1.00 | 43.90 |
| ATOM | 29 | CA  | PRO | 194 | -3.638 | 12.690 | 13.546 | 1.00 | 43.17 |
| ATOM | 30 | CB  | PRO | 194 | -2.493 | 12.691 | 12.536 | 1.00 | 43.02 |
| ATOM | 31 | CG  | PRO | 194 | -1.571 | 13.753 | 13.016 | 1.00 | 43.69 |
| ATOM | 32 | C   | PRO | 194 | -4.068 | 11.265 | 13.819 | 1.00 | 43.70 |
| ATOM | 33 | O   | PRO | 194 | -3.519 | 10.595 | 14.691 | 1.00 | 44.16 |
| ATOM | 34 | N   | ALA | 195 | -5.031 | 10.794 | 13.038 | 1.00 | 43.76 |
| ATOM | 35 | CA  | ALA | 195 | -5.522 | 9.433  | 13.176 | 1.00 | 43.44 |
| ATOM | 36 | CB  | ALA | 195 | -6.782 | 9.247  | 12.327 | 1.00 | 44.50 |
| ATOM | 37 | C   | ALA | 195 | -4.422 | 8.466  | 12.732 | 1.00 | 42.59 |
| ATOM | 38 | O   | ALA | 195 | -4.320 | 7.345  | 13.235 | 1.00 | 43.20 |
| ATOM | 39 | N   | SER | 196 | -3.607 | 8.914  | 11.783 | 1.00 | 41.07 |
| ATOM | 40 | CA  | SER | 196 | -2.507 | 8.117  | 11.255 | 1.00 | 40.13 |
| ATOM | 41 | CB  | SER | 196 | -2.859 | 7.604  | 9.851  | 1.00 | 41.51 |
| ATOM | 42 | OG  | SER | 196 | -3.572 | 8.583  | 9.106  | 1.00 | 43.93 |
| ATOM | 43 | C   | SER | 196 | -1.225 | 8.957  | 11.233 | 1.00 | 37.38 |
| ATOM | 44 | O   | SER | 196 | -1.274 | 10.181 | 11.393 | 1.00 | 36.47 |
| ATOM | 45 | N   | PHE | 197 | -0.082 | 8.303  | 11.037 | 1.00 | 35.00 |
| ATOM | 46 | CA  | PHE | 197 | 1.193  | 9.017  | 11.014 | 1.00 | 31.57 |
| ATOM | 47 | CB  | PHE | 197 | 2.373  | 8.079  | 10.744 | 1.00 | 28.81 |
| ATOM | 48 | CG  | PHE | 197 | 3.697  | 8.794  | 10.693 | 1.00 | 25.08 |
| ATOM | 49 | CD1 | PHE | 197 | 4.343  | 9.162  | 11.863 | 1.00 | 23.41 |
| ATOM | 50 | CD2 | PHE | 197 | 4.254  | 9.167  | 9.482  | 1.00 | 23.23 |
| ATOM | 51 | CE1 | PHE | 197 | 5.505  | 9.887  | 11.824 | 1.00 | 21.81 |
| ATOM | 52 | CE2 | PHE | 197 | 5.420  | 9.894  | 9.437  | 1.00 | 21.64 |
| ATOM | 53 | CZ  | PHE | 197 | 6.045  | 10.256 | 10.606 | 1.00 | 22.04 |

FIGURE 1 (cont.)

| | | | | | | | | |
|---|---|---|---|---|---|---|---|---|
| ATOM | 54 | C | PHE | 197 | 1.262 | 10.163 | 10.020 | 1.00 30.70 |
| ATOM | 55 | O | PHE | 197 | 1.089 | 9.965 | 8.816 | 1.00 31.02 |
| ATOM | 56 | N | GLN | 198 | 1.582 | 11.345 | 10.536 | 1.00 30.64 |
| ATOM | 57 | CA | GLN | 198 | 1.731 | 12.550 | 9.732 | 1.00 30.20 |
| ATOM | 58 | CB | GLN | 198 | 0.478 | 13.438 | 9.818 | 1.00 33.70 |
| ATOM | 59 | CG | GLN | 198 | -0.893 | 12.720 | 9.747 | 1.00 38.79 |
| ATOM | 60 | CD | GLN | 198 | -1.331 | 12.268 | 8.350 | 1.00 41.73 |
| ATOM | 61 | OE1 | GLN | 198 | -2.254 | 11.462 | 8.218 | 1.00 44.20 |
| ATOM | 62 | NE2 | GLN | 198 | -0.696 | 12.802 | 7.310 | 1.00 44.35 |
| ATOM | 63 | C | GLN | 198 | 2.921 | 13.340 | 10.279 | 1.00 28.49 |
| ATOM | 64 | O | GLN | 198 | 3.341 | 13.148 | 11.423 | 1.00 27.20 |
| ATOM | 65 | N | VAL | 199 | 3.485 | 14.191 | 9.431 | 1.00 28.09 |
| ATOM | 66 | CA | VAL | 199 | 4.595 | 15.074 | 9.786 | 1.00 27.30 |
| ATOM | 67 | CB | VAL | 199 | 5.798 | 14.949 | 8.803 | 1.00 27.93 |
| ATOM | 68 | CG1 | VAL | 199 | 6.783 | 16.106 | 9.018 | 1.00 26.84 |
| ATOM | 69 | CG2 | VAL | 199 | 6.510 | 13.607 | 8.984 | 1.00 27.42 |
| ATOM | 70 | C | VAL | 199 | 3.989 | 16.464 | 9.624 | 1.00 26.70 |
| ATOM | 71 | O | VAL | 199 | 3.425 | 16.784 | 8.579 | 1.00 26.24 |
| ATOM | 72 | N | ALA | 200 | 4.115 | 17.298 | 10.640 | 1.00 26.58 |
| ATOM | 73 | CA | ALA | 200 | 3.538 | 18.624 | 10.574 | 1.00 25.57 |
| ATOM | 74 | CB | ALA | 200 | 2.364 | 18.725 | 11.544 | 1.00 24.63 |
| ATOM | 75 | C | ALA | 200 | 4.567 | 19.677 | 10.906 | 1.00 25.17 |
| ATOM | 76 | O | ALA | 200 | 5.569 | 19.400 | 11.558 | 1.00 24.12 |
| ATOM | 77 | N | HIS | 201 | 4.306 | 20.891 | 10.442 | 1.00 25.38 |
| ATOM | 78 | CA | HIS | 201 | 5.178 | 22.022 | 10.698 | 1.00 25.85 |
| ATOM | 79 | CB | HIS | 201 | 5.417 | 22.812 | 9.413 | 1.00 24.66 |
| ATOM | 80 | CG | HIS | 201 | 6.130 | 22.041 | 8.353 | 1.00 24.83 |
| ATOM | 81 | CD2 | HIS | 201 | 5.683 | 21.125 | 7.461 | 1.00 26.76 |
| ATOM | 82 | ND1 | HIS | 201 | 7.480 | 22.171 | 8.124 | 1.00 24.29 |
| ATOM | 83 | CE1 | HIS | 201 | 7.838 | 21.367 | 7.139 | 1.00 27.15 |
| ATOM | 84 | NE2 | HIS | 201 | 6.767 | 20.722 | 6.719 | 1.00 28.31 |
| ATOM | 85 | C | HIS | 201 | 4.469 | 22.927 | 11.689 | 1.00 26.56 |
| ATOM | 86 | O | HIS | 201 | 3.264 | 23.163 | 11.556 | 1.00 27.65 |
| ATOM | 87 | N | LEU | 202 | 5.191 | 23.399 | 12.698 | 1.00 26.07 |
| ATOM | 88 | CA | LEU | 202 | 4.601 | 24.317 | 13.659 | 1.00 25.58 |
| ATOM | 89 | CB | LEU | 202 | 4.621 | 23.756 | 15.085 | 1.00 25.67 |
| ATOM | 90 | CG | LEU | 202 | 4.182 | 24.740 | 16.183 | 1.00 25.11 |
| ATOM | 91 | CD1 | LEU | 202 | 2.710 | 25.088 | 16.033 | 1.00 22.05 |
| ATOM | 92 | CD2 | LEU | 202 | 4.459 | 24.159 | 17.554 | 1.00 23.90 |
| ATOM | 93 | C | LEU | 202 | 5.398 | 25.609 | 13.585 | 1.00 25.03 |
| ATOM | 94 | O | LEU | 202 | 6.563 | 25.645 | 13.962 | 1.00 26.19 |
| ATOM | 95 | N | HIS | 203 | 4.796 | 26.637 | 13.000 | 1.00 24.59 |
| ATOM | 96 | CA | HIS | 203 | 5.449 | 27.923 | 12.874 | 1.00 26.20 |
| ATOM | 97 | CB | HIS | 203 | 5.295 | 28.476 | 11.451 | 1.00 25.91 |
| ATOM | 98 | CG | HIS | 203 | 5.862 | 27.588 | 10.384 | 1.00 24.03 |
| ATOM | 99 | CD2 | HIS | 203 | 5.581 | 27.497 | 9.062 | 1.00 24.35 |
| ATOM | 100 | ND1 | HIS | 203 | 6.827 | 26.637 | 10.633 | 1.00 25.58 |
| ATOM | 101 | CE1 | HIS | 203 | 7.115 | 25.994 | 9.517 | 1.00 23.23 |
| ATOM | 102 | NE2 | HIS | 203 | 6.372 | 26.498 | 8.548 | 1.00 24.13 |
| ATOM | 103 | C | HIS | 203 | 4.763 | 28.836 | 13.877 | 1.00 28.92 |
| ATOM | 104 | O | HIS | 203 | 3.590 | 29.174 | 13.711 | 1.00 29.53 |
| ATOM | 105 | N | ALA | 204 | 5.479 | 29.191 | 14.939 | 1.00 30.12 |
| ATOM | 106 | CA | ALA | 204 | 4.936 | 30.043 | 15.982 | 1.00 30.61 |
| ATOM | 107 | CB | ALA | 204 | 4.275 | 29.193 | 17.066 | 1.00 30.68 |
| ATOM | 108 | C | ALA | 204 | 6.093 | 30.831 | 16.556 | 1.00 31.44 |
| ATOM | 109 | O | ALA | 204 | 7.201 | 30.310 | 16.662 | 1.00 32.28 |
| ATOM | 110 | N | PRO | 205 | 5.847 | 32.092 | 16.957 | 1.00 32.18 |
| ATOM | 111 | CD | PRO | 205 | 4.523 | 32.742 | 16.982 | 1.00 32.11 |

FIGURE 1 (cont.)

| ATOM | 112 | CA  | PRO | 205 | 6.872  | 32.978 | 17.524 | 1.00 | 31.56 |
|------|-----|-----|-----|-----|--------|--------|--------|------|-------|
| ATOM | 113 | CB  | PRO | 205 | 6.102  | 34.282 | 17.748 | 1.00 | 31.92 |
| ATOM | 114 | CG  | PRO | 205 | 4.708  | 33.804 | 18.033 | 1.00 | 31.71 |
| ATOM | 115 | C   | PRO | 205 | 7.525  | 32.474 | 18.805 | 1.00 | 30.91 |
| ATOM | 116 | O   | PRO | 205 | 6.924  | 31.728 | 19.566 | 1.00 | 30.86 |
| ATOM | 117 | N   | THR | 206 | 8.764  | 32.888 | 19.037 | 1.00 | 31.28 |
| ATOM | 118 | CA  | THR | 206 | 9.492  | 32.486 | 20.228 | 1.00 | 32.05 |
| ATOM | 119 | CB  | THR | 206 | 10.872 | 33.160 | 20.276 | 1.00 | 32.26 |
| ATOM | 120 | OG1 | THR | 206 | 11.616 | 32.779 | 19.115 | 1.00 | 35.41 |
| ATOM | 121 | CG2 | THR | 206 | 11.641 | 32.740 | 21.506 | 1.00 | 32.09 |
| ATOM | 122 | C   | THR | 206 | 8.674  | 32.894 | 21.444 | 1.00 | 32.25 |
| ATOM | 123 | O   | THR | 206 | 8.038  | 33.942 | 21.439 | 1.00 | 34.50 |
| ATOM | 124 | N   | GLY | 207 | 8.664  | 32.052 | 22.470 | 1.00 | 31.86 |
| ATOM | 125 | CA  | GLY | 207 | 7.894  | 32.358 | 23.661 | 1.00 | 31.13 |
| ATOM | 126 | C   | GLY | 207 | 6.455  | 31.860 | 23.626 | 1.00 | 30.15 |
| ATOM | 127 | O   | GLY | 207 | 5.765  | 31.891 | 24.642 | 1.00 | 31.27 |
| ATOM | 128 | N   | SER | 208 | 6.005  | 31.362 | 22.480 | 1.00 | 29.48 |
| ATOM | 129 | CA  | SER | 208 | 4.642  | 30.868 | 22.374 | 1.00 | 28.52 |
| ATOM | 130 | CB  | SER | 208 | 4.182  | 30.872 | 20.908 | 1.00 | 27.20 |
| ATOM | 131 | OG  | SER | 208 | 5.029  | 30.097 | 20.086 | 1.00 | 25.55 |
| ATOM | 132 | C   | SER | 208 | 4.415  | 29.497 | 23.033 | 1.00 | 28.55 |
| ATOM | 133 | O   | SER | 208 | 3.271  | 29.044 | 23.149 | 1.00 | 29.28 |
| ATOM | 134 | N   | GLY | 209 | 5.494  | 28.840 | 23.463 | 1.00 | 28.23 |
| ATOM | 135 | CA  | GLY | 209 | 5.367  | 27.540 | 24.120 | 1.00 | 28.17 |
| ATOM | 136 | C   | GLY | 209 | 5.508  | 26.273 | 23.279 | 1.00 | 29.13 |
| ATOM | 137 | O   | GLY | 209 | 5.108  | 25.181 | 23.721 | 1.00 | 27.88 |
| ATOM | 138 | N   | LYS | 210 | 6.110  | 26.398 | 22.096 | 1.00 | 29.07 |
| ATOM | 139 | CA  | LYS | 210 | 6.318  | 25.267 | 21.180 | 1.00 | 28.86 |
| ATOM | 140 | CB  | LYS | 210 | 7.066  | 25.726 | 19.920 | 1.00 | 29.78 |
| ATOM | 141 | CG  | LYS | 210 | 6.367  | 26.802 | 19.103 | 1.00 | 30.86 |
| ATOM | 142 | CD  | LYS | 210 | 7.072  | 27.040 | 17.770 | 1.00 | 30.40 |
| ATOM | 143 | CE  | LYS | 210 | 8.506  | 27.502 | 17.959 | 1.00 | 31.43 |
| ATOM | 144 | NZ  | LYS | 210 | 8.607  | 28.803 | 18.689 | 1.00 | 33.79 |
| ATOM | 145 | C   | LYS | 210 | 7.092  | 24.098 | 21.797 | 1.00 | 28.32 |
| ATOM | 146 | O   | LYS | 210 | 6.829  | 22.935 | 21.498 | 1.00 | 28.11 |
| ATOM | 147 | N   | SER | 211 | 8.072  | 24.411 | 22.630 | 1.00 | 28.62 |
| ATOM | 148 | CA  | SER | 211 | 8.876  | 23.377 | 23.256 | 1.00 | 28.88 |
| ATOM | 149 | CB  | SER | 211 | 10.348 | 23.763 | 23.172 | 1.00 | 30.34 |
| ATOM | 150 | OG  | SER | 211 | 10.516 | 25.162 | 23.338 | 1.00 | 32.24 |
| ATOM | 151 | C   | SER | 211 | 8.509  | 23.084 | 24.700 | 1.00 | 28.90 |
| ATOM | 152 | O   | SER | 211 | 9.241  | 22.376 | 25.384 | 1.00 | 29.14 |
| ATOM | 153 | N   | THR | 212 | 7.367  | 23.599 | 25.152 | 1.00 | 29.90 |
| ATOM | 154 | CA  | THR | 212 | 6.925  | 23.399 | 26.532 | 1.00 | 29.80 |
| ATOM | 155 | CB  | THR | 212 | 7.371  | 24.579 | 27.415 | 1.00 | 28.95 |
| ATOM | 156 | OG1 | THR | 212 | 7.033  | 25.814 | 26.768 | 1.00 | 29.28 |
| ATOM | 157 | CG2 | THR | 212 | 8.870  | 24.531 | 27.651 | 1.00 | 26.88 |
| ATOM | 158 | C   | THR | 212 | 5.412  | 23.193 | 26.686 | 1.00 | 29.89 |
| ATOM | 159 | O   | THR | 212 | 4.949  | 22.153 | 27.166 | 1.00 | 29.41 |
| ATOM | 160 | N   | LYS | 213 | 4.641  | 24.191 | 26.277 | 1.00 | 31.79 |
| ATOM | 161 | CA  | LYS | 213 | 3.185  | 24.128 | 26.374 | 1.00 | 31.17 |
| ATOM | 162 | CB  | LYS | 213 | 2.576  | 25.486 | 26.013 | 1.00 | 31.92 |
| ATOM | 163 | CG  | LYS | 213 | 1.066  | 25.565 | 26.123 | 1.00 | 33.79 |
| ATOM | 164 | CD  | LYS | 213 | 0.627  | 27.019 | 26.126 | 1.00 | 36.61 |
| ATOM | 165 | CE  | LYS | 213 | -0.887 | 27.169 | 26.155 | 1.00 | 38.22 |
| ATOM | 166 | NZ  | LYS | 213 | -1.254 | 28.563 | 26.558 | 1.00 | 38.71 |
| ATOM | 167 | C   | LYS | 213 | 2.636  | 23.043 | 25.464 | 1.00 | 30.15 |
| ATOM | 168 | O   | LYS | 213 | 1.836  | 22.212 | 25.894 | 1.00 | 29.46 |
| ATOM | 169 | N   | VAL | 214 | 3.110  | 23.026 | 24.222 | 1.00 | 29.37 |

FIGURE 1 (cont.)

| | | | | | | | | |
|---|---|---|---|---|---|---|---|---|
| ATOM | 170 | CA | VAL | 214 | 2.657 | 22.042 | 23.247 | 1.00 29.35 |
| ATOM | 171 | CB | VAL | 214 | 3.274 | 22.317 | 21.845 | 1.00 30.43 |
| ATOM | 172 | CG1 | VAL | 214 | 2.805 | 21.296 | 20.826 | 1.00 29.20 |
| ATOM | 173 | CG2 | VAL | 214 | 2.881 | 23.719 | 21.381 | 1.00 31.27 |
| ATOM | 174 | C | VAL | 214 | 2.903 | 20.604 | 23.725 | 1.00 27.79 |
| ATOM | 175 | O | VAL | 214 | 1.980 | 19.781 | 23.722 | 1.00 29.24 |
| ATOM | 176 | N | PRO | 215 | 4.146 | 20.268 | 24.125 | 1.00 25.78 |
| ATOM | 177 | CD | PRO | 215 | 5.439 | 20.966 | 24.012 | 1.00 24.07 |
| ATOM | 178 | CA | PRO | 215 | 4.338 | 18.887 | 24.586 | 1.00 24.86 |
| ATOM | 179 | CB | PRO | 215 | 5.862 | 18.782 | 24.767 | 1.00 22.92 |
| ATOM | 180 | CG | PRO | 215 | 6.298 | 20.185 | 24.983 | 1.00 23.18 |
| ATOM | 181 | C | PRO | 215 | 3.556 | 18.590 | 25.878 | 1.00 23.85 |
| ATOM | 182 | O | PRO | 215 | 3.157 | 17.448 | 26.109 | 1.00 24.03 |
| ATOM | 183 | N | ALA | 216 | 3.322 | 19.615 | 26.700 | 1.00 24.13 |
| ATOM | 184 | CA | ALA | 216 | 2.555 | 19.466 | 27.946 | 1.00 24.64 |
| ATOM | 185 | CB | ALA | 216 | 2.592 | 20.754 | 28.741 | 1.00 23.09 |
| ATOM | 186 | C | ALA | 216 | 1.100 | 19.089 | 27.616 | 1.00 25.20 |
| ATOM | 187 | O | ALA | 216 | 0.517 | 18.192 | 28.232 | 1.00 25.36 |
| ATOM | 188 | N | ALA | 217 | 0.524 | 19.773 | 26.631 | 1.00 25.49 |
| ATOM | 189 | CA | ALA | 217 | -0.836 | 19.501 | 26.187 | 1.00 25.40 |
| ATOM | 190 | CB | ALA | 217 | -1.277 | 20.565 | 25.194 | 1.00 23.76 |
| ATOM | 191 | C | ALA | 217 | -0.905 | 18.104 | 25.547 | 1.00 25.48 |
| ATOM | 192 | O | ALA | 217 | -1.878 | 17.373 | 25.725 | 1.00 25.77 |
| ATOM | 193 | N | TYR | 218 | 0.136 | 17.735 | 24.807 | 1.00 25.42 |
| ATOM | 194 | CA | TYR | 218 | 0.191 | 16.422 | 24.165 | 1.00 24.86 |
| ATOM | 195 | CB | TYR | 218 | 1.410 | 16.306 | 23.243 | 1.00 24.75 |
| ATOM | 196 | CG | TYR | 218 | 1.253 | 16.946 | 21.882 | 1.00 24.58 |
| ATOM | 197 | CD1 | TYR | 218 | 0.072 | 16.795 | 21.146 | 1.00 23.47 |
| ATOM | 198 | CE1 | TYR | 218 | -0.048 | 17.332 | 19.858 | 1.00 24.75 |
| ATOM | 199 | CD2 | TYR | 218 | 2.310 | 17.656 | 21.303 | 1.00 23.47 |
| ATOM | 200 | CE2 | TYR | 218 | 2.205 | 18.192 | 20.021 | 1.00 23.76 |
| ATOM | 201 | CZ | TYR | 218 | 1.025 | 18.028 | 19.299 | 1.00 25.01 |
| ATOM | 202 | OH | TYR | 218 | 0.924 | 18.553 | 18.023 | 1.00 24.22 |
| ATOM | 203 | C | TYR | 218 | 0.245 | 15.294 | 25.183 | 1.00 23.95 |
| ATOM | 204 | O | TYR | 218 | -0.499 | 14.324 | 25.065 | 1.00 25.49 |
| ATOM | 205 | N | ALA | 219 | 1.140 | 15.410 | 26.160 | 1.00 23.90 |
| ATOM | 206 | CA | ALA | 219 | 1.305 | 14.388 | 27.204 | 1.00 25.10 |
| ATOM | 207 | CB | ALA | 219 | 2.553 | 14.673 | 28.033 | 1.00 23.15 |
| ATOM | 208 | C | ALA | 219 | 0.079 | 14.281 | 28.115 | 1.00 26.52 |
| ATOM | 209 | O | ALA | 219 | -0.257 | 13.193 | 28.595 | 1.00 26.05 |
| ATOM | 210 | N | ALA | 220 | -0.591 | 15.416 | 28.328 | 1.00 28.32 |
| ATOM | 211 | CA | ALA | 220 | -1.789 | 15.484 | 29.161 | 1.00 27.69 |
| ATOM | 212 | CB | ALA | 220 | -2.224 | 16.933 | 29.346 | 1.00 28.77 |
| ATOM | 213 | C | ALA | 220 | -2.904 | 14.666 | 28.528 | 1.00 27.42 |
| ATOM | 214 | O | ALA | 220 | -3.873 | 14.315 | 29.190 | 1.00 27.84 |
| ATOM | 215 | N | GLN | 221 | -2.762 | 14.380 | 27.236 | 1.00 28.01 |
| ATOM | 216 | CA | GLN | 221 | -3.733 | 13.576 | 26.492 | 1.00 27.15 |
| ATOM | 217 | CB | GLN | 221 | -3.782 | 13.991 | 25.027 | 1.00 28.76 |
| ATOM | 218 | CG | GLN | 221 | -4.413 | 15.331 | 24.739 | 1.00 30.06 |
| ATOM | 219 | CD | GLN | 221 | -4.084 | 15.798 | 23.335 | 1.00 32.54 |
| ATOM | 220 | OE1 | GLN | 221 | -4.457 | 15.159 | 22.346 | 1.00 34.37 |
| ATOM | 221 | NE2 | GLN | 221 | -3.350 | 16.895 | 23.238 | 1.00 34.38 |
| ATOM | 222 | C | GLN | 221 | -3.321 | 12.119 | 26.554 | 1.00 26.58 |
| ATOM | 223 | O | GLN | 221 | -3.881 | 11.284 | 25.851 | 1.00 27.44 |
| ATOM | 224 | N | GLY | 222 | -2.285 | 11.833 | 27.334 | 1.00 25.93 |
| ATOM | 225 | CA | GLY | 222 | -1.828 | 10.472 | 27.487 | 1.00 24.98 |
| ATOM | 226 | C | GLY | 222 | -0.767 | 9.987 | 26.530 | 1.00 26.33 |
| ATOM | 227 | O | GLY | 222 | -0.561 | 8.783 | 26.414 | 1.00 27.70 |

FIGURE 1 (cont.)

| ATOM | 228 | N   | TYR | 223 | -0.057 | 10.896 | 25.875 | 1.00 | 26.89 |
|------|-----|-----|-----|-----|--------|--------|--------|------|-------|
| ATOM | 229 | CA  | TYR | 223 | 0.995  | 10.498 | 24.940 | 1.00 | 25.87 |
| ATOM | 230 | CB  | TYR | 223 | 0.901  | 11.316 | 23.665 | 1.00 | 25.29 |
| ATOM | 231 | CG  | TYR | 223 | -0.373 | 11.111 | 22.906 | 1.00 | 25.96 |
| ATOM | 232 | CD1 | TYR | 223 | -1.399 | 12.045 | 22.974 | 1.00 | 25.65 |
| ATOM | 233 | CE1 | TYR | 223 | -2.559 | 11.873 | 22.250 | 1.00 | 27.75 |
| ATOM | 234 | CD2 | TYR | 223 | -0.542 | 9.993  | 22.096 | 1.00 | 26.27 |
| ATOM | 235 | CE2 | TYR | 223 | -1.692 | 9.808  | 21.372 | 1.00 | 27.03 |
| ATOM | 236 | CZ  | TYR | 223 | -2.698 | 10.749 | 21.446 | 1.00 | 28.75 |
| ATOM | 237 | OH  | TYR | 223 | -3.839 | 10.573 | 20.695 | 1.00 | 32.89 |
| ATOM | 238 | C   | TYR | 223 | 2.415  | 10.629 | 25.483 | 1.00 | 26.22 |
| ATOM | 239 | O   | TYR | 223 | 2.697  | 11.441 | 26.373 | 1.00 | 25.06 |
| ATOM | 240 | N   | LYS | 224 | 3.308  | 9.826  | 24.919 | 1.00 | 27.21 |
| ATOM | 241 | CA  | LYS | 224 | 4.721  | 9.850  | 25.270 | 1.00 | 27.71 |
| ATOM | 242 | CB  | LYS | 224 | 5.325  | 8.460  | 25.107 | 1.00 | 29.76 |
| ATOM | 243 | CG  | LYS | 224 | 4.827  | 7.470  | 26.139 | 1.00 | 35.42 |
| ATOM | 244 | CD  | LYS | 224 | 5.314  | 7.887  | 27.525 | 1.00 | 39.88 |
| ATOM | 245 | CE  | LYS | 224 | 4.771  | 7.005  | 28.652 | 1.00 | 41.50 |
| ATOM | 246 | NZ  | LYS | 224 | 5.385  | 7.396  | 29.969 | 1.00 | 42.40 |
| ATOM | 247 | C   | LYS | 224 | 5.309  | 10.821 | 24.258 | 1.00 | 26.68 |
| ATOM | 248 | O   | LYS | 224 | 5.265  | 10.571 | 23.047 | 1.00 | 27.78 |
| ATOM | 249 | N   | VAL | 225 | 5.785  | 11.959 | 24.746 | 1.00 | 25.81 |
| ATOM | 250 | CA  | VAL | 225 | 6.333  | 12.998 | 23.883 | 1.00 | 24.37 |
| ATOM | 251 | CB  | VAL | 225 | 5.649  | 14.354 | 24.161 | 1.00 | 24.83 |
| ATOM | 252 | CG1 | VAL | 225 | 5.997  | 15.359 | 23.075 | 1.00 | 23.06 |
| ATOM | 253 | CG2 | VAL | 225 | 4.137  | 14.166 | 24.274 | 1.00 | 25.36 |
| ATOM | 254 | C   | VAL | 225 | 7.834  | 13.190 | 24.046 | 1.00 | 23.03 |
| ATOM | 255 | O   | VAL | 225 | 8.355  | 13.220 | 25.166 | 1.00 | 20.40 |
| ATOM | 256 | N   | LEU | 226 | 8.513  | 13.330 | 22.914 | 1.00 | 22.55 |
| ATOM | 257 | CA  | LEU | 226 | 9.954  | 13.551 | 22.878 | 1.00 | 21.32 |
| ATOM | 258 | CB  | LEU | 226 | 10.627 | 12.471 | 22.037 | 1.00 | 18.45 |
| ATOM | 259 | CG  | LEU | 226 | 12.082 | 12.710 | 21.656 | 1.00 | 18.51 |
| ATOM | 260 | CD1 | LEU | 226 | 12.985 | 12.577 | 22.884 | 1.00 | 16.54 |
| ATOM | 261 | CD2 | LEU | 226 | 12.473 | 11.717 | 20.570 | 1.00 | 19.37 |
| ATOM | 262 | C   | LEU | 226 | 10.192 | 14.926 | 22.253 | 1.00 | 20.71 |
| ATOM | 263 | O   | LEU | 226 | 9.629  | 15.245 | 21.202 | 1.00 | 20.63 |
| ATOM | 264 | N   | VAL | 227 | 10.993 | 15.752 | 22.912 | 1.00 | 22.06 |
| ATOM | 265 | CA  | VAL | 227 | 11.290 | 17.087 | 22.404 | 1.00 | 22.02 |
| ATOM | 266 | CB  | VAL | 227 | 10.915 | 18.173 | 23.425 | 1.00 | 20.33 |
| ATOM | 267 | CG1 | VAL | 227 | 10.933 | 19.532 | 22.757 | 1.00 | 19.96 |
| ATOM | 268 | CG2 | VAL | 227 | 9.561  | 17.881 | 24.043 | 1.00 | 19.10 |
| ATOM | 269 | C   | VAL | 227 | 12.787 | 17.165 | 22.111 | 1.00 | 22.26 |
| ATOM | 270 | O   | VAL | 227 | 13.612 | 17.040 | 23.023 | 1.00 | 23.12 |
| ATOM | 271 | N   | LEU | 228 | 13.135 | 17.322 | 20.839 | 1.00 | 21.87 |
| ATOM | 272 | CA  | LEU | 228 | 14.534 | 17.397 | 20.435 | 1.00 | 21.87 |
| ATOM | 273 | CB  | LEU | 228 | 14.770 | 16.590 | 19.162 | 1.00 | 20.02 |
| ATOM | 274 | CG  | LEU | 228 | 14.576 | 15.079 | 19.254 | 1.00 | 18.46 |
| ATOM | 275 | CD1 | LEU | 228 | 14.817 | 14.488 | 17.874 | 1.00 | 17.50 |
| ATOM | 276 | CD2 | LEU | 228 | 15.522 | 14.477 | 20.304 | 1.00 | 15.84 |
| ATOM | 277 | C   | LEU | 228 | 14.961 | 18.833 | 20.216 | 1.00 | 22.19 |
| ATOM | 278 | O   | LEU | 228 | 14.338 | 19.566 | 19.450 | 1.00 | 23.01 |
| ATOM | 279 | N   | ASN | 229 | 16.063 | 19.211 | 20.849 | 1.00 | 22.54 |
| ATOM | 280 | CA  | ASN | 229 | 16.587 | 20.567 | 20.756 | 1.00 | 22.64 |
| ATOM | 281 | CB  | ASN | 229 | 16.276 | 21.301 | 22.067 | 1.00 | 23.81 |
| ATOM | 282 | CG  | ASN | 229 | 16.582 | 22.770 | 22.008 | 1.00 | 24.90 |
| ATOM | 283 | OD1 | ASN | 229 | 17.732 | 23.196 | 22.184 | 1.00 | 26.02 |
| ATOM | 284 | ND2 | ASN | 229 | 15.548 | 23.568 | 21.794 | 1.00 | 24.10 |
| ATOM | 285 | C   | ASN | 229 | 18.101 | 20.482 | 20.517 | 1.00 | 22.10 |

FIGURE 1 (cont.)

| ATOM | 286 | O   | ASN | 229 | 18.756 | 19.525 | 20.938 | 1.00 | 19.92 |
|------|-----|-----|-----|-----|--------|--------|--------|------|-------|
| ATOM | 287 | N   | PRO | 230 | 18.659 | 21.429 | 19.753 | 1.00 | 23.12 |
| ATOM | 288 | CD  | PRO | 230 | 17.987 | 22.400 | 18.872 | 1.00 | 21.71 |
| ATOM | 289 | CA  | PRO | 230 | 20.107 | 21.397 | 19.495 | 1.00 | 23.95 |
| ATOM | 290 | CB  | PRO | 230 | 20.269 | 22.383 | 18.336 | 1.00 | 23.83 |
| ATOM | 291 | CG  | PRO | 230 | 19.114 | 23.319 | 18.510 | 1.00 | 23.76 |
| ATOM | 292 | C   | PRO | 230 | 21.011 | 21.755 | 20.688 | 1.00 | 24.47 |
| ATOM | 293 | O   | PRO | 230 | 22.114 | 21.211 | 20.834 | 1.00 | 25.45 |
| ATOM | 294 | N   | SER | 231 | 20.512 | 22.595 | 21.584 | 1.00 | 24.28 |
| ATOM | 295 | CA  | SER | 231 | 21.290 | 23.036 | 22.727 | 1.00 | 24.31 |
| ATOM | 296 | CB  | SER | 231 | 20.886 | 24.461 | 23.088 | 1.00 | 23.88 |
| ATOM | 297 | OG  | SER | 231 | 21.566 | 24.896 | 24.251 | 1.00 | 27.81 |
| ATOM | 298 | C   | SER | 231 | 21.236 | 22.165 | 23.975 | 1.00 | 25.03 |
| ATOM | 299 | O   | SER | 231 | 20.157 | 21.870 | 24.496 | 1.00 | 25.25 |
| ATOM | 300 | N   | VAL | 232 | 22.413 | 21.805 | 24.480 | 1.00 | 24.64 |
| ATOM | 301 | CA  | VAL | 232 | 22.525 | 21.011 | 25.694 | 1.00 | 24.77 |
| ATOM | 302 | CB  | VAL | 232 | 24.006 | 20.628 | 25.975 | 1.00 | 24.98 |
| ATOM | 303 | CG1 | VAL | 232 | 24.184 | 20.163 | 27.417 | 1.00 | 24.08 |
| ATOM | 304 | CG2 | VAL | 232 | 24.458 | 19.534 | 25.019 | 1.00 | 20.75 |
| ATOM | 305 | C   | VAL | 232 | 21.976 | 21.862 | 26.852 | 1.00 | 26.64 |
| ATOM | 306 | O   | VAL | 232 | 21.174 | 21.394 | 27.668 | 1.00 | 28.40 |
| ATOM | 307 | N   | ALA | 233 | 22.365 | 23.133 | 26.879 | 1.00 | 26.57 |
| ATOM | 308 | CA  | ALA | 233 | 21.916 | 24.051 | 27.922 | 1.00 | 26.13 |
| ATOM | 309 | CB  | ALA | 233 | 22.592 | 25.417 | 27.759 | 1.00 | 25.46 |
| ATOM | 310 | C   | ALA | 233 | 20.401 | 24.203 | 27.907 | 1.00 | 25.51 |
| ATOM | 311 | O   | ALA | 233 | 19.764 | 24.124 | 28.952 | 1.00 | 26.22 |
| ATOM | 312 | N   | ALA | 234 | 19.831 | 24.397 | 26.718 | 1.00 | 25.47 |
| ATOM | 313 | CA  | ALA | 234 | 18.385 | 24.553 | 26.567 | 1.00 | 24.61 |
| ATOM | 314 | CB  | ALA | 234 | 18.031 | 24.857 | 25.138 | 1.00 | 23.89 |
| ATOM | 315 | C   | ALA | 234 | 17.653 | 23.304 | 27.015 | 1.00 | 25.81 |
| ATOM | 316 | O   | ALA | 234 | 16.652 | 23.393 | 27.728 | 1.00 | 25.42 |
| ATOM | 317 | N   | THR | 235 | 18.157 | 22.144 | 26.591 | 1.00 | 26.43 |
| ATOM | 318 | CA  | THR | 235 | 17.556 | 20.868 | 26.951 | 1.00 | 26.97 |
| ATOM | 319 | CB  | THR | 235 | 18.339 | 19.673 | 26.345 | 1.00 | 27.79 |
| ATOM | 320 | OG1 | THR | 235 | 18.322 | 19.768 | 24.916 | 1.00 | 27.58 |
| ATOM | 321 | CG2 | THR | 235 | 17.704 | 18.343 | 26.748 | 1.00 | 26.60 |
| ATOM | 322 | C   | THR | 235 | 17.499 | 20.746 | 28.472 | 1.00 | 27.43 |
| ATOM | 323 | O   | THR | 235 | 16.440 | 20.488 | 29.035 | 1.00 | 28.23 |
| ATOM | 324 | N   | LEU | 236 | 18.624 | 20.984 | 29.138 | 1.00 | 27.19 |
| ATOM | 325 | CA  | LEU | 236 | 18.670 | 20.898 | 30.595 | 1.00 | 27.35 |
| ATOM | 326 | CB  | LEU | 236 | 20.086 | 21.185 | 31.096 | 1.00 | 28.04 |
| ATOM | 327 | CG  | LEU | 236 | 21.174 | 20.151 | 30.842 | 1.00 | 27.41 |
| ATOM | 328 | CD1 | LEU | 236 | 22.519 | 20.838 | 30.894 | 1.00 | 28.18 |
| ATOM | 329 | CD2 | LEU | 236 | 21.086 | 19.028 | 31.858 | 1.00 | 26.49 |
| ATOM | 330 | C   | LEU | 236 | 17.715 | 21.898 | 31.235 | 1.00 | 26.83 |
| ATOM | 331 | O   | LEU | 236 | 17.054 | 21.601 | 32.232 | 1.00 | 27.18 |
| ATOM | 332 | N   | GLY | 237 | 17.651 | 23.086 | 30.648 | 1.00 | 26.16 |
| ATOM | 333 | CA  | GLY | 237 | 16.804 | 24.131 | 31.178 | 1.00 | 26.03 |
| ATOM | 334 | C   | GLY | 237 | 15.333 | 23.812 | 31.228 | 1.00 | 25.39 |
| ATOM | 335 | O   | GLY | 237 | 14.651 | 24.230 | 32.151 | 1.00 | 25.99 |
| ATOM | 336 | N   | PHE | 238 | 14.841 | 23.065 | 30.252 | 1.00 | 25.78 |
| ATOM | 337 | CA  | PHE | 238 | 13.428 | 22.721 | 30.205 | 1.00 | 27.27 |
| ATOM | 338 | CB  | PHE | 238 | 13.138 | 21.811 | 29.013 | 1.00 | 27.38 |
| ATOM | 339 | CG  | PHE | 238 | 13.274 | 22.495 | 27.691 | 1.00 | 29.37 |
| ATOM | 340 | CD1 | PHE | 238 | 12.493 | 23.610 | 27.388 | 1.00 | 29.67 |
| ATOM | 341 | CD2 | PHE | 238 | 14.202 | 22.052 | 26.756 | 1.00 | 29.17 |
| ATOM | 342 | CE1 | PHE | 238 | 12.641 | 24.273 | 26.169 | 1.00 | 29.22 |
| ATOM | 343 | CE2 | PHE | 238 | 14.354 | 22.707 | 25.541 | 1.00 | 28.63 |

FIGURE 1 (cont.)

```
ATOM    344  CZ  PHE   238     13.571  23.822  25.248  1.00  27.73
ATOM    345  C   PHE   238     12.908  22.087  31.488  1.00  28.44
ATOM    346  O   PHE   238     11.740  22.267  31.838  1.00  28.75
ATOM    347  N   GLY   239     13.782  21.377  32.199  1.00  29.43
ATOM    348  CA  GLY   239     13.387  20.728  33.439  1.00  30.17
ATOM    349  C   GLY   239     12.724  21.653  34.447  1.00  30.46
ATOM    350  O   GLY   239     11.590  21.420  34.874  1.00  30.46
ATOM    351  N   ALA   240     13.429  22.711  34.825  1.00  30.54
ATOM    352  CA  ALA   240     12.904  23.667  35.785  1.00  31.68
ATOM    353  CB  ALA   240     14.007  24.611  36.258  1.00  30.45
ATOM    354  C   ALA   240     11.732  24.460  35.216  1.00  31.56
ATOM    355  O   ALA   240     10.736  24.673  35.904  1.00  32.32
ATOM    356  N   TYR   241     11.836  24.873  33.957  1.00  31.75
ATOM    357  CA  TYR   241     10.770  25.653  33.340  1.00  30.92
ATOM    358  CB  TYR   241     11.139  26.095  31.920  1.00  31.44
ATOM    359  CG  TYR   241     10.037  26.903  31.250  1.00  33.57
ATOM    360  CD1 TYR   241     10.086  28.294  31.220  1.00  35.11
ATOM    361  CE1 TYR   241      9.052  29.038  30.657  1.00  36.03
ATOM    362  CD2 TYR   241      8.919  26.276  30.690  1.00  33.41
ATOM    363  CE2 TYR   241      7.889  27.006  30.133  1.00  34.12
ATOM    364  CZ  TYR   241      7.958  28.384  30.122  1.00  36.46
ATOM    365  OH  TYR   241      6.915  29.107  29.601  1.00  39.06
ATOM    366  C   TYR   241      9.464  24.885  33.288  1.00  29.43
ATOM    367  O   TYR   241      8.402  25.452  33.500  1.00  28.88
ATOM    368  N   MET   242      9.547  23.613  32.932  1.00  28.93
ATOM    369  CA  MET   242      8.368  22.767  32.824  1.00  29.09
ATOM    370  CB  MET   242      8.735  21.464  32.106  1.00  28.71
ATOM    371  CG  MET   242      8.956  21.646  30.602  1.00  27.19
ATOM    372  SD  MET   242      7.445  22.198  29.767  1.00  24.74
ATOM    373  CE  MET   242      6.543  20.617  29.574  1.00  25.21
ATOM    374  C   MET   242      7.732  22.501  34.191  1.00  28.87
ATOM    375  O   MET   242      6.507  22.451  34.339  1.00  25.61
ATOM    376  N   SER   243      8.581  22.366  35.195  1.00  31.13
ATOM    377  CA  SER   243      8.125  22.137  36.543  1.00  31.64
ATOM    378  CB  SER   243      9.325  21.864  37.445  1.00  32.82
ATOM    379  OG  SER   243      8.916  21.422  38.725  1.00  37.37
ATOM    380  C   SER   243      7.378  23.390  36.994  1.00  31.87
ATOM    381  O   SER   243      6.226  23.320  37.420  1.00  32.45
ATOM    382  N   ALA   244      8.000  24.547  36.806  1.00  31.20
ATOM    383  CA  ALA   244      7.387  25.806  37.218  1.00  30.80
ATOM    384  CB  ALA   244      8.414  26.947  37.163  1.00  30.58
ATOM    385  C   ALA   244      6.148  26.182  36.420  1.00  29.56
ATOM    386  O   ALA   244      5.144  26.608  36.985  1.00  30.91
ATOM    387  N   ALA   245      6.205  25.994  35.113  1.00  27.79
ATOM    388  CA  ALA   245      5.093  26.369  34.261  1.00  27.16
ATOM    389  CB  ALA   245      5.601  26.694  32.871  1.00  26.05
ATOM    390  C   ALA   245      3.966  25.363  34.171  1.00  27.41
ATOM    391  O   ALA   245      2.804  25.742  34.001  1.00  27.65
ATOM    392  N   HIS   246      4.295  24.083  34.278  1.00  27.72
ATOM    393  CA  HIS   246      3.280  23.050  34.134  1.00  26.52
ATOM    394  CB  HIS   246      3.437  22.414  32.751  1.00  26.99
ATOM    395  CG  HIS   246      3.348  23.395  31.626  1.00  24.43
ATOM    396  CD2 HIS   246      4.309  23.992  30.882  1.00  26.07
ATOM    397  ND1 HIS   246      2.147  23.885  31.161  1.00  26.33
ATOM    398  CE1 HIS   246      2.369  24.741  30.179  1.00  25.34
ATOM    399  NE2 HIS   246      3.673  24.825  29.991  1.00  26.40
ATOM    400  C   HIS   246      3.245  21.961  35.208  1.00  26.80
ATOM    401  O   HIS   246      2.446  21.035  35.119  1.00  25.51
```

FIGURE 1 (cont.)

```
ATOM    402  N    GLY   247       4.097  22.073  36.223  1.00 26.76
ATOM    403  CA   GLY   247       4.123  21.069  37.267  1.00 26.09
ATOM    404  C    GLY   247       4.509  19.740  36.657  1.00 27.58
ATOM    405  O    GLY   247       3.899  18.701  36.945  1.00 28.05
ATOM    406  N    VAL   248       5.497  19.782  35.768  1.00 27.72
ATOM    407  CA   VAL   248       5.985  18.589  35.088  1.00 27.72
ATOM    408  CB   VAL   248       5.712  18.668  33.558  1.00 28.05
ATOM    409  CG1  VAL   248       6.274  17.450  32.854  1.00 28.78
ATOM    410  CG2  VAL   248       4.220  18.792  33.278  1.00 27.03
ATOM    411  C    VAL   248       7.488  18.441  35.307  1.00 27.70
ATOM    412  O    VAL   248       8.229  19.414  35.224  1.00 27.56
ATOM    413  N    ASP   249       7.923  17.228  35.622  1.00 29.51
ATOM    414  CA   ASP   249       9.342  16.928  35.813  1.00 31.97
ATOM    415  CB   ASP   249       9.563  16.290  37.187  1.00 36.65
ATOM    416  CG   ASP   249       8.834  17.029  38.296  1.00 42.98
ATOM    417  OD1  ASP   249       9.183  18.198  38.578  1.00 48.26
ATOM    418  OD2  ASP   249       7.897  16.448  38.884  1.00 47.15
ATOM    419  C    ASP   249       9.655  15.927  34.697  1.00 30.40
ATOM    420  O    ASP   249       9.444  14.721  34.854  1.00 32.54
ATOM    421  N    PRO   250      10.112  16.412  33.531  1.00 28.60
ATOM    422  CD   PRO   250      10.397  17.809  33.145  1.00 28.10
ATOM    423  CA   PRO   250      10.411  15.500  32.424  1.00 27.32
ATOM    424  CB   PRO   250      10.356  16.432  31.218  1.00 25.82
ATOM    425  CG   PRO   250      10.998  17.658  31.748  1.00 25.77
ATOM    426  C    PRO   250      11.756  14.787  32.504  1.00 27.35
ATOM    427  O    PRO   250      12.581  15.083  33.368  1.00 27.56
ATOM    428  N    ASN   251      11.944  13.805  31.629  1.00 27.78
ATOM    429  CA   ASN   251      13.213  13.090  31.553  1.00 27.99
ATOM    430  CB   ASN   251      13.046  11.776  30.802  1.00 27.88
ATOM    431  CG   ASN   251      11.944  10.914  31.380  1.00 29.52
ATOM    432  OD1  ASN   251      12.136  10.211  32.377  1.00 29.08
ATOM    433  ND2  ASN   251      10.770  10.978  30.768  1.00 30.24
ATOM    434  C    ASN   251      14.131  14.026  30.763  1.00 28.29
ATOM    435  O    ASN   251      13.687  14.685  29.808  1.00 27.76
ATOM    436  N    ILE   252      15.387  14.131  31.185  1.00 28.26
ATOM    437  CA   ILE   252      16.349  15.004  30.517  1.00 27.72
ATOM    438  CB   ILE   252      16.891  16.081  31.491  1.00 25.56
ATOM    439  CG2  ILE   252      17.909  16.978  30.780  1.00 24.45
ATOM    440  CG1  ILE   252      15.731  16.880  32.116  1.00 23.07
ATOM    441  CD1  ILE   252      14.946  17.753  31.147  1.00 20.19
ATOM    442  C    ILE   252      17.511  14.157  29.995  1.00 29.20
ATOM    443  O    ILE   252      18.148  13.435  30.759  1.00 29.28
ATOM    444  N    ARG   253      17.776  14.230  28.695  1.00 29.57
ATOM    445  CA   ARG   253      18.862  13.455  28.109  1.00 29.87
ATOM    446  CB   ARG   253      18.306  12.366  27.207  1.00 30.75
ATOM    447  CG   ARG   253      17.023  11.733  27.695  1.00 32.49
ATOM    448  CD   ARG   253      16.943  10.331  27.175  1.00 35.54
ATOM    449  NE   ARG   253      18.046   9.553  27.726  1.00 40.71
ATOM    450  CZ   ARG   253      18.431   8.369  27.272  1.00 41.75
ATOM    451  NH1  ARG   253      19.449   7.743  27.846  1.00 42.45
ATOM    452  NH2  ARG   253      17.814   7.822  26.233  1.00 44.21
ATOM    453  C    ARG   253      19.858  14.296  27.309  1.00 31.31
ATOM    454  O    ARG   253      19.547  14.791  26.218  1.00 30.51
ATOM    455  N    THR   254      21.046  14.484  27.876  1.00 32.71
ATOM    456  CA   THR   254      22.114  15.225  27.214  1.00 33.25
ATOM    457  CB   THR   254      22.386  16.599  27.876  1.00 31.25
ATOM    458  OG1  THR   254      22.880  16.414  29.206  1.00 29.55
ATOM    459  CG2  THR   254      21.118  17.427  27.921  1.00 30.34
```

FIGURE 1 (cont.)

```
ATOM    460  C    THR   254      23.374   14.370   27.289  1.00  35.29
ATOM    461  O    THR   254      23.378   13.313   27.926  1.00  34.39
ATOM    462  N    GLY   255      24.435   14.818   26.625  1.00  37.19
ATOM    463  CA   GLY   255      25.680   14.075   26.656  1.00  38.93
ATOM    464  C    GLY   255      26.217   14.023   28.072  1.00  40.31
ATOM    465  O    GLY   255      26.605   12.963   28.566  1.00  40.42
ATOM    466  N    VAL   256      26.192   15.169   28.744  1.00  41.59
ATOM    467  CA   VAL   256      26.684   15.252   30.111  1.00  43.59
ATOM    468  CB   VAL   256      26.869   16.712   30.597  1.00  43.46
ATOM    469  CG1  VAL   256      28.182   17.268   30.084  1.00  46.24
ATOM    470  CG2  VAL   256      25.705   17.591   30.153  1.00  43.43
ATOM    471  C    VAL   256      25.839   14.516   31.137  1.00  44.62
ATOM    472  O    VAL   256      26.356   13.667   31.860  1.00  45.65
ATOM    473  N    ARG   257      24.540   14.810   31.172  1.00  45.28
ATOM    474  CA   ARG   257      23.651   14.203   32.156  1.00  44.14
ATOM    475  CB   ARG   257      23.445   15.197   33.311  1.00  45.53
ATOM    476  CG   ARG   257      22.434   14.762   34.357  1.00  49.87
ATOM    477  CD   ARG   257      22.485   15.627   35.618  1.00  52.65
ATOM    478  NE   ARG   257      21.615   15.118   36.686  1.00  56.84
ATOM    479  CZ   ARG   257      21.608   13.858   37.140  1.00  58.71
ATOM    480  NH1  ARG   257      22.424   12.935   36.632  1.00  58.53
ATOM    481  NH2  ARG   257      20.778   13.513   38.119  1.00  59.13
ATOM    482  C    ARG   257      22.291   13.718   31.654  1.00  42.81
ATOM    483  O    ARG   257      21.629   14.385   30.856  1.00  42.13
ATOM    484  N    THR   258      21.896   12.544   32.136  1.00  42.22
ATOM    485  CA   THR   258      20.601   11.949   31.834  1.00  41.75
ATOM    486  CB   THR   258      20.730   10.521   31.268  1.00  41.55
ATOM    487  OG1  THR   258      21.112   10.588   29.890  1.00  43.65
ATOM    488  CG2  THR   258      19.411    9.770   31.376  1.00  41.26
ATOM    489  C    THR   258      19.864   11.902   33.173  1.00  41.88
ATOM    490  O    THR   258      20.431   11.489   34.191  1.00  43.37
ATOM    491  N    ILE   259      18.635   12.398   33.184  1.00  40.14
ATOM    492  CA   ILE   259      17.815   12.424   34.382  1.00  38.42
ATOM    493  CB   ILE   259      17.506   13.870   34.799  1.00  37.89
ATOM    494  CG2  ILE   259      16.631   13.891   36.043  1.00  38.14
ATOM    495  CG1  ILE   259      18.805   14.649   35.011  1.00  37.37
ATOM    496  CD1  ILE   259      18.593   16.115   35.332  1.00  37.01
ATOM    497  C    ILE   259      16.516   11.736   33.998  1.00  38.66
ATOM    498  O    ILE   259      15.754   12.258   33.185  1.00  38.35
ATOM    499  N    THR   260      16.307   10.532   34.510  1.00  39.27
ATOM    500  CA   THR   260      15.090    9.790   34.208  1.00  40.28
ATOM    501  CB   THR   260      15.384    8.297   33.979  1.00  41.32
ATOM    502  OG1  THR   260      16.401    8.165   32.977  1.00  42.58
ATOM    503  CG2  THR   260      14.125    7.573   33.504  1.00  42.71
ATOM    504  C    THR   260      14.075    9.989   35.333  1.00  39.99
ATOM    505  O    THR   260      14.356    9.733   36.504  1.00  39.99
ATOM    506  N    THR   261      12.894   10.452   34.958  1.00  39.53
ATOM    507  CA   THR   261      11.842   10.740   35.910  1.00  39.43
ATOM    508  CB   THR   261      11.392   12.185   35.717  1.00  40.25
ATOM    509  OG1  THR   261      12.527   13.049   35.864  1.00  42.32
ATOM    510  CG2  THR   261      10.337   12.562   36.723  1.00  42.64
ATOM    511  C    THR   261      10.628    9.829   35.793  1.00  38.62
ATOM    512  O    THR   261       9.843    9.700   36.736  1.00  39.27
ATOM    513  N    GLY   262      10.476    9.177   34.648  1.00  36.63
ATOM    514  CA   GLY   262       9.316    8.323   34.462  1.00  34.27
ATOM    515  C    GLY   262       8.185    9.149   33.875  1.00  32.70
ATOM    516  O    GLY   262       7.037    8.708   33.802  1.00  32.40
ATOM    517  N    SER   263       8.525   10.368   33.464  1.00  30.97
```

FIGURE 1 (cont.)

| | | | | | | | | |
|---|---|---|---|---|---|---|---|---|
| ATOM | 518 | CA | SER | 263 | 7.571 | 11.282 | 32.861 | 1.00 28.52 |
| ATOM | 519 | CB | SER | 263 | 8.148 | 12.705 | 32.871 | 1.00 27.84 |
| ATOM | 520 | OG | SER | 263 | 7.276 | 13.641 | 32.251 | 1.00 26.21 |
| ATOM | 521 | C | SER | 263 | 7.286 | 10.852 | 31.420 | 1.00 27.13 |
| ATOM | 522 | O | SER | 263 | 8.092 | 10.151 | 30.796 | 1.00 25.11 |
| ATOM | 523 | N | PRO | 264 | 6.091 | 11.189 | 30.907 | 1.00 25.91 |
| ATOM | 524 | CD | PRO | 264 | 4.919 | 11.756 | 31.593 | 1.00 24.44 |
| ATOM | 525 | CA | PRO | 264 | 5.757 | 10.825 | 29.528 | 1.00 25.37 |
| ATOM | 526 | CB | PRO | 264 | 4.252 | 11.072 | 29.466 | 1.00 24.70 |
| ATOM | 527 | CG | PRO | 264 | 4.059 | 12.176 | 30.433 | 1.00 25.43 |
| ATOM | 528 | C | PRO | 264 | 6.516 | 11.761 | 28.575 | 1.00 25.19 |
| ATOM | 529 | O | PRO | 264 | 6.637 | 11.488 | 27.378 | 1.00 24.68 |
| ATOM | 530 | N | ILE | 265 | 7.009 | 12.874 | 29.113 | 1.00 25.11 |
| ATOM | 531 | CA | ILE | 265 | 7.760 | 13.839 | 28.323 | 1.00 24.64 |
| ATOM | 532 | CB | ILE | 265 | 7.395 | 15.284 | 28.689 | 1.00 24.85 |
| ATOM | 533 | CG2 | ILE | 265 | 8.045 | 16.250 | 27.706 | 1.00 24.63 |
| ATOM | 534 | CG1 | ILE | 265 | 5.880 | 15.463 | 28.623 | 1.00 25.72 |
| ATOM | 535 | CD1 | ILE | 265 | 5.398 | 16.810 | 29.116 | 1.00 27.30 |
| ATOM | 536 | C | ILE | 265 | 9.257 | 13.646 | 28.498 | 1.00 23.56 |
| ATOM | 537 | O | ILE | 265 | 9.756 | 13.474 | 29.612 | 1.00 23.63 |
| ATOM | 538 | N | THR | 266 | 9.974 | 13.683 | 27.386 | 1.00 23.74 |
| ATOM | 539 | CA | THR | 266 | 11.419 | 13.510 | 27.391 | 1.00 22.48 |
| ATOM | 540 | CB | THR | 266 | 11.799 | 12.115 | 26.833 | 1.00 21.23 |
| ATOM | 541 | OG1 | THR | 266 | 11.288 | 11.107 | 27.707 | 1.00 20.89 |
| ATOM | 542 | CG2 | THR | 266 | 13.295 | 11.952 | 26.716 | 1.00 21.86 |
| ATOM | 543 | C | THR | 266 | 12.060 | 14.585 | 26.530 | 1.00 21.76 |
| ATOM | 544 | O | THR | 266 | 11.674 | 14.770 | 25.376 | 1.00 20.29 |
| ATOM | 545 | N | TYR | 267 | 12.981 | 15.341 | 27.119 | 1.00 21.86 |
| ATOM | 546 | CA | TYR | 267 | 13.702 | 16.372 | 26.388 | 1.00 22.28 |
| ATOM | 547 | CB | TYR | 267 | 13.833 | 17.654 | 27.211 | 1.00 22.75 |
| ATOM | 548 | CG | TYR | 267 | 12.563 | 18.464 | 27.278 | 1.00 24.36 |
| ATOM | 549 | CD1 | TYR | 267 | 11.666 | 18.297 | 28.327 | 1.00 22.30 |
| ATOM | 550 | CE1 | TYR | 267 | 10.493 | 19.034 | 28.386 | 1.00 22.80 |
| ATOM | 551 | CD2 | TYR | 267 | 12.253 | 19.396 | 26.281 | 1.00 23.66 |
| ATOM | 552 | CE2 | TYR | 267 | 11.080 | 20.139 | 26.332 | 1.00 24.13 |
| ATOM | 553 | CZ | TYR | 267 | 10.206 | 19.949 | 27.391 | 1.00 23.99 |
| ATOM | 554 | OH | TYR | 267 | 9.045 | 20.674 | 27.465 | 1.00 23.95 |
| ATOM | 555 | C | TYR | 267 | 15.078 | 15.805 | 26.108 | 1.00 22.43 |
| ATOM | 556 | O | TYR | 267 | 15.679 | 15.165 | 26.978 | 1.00 23.25 |
| ATOM | 557 | N | SER | 268 | 15.573 | 16.031 | 24.900 | 1.00 22.28 |
| ATOM | 558 | CA | SER | 268 | 16.884 | 15.532 | 24.512 | 1.00 22.21 |
| ATOM | 559 | CB | SER | 268 | 16.750 | 14.082 | 24.010 | 1.00 22.96 |
| ATOM | 560 | OG | SER | 268 | 17.948 | 13.556 | 23.441 | 1.00 19.87 |
| ATOM | 561 | C | SER | 268 | 17.484 | 16.401 | 23.419 | 1.00 22.55 |
| ATOM | 562 | O | SER | 268 | 16.774 | 17.111 | 22.706 | 1.00 23.40 |
| ATOM | 563 | N | THR | 269 | 18.809 | 16.391 | 23.348 | 1.00 23.70 |
| ATOM | 564 | CA | THR | 269 | 19.547 | 17.102 | 22.310 | 1.00 22.50 |
| ATOM | 565 | CB | THR | 269 | 21.031 | 17.245 | 22.694 | 1.00 22.70 |
| ATOM | 566 | OG1 | THR | 269 | 21.510 | 15.986 | 23.193 | 1.00 19.49 |
| ATOM | 567 | CG2 | THR | 269 | 21.218 | 18.313 | 23.744 | 1.00 20.70 |
| ATOM | 568 | C | THR | 269 | 19.495 | 16.149 | 21.110 | 1.00 22.45 |
| ATOM | 569 | O | THR | 269 | 19.222 | 14.950 | 21.269 | 1.00 22.71 |
| ATOM | 570 | N | TYR | 270 | 19.746 | 16.656 | 19.910 | 1.00 22.86 |
| ATOM | 571 | CA | TYR | 270 | 19.746 | 15.777 | 18.747 | 1.00 22.07 |
| ATOM | 572 | CB | TYR | 270 | 19.812 | 16.581 | 17.446 | 1.00 20.62 |
| ATOM | 573 | CG | TYR | 270 | 18.535 | 17.330 | 17.123 | 1.00 19.62 |
| ATOM | 574 | CD1 | TYR | 270 | 18.392 | 18.677 | 17.452 | 1.00 20.22 |
| ATOM | 575 | CE1 | TYR | 270 | 17.242 | 19.389 | 17.118 | 1.00 18.98 |

FIGURE 1 (cont.)

| | | | | | | | | |
|---|---|---|---|---|---|---|---|---|
| ATOM | 576 | CD2 | TYR | 270 | 17.488 | 16.704 | 16.454 | 1.00 18.83 |
| ATOM | 577 | CE2 | TYR | 270 | 16.331 | 17.406 | 16.115 | 1.00 20.81 |
| ATOM | 578 | CZ | TYR | 270 | 16.218 | 18.752 | 16.451 | 1.00 20.32 |
| ATOM | 579 | OH | TYR | 270 | 15.086 | 19.457 | 16.112 | 1.00 18.84 |
| ATOM | 580 | C | TYR | 270 | 20.943 | 14.828 | 18.852 | 1.00 21.56 |
| ATOM | 581 | O | TYR | 270 | 20.850 | 13.654 | 18.486 | 1.00 23.69 |
| ATOM | 582 | N | GLY | 271 | 22.043 | 15.333 | 19.406 | 1.00 19.54 |
| ATOM | 583 | CA | GLY | 271 | 23.242 | 14.534 | 19.555 | 1.00 19.07 |
| ATOM | 584 | C | GLY | 271 | 23.012 | 13.299 | 20.394 | 1.00 19.18 |
| ATOM | 585 | O | GLY | 271 | 23.330 | 12.192 | 19.980 | 1.00 19.27 |
| ATOM | 586 | N | LYS | 272 | 22.494 | 13.499 | 21.600 | 1.00 21.00 |
| ATOM | 587 | CA | LYS | 272 | 22.209 | 12.399 | 22.516 | 1.00 22.97 |
| ATOM | 588 | CB | LYS | 272 | 21.709 | 12.968 | 23.850 | 1.00 24.05 |
| ATOM | 589 | CG | LYS | 272 | 21.538 | 11.960 | 24.963 | 1.00 26.57 |
| ATOM | 590 | CD | LYS | 272 | 22.761 | 11.085 | 25.118 | 1.00 28.96 |
| ATOM | 591 | CE | LYS | 272 | 22.573 | 10.081 | 26.243 | 1.00 30.16 |
| ATOM | 592 | NZ | LYS | 272 | 23.623 | 9.033 | 26.198 | 1.00 31.88 |
| ATOM | 593 | C | LYS | 272 | 21.187 | 11.424 | 21.885 | 1.00 23.97 |
| ATOM | 594 | O | LYS | 272 | 21.351 | 10.198 | 21.964 | 1.00 24.73 |
| ATOM | 595 | N | PHE | 273 | 20.173 | 11.967 | 21.204 | 1.00 23.94 |
| ATOM | 596 | CA | PHE | 273 | 19.151 | 11.153 | 20.538 | 1.00 22.60 |
| ATOM | 597 | CB | PHE | 273 | 18.170 | 12.068 | 19.790 | 1.00 20.76 |
| ATOM | 598 | CG | PHE | 273 | 17.188 | 11.333 | 18.917 | 1.00 19.28 |
| ATOM | 599 | CD1 | PHE | 273 | 16.138 | 10.611 | 19.476 | 1.00 19.37 |
| ATOM | 600 | CD2 | PHE | 273 | 17.299 | 11.382 | 17.536 | 1.00 17.87 |
| ATOM | 601 | CE1 | PHE | 273 | 15.211 | 9.951 | 18.670 | 1.00 18.22 |
| ATOM | 602 | CE2 | PHE | 273 | 16.382 | 10.727 | 16.724 | 1.00 19.02 |
| ATOM | 603 | CZ | PHE | 273 | 15.334 | 10.010 | 17.293 | 1.00 17.46 |
| ATOM | 604 | C | PHE | 273 | 19.840 | 10.191 | 19.561 | 1.00 21.90 |
| ATOM | 605 | O | PHE | 273 | 19.619 | 8.970 | 19.580 | 1.00 20.97 |
| ATOM | 606 | N | LEU | 274 | 20.685 | 10.766 | 18.712 | 1.00 22.63 |
| ATOM | 607 | CA | LEU | 274 | 21.455 | 10.020 | 17.726 | 1.00 21.66 |
| ATOM | 608 | CB | LEU | 274 | 22.324 | 10.989 | 16.921 | 1.00 21.04 |
| ATOM | 609 | CG | LEU | 274 | 21.624 | 11.852 | 15.874 | 1.00 18.37 |
| ATOM | 610 | CD1 | LEU | 274 | 22.546 | 12.969 | 15.437 | 1.00 16.98 |
| ATOM | 611 | CD2 | LEU | 274 | 21.233 | 10.972 | 14.697 | 1.00 16.49 |
| ATOM | 612 | C | LEU | 274 | 22.346 | 8.971 | 18.403 | 1.00 21.93 |
| ATOM | 613 | O | LEU | 274 | 22.503 | 7.853 | 17.903 | 1.00 19.56 |
| ATOM | 614 | N | ALA | 275 | 22.944 | 9.362 | 19.525 | 1.00 23.03 |
| ATOM | 615 | CA | ALA | 275 | 23.818 | 8.493 | 20.300 | 1.00 24.57 |
| ATOM | 616 | CB | ALA | 275 | 24.585 | 9.301 | 21.322 | 1.00 21.93 |
| ATOM | 617 | C | ALA | 275 | 23.033 | 7.381 | 20.992 | 1.00 26.77 |
| ATOM | 618 | O | ALA | 275 | 23.580 | 6.302 | 21.237 | 1.00 28.37 |
| ATOM | 619 | N | ASP | 276 | 21.764 | 7.631 | 21.314 | 1.00 27.59 |
| ATOM | 620 | CA | ASP | 276 | 20.952 | 6.604 | 21.968 | 1.00 28.62 |
| ATOM | 621 | CB | ASP | 276 | 19.859 | 7.225 | 22.847 | 1.00 28.88 |
| ATOM | 622 | CG | ASP | 276 | 20.412 | 7.872 | 24.107 | 1.00 28.41 |
| ATOM | 623 | OD1 | ASP | 276 | 21.515 | 7.500 | 24.553 | 1.00 28.79 |
| ATOM | 624 | OD2 | ASP | 276 | 19.741 | 8.767 | 24.649 | 1.00 29.37 |
| ATOM | 625 | C | ASP | 276 | 20.350 | 5.614 | 20.971 | 1.00 29.04 |
| ATOM | 626 | O | ASP | 276 | 19.589 | 4.719 | 21.346 | 1.00 30.14 |
| ATOM | 627 | N | GLY | 277 | 20.700 | 5.775 | 19.701 | 1.00 29.48 |
| ATOM | 628 | CA | GLY | 277 | 20.201 | 4.876 | 18.677 | 1.00 29.82 |
| ATOM | 629 | C | GLY | 277 | 18.987 | 5.363 | 17.904 | 1.00 30.86 |
| ATOM | 630 | O | GLY | 277 | 18.343 | 4.574 | 17.211 | 1.00 31.50 |
| ATOM | 631 | N | GLY | 278 | 18.667 | 6.650 | 17.997 | 1.00 30.29 |
| ATOM | 632 | CA | GLY | 278 | 17.517 | 7.152 | 17.269 | 1.00 29.28 |
| ATOM | 633 | C | GLY | 278 | 16.193 | 6.655 | 17.827 | 1.00 28.58 |

FIGURE 1 (cont.)

| ATOM | 634 | O | GLY | 278 | 16.005 | 6.611 | 19.037 | 1.00 | 28.84 |
|---|---|---|---|---|---|---|---|---|---|
| ATOM | 635 | N | CME | 279 | 15.279 | 6.255 | 16.956 | 1.00 | 27.25 |
| ATOM | 636 | CA | CME | 279 | 13.973 | 5.792 | 17.394 | 1.00 | 28.61 |
| ATOM | 637 | C | CME | 279 | 13.976 | 4.530 | 18.265 | 1.00 | 30.15 |
| ATOM | 638 | O | CME | 279 | 13.004 | 4.243 | 18.959 | 1.00 | 31.77 |
| ATOM | 639 | CB | CME | 279 | 13.043 | 5.619 | 16.190 | 1.00 | 27.21 |
| ATOM | 640 | SG | CME | 279 | 12.348 | 7.190 | 15.561 | 1.00 | 27.85 |
| ATOM | 641 | 2SG | CME | 279 | 11.574 | 8.053 | 17.229 | 1.00 | 28.77 |
| ATOM | 642 | 2CB | CME | 279 | 9.954 | 7.230 | 17.445 | 1.00 | 24.45 |
| ATOM | 643 | 2CA | CME | 279 | 9.943 | 5.999 | 18.329 | 1.00 | 22.60 |
| ATOM | 644 | OG | CME | 279 | 10.230 | 6.331 | 19.673 | 1.00 | 21.99 |
| ATOM | 645 | N | SER | 280 | 15.075 | 3.788 | 18.256 | 1.00 | 32.02 |
| ATOM | 646 | CA | SER | 280 | 15.171 | 2.566 | 19.054 | 1.00 | 31.88 |
| ATOM | 647 | CB | SER | 280 | 16.161 | 1.604 | 18.408 | 1.00 | 32.23 |
| ATOM | 648 | OG | SER | 280 | 17.471 | 2.145 | 18.447 | 1.00 | 33.11 |
| ATOM | 649 | C | SER | 280 | 15.637 | 2.873 | 20.467 | 1.00 | 32.76 |
| ATOM | 650 | O | SER | 280 | 15.710 | 1.978 | 21.299 | 1.00 | 34.40 |
| ATOM | 651 | N | GLY | 281 | 16.014 | 4.127 | 20.710 | 1.00 | 33.60 |
| ATOM | 652 | CA | GLY | 281 | 16.479 | 4.540 | 22.022 | 1.00 | 33.70 |
| ATOM | 653 | C | GLY | 281 | 15.357 | 4.781 | 23.017 | 1.00 | 34.64 |
| ATOM | 654 | O | GLY | 281 | 15.609 | 4.974 | 24.210 | 1.00 | 35.32 |
| ATOM | 655 | N | GLY | 282 | 14.119 | 4.767 | 22.531 | 1.00 | 34.83 |
| ATOM | 656 | CA | GLY | 282 | 12.963 | 4.979 | 23.388 | 1.00 | 34.77 |
| ATOM | 657 | C | GLY | 282 | 11.697 | 4.820 | 22.571 | 1.00 | 34.68 |
| ATOM | 658 | O | GLY | 282 | 11.780 | 4.727 | 21.346 | 1.00 | 36.05 |
| ATOM | 659 | N | ALA | 283 | 10.536 | 4.761 | 23.222 | 1.00 | 33.24 |
| ATOM | 660 | CA | ALA | 283 | 9.276 | 4.615 | 22.495 | 1.00 | 32.26 |
| ATOM | 661 | CB | ALA | 283 | 8.515 | 3.397 | 22.983 | 1.00 | 34.72 |
| ATOM | 662 | C | ALA | 283 | 8.479 | 5.879 | 22.732 | 1.00 | 31.42 |
| ATOM | 663 | O | ALA | 283 | 8.072 | 6.157 | 23.857 | 1.00 | 33.31 |
| ATOM | 664 | N | TYR | 284 | 8.286 | 6.655 | 21.673 | 1.00 | 29.86 |
| ATOM | 665 | CA | TYR | 284 | 7.590 | 7.930 | 21.756 | 1.00 | 26.87 |
| ATOM | 666 | CB | TYR | 284 | 8.586 | 9.068 | 21.499 | 1.00 | 25.67 |
| ATOM | 667 | CG | TYR | 284 | 9.898 | 8.953 | 22.270 | 1.00 | 25.12 |
| ATOM | 668 | CD1 | TYR | 284 | 11.066 | 8.484 | 21.650 | 1.00 | 24.08 |
| ATOM | 669 | CE1 | TYR | 284 | 12.280 | 8.406 | 22.342 | 1.00 | 23.42 |
| ATOM | 670 | CD2 | TYR | 284 | 9.977 | 9.338 | 23.611 | 1.00 | 25.92 |
| ATOM | 671 | CE2 | TYR | 284 | 11.186 | 9.263 | 24.316 | 1.00 | 26.34 |
| ATOM | 672 | CZ | TYR | 284 | 12.334 | 8.800 | 23.675 | 1.00 | 27.01 |
| ATOM | 673 | OH | TYR | 284 | 13.526 | 8.765 | 24.383 | 1.00 | 26.66 |
| ATOM | 674 | C | TYR | 284 | 6.501 | 7.977 | 20.706 | 1.00 | 27.07 |
| ATOM | 675 | O | TYR | 284 | 6.697 | 7.507 | 19.583 | 1.00 | 27.54 |
| ATOM | 676 | N | ASP | 285 | 5.360 | 8.562 | 21.060 | 1.00 | 26.33 |
| ATOM | 677 | CA | ASP | 285 | 4.237 | 8.665 | 20.128 | 1.00 | 25.48 |
| ATOM | 678 | CB | ASP | 285 | 2.906 | 8.695 | 20.888 | 1.00 | 27.66 |
| ATOM | 679 | CG | ASP | 285 | 2.754 | 7.540 | 21.867 | 1.00 | 29.66 |
| ATOM | 680 | OD1 | ASP | 285 | 2.833 | 6.357 | 21.451 | 1.00 | 30.75 |
| ATOM | 681 | OD2 | ASP | 285 | 2.537 | 7.822 | 23.060 | 1.00 | 30.49 |
| ATOM | 682 | C | ASP | 285 | 4.365 | 9.942 | 19.308 | 1.00 | 24.75 |
| ATOM | 683 | O | ASP | 285 | 4.021 | 9.982 | 18.122 | 1.00 | 24.16 |
| ATOM | 684 | N | ILE | 286 | 4.864 | 10.991 | 19.957 | 1.00 | 24.04 |
| ATOM | 685 | CA | ILE | 286 | 5.025 | 12.289 | 19.321 | 1.00 | 22.60 |
| ATOM | 686 | CB | ILE | 286 | 4.036 | 13.310 | 19.936 | 1.00 | 21.83 |
| ATOM | 687 | CG2 | ILE | 286 | 4.185 | 14.677 | 19.265 | 1.00 | 19.78 |
| ATOM | 688 | CG1 | ILE | 286 | 2.601 | 12.776 | 19.805 | 1.00 | 20.82 |
| ATOM | 689 | CD1 | ILE | 286 | 1.539 | 13.664 | 20.395 | 1.00 | 19.00 |
| ATOM | 690 | C | ILE | 286 | 6.458 | 12.804 | 19.470 | 1.00 | 22.69 |
| ATOM | 691 | O | ILE | 286 | 7.052 | 12.730 | 20.556 | 1.00 | 22.52 |

FIGURE 1 (cont.)

| ATOM | 692 | N   | ILE | 287 | 7.028  | 13.274 | 18.361 | 1.00 | 22.96 |
|------|-----|-----|-----|-----|--------|--------|--------|------|-------|
| ATOM | 693 | CA  | ILE | 287 | 8.381  | 13.822 | 18.373 | 1.00 | 22.01 |
| ATOM | 694 | CB  | ILE | 287 | 9.375  | 13.029 | 17.459 | 1.00 | 21.82 |
| ATOM | 695 | CG2 | ILE | 287 | 10.741 | 13.732 | 17.432 | 1.00 | 20.37 |
| ATOM | 696 | CG1 | ILE | 287 | 9.543  | 11.586 | 17.945 | 1.00 | 20.76 |
| ATOM | 697 | CD1 | ILE | 287 | 8.661  | 10.601 | 17.227 | 1.00 | 19.72 |
| ATOM | 698 | C   | ILE | 287 | 8.348  | 15.267 | 17.890 | 1.00 | 20.35 |
| ATOM | 699 | O   | ILE | 287 | 7.944  | 15.540 | 16.756 | 1.00 | 18.88 |
| ATOM | 700 | N   | ILE | 288 | 8.746  | 16.184 | 18.763 | 1.00 | 20.27 |
| ATOM | 701 | CA  | ILE | 288 | 8.792  | 17.595 | 18.420 | 1.00 | 22.23 |
| ATOM | 702 | CB  | ILE | 288 | 8.399  | 18.525 | 19.624 | 1.00 | 24.13 |
| ATOM | 703 | CG2 | ILE | 288 | 8.370  | 19.992 | 19.183 | 1.00 | 23.03 |
| ATOM | 704 | CG1 | ILE | 288 | 7.041  | 18.132 | 20.224 | 1.00 | 25.74 |
| ATOM | 705 | CD1 | ILE | 288 | 5.866  | 18.329 | 19.292 | 1.00 | 27.52 |
| ATOM | 706 | C   | ILE | 288 | 10.247 | 17.883 | 18.076 | 1.00 | 20.12 |
| ATOM | 707 | O   | ILE | 288 | 11.118 | 17.740 | 18.925 | 1.00 | 20.16 |
| ATOM | 708 | N   | CYS | 289 | 10.514 | 18.173 | 16.810 | 1.00 | 20.26 |
| ATOM | 709 | CA  | CYS | 289 | 11.855 | 18.520 | 16.349 | 1.00 | 19.98 |
| ATOM | 710 | CB  | CYS | 289 | 12.057 | 18.095 | 14.899 | 1.00 | 18.98 |
| ATOM | 711 | SG  | CYS | 289 | 12.188 | 16.314 | 14.684 | 1.00 | 18.93 |
| ATOM | 712 | C   | CYS | 289 | 11.916 | 20.030 | 16.466 | 1.00 | 20.28 |
| ATOM | 713 | O   | CYS | 289 | 11.550 | 20.757 | 15.542 | 1.00 | 21.53 |
| ATOM | 714 | N   | ASP | 290 | 12.322 | 20.482 | 17.642 | 1.00 | 20.55 |
| ATOM | 715 | CA  | ASP | 290 | 12.407 | 21.892 | 17.969 | 1.00 | 22.05 |
| ATOM | 716 | CB  | ASP | 290 | 12.530 | 22.030 | 19.490 | 1.00 | 22.57 |
| ATOM | 717 | CG  | ASP | 290 | 12.197 | 23.413 | 19.979 | 1.00 | 24.81 |
| ATOM | 718 | OD1 | ASP | 290 | 12.731 | 23.789 | 21.040 | 1.00 | 25.61 |
| ATOM | 719 | OD2 | ASP | 290 | 11.410 | 24.127 | 19.312 | 1.00 | 27.06 |
| ATOM | 720 | C   | ASP | 290 | 13.564 | 22.591 | 17.247 | 1.00 | 22.93 |
| ATOM | 721 | O   | ASP | 290 | 14.611 | 21.983 | 17.004 | 1.00 | 24.56 |
| ATOM | 722 | N   | GLU | 291 | 13.364 | 23.866 | 16.905 | 1.00 | 22.47 |
| ATOM | 723 | CA  | GLU | 291 | 14.361 | 24.674 | 16.190 | 1.00 | 21.59 |
| ATOM | 724 | CB  | GLU | 291 | 15.600 | 24.947 | 17.055 | 1.00 | 22.46 |
| ATOM | 725 | CG  | GLU | 291 | 15.341 | 25.261 | 18.533 | 1.00 | 23.21 |
| ATOM | 726 | CD  | GLU | 291 | 14.639 | 26.573 | 18.786 | 1.00 | 24.42 |
| ATOM | 727 | OE1 | GLU | 291 | 14.159 | 27.222 | 17.840 | 1.00 | 27.28 |
| ATOM | 728 | OE2 | GLU | 291 | 14.552 | 26.961 | 19.964 | 1.00 | 28.33 |
| ATOM | 729 | C   | GLU | 291 | 14.783 | 23.938 | 14.922 | 1.00 | 20.30 |
| ATOM | 730 | O   | GLU | 291 | 15.945 | 23.954 | 14.535 | 1.00 | 20.16 |
| ATOM | 731 | N   | CYS | 292 | 13.804 | 23.375 | 14.228 | 1.00 | 20.51 |
| ATOM | 732 | CA  | CYS | 292 | 14.057 | 22.608 | 13.021 | 1.00 | 20.48 |
| ATOM | 733 | CB  | CYS | 292 | 12.762 | 21.929 | 12.573 | 1.00 | 21.07 |
| ATOM | 734 | SG  | CYS | 292 | 11.485 | 23.089 | 12.067 | 1.00 | 22.23 |
| ATOM | 735 | C   | CYS | 292 | 14.682 | 23.411 | 11.880 | 1.00 | 19.98 |
| ATOM | 736 | O   | CYS | 292 | 14.876 | 22.906 | 10.777 | 1.00 | 18.04 |
| ATOM | 737 | N   | HIS | 293 | 14.962 | 24.683 | 12.144 | 1.00 | 22.14 |
| ATOM | 738 | CA  | HIS | 293 | 15.592 | 25.557 | 11.157 | 1.00 | 22.17 |
| ATOM | 739 | CB  | HIS | 293 | 15.198 | 27.009 | 11.419 | 1.00 | 20.03 |
| ATOM | 740 | CG  | HIS | 293 | 15.718 | 27.534 | 12.718 | 1.00 | 20.67 |
| ATOM | 741 | CD2 | HIS | 293 | 16.944 | 27.991 | 13.068 | 1.00 | 20.00 |
| ATOM | 742 | ND1 | HIS | 293 | 14.962 | 27.549 | 13.868 | 1.00 | 21.26 |
| ATOM | 743 | CE1 | HIS | 293 | 15.701 | 27.986 | 14.872 | 1.00 | 21.87 |
| ATOM | 744 | NE2 | HIS | 293 | 16.907 | 28.261 | 14.413 | 1.00 | 20.16 |
| ATOM | 745 | C   | HIS | 293 | 17.121 | 25.434 | 11.259 | 1.00 | 22.50 |
| ATOM | 746 | O   | HIS | 293 | 17.834 | 25.959 | 10.414 | 1.00 | 23.46 |
| ATOM | 747 | N   | SER | 294 | 17.611 | 24.787 | 12.319 | 1.00 | 23.32 |
| ATOM | 748 | CA  | SER | 294 | 19.049 | 24.621 | 12.553 | 1.00 | 23.42 |
| ATOM | 749 | CB  | SER | 294 | 19.294 | 23.913 | 13.878 | 1.00 | 21.98 |

FIGURE 1 (cont.)

| | | | | | | | | | |
|---|---|---|---|---|---|---|---|---|---|
| ATOM | 750 | OG  | SER | 294 | 18.708 | 24.650 | 14.930 | 1.00 | 25.79 |
| ATOM | 751 | C   | SER | 294 | 19.767 | 23.878 | 11.441 | 1.00 | 24.00 |
| ATOM | 752 | O   | SER | 294 | 19.379 | 22.774 | 11.061 | 1.00 | 24.59 |
| ATOM | 753 | N   | THR | 295 | 20.845 | 24.473 | 10.946 | 1.00 | 24.29 |
| ATOM | 754 | CA  | THR | 295 | 21.590 | 23.866 | 9.868  | 1.00 | 24.56 |
| ATOM | 755 | CB  | THR | 295 | 21.764 | 24.855 | 8.697  | 1.00 | 25.03 |
| ATOM | 756 | OG1 | THR | 295 | 22.307 | 26.091 | 9.175  | 1.00 | 24.69 |
| ATOM | 757 | CG2 | THR | 295 | 20.411 | 25.132 | 8.038  | 1.00 | 24.54 |
| ATOM | 758 | C   | THR | 295 | 22.916 | 23.247 | 10.297 | 1.00 | 25.11 |
| ATOM | 759 | O   | THR | 295 | 23.773 | 22.952 | 9.467  | 1.00 | 25.90 |
| ATOM | 760 | N   | ASP | 296 | 23.083 | 23.035 | 11.596 | 1.00 | 24.58 |
| ATOM | 761 | CA  | ASP | 296 | 24.297 | 22.405 | 12.097 | 1.00 | 25.65 |
| ATOM | 762 | CB  | ASP | 296 | 24.430 | 22.642 | 13.593 | 1.00 | 28.87 |
| ATOM | 763 | CG  | ASP | 296 | 23.307 | 22.010 | 14.372 | 1.00 | 32.27 |
| ATOM | 764 | OD1 | ASP | 296 | 22.182 | 22.547 | 14.308 | 1.00 | 34.23 |
| ATOM | 765 | OD2 | ASP | 296 | 23.541 | 20.956 | 15.009 | 1.00 | 35.53 |
| ATOM | 766 | C   | ASP | 296 | 24.142 | 20.904 | 11.806 | 1.00 | 24.87 |
| ATOM | 767 | O   | ASP | 296 | 23.027 | 20.374 | 11.883 | 1.00 | 24.43 |
| ATOM | 768 | N   | ALA | 297 | 25.251 | 20.220 | 11.524 | 1.00 | 23.24 |
| ATOM | 769 | CA  | ALA | 297 | 25.228 | 18.796 | 11.185 | 1.00 | 22.47 |
| ATOM | 770 | CB  | ALA | 297 | 26.633 | 18.247 | 11.066 | 1.00 | 20.82 |
| ATOM | 771 | C   | ALA | 297 | 24.414 | 17.923 | 12.122 | 1.00 | 21.78 |
| ATOM | 772 | O   | ALA | 297 | 23.643 | 17.079 | 11.672 | 1.00 | 22.68 |
| ATOM | 773 | N   | THR | 298 | 24.571 | 18.134 | 13.420 | 1.00 | 22.79 |
| ATOM | 774 | CA  | THR | 298 | 23.846 | 17.338 | 14.404 | 1.00 | 24.28 |
| ATOM | 775 | CB  | THR | 298 | 24.334 | 17.649 | 15.813 | 1.00 | 24.90 |
| ATOM | 776 | OG1 | THR | 298 | 25.767 | 17.588 | 15.822 | 1.00 | 26.90 |
| ATOM | 777 | CG2 | THR | 298 | 23.780 | 16.639 | 16.800 | 1.00 | 24.31 |
| ATOM | 778 | C   | THR | 298 | 22.320 | 17.460 | 14.321 | 1.00 | 21.89 |
| ATOM | 779 | O   | THR | 298 | 21.614 | 16.458 | 14.441 | 1.00 | 21.95 |
| ATOM | 780 | N   | SER | 299 | 21.817 | 18.665 | 14.074 | 1.00 | 20.47 |
| ATOM | 781 | CA  | SER | 299 | 20.373 | 18.865 | 13.969 | 1.00 | 19.52 |
| ATOM | 782 | CB  | SER | 299 | 20.025 | 20.352 | 14.038 | 1.00 | 16.97 |
| ATOM | 783 | OG  | SER | 299 | 20.393 | 20.874 | 15.300 | 1.00 | 15.99 |
| ATOM | 784 | C   | SER | 299 | 19.835 | 18.243 | 12.688 | 1.00 | 18.61 |
| ATOM | 785 | O   | SER | 299 | 18.810 | 17.570 | 12.698 | 1.00 | 18.83 |
| ATOM | 786 | N   | ILE | 300 | 20.567 | 18.418 | 11.597 | 1.00 | 18.65 |
| ATOM | 787 | CA  | ILE | 300 | 20.155 | 17.863 | 10.322 | 1.00 | 19.88 |
| ATOM | 788 | CB  | ILE | 300 | 21.085 | 18.343 | 9.190  | 1.00 | 20.48 |
| ATOM | 789 | CG2 | ILE | 300 | 20.691 | 17.693 | 7.846  | 1.00 | 19.34 |
| ATOM | 790 | CG1 | ILE | 300 | 21.022 | 19.867 | 9.098  | 1.00 | 19.44 |
| ATOM | 791 | CD1 | ILE | 300 | 22.063 | 20.436 | 8.226  | 1.00 | 20.43 |
| ATOM | 792 | C   | ILE | 300 | 20.135 | 16.337 | 10.358 | 1.00 | 20.31 |
| ATOM | 793 | O   | ILE | 300 | 19.194 | 15.717 | 9.867  | 1.00 | 21.85 |
| ATOM | 794 | N   | LEU | 301 | 21.161 | 15.733 | 10.950 | 1.00 | 20.00 |
| ATOM | 795 | CA  | LEU | 301 | 21.243 | 14.280 | 11.022 | 1.00 | 19.61 |
| ATOM | 796 | CB  | LEU | 301 | 22.626 | 13.852 | 11.516 | 1.00 | 20.91 |
| ATOM | 797 | CG  | LEU | 301 | 22.986 | 12.379 | 11.326 | 1.00 | 23.01 |
| ATOM | 798 | CD1 | LEU | 301 | 23.023 | 12.031 | 9.851  | 1.00 | 21.44 |
| ATOM | 799 | CD2 | LEU | 301 | 24.336 | 12.111 | 11.964 | 1.00 | 24.76 |
| ATOM | 800 | C   | LEU | 301 | 20.156 | 13.742 | 11.942 | 1.00 | 19.65 |
| ATOM | 801 | O   | LEU | 301 | 19.517 | 12.729 | 11.642 | 1.00 | 19.47 |
| ATOM | 802 | N   | GLY | 302 | 19.929 | 14.450 | 13.044 | 1.00 | 19.18 |
| ATOM | 803 | CA  | GLY | 302 | 18.919 | 14.048 | 14.002 | 1.00 | 18.63 |
| ATOM | 804 | C   | GLY | 302 | 17.522 | 14.119 | 13.425 | 1.00 | 19.58 |
| ATOM | 805 | O   | GLY | 302 | 16.731 | 13.194 | 13.606 | 1.00 | 20.16 |
| ATOM | 806 | N   | ILE | 303 | 17.220 | 15.206 | 12.719 | 1.00 | 19.27 |
| ATOM | 807 | CA  | ILE | 303 | 15.906 | 15.383 | 12.113 | 1.00 | 19.24 |

FIGURE 1 (cont.)

| ATOM | 808 | CB  | ILE | 303 | 15.732 | 16.799 | 11.518 | 1.00 | 18.46 |
|------|-----|-----|-----|-----|--------|--------|--------|------|-------|
| ATOM | 809 | CG2 | ILE | 303 | 14.466 | 16.879 | 10.680 | 1.00 | 19.48 |
| ATOM | 810 | CG1 | ILE | 303 | 15.646 | 17.818 | 12.653 | 1.00 | 18.58 |
| ATOM | 811 | CD1 | ILE | 303 | 15.483 | 19.232 | 12.199 | 1.00 | 19.42 |
| ATOM | 812 | C   | ILE | 303 | 15.675 | 14.324 | 11.057 | 1.00 | 19.21 |
| ATOM | 813 | O   | ILE | 303 | 14.631 | 13.685 | 11.044 | 1.00 | 21.27 |
| ATOM | 814 | N   | GLY | 304 | 16.662 | 14.120 | 10.191 | 1.00 | 20.04 |
| ATOM | 815 | CA  | GLY | 304 | 16.547 | 13.110 | 9.160  | 1.00 | 20.49 |
| ATOM | 816 | C   | GLY | 304 | 16.323 | 11.730 | 9.765  | 1.00 | 21.95 |
| ATOM | 817 | O   | GLY | 304 | 15.555 | 10.930 | 9.226  | 1.00 | 22.92 |
| ATOM | 818 | N   | THR | 305 | 17.009 | 11.435 | 10.869 | 1.00 | 22.89 |
| ATOM | 819 | CA  | THR | 305 | 16.854 | 10.150 | 11.552 | 1.00 | 23.21 |
| ATOM | 820 | CB  | THR | 305 | 17.722 | 10.087 | 12.830 | 1.00 | 22.58 |
| ATOM | 821 | OG1 | THR | 305 | 19.101 | 10.155 | 12.458 | 1.00 | 26.30 |
| ATOM | 822 | CG2 | THR | 305 | 17.494 | 8.794  | 13.603 | 1.00 | 20.55 |
| ATOM | 823 | C   | THR | 305 | 15.377 | 9.988  | 11.919 | 1.00 | 23.59 |
| ATOM | 824 | O   | THR | 305 | 14.734 | 9.028  | 11.504 | 1.00 | 22.98 |
| ATOM | 825 | N   | VAL | 306 | 14.830 | 10.974 | 12.632 | 1.00 | 24.39 |
| ATOM | 826 | CA  | VAL | 306 | 13.423 | 10.954 | 13.039 | 1.00 | 22.55 |
| ATOM | 827 | CB  | VAL | 306 | 13.022 | 12.258 | 13.751 | 1.00 | 19.96 |
| ATOM | 828 | CG1 | VAL | 306 | 11.516 | 12.293 | 13.977 | 1.00 | 19.45 |
| ATOM | 829 | CG2 | VAL | 306 | 13.748 | 12.380 | 15.061 | 1.00 | 18.75 |
| ATOM | 830 | C   | VAL | 306 | 12.499 | 10.773 | 11.837 | 1.00 | 21.61 |
| ATOM | 831 | O   | VAL | 306 | 11.629 | 9.908  | 11.840 | 1.00 | 22.37 |
| ATOM | 832 | N   | LEU | 307 | 12.701 | 11.581 | 10.805 | 1.00 | 21.43 |
| ATOM | 833 | CA  | LEU | 307 | 11.855 | 11.513 | 9.622  | 1.00 | 21.34 |
| ATOM | 834 | CB  | LEU | 307 | 12.238 | 12.605 | 8.626  | 1.00 | 19.20 |
| ATOM | 835 | CG  | LEU | 307 | 11.804 | 14.002 | 9.057  | 1.00 | 17.60 |
| ATOM | 836 | CD1 | LEU | 307 | 12.361 | 15.033 | 8.111  | 1.00 | 17.57 |
| ATOM | 837 | CD2 | LEU | 307 | 10.293 | 14.074 | 9.095  | 1.00 | 16.93 |
| ATOM | 838 | C   | LEU | 307 | 11.891 | 10.155 | 8.960  | 1.00 | 22.33 |
| ATOM | 839 | O   | LEU | 307 | 10.875 | 9.661  | 8.490  | 1.00 | 24.71 |
| ATOM | 840 | N   | ASP | 308 | 13.051 | 9.522  | 8.971  | 1.00 | 23.84 |
| ATOM | 841 | CA  | ASP | 308 | 13.184 | 8.221  | 8.356  | 1.00 | 23.32 |
| ATOM | 842 | CB  | ASP | 308 | 14.655 | 7.938  | 8.062  | 1.00 | 23.50 |
| ATOM | 843 | CG  | ASP | 308 | 14.859 | 6.634  | 7.316  | 1.00 | 23.73 |
| ATOM | 844 | OD1 | ASP | 308 | 14.468 | 6.559  | 6.136  | 1.00 | 25.35 |
| ATOM | 845 | OD2 | ASP | 308 | 15.403 | 5.682  | 7.907  | 1.00 | 22.72 |
| ATOM | 846 | C   | ASP | 308 | 12.617 | 7.111  | 9.230  | 1.00 | 23.73 |
| ATOM | 847 | O   | ASP | 308 | 11.878 | 6.259  | 8.752  | 1.00 | 24.61 |
| ATOM | 848 | N   | GLN | 309 | 12.927 | 7.159  | 10.518 | 1.00 | 23.54 |
| ATOM | 849 | CA  | GLN | 309 | 12.529 | 6.130  | 11.465 | 1.00 | 24.40 |
| ATOM | 850 | CB  | GLN | 309 | 13.609 | 6.003  | 12.538 | 1.00 | 24.46 |
| ATOM | 851 | CG  | GLN | 309 | 14.985 | 5.638  | 12.022 | 1.00 | 24.18 |
| ATOM | 852 | CD  | GLN | 309 | 16.023 | 5.622  | 13.128 | 1.00 | 23.84 |
| ATOM | 853 | OE1 | GLN | 309 | 15.702 | 5.805  | 14.301 | 1.00 | 24.42 |
| ATOM | 854 | NE2 | GLN | 309 | 17.276 | 5.415  | 12.760 | 1.00 | 25.37 |
| ATOM | 855 | C   | GLN | 309 | 11.169 | 6.173  | 12.168 | 1.00 | 26.09 |
| ATOM | 856 | O   | GLN | 309 | 10.580 | 5.116  | 12.401 | 1.00 | 25.68 |
| ATOM | 857 | N   | ALA | 310 | 10.698 | 7.367  | 12.537 | 1.00 | 27.06 |
| ATOM | 858 | CA  | ALA | 310 | 9.432  | 7.554  | 13.273 | 1.00 | 28.07 |
| ATOM | 859 | CB  | ALA | 310 | 8.983  | 9.012  | 13.224 | 1.00 | 27.02 |
| ATOM | 860 | C   | ALA | 310 | 8.251  | 6.646  | 12.956 | 1.00 | 28.11 |
| ATOM | 861 | O   | ALA | 310 | 7.831  | 5.866  | 13.814 | 1.00 | 28.35 |
| ATOM | 862 | N   | GLU | 311 | 7.714  | 6.735  | 11.742 | 1.00 | 29.49 |
| ATOM | 863 | CA  | GLU | 311 | 6.560  | 5.916  | 11.376 | 1.00 | 31.72 |
| ATOM | 864 | CB  | GLU | 311 | 6.125  | 6.161  | 9.932  | 1.00 | 31.31 |
| ATOM | 865 | CG  | GLU | 311 | 4.847  | 5.405  | 9.558  | 1.00 | 33.59 |

FIGURE 1 (cont.)

```
ATOM    866  CD   GLU  311       4.180   5.925   8.291  1.00 34.98
ATOM    867  OE1  GLU  311       2.993   5.602   8.065  1.00 36.53
ATOM    868  OE2  GLU  311       4.834   6.657   7.519  1.00 37.12
ATOM    869  C    GLU  311       6.784   4.429  11.614  1.00 33.13
ATOM    870  O    GLU  311       5.993   3.784  12.303  1.00 35.45
ATOM    871  N    THR  312       7.880   3.898  11.085  1.00 32.86
ATOM    872  CA   THR  312       8.200   2.487  11.249  1.00 32.32
ATOM    873  CB   THR  312       9.488   2.140  10.477  1.00 32.72
ATOM    874  OG1  THR  312       9.289   2.449   9.092  1.00 33.20
ATOM    875  CG2  THR  312       9.829   0.661  10.611  1.00 31.35
ATOM    876  C    THR  312       8.329   2.104  12.727  1.00 31.60
ATOM    877  O    THR  312       8.016   0.980  13.114  1.00 32.69
ATOM    878  N    ALA  313       8.741   3.057  13.554  1.00 30.31
ATOM    879  CA   ALA  313       8.899   2.806  14.977  1.00 29.28
ATOM    880  CB   ALA  313       9.949   3.731  15.563  1.00 28.71
ATOM    881  C    ALA  313       7.575   2.950  15.722  1.00 28.65
ATOM    882  O    ALA  313       7.520   2.786  16.939  1.00 29.03
ATOM    883  N    GLY  314       6.514   3.278  14.996  1.00 28.36
ATOM    884  CA   GLY  314       5.207   3.409  15.618  1.00 29.07
ATOM    885  C    GLY  314       4.836   4.749  16.231  1.00 28.95
ATOM    886  O    GLY  314       4.048   4.822  17.173  1.00 28.57
ATOM    887  N    ALA  315       5.418   5.821  15.724  1.00 29.15
ATOM    888  CA   ALA  315       5.080   7.131  16.239  1.00 27.89
ATOM    889  CB   ALA  315       6.218   8.106  15.987  1.00 27.99
ATOM    890  C    ALA  315       3.820   7.561  15.499  1.00 27.19
ATOM    891  O    ALA  315       3.509   7.042  14.421  1.00 25.84
ATOM    892  N    ARG  316       3.090   8.493  16.092  1.00 27.55
ATOM    893  CA   ARG  316       1.863   9.010  15.502  1.00 27.08
ATOM    894  CB   ARG  316       0.777   9.155  16.582  1.00 31.00
ATOM    895  CG   ARG  316      -0.529   9.805  16.099  1.00 35.35
ATOM    896  CD   ARG  316      -1.404   8.835  15.306  1.00 38.97
ATOM    897  NE   ARG  316      -1.989   7.798  16.158  1.00 42.10
ATOM    898  CZ   ARG  316      -2.953   8.008  17.055  1.00 43.29
ATOM    899  NH1  ARG  316      -3.462   9.220  17.232  1.00 43.63
ATOM    900  NH2  ARG  316      -3.393   7.004  17.799  1.00 43.76
ATOM    901  C    ARG  316       2.095  10.366  14.854  1.00 25.15
ATOM    902  O    ARG  316       1.521  10.679  13.805  1.00 25.12
ATOM    903  N    LEU  317       2.962  11.164  15.457  1.00 22.37
ATOM    904  CA   LEU  317       3.185  12.493  14.931  1.00 20.99
ATOM    905  CB   LEU  317       2.234  13.482  15.648  1.00 18.70
ATOM    906  CG   LEU  317       2.297  14.999  15.402  1.00 16.65
ATOM    907  CD1  LEU  317       1.898  15.327  13.972  1.00 15.36
ATOM    908  CD2  LEU  317       1.384  15.723  16.375  1.00 16.28
ATOM    909  C    LEU  317       4.612  12.987  15.060  1.00 21.09
ATOM    910  O    LEU  317       5.293  12.705  16.053  1.00 21.51
ATOM    911  N    VAL  318       5.061  13.686  14.020  1.00 20.92
ATOM    912  CA   VAL  318       6.368  14.319  14.009  1.00 21.69
ATOM    913  CB   VAL  318       7.324  13.760  12.924  1.00 21.79
ATOM    914  CG1  VAL  318       8.541  14.686  12.772  1.00 20.61
ATOM    915  CG2  VAL  318       7.801  12.375  13.320  1.00 21.19
ATOM    916  C    VAL  318       6.061  15.787  13.736  1.00 21.64
ATOM    917  O    VAL  318       5.367  16.112  12.767  1.00 20.75
ATOM    918  N    VAL  319       6.523  16.660  14.626  1.00 21.64
ATOM    919  CA   VAL  319       6.291  18.088  14.489  1.00 21.71
ATOM    920  CB   VAL  319       5.581  18.679  15.751  1.00 21.72
ATOM    921  CG1  VAL  319       5.321  20.171  15.579  1.00 19.36
ATOM    922  CG2  VAL  319       4.280  17.947  16.020  1.00 21.02
ATOM    923  C    VAL  319       7.619  18.793  14.308  1.00 20.25
```

FIGURE 1 (cont.)

```
ATOM    924  O    VAL  319       8.520  18.635  15.127  1.00 19.92
ATOM    925  N    LEU  320       7.739  19.555  13.226  1.00 20.09
ATOM    926  CA   LEU  320       8.946  20.323  12.934  1.00 18.99
ATOM    927  CB   LEU  320       9.276  20.236  11.442  1.00 18.78
ATOM    928  CG   LEU  320       9.265  18.835  10.803  1.00 20.01
ATOM    929  CD1  LEU  320       9.449  18.951   9.309  1.00 20.04
ATOM    930  CD2  LEU  320      10.342  17.940  11.400  1.00 20.17
ATOM    931  C    LEU  320       8.609  21.754  13.352  1.00 17.86
ATOM    932  O    LEU  320       7.887  22.459  12.655  1.00 17.59
ATOM    933  N    ALA  321       9.102  22.160  14.515  1.00 18.47
ATOM    934  CA   ALA  321       8.807  23.476  15.055  1.00 20.27
ATOM    935  CB   ALA  321       8.365  23.354  16.522  1.00 19.53
ATOM    936  C    ALA  321       9.926  24.499  14.935  1.00 22.46
ATOM    937  O    ALA  321      11.105  24.199  15.192  1.00 22.78
ATOM    938  N    THR  322       9.531  25.732  14.615  1.00 23.57
ATOM    939  CA   THR  322      10.463  26.839  14.463  1.00 24.42
ATOM    940  CB   THR  322      11.384  26.632  13.224  1.00 23.87
ATOM    941  OG1  THR  322      12.368  27.677  13.159  1.00 22.26
ATOM    942  CG2  THR  322      10.561  26.606  11.935  1.00 20.90
ATOM    943  C    THR  322       9.721  28.166  14.301  1.00 25.40
ATOM    944  O    THR  322       8.632  28.227  13.719  1.00 25.14
ATOM    945  N    ALA  323      10.317  29.220  14.841  1.00 25.81
ATOM    946  CA   ALA  323       9.768  30.559  14.729  1.00 25.79
ATOM    947  CB   ALA  323      10.219  31.412  15.902  1.00 25.93
ATOM    948  C    ALA  323      10.288  31.153  13.423  1.00 26.98
ATOM    949  O    ALA  323       9.758  32.153  12.932  1.00 28.83
ATOM    950  N    THR  324      11.325  30.531  12.862  1.00 25.90
ATOM    951  CA   THR  324      11.925  31.003  11.617  1.00 24.88
ATOM    952  CB   THR  324      13.319  31.611  11.876  1.00 24.01
ATOM    953  OG1  THR  324      14.106  30.689  12.641  1.00 25.50
ATOM    954  CG2  THR  324      13.201  32.908  12.648  1.00 23.67
ATOM    955  C    THR  324      12.048  29.943  10.508  1.00 24.40
ATOM    956  O    THR  324      13.123  29.369  10.293  1.00 24.97
ATOM    957  N    PRO  325      10.935  29.624   9.829  1.00 22.47
ATOM    958  CD   PRO  325       9.557  30.088  10.041  1.00 21.14
ATOM    959  CA   PRO  325      10.978  28.634   8.755  1.00 22.40
ATOM    960  CB   PRO  325       9.500  28.446   8.422  1.00 20.85
ATOM    961  CG   PRO  325       8.922  29.769   8.720  1.00 19.94
ATOM    962  C    PRO  325      11.756  29.190   7.559  1.00 23.10
ATOM    963  O    PRO  325      12.008  30.396   7.486  1.00 23.30
ATOM    964  N    PRO  326      12.159  28.319   6.609  1.00 23.99
ATOM    965  CD   PRO  326      12.034  26.849   6.583  1.00 23.51
ATOM    966  CA   PRO  326      12.908  28.793   5.437  1.00 23.61
ATOM    967  CB   PRO  326      12.949  27.553   4.544  1.00 22.60
ATOM    968  CG   PRO  326      13.058  26.456   5.545  1.00 22.79
ATOM    969  C    PRO  326      12.245  29.985   4.740  1.00 22.55
ATOM    970  O    PRO  326      11.019  30.087   4.696  1.00 23.41
ATOM    971  N    GLY  327      13.070  30.901   4.249  1.00 20.16
ATOM    972  CA   GLY  327      12.576  32.077   3.561  1.00 20.04
ATOM    973  C    GLY  327      12.224  33.207   4.501  1.00 20.56
ATOM    974  O    GLY  327      11.681  34.216   4.075  1.00 21.64
ATOM    975  N    SER  328      12.544  33.044   5.779  1.00 22.07
ATOM    976  CA   SER  328      12.245  34.056   6.783  1.00 21.35
ATOM    977  CB   SER  328      12.379  33.466   8.189  1.00 20.72
ATOM    978  OG   SER  328      11.326  32.565   8.454  1.00 20.21
ATOM    979  C    SER  328      13.088  35.322   6.689  1.00 22.21
ATOM    980  O    SER  328      14.185  35.333   6.115  1.00 21.32
ATOM    981  N    VAL  329      12.552  36.387   7.275  1.00 21.78
```

FIGURE 1 (cont.)

| ATOM | 982  | CA  | VAL | 329 | 13.207 | 37.678 | 7.325  | 1.00 | 21.67 |
|------|------|-----|-----|-----|--------|--------|--------|------|-------|
| ATOM | 983  | CB  | VAL | 329 | 12.634 | 38.651 | 6.278  | 1.00 | 21.56 |
| ATOM | 984  | CG1 | VAL | 329 | 13.039 | 38.203 | 4.867  | 1.00 | 21.42 |
| ATOM | 985  | CG2 | VAL | 329 | 11.123 | 38.747 | 6.410  | 1.00 | 19.14 |
| ATOM | 986  | C   | VAL | 329 | 12.960 | 38.192 | 8.737  | 1.00 | 21.96 |
| ATOM | 987  | O   | VAL | 329 | 12.080 | 37.683 | 9.424  | 1.00 | 21.78 |
| ATOM | 988  | N   | THR | 330 | 13.786 | 39.132 | 9.187  | 1.00 | 23.09 |
| ATOM | 989  | CA  | THR | 330 | 13.681 | 39.708 | 10.523 | 1.00 | 24.47 |
| ATOM | 990  | CB  | THR | 330 | 15.073 | 40.131 | 11.047 | 1.00 | 24.34 |
| ATOM | 991  | OG1 | THR | 330 | 15.958 | 39.009 | 10.972 | 1.00 | 25.56 |
| ATOM | 992  | CG2 | THR | 330 | 14.997 | 40.577 | 12.490 | 1.00 | 23.96 |
| ATOM | 993  | C   | THR | 330 | 12.719 | 40.888 | 10.521 | 1.00 | 25.81 |
| ATOM | 994  | O   | THR | 330 | 13.062 | 42.014 | 10.134 | 1.00 | 25.19 |
| ATOM | 995  | N   | VAL | 331 | 11.507 | 40.600 | 10.972 | 1.00 | 27.46 |
| ATOM | 996  | CA  | VAL | 331 | 10.415 | 41.558 | 11.029 | 1.00 | 29.93 |
| ATOM | 997  | CB  | VAL | 331 | 9.065  | 40.789 | 10.871 | 1.00 | 30.69 |
| ATOM | 998  | CG1 | VAL | 331 | 7.885  | 41.620 | 11.359 | 1.00 | 33.40 |
| ATOM | 999  | CG2 | VAL | 331 | 8.871  | 40.366 | 9.408  | 1.00 | 28.41 |
| ATOM | 1000 | C   | VAL | 331 | 10.431 | 42.356 | 12.330 | 1.00 | 30.66 |
| ATOM | 1001 | O   | VAL | 331 | 10.942 | 41.880 | 13.347 | 1.00 | 30.44 |
| ATOM | 1002 | N   | PRO | 332 | 9.923  | 43.601 | 12.296 | 1.00 | 31.80 |
| ATOM | 1003 | CD  | PRO | 332 | 9.525  | 44.351 | 11.088 | 1.00 | 32.94 |
| ATOM | 1004 | CA  | PRO | 332 | 9.868  | 44.471 | 13.469 | 1.00 | 32.90 |
| ATOM | 1005 | CB  | PRO | 332 | 8.882  | 45.544 | 13.029 | 1.00 | 33.03 |
| ATOM | 1006 | CG  | PRO | 332 | 9.299  | 45.772 | 11.616 | 1.00 | 32.19 |
| ATOM | 1007 | C   | PRO | 332 | 9.403  | 43.751 | 14.726 | 1.00 | 33.35 |
| ATOM | 1008 | O   | PRO | 332 | 8.539  | 42.879 | 14.673 | 1.00 | 33.22 |
| ATOM | 1009 | N   | HIS | 333 | 10.042 | 44.092 | 15.840 | 1.00 | 34.93 |
| ATOM | 1010 | CA  | HIS | 333 | 9.747  | 43.526 | 17.149 | 1.00 | 35.66 |
| ATOM | 1011 | CB  | HIS | 333 | 11.040 | 43.034 | 17.801 | 1.00 | 35.75 |
| ATOM | 1012 | CG  | HIS | 333 | 10.864 | 42.519 | 19.196 | 1.00 | 35.91 |
| ATOM | 1013 | CD2 | HIS | 333 | 11.036 | 41.281 | 19.717 | 1.00 | 37.50 |
| ATOM | 1014 | ND1 | HIS | 333 | 10.494 | 43.327 | 20.250 | 1.00 | 35.51 |
| ATOM | 1015 | CE1 | HIS | 333 | 10.448 | 42.610 | 21.359 | 1.00 | 35.57 |
| ATOM | 1016 | NE2 | HIS | 333 | 10.774 | 41.366 | 21.063 | 1.00 | 37.41 |
| ATOM | 1017 | C   | HIS | 333 | 9.152  | 44.666 | 17.967 | 1.00 | 36.79 |
| ATOM | 1018 | O   | HIS | 333 | 9.616  | 45.804 | 17.878 | 1.00 | 37.38 |
| ATOM | 1019 | N   | PRO | 334 | 8.174  | 44.362 | 18.833 | 1.00 | 37.08 |
| ATOM | 1020 | CD  | PRO | 334 | 7.664  | 43.006 | 19.111 | 1.00 | 36.74 |
| ATOM | 1021 | CA  | PRO | 334 | 7.509  | 45.364 | 19.680 | 1.00 | 37.36 |
| ATOM | 1022 | CB  | PRO | 334 | 6.622  | 44.508 | 20.589 | 1.00 | 38.15 |
| ATOM | 1023 | CG  | PRO | 334 | 6.344  | 43.286 | 19.753 | 1.00 | 38.80 |
| ATOM | 1024 | C   | PRO | 334 | 8.458  | 46.225 | 20.521 | 1.00 | 37.12 |
| ATOM | 1025 | O   | PRO | 334 | 8.426  | 47.448 | 20.447 | 1.00 | 37.73 |
| ATOM | 1026 | N   | ASN | 335 | 9.283  | 45.564 | 21.330 | 1.00 | 36.19 |
| ATOM | 1027 | CA  | ASN | 335 | 10.231 | 46.226 | 22.228 | 1.00 | 35.31 |
| ATOM | 1028 | CB  | ASN | 335 | 10.616 | 45.294 | 23.385 | 1.00 | 36.70 |
| ATOM | 1029 | CG  | ASN | 335 | 9.433  | 44.782 | 24.146 | 1.00 | 38.17 |
| ATOM | 1030 | OD1 | ASN | 335 | 8.393  | 45.429 | 24.192 | 1.00 | 41.02 |
| ATOM | 1031 | ND2 | ASN | 335 | 9.579  | 43.602 | 24.751 | 1.00 | 37.75 |
| ATOM | 1032 | C   | ASN | 335 | 11.547 | 46.676 | 21.640 | 1.00 | 33.43 |
| ATOM | 1033 | O   | ASN | 335 | 12.410 | 47.100 | 22.404 | 1.00 | 35.07 |
| ATOM | 1034 | N   | ILE | 336 | 11.732 | 46.613 | 20.325 | 1.00 | 30.99 |
| ATOM | 1035 | CA  | ILE | 336 | 13.043 | 46.972 | 19.783 | 1.00 | 27.79 |
| ATOM | 1036 | CB  | ILE | 336 | 13.771 | 45.706 | 19.242 | 1.00 | 26.56 |
| ATOM | 1037 | CG2 | ILE | 336 | 15.209 | 46.038 | 18.847 | 1.00 | 23.81 |
| ATOM | 1038 | CG1 | ILE | 336 | 13.786 | 44.609 | 20.312 | 1.00 | 24.10 |
| ATOM | 1039 | CD1 | ILE | 336 | 14.260 | 43.272 | 19.819 | 1.00 | 22.21 |

FIGURE 1 (cont.)

| ATOM | 1040 | C   | ILE | 336 | 13.131 | 48.077 | 18.738 | 1.00 | 28.12 |
|------|------|-----|-----|-----|--------|--------|--------|------|-------|
| ATOM | 1041 | O   | ILE | 336 | 12.731 | 47.896 | 17.588 | 1.00 | 28.53 |
| ATOM | 1042 | N   | GLU | 337 | 13.694 | 49.213 | 19.128 | 1.00 | 27.62 |
| ATOM | 1043 | CA  | GLU | 337 | 13.879 | 50.309 | 18.189 | 1.00 | 28.28 |
| ATOM | 1044 | CB  | GLU | 337 | 14.019 | 51.634 | 18.931 | 1.00 | 29.84 |
| ATOM | 1045 | CG  | GLU | 337 | 14.335 | 52.802 | 18.002 | 1.00 | 33.89 |
| ATOM | 1046 | CD  | GLU | 337 | 14.754 | 54.067 | 18.730 | 1.00 | 36.64 |
| ATOM | 1047 | OE1 | GLU | 337 | 14.866 | 54.049 | 19.978 | 1.00 | 39.22 |
| ATOM | 1048 | OE2 | GLU | 337 | 14.987 | 55.084 | 18.041 | 1.00 | 38.86 |
| ATOM | 1049 | C   | GLU | 337 | 15.168 | 50.031 | 17.401 | 1.00 | 27.48 |
| ATOM | 1050 | O   | GLU | 337 | 16.224 | 49.807 | 17.990 | 1.00 | 27.75 |
| ATOM | 1051 | N   | GLU | 338 | 15.092 | 50.053 | 16.078 | 1.00 | 26.13 |
| ATOM | 1052 | CA  | GLU | 338 | 16.264 | 49.791 | 15.260 | 1.00 | 25.01 |
| ATOM | 1053 | CB  | GLU | 338 | 15.939 | 48.745 | 14.200 | 1.00 | 25.16 |
| ATOM | 1054 | CG  | GLU | 338 | 15.433 | 47.431 | 14.770 | 1.00 | 26.26 |
| ATOM | 1055 | CD  | GLU | 338 | 15.271 | 46.355 | 13.720 | 1.00 | 25.40 |
| ATOM | 1056 | OE1 | GLU | 338 | 14.396 | 45.490 | 13.896 | 1.00 | 26.96 |
| ATOM | 1057 | OE2 | GLU | 338 | 16.020 | 46.363 | 12.723 | 1.00 | 26.71 |
| ATOM | 1058 | C   | GLU | 338 | 16.794 | 51.050 | 14.594 | 1.00 | 25.30 |
| ATOM | 1059 | O   | GLU | 338 | 16.033 | 51.835 | 14.033 | 1.00 | 27.51 |
| ATOM | 1060 | N   | VAL | 339 | 18.103 | 51.250 | 14.646 | 1.00 | 24.09 |
| ATOM | 1061 | CA  | VAL | 339 | 18.690 | 52.421 | 14.027 | 1.00 | 22.82 |
| ATOM | 1062 | CB  | VAL | 339 | 18.667 | 53.653 | 14.986 | 1.00 | 22.08 |
| ATOM | 1063 | CG1 | VAL | 339 | 18.756 | 53.221 | 16.424 | 1.00 | 21.99 |
| ATOM | 1064 | CG2 | VAL | 339 | 19.763 | 54.646 | 14.637 | 1.00 | 19.75 |
| ATOM | 1065 | C   | VAL | 339 | 20.064 | 52.174 | 13.411 | 1.00 | 22.67 |
| ATOM | 1066 | O   | VAL | 339 | 20.951 | 51.593 | 14.027 | 1.00 | 23.55 |
| ATOM | 1067 | N   | ALA | 340 | 20.189 | 52.567 | 12.150 | 1.00 | 22.35 |
| ATOM | 1068 | CA  | ALA | 340 | 21.416 | 52.428 | 11.384 | 1.00 | 23.06 |
| ATOM | 1069 | CB  | ALA | 340 | 21.169 | 52.877 |  9.952 | 1.00 | 20.82 |
| ATOM | 1070 | C   | ALA | 340 | 22.559 | 53.240 | 11.969 | 1.00 | 23.85 |
| ATOM | 1071 | O   | ALA | 340 | 22.354 | 54.337 | 12.485 | 1.00 | 25.71 |
| ATOM | 1072 | N   | LEU | 341 | 23.761 | 52.686 | 11.929 | 1.00 | 23.84 |
| ATOM | 1073 | CA  | LEU | 341 | 24.920 | 53.417 | 12.404 | 1.00 | 23.48 |
| ATOM | 1074 | CB  | LEU | 341 | 26.069 | 52.468 | 12.729 | 1.00 | 22.83 |
| ATOM | 1075 | CG  | LEU | 341 | 25.938 | 51.583 | 13.960 | 1.00 | 21.53 |
| ATOM | 1076 | CD1 | LEU | 341 | 27.012 | 50.509 | 13.925 | 1.00 | 22.65 |
| ATOM | 1077 | CD2 | LEU | 341 | 26.054 | 52.427 | 15.203 | 1.00 | 21.05 |
| ATOM | 1078 | C   | LEU | 341 | 25.307 | 54.276 | 11.206 | 1.00 | 25.07 |
| ATOM | 1079 | O   | LEU | 341 | 24.967 | 53.939 | 10.064 | 1.00 | 25.58 |
| ATOM | 1080 | N   | SER | 342 | 25.988 | 55.388 | 11.459 | 1.00 | 25.28 |
| ATOM | 1081 | CA  | SER | 342 | 26.426 | 56.272 | 10.391 | 1.00 | 25.74 |
| ATOM | 1082 | CB  | SER | 342 | 25.832 | 57.680 | 10.569 | 1.00 | 25.63 |
| ATOM | 1083 | OG  | SER | 342 | 26.162 | 58.252 | 11.831 | 1.00 | 26.66 |
| ATOM | 1084 | C   | SER | 342 | 27.946 | 56.313 | 10.422 | 1.00 | 26.04 |
| ATOM | 1085 | O   | SER | 342 | 28.588 | 55.459 | 11.030 | 1.00 | 26.02 |
| ATOM | 1086 | N   | THR | 343 | 28.528 | 57.276 |  9.727 | 1.00 | 27.63 |
| ATOM | 1087 | CA  | THR | 343 | 29.972 | 57.416 |  9.712 | 1.00 | 28.59 |
| ATOM | 1088 | CB  | THR | 343 | 30.429 | 58.057 |  8.404 | 1.00 | 29.62 |
| ATOM | 1089 | OG1 | THR | 343 | 29.514 | 59.101 |  8.050 | 1.00 | 30.43 |
| ATOM | 1090 | CG2 | THR | 343 | 30.455 | 57.019 |  7.302 | 1.00 | 32.51 |
| ATOM | 1091 | C   | THR | 343 | 30.422 | 58.275 | 10.890 | 1.00 | 28.11 |
| ATOM | 1092 | O   | THR | 343 | 31.614 | 58.399 | 11.171 | 1.00 | 29.07 |
| ATOM | 1093 | N   | THR | 344 | 29.459 | 58.863 | 11.583 | 1.00 | 27.10 |
| ATOM | 1094 | CA  | THR | 344 | 29.767 | 59.710 | 12.714 | 1.00 | 27.21 |
| ATOM | 1095 | CB  | THR | 344 | 28.729 | 60.827 | 12.825 | 1.00 | 27.65 |
| ATOM | 1096 | OG1 | THR | 344 | 28.658 | 61.514 | 11.568 | 1.00 | 28.57 |
| ATOM | 1097 | CG2 | THR | 344 | 29.100 | 61.805 | 13.924 | 1.00 | 27.24 |

FIGURE 1 (cont.)

| ATOM | 1098 | C   | THR | 344 | 29.842 | 58.908 | 14.008 | 1.00 | 27.63 |
|------|------|-----|-----|-----|--------|--------|--------|------|-------|
| ATOM | 1099 | O   | THR | 344 | 28.884 | 58.225 | 14.396 | 1.00 | 27.69 |
| ATOM | 1100 | N   | GLY | 345 | 31.003 | 58.969 | 14.649 | 1.00 | 26.95 |
| ATOM | 1101 | CA  | GLY | 345 | 31.211 | 58.260 | 15.890 | 1.00 | 26.75 |
| ATOM | 1102 | C   | GLY | 345 | 32.688 | 58.168 | 16.189 | 1.00 | 28.21 |
| ATOM | 1103 | O   | GLY | 345 | 33.512 | 58.276 | 15.285 | 1.00 | 28.29 |
| ATOM | 1104 | N   | GLU | 346 | 33.023 | 57.926 | 17.451 | 1.00 | 28.51 |
| ATOM | 1105 | CA  | GLU | 346 | 34.414 | 57.832 | 17.863 | 1.00 | 29.04 |
| ATOM | 1106 | CB  | GLU | 346 | 34.541 | 58.020 | 19.378 | 1.00 | 30.35 |
| ATOM | 1107 | CG  | GLU | 346 | 34.291 | 59.439 | 19.880 | 1.00 | 32.52 |
| ATOM | 1108 | CD  | GLU | 346 | 32.888 | 59.926 | 19.593 | 1.00 | 32.87 |
| ATOM | 1109 | OE1 | GLU | 346 | 31.929 | 59.174 | 19.854 | 1.00 | 32.23 |
| ATOM | 1110 | OE2 | GLU | 346 | 32.747 | 61.057 | 19.086 | 1.00 | 35.06 |
| ATOM | 1111 | C   | GLU | 346 | 35.084 | 56.523 | 17.479 | 1.00 | 28.20 |
| ATOM | 1112 | O   | GLU | 346 | 36.283 | 56.502 | 17.218 | 1.00 | 29.40 |
| ATOM | 1113 | N   | ILE | 347 | 34.321 | 55.431 | 17.457 | 1.00 | 28.52 |
| ATOM | 1114 | CA  | ILE | 347 | 34.889 | 54.110 | 17.153 | 1.00 | 26.91 |
| ATOM | 1115 | CB  | ILE | 347 | 34.453 | 53.035 | 18.192 | 1.00 | 27.90 |
| ATOM | 1116 | CG2 | ILE | 347 | 35.250 | 51.776 | 18.005 | 1.00 | 28.31 |
| ATOM | 1117 | CG1 | ILE | 347 | 34.645 | 53.537 | 19.620 | 1.00 | 29.70 |
| ATOM | 1118 | CD1 | ILE | 347 | 33.400 | 54.194 | 20.186 | 1.00 | 32.81 |
| ATOM | 1119 | C   | ILE | 347 | 34.551 | 53.550 | 15.781 | 1.00 | 24.52 |
| ATOM | 1120 | O   | ILE | 347 | 33.392 | 53.258 | 15.490 | 1.00 | 23.00 |
| ATOM | 1121 | N   | PRO | 348 | 35.559 | 53.398 | 14.914 | 1.00 | 23.86 |
| ATOM | 1122 | CD  | PRO | 348 | 36.947 | 53.871 | 15.026 | 1.00 | 23.37 |
| ATOM | 1123 | CA  | PRO | 348 | 35.302 | 52.854 | 13.582 | 1.00 | 24.53 |
| ATOM | 1124 | CB  | PRO | 348 | 36.692 | 52.834 | 12.959 | 1.00 | 24.34 |
| ATOM | 1125 | CG  | PRO | 348 | 37.338 | 54.030 | 13.588 | 1.00 | 23.28 |
| ATOM | 1126 | C   | PRO | 348 | 34.759 | 51.449 | 13.786 | 1.00 | 25.57 |
| ATOM | 1127 | O   | PRO | 348 | 35.290 | 50.696 | 14.606 | 1.00 | 25.45 |
| ATOM | 1128 | N   | PHE | 349 | 33.677 | 51.118 | 13.084 | 1.00 | 25.89 |
| ATOM | 1129 | CA  | PHE | 349 | 33.041 | 49.812 | 13.216 | 1.00 | 24.50 |
| ATOM | 1130 | CB  | PHE | 349 | 31.971 | 49.860 | 14.318 | 1.00 | 23.29 |
| ATOM | 1131 | CG  | PHE | 349 | 31.358 | 48.522 | 14.632 | 1.00 | 25.07 |
| ATOM | 1132 | CD1 | PHE | 349 | 32.025 | 47.610 | 15.447 | 1.00 | 26.07 |
| ATOM | 1133 | CD2 | PHE | 349 | 30.111 | 48.175 | 14.119 | 1.00 | 25.08 |
| ATOM | 1134 | CE1 | PHE | 349 | 31.461 | 46.372 | 15.750 | 1.00 | 25.64 |
| ATOM | 1135 | CE2 | PHE | 349 | 29.535 | 46.945 | 14.411 | 1.00 | 25.25 |
| ATOM | 1136 | CZ  | PHE | 349 | 30.211 | 46.038 | 15.230 | 1.00 | 26.19 |
| ATOM | 1137 | C   | PHE | 349 | 32.437 | 49.321 | 11.904 | 1.00 | 23.33 |
| ATOM | 1138 | O   | PHE | 349 | 31.361 | 49.749 | 11.501 | 1.00 | 22.31 |
| ATOM | 1139 | N   | TYR | 350 | 33.154 | 48.418 | 11.247 | 1.00 | 23.43 |
| ATOM | 1140 | CA  | TYR | 350 | 32.725 | 47.820 |  9.986 | 1.00 | 23.78 |
| ATOM | 1141 | CB  | TYR | 350 | 31.636 | 46.759 | 10.230 | 1.00 | 21.13 |
| ATOM | 1142 | CG  | TYR | 350 | 32.133 | 45.531 | 10.967 | 1.00 | 20.42 |
| ATOM | 1143 | CD1 | TYR | 350 | 32.302 | 45.552 | 12.344 | 1.00 | 19.57 |
| ATOM | 1144 | CE1 | TYR | 350 | 32.794 | 44.440 | 13.028 | 1.00 | 20.40 |
| ATOM | 1145 | CD2 | TYR | 350 | 32.465 | 44.353 | 10.279 | 1.00 | 21.51 |
| ATOM | 1146 | CE2 | TYR | 350 | 32.963 | 43.224 | 10.958 | 1.00 | 19.67 |
| ATOM | 1147 | CZ  | TYR | 350 | 33.126 | 43.282 | 12.335 | 1.00 | 20.56 |
| ATOM | 1148 | OH  | TYR | 350 | 33.648 | 42.212 | 13.040 | 1.00 | 20.53 |
| ATOM | 1149 | C   | TYR | 350 | 32.280 | 48.823 |  8.920 | 1.00 | 25.07 |
| ATOM | 1150 | O   | TYR | 350 | 31.215 | 48.680 |  8.324 | 1.00 | 26.53 |
| ATOM | 1151 | N   | GLY | 351 | 33.118 | 49.817 |  8.656 | 1.00 | 25.52 |
| ATOM | 1152 | CA  | GLY | 351 | 32.789 | 50.802 |  7.644 | 1.00 | 26.67 |
| ATOM | 1153 | C   | GLY | 351 | 32.054 | 52.000 |  8.205 | 1.00 | 27.75 |
| ATOM | 1154 | O   | GLY | 351 | 32.097 | 53.088 |  7.624 | 1.00 | 29.56 |
| ATOM | 1155 | N   | LYS | 352 | 31.332 | 51.788 |  9.300 | 1.00 | 28.35 |

FIGURE 1 (cont.)

| ATOM | 1156 | CA | LYS | 352 | 30.596 | 52.858 | 9.962 | 1.00 | 26.46 |
|------|------|-----|-----|-----|--------|--------|--------|------|-------|
| ATOM | 1157 | CB | LYS | 352 | 29.182 | 52.405 | 10.332 | 1.00 | 26.95 |
| ATOM | 1158 | CG | LYS | 352 | 28.352 | 51.994 | 9.145 | 1.00 | 28.09 |
| ATOM | 1159 | CD | LYS | 352 | 28.138 | 53.145 | 8.186 | 1.00 | 29.10 |
| ATOM | 1160 | CE | LYS | 352 | 27.767 | 52.615 | 6.811 | 1.00 | 31.84 |
| ATOM | 1161 | NZ | LYS | 352 | 26.677 | 51.594 | 6.876 | 1.00 | 34.67 |
| ATOM | 1162 | C | LYS | 352 | 31.373 | 53.197 | 11.213 | 1.00 | 25.16 |
| ATOM | 1163 | O | LYS | 352 | 32.560 | 52.903 | 11.313 | 1.00 | 24.74 |
| ATOM | 1164 | N | ALA | 353 | 30.704 | 53.811 | 12.170 | 1.00 | 26.04 |
| ATOM | 1165 | CA | ALA | 353 | 31.353 | 54.186 | 13.407 | 1.00 | 27.08 |
| ATOM | 1166 | CB | ALA | 353 | 31.987 | 55.568 | 13.267 | 1.00 | 26.55 |
| ATOM | 1167 | C | ALA | 353 | 30.332 | 54.172 | 14.533 | 1.00 | 27.81 |
| ATOM | 1168 | O | ALA | 353 | 29.122 | 54.285 | 14.297 | 1.00 | 29.07 |
| ATOM | 1169 | N | ILE | 354 | 30.816 | 53.977 | 15.750 | 1.00 | 26.83 |
| ATOM | 1170 | CA | ILE | 354 | 29.944 | 53.949 | 16.903 | 1.00 | 26.78 |
| ATOM | 1171 | CB | ILE | 354 | 30.136 | 52.664 | 17.758 | 1.00 | 26.37 |
| ATOM | 1172 | CG2 | ILE | 354 | 29.224 | 52.705 | 18.989 | 1.00 | 23.34 |
| ATOM | 1173 | CG1 | ILE | 354 | 29.864 | 51.409 | 16.922 | 1.00 | 26.07 |
| ATOM | 1174 | CD1 | ILE | 354 | 30.151 | 50.093 | 17.660 | 1.00 | 26.73 |
| ATOM | 1175 | C | ILE | 354 | 30.269 | 55.147 | 17.770 | 1.00 | 27.53 |
| ATOM | 1176 | O | ILE | 354 | 31.446 | 55.480 | 17.980 | 1.00 | 27.83 |
| ATOM | 1177 | N | PRO | 355 | 29.231 | 55.890 | 18.172 | 1.00 | 27.07 |
| ATOM | 1178 | CD | PRO | 355 | 27.876 | 55.817 | 17.601 | 1.00 | 26.53 |
| ATOM | 1179 | CA | PRO | 355 | 29.379 | 57.069 | 19.026 | 1.00 | 27.16 |
| ATOM | 1180 | CB | PRO | 355 | 28.042 | 57.794 | 18.851 | 1.00 | 27.57 |
| ATOM | 1181 | CG | PRO | 355 | 27.507 | 57.257 | 17.531 | 1.00 | 28.35 |
| ATOM | 1182 | C | PRO | 355 | 29.521 | 56.570 | 20.463 | 1.00 | 27.80 |
| ATOM | 1183 | O | PRO | 355 | 28.665 | 55.825 | 20.951 | 1.00 | 28.66 |
| ATOM | 1184 | N | LEU | 356 | 30.602 | 56.955 | 21.133 | 1.00 | 27.31 |
| ATOM | 1185 | CA | LEU | 356 | 30.821 | 56.537 | 22.512 | 1.00 | 26.78 |
| ATOM | 1186 | CB | LEU | 356 | 32.024 | 57.269 | 23.110 | 1.00 | 27.84 |
| ATOM | 1187 | CG | LEU | 356 | 33.384 | 56.622 | 22.838 | 1.00 | 27.71 |
| ATOM | 1188 | CD1 | LEU | 356 | 34.515 | 57.553 | 23.275 | 1.00 | 27.97 |
| ATOM | 1189 | CD2 | LEU | 356 | 33.457 | 55.297 | 23.568 | 1.00 | 25.40 |
| ATOM | 1190 | C | LEU | 356 | 29.591 | 56.787 | 23.367 | 1.00 | 25.92 |
| ATOM | 1191 | O | LEU | 356 | 29.272 | 56.004 | 24.257 | 1.00 | 25.15 |
| ATOM | 1192 | N | ALA | 357 | 28.887 | 57.872 | 23.069 | 1.00 | 26.25 |
| ATOM | 1193 | CA | ALA | 357 | 27.685 | 58.241 | 23.813 | 1.00 | 26.44 |
| ATOM | 1194 | CB | ALA | 357 | 27.072 | 59.522 | 23.228 | 1.00 | 25.83 |
| ATOM | 1195 | C | ALA | 357 | 26.638 | 57.124 | 23.873 | 1.00 | 26.65 |
| ATOM | 1196 | O | ALA | 357 | 26.011 | 56.918 | 24.911 | 1.00 | 26.75 |
| ATOM | 1197 | N | VAL | 358 | 26.502 | 56.360 | 22.791 | 1.00 | 26.24 |
| ATOM | 1198 | CA | VAL | 358 | 25.506 | 55.295 | 22.758 | 1.00 | 26.40 |
| ATOM | 1199 | CB | VAL | 358 | 25.119 | 54.892 | 21.298 | 1.00 | 25.09 |
| ATOM | 1200 | CG1 | VAL | 358 | 24.714 | 56.119 | 20.511 | 1.00 | 23.26 |
| ATOM | 1201 | CG2 | VAL | 358 | 26.266 | 54.180 | 20.597 | 1.00 | 24.96 |
| ATOM | 1202 | C | VAL | 358 | 25.881 | 54.069 | 23.590 | 1.00 | 26.35 |
| ATOM | 1203 | O | VAL | 358 | 25.050 | 53.179 | 23.797 | 1.00 | 27.18 |
| ATOM | 1204 | N | ILE | 359 | 27.121 | 54.021 | 24.074 | 1.00 | 25.51 |
| ATOM | 1205 | CA | ILE | 359 | 27.567 | 52.892 | 24.893 | 1.00 | 24.89 |
| ATOM | 1206 | CB | ILE | 359 | 28.582 | 51.982 | 24.136 | 1.00 | 22.23 |
| ATOM | 1207 | CG2 | ILE | 359 | 27.857 | 51.199 | 23.029 | 1.00 | 21.17 |
| ATOM | 1208 | CG1 | ILE | 359 | 29.756 | 52.814 | 23.600 | 1.00 | 21.55 |
| ATOM | 1209 | CD1 | ILE | 359 | 30.892 | 52.026 | 22.995 | 1.00 | 17.63 |
| ATOM | 1210 | C | ILE | 359 | 28.159 | 53.308 | 26.237 | 1.00 | 25.79 |
| ATOM | 1211 | O | ILE | 359 | 28.437 | 52.459 | 27.076 | 1.00 | 25.36 |
| ATOM | 1212 | N | ALA | 360 | 28.304 | 54.616 | 26.449 | 1.00 | 29.45 |
| ATOM | 1213 | CA | ALA | 360 | 28.879 | 55.171 | 27.681 | 1.00 | 31.32 |

FIGURE 1 (cont.)

| ATOM | 1214 | CB | ALA | 360 | 28.880 | 56.691 | 27.621 | 1.00 | 30.01 |
|------|------|-----|-----|-----|--------|--------|--------|------|-------|
| ATOM | 1215 | C | ALA | 360 | 28.207 | 54.684 | 28.972 | 1.00 | 32.84 |
| ATOM | 1216 | O | ALA | 360 | 28.889 | 54.369 | 29.960 | 1.00 | 33.70 |
| ATOM | 1217 | N | GLY | 361 | 26.880 | 54.659 | 28.981 | 1.00 | 32.93 |
| ATOM | 1218 | CA | GLY | 361 | 26.172 | 54.179 | 30.154 | 1.00 | 32.53 |
| ATOM | 1219 | C | GLY | 361 | 25.285 | 53.020 | 29.739 | 1.00 | 32.16 |
| ATOM | 1220 | O | GLY | 361 | 24.892 | 52.945 | 28.579 | 1.00 | 33.01 |
| ATOM | 1221 | N | GLY | 362 | 24.978 | 52.115 | 30.664 | 1.00 | 31.44 |
| ATOM | 1222 | CA | GLY | 362 | 24.124 | 50.980 | 30.352 | 1.00 | 28.17 |
| ATOM | 1223 | C | GLY | 362 | 24.894 | 49.725 | 29.979 | 1.00 | 28.18 |
| ATOM | 1224 | O | GLY | 362 | 26.128 | 49.699 | 30.060 | 1.00 | 28.64 |
| ATOM | 1225 | N | ARG | 363 | 24.168 | 48.677 | 29.597 | 1.00 | 25.54 |
| ATOM | 1226 | CA | ARG | 363 | 24.762 | 47.404 | 29.196 | 1.00 | 25.19 |
| ATOM | 1227 | CB | ARG | 363 | 24.135 | 46.256 | 29.985 | 1.00 | 25.16 |
| ATOM | 1228 | CG | ARG | 363 | 23.726 | 46.631 | 31.401 | 1.00 | 26.44 |
| ATOM | 1229 | CD | ARG | 363 | 23.093 | 45.460 | 32.123 | 1.00 | 29.20 |
| ATOM | 1230 | NE | ARG | 363 | 24.075 | 44.760 | 32.935 | 1.00 | 34.10 |
| ATOM | 1231 | CZ | ARG | 363 | 24.655 | 43.608 | 32.616 | 1.00 | 35.13 |
| ATOM | 1232 | NH1 | ARG | 363 | 24.358 | 42.977 | 31.494 | 1.00 | 34.77 |
| ATOM | 1233 | NH2 | ARG | 363 | 25.613 | 43.130 | 33.389 | 1.00 | 36.31 |
| ATOM | 1234 | C | ARG | 363 | 24.504 | 47.226 | 27.695 | 1.00 | 24.94 |
| ATOM | 1235 | O | ARG | 363 | 23.377 | 47.393 | 27.222 | 1.00 | 24.76 |
| ATOM | 1236 | N | HIS | 364 | 25.542 | 46.910 | 26.934 | 1.00 | 24.18 |
| ATOM | 1237 | CA | HIS | 364 | 25.385 | 46.776 | 25.494 | 1.00 | 23.64 |
| ATOM | 1238 | CB | HIS | 364 | 25.891 | 48.048 | 24.830 | 1.00 | 23.19 |
| ATOM | 1239 | CG | HIS | 364 | 25.367 | 49.291 | 25.478 | 1.00 | 25.11 |
| ATOM | 1240 | CD2 | HIS | 364 | 25.895 | 50.084 | 26.438 | 1.00 | 24.33 |
| ATOM | 1241 | ND1 | HIS | 364 | 24.116 | 49.803 | 25.205 | 1.00 | 26.29 |
| ATOM | 1242 | CE1 | HIS | 364 | 23.894 | 50.856 | 25.970 | 1.00 | 25.44 |
| ATOM | 1243 | NE2 | HIS | 364 | 24.959 | 51.047 | 26.726 | 1.00 | 25.09 |
| ATOM | 1244 | C | HIS | 364 | 26.133 | 45.559 | 24.993 | 1.00 | 23.60 |
| ATOM | 1245 | O | HIS | 364 | 27.098 | 45.128 | 25.628 | 1.00 | 24.11 |
| ATOM | 1246 | N | LEU | 365 | 25.645 | 44.976 | 23.900 | 1.00 | 22.16 |
| ATOM | 1247 | CA | LEU | 365 | 26.247 | 43.784 | 23.310 | 1.00 | 21.25 |
| ATOM | 1248 | CB | LEU | 365 | 25.241 | 42.635 | 23.316 | 1.00 | 20.31 |
| ATOM | 1249 | CG | LEU | 365 | 25.667 | 41.278 | 22.749 | 1.00 | 19.06 |
| ATOM | 1250 | CD1 | LEU | 365 | 26.952 | 40.821 | 23.413 | 1.00 | 18.55 |
| ATOM | 1251 | CD2 | LEU | 365 | 24.562 | 40.252 | 22.966 | 1.00 | 16.61 |
| ATOM | 1252 | C | LEU | 365 | 26.672 | 44.079 | 21.883 | 1.00 | 21.19 |
| ATOM | 1253 | O | LEU | 365 | 25.836 | 44.377 | 21.031 | 1.00 | 21.03 |
| ATOM | 1254 | N | ILE | 366 | 27.966 | 43.978 | 21.615 | 1.00 | 20.98 |
| ATOM | 1255 | CA | ILE | 366 | 28.473 | 44.255 | 20.283 | 1.00 | 21.20 |
| ATOM | 1256 | CB | ILE | 366 | 29.646 | 45.254 | 20.322 | 1.00 | 21.57 |
| ATOM | 1257 | CG2 | ILE | 366 | 30.113 | 45.572 | 18.911 | 1.00 | 19.27 |
| ATOM | 1258 | CG1 | ILE | 366 | 29.225 | 46.536 | 21.051 | 1.00 | 21.36 |
| ATOM | 1259 | CD1 | ILE | 366 | 30.303 | 47.607 | 21.078 | 1.00 | 20.61 |
| ATOM | 1260 | C | ILE | 366 | 28.925 | 42.974 | 19.605 | 1.00 | 21.06 |
| ATOM | 1261 | O | ILE | 366 | 29.825 | 42.296 | 20.093 | 1.00 | 20.15 |
| ATOM | 1262 | N | PHE | 367 | 28.274 | 42.635 | 18.495 | 1.00 | 20.98 |
| ATOM | 1263 | CA | PHE | 367 | 28.610 | 41.438 | 17.747 | 1.00 | 21.40 |
| ATOM | 1264 | CB | PHE | 367 | 27.364 | 40.804 | 17.125 | 1.00 | 20.48 |
| ATOM | 1265 | CG | PHE | 367 | 26.556 | 39.975 | 18.093 | 1.00 | 20.75 |
| ATOM | 1266 | CD1 | PHE | 367 | 25.393 | 40.487 | 18.671 | 1.00 | 20.80 |
| ATOM | 1267 | CD2 | PHE | 367 | 26.951 | 38.675 | 18.416 | 1.00 | 19.09 |
| ATOM | 1268 | CE1 | PHE | 367 | 24.633 | 39.711 | 19.557 | 1.00 | 19.99 |
| ATOM | 1269 | CE2 | PHE | 367 | 26.210 | 37.899 | 19.291 | 1.00 | 19.22 |
| ATOM | 1270 | CZ | PHE | 367 | 25.043 | 38.417 | 19.865 | 1.00 | 20.05 |
| ATOM | 1271 | C | PHE | 367 | 29.644 | 41.705 | 16.670 | 1.00 | 22.44 |

FIGURE 1 (cont.)

| ATOM | 1272 | O   | PHE | 367 | 29.478 | 42.596 | 15.829 | 1.00 | 21.74 |
|------|------|-----|-----|-----|--------|--------|--------|------|-------|
| ATOM | 1273 | N   | CYS | 368 | 30.728 | 40.942 | 16.728 | 1.00 | 22.95 |
| ATOM | 1274 | CA  | CYS | 368 | 31.807 | 41.032 | 15.761 | 1.00 | 23.17 |
| ATOM | 1275 | CB  | CYS | 368 | 33.126 | 41.385 | 16.464 | 1.00 | 23.99 |
| ATOM | 1276 | SG  | CYS | 368 | 33.120 | 43.017 | 17.283 | 1.00 | 21.99 |
| ATOM | 1277 | C   | CYS | 368 | 31.863 | 39.650 | 15.106 | 1.00 | 23.06 |
| ATOM | 1278 | O   | CYS | 368 | 31.433 | 38.658 | 15.699 | 1.00 | 21.98 |
| ATOM | 1279 | N   | HIS | 369 | 32.358 | 39.578 | 13.877 | 1.00 | 23.71 |
| ATOM | 1280 | CA  | HIS | 369 | 32.402 | 38.291 | 13.185 | 1.00 | 24.68 |
| ATOM | 1281 | CB  | HIS | 369 | 32.429 | 38.498 | 11.667 | 1.00 | 24.85 |
| ATOM | 1282 | CG  | HIS | 369 | 33.754 | 38.951 | 11.138 | 1.00 | 27.37 |
| ATOM | 1283 | CD2 | HIS | 369 | 34.644 | 38.338 | 10.323 | 1.00 | 28.58 |
| ATOM | 1284 | ND1 | HIS | 369 | 34.306 | 40.175 | 11.452 | 1.00 | 29.21 |
| ATOM | 1285 | CE1 | HIS | 369 | 35.480 | 40.295 | 10.859 | 1.00 | 29.19 |
| ATOM | 1286 | NE2 | HIS | 369 | 35.708 | 39.194 | 10.168 | 1.00 | 29.69 |
| ATOM | 1287 | C   | HIS | 369 | 33.550 | 37.372 | 13.606 | 1.00 | 24.39 |
| ATOM | 1288 | O   | HIS | 369 | 33.440 | 36.153 | 13.506 | 1.00 | 24.00 |
| ATOM | 1289 | N   | SER | 370 | 34.641 | 37.959 | 14.087 | 1.00 | 24.30 |
| ATOM | 1290 | CA  | SER | 370 | 35.814 | 37.189 | 14.479 | 1.00 | 24.06 |
| ATOM | 1291 | CB  | SER | 370 | 36.949 | 37.460 | 13.494 | 1.00 | 24.57 |
| ATOM | 1292 | OG  | SER | 370 | 37.431 | 38.784 | 13.648 | 1.00 | 26.06 |
| ATOM | 1293 | C   | SER | 370 | 36.269 | 37.518 | 15.892 | 1.00 | 23.01 |
| ATOM | 1294 | O   | SER | 370 | 35.936 | 38.574 | 16.433 | 1.00 | 23.58 |
| ATOM | 1295 | N   | LYS | 371 | 37.076 | 36.633 | 16.461 | 1.00 | 23.64 |
| ATOM | 1296 | CA  | LYS | 371 | 37.587 | 36.797 | 17.817 | 1.00 | 25.06 |
| ATOM | 1297 | CB  | LYS | 371 | 38.146 | 35.466 | 18.320 | 1.00 | 24.91 |
| ATOM | 1298 | CG  | LYS | 371 | 37.086 | 34.372 | 18.306 | 1.00 | 27.06 |
| ATOM | 1299 | CD  | LYS | 371 | 37.648 | 32.979 | 18.078 | 1.00 | 28.04 |
| ATOM | 1300 | CE  | LYS | 371 | 38.277 | 32.415 | 19.318 | 1.00 | 28.77 |
| ATOM | 1301 | NZ  | LYS | 371 | 38.642 | 30.999 | 19.107 | 1.00 | 31.47 |
| ATOM | 1302 | C   | LYS | 371 | 38.625 | 37.904 | 17.877 | 1.00 | 25.64 |
| ATOM | 1303 | O   | LYS | 371 | 38.689 | 38.650 | 18.849 | 1.00 | 27.42 |
| ATOM | 1304 | N   | LYS | 372 | 39.379 | 38.061 | 16.795 | 1.00 | 27.32 |
| ATOM | 1305 | CA  | LYS | 372 | 40.402 | 39.100 | 16.707 | 1.00 | 28.80 |
| ATOM | 1306 | CB  | LYS | 372 | 41.136 | 39.010 | 15.366 | 1.00 | 29.78 |
| ATOM | 1307 | CG  | LYS | 372 | 42.339 | 39.923 | 15.243 | 1.00 | 30.84 |
| ATOM | 1308 | CD  | LYS | 372 | 42.976 | 39.812 | 13.866 | 1.00 | 31.69 |
| ATOM | 1309 | C   | LYS | 372 | 39.729 | 40.455 | 16.842 | 1.00 | 28.53 |
| ATOM | 1310 | O   | LYS | 372 | 40.095 | 41.255 | 17.696 | 1.00 | 28.67 |
| ATOM | 1311 | N   | LYS | 373 | 38.720 | 40.688 | 16.008 | 1.00 | 29.86 |
| ATOM | 1312 | CA  | LYS | 373 | 37.966 | 41.935 | 16.040 | 1.00 | 30.80 |
| ATOM | 1313 | CB  | LYS | 373 | 36.864 | 41.927 | 14.975 | 1.00 | 32.75 |
| ATOM | 1314 | CG  | LYS | 373 | 37.131 | 42.879 | 13.817 | 1.00 | 38.26 |
| ATOM | 1315 | CD  | LYS | 373 | 38.427 | 42.514 | 13.101 | 1.00 | 42.40 |
| ATOM | 1316 | CE  | LYS | 373 | 38.993 | 43.676 | 12.295 | 1.00 | 43.70 |
| ATOM | 1317 | NZ  | LYS | 373 | 40.324 | 43.301 | 11.729 | 1.00 | 45.18 |
| ATOM | 1318 | C   | LYS | 373 | 37.362 | 42.209 | 17.422 | 1.00 | 30.08 |
| ATOM | 1319 | O   | LYS | 373 | 37.301 | 43.359 | 17.850 | 1.00 | 31.06 |
| ATOM | 1320 | N   | CYS | 374 | 36.923 | 41.157 | 18.114 | 1.00 | 28.22 |
| ATOM | 1321 | CA  | CYS | 374 | 36.334 | 41.310 | 19.438 | 1.00 | 26.08 |
| ATOM | 1322 | CB  | CYS | 374 | 35.800 | 39.970 | 19.964 | 1.00 | 23.42 |
| ATOM | 1323 | SG  | CYS | 374 | 34.336 | 39.310 | 19.100 | 1.00 | 23.17 |
| ATOM | 1324 | C   | CYS | 374 | 37.402 | 41.851 | 20.375 | 1.00 | 27.53 |
| ATOM | 1325 | O   | CYS | 374 | 37.162 | 42.805 | 21.110 | 1.00 | 25.72 |
| ATOM | 1326 | N   | ASP | 375 | 38.588 | 41.239 | 20.322 | 1.00 | 29.96 |
| ATOM | 1327 | CA  | ASP | 375 | 39.735 | 41.633 | 21.149 | 1.00 | 31.23 |
| ATOM | 1328 | CB  | ASP | 375 | 40.945 | 40.738 | 20.860 | 1.00 | 30.10 |
| ATOM | 1329 | CG  | ASP | 375 | 40.737 | 39.312 | 21.296 | 1.00 | 29.63 |

FIGURE 1 (cont.)

| ATOM | 1330 | OD1 | ASP | 375 | 39.996 | 39.076 | 22.274 | 1.00 | 28.42 |
|---|---|---|---|---|---|---|---|---|---|
| ATOM | 1331 | OD2 | ASP | 375 | 41.332 | 38.423 | 20.657 | 1.00 | 30.89 |
| ATOM | 1332 | C | ASP | 375 | 40.135 | 43.069 | 20.861 | 1.00 | 31.74 |
| ATOM | 1333 | O | ASP | 375 | 40.304 | 43.872 | 21.783 | 1.00 | 33.16 |
| ATOM | 1334 | N | GLU | 376 | 40.301 | 43.371 | 19.577 | 1.00 | 31.73 |
| ATOM | 1335 | CA | GLU | 376 | 40.686 | 44.701 | 19.127 | 1.00 | 33.34 |
| ATOM | 1336 | CB | GLU | 376 | 40.848 | 44.715 | 17.603 | 1.00 | 34.63 |
| ATOM | 1337 | CG | GLU | 376 | 41.791 | 43.621 | 17.095 | 1.00 | 38.95 |
| ATOM | 1338 | CD | GLU | 376 | 42.234 | 43.797 | 15.646 | 1.00 | 40.85 |
| ATOM | 1339 | OE1 | GLU | 376 | 41.453 | 44.311 | 14.813 | 1.00 | 42.74 |
| ATOM | 1340 | OE2 | GLU | 376 | 43.380 | 43.401 | 15.340 | 1.00 | 42.32 |
| ATOM | 1341 | C | GLU | 376 | 39.696 | 45.776 | 19.581 | 1.00 | 32.36 |
| ATOM | 1342 | O | GLU | 376 | 40.099 | 46.831 | 20.067 | 1.00 | 32.77 |
| ATOM | 1343 | N | LEU | 377 | 38.404 | 45.493 | 19.464 | 1.00 | 31.01 |
| ATOM | 1344 | CA | LEU | 377 | 37.398 | 46.456 | 19.871 | 1.00 | 29.80 |
| ATOM | 1345 | CB | LEU | 377 | 36.014 | 46.042 | 19.375 | 1.00 | 27.58 |
| ATOM | 1346 | CG | LEU | 377 | 34.886 | 47.037 | 19.646 | 1.00 | 25.16 |
| ATOM | 1347 | CD1 | LEU | 377 | 35.306 | 48.433 | 19.220 | 1.00 | 26.04 |
| ATOM | 1348 | CD2 | LEU | 377 | 33.635 | 46.611 | 18.901 | 1.00 | 24.83 |
| ATOM | 1349 | C | LEU | 377 | 37.408 | 46.603 | 21.384 | 1.00 | 31.08 |
| ATOM | 1350 | O | LEU | 377 | 37.488 | 47.713 | 21.908 | 1.00 | 32.49 |
| ATOM | 1351 | N | ALA | 378 | 37.362 | 45.481 | 22.089 | 1.00 | 31.01 |
| ATOM | 1352 | CA | ALA | 378 | 37.372 | 45.516 | 23.541 | 1.00 | 31.90 |
| ATOM | 1353 | CB | ALA | 378 | 37.518 | 44.102 | 24.109 | 1.00 | 30.31 |
| ATOM | 1354 | C | ALA | 378 | 38.532 | 46.398 | 23.990 | 1.00 | 33.00 |
| ATOM | 1355 | O | ALA | 378 | 38.350 | 47.303 | 24.800 | 1.00 | 32.23 |
| ATOM | 1356 | N | ALA | 379 | 39.703 | 46.171 | 23.399 | 1.00 | 34.63 |
| ATOM | 1357 | CA | ALA | 379 | 40.906 | 46.931 | 23.725 | 1.00 | 36.26 |
| ATOM | 1358 | CB | ALA | 379 | 42.087 | 46.423 | 22.915 | 1.00 | 36.36 |
| ATOM | 1359 | C | ALA | 379 | 40.690 | 48.416 | 23.471 | 1.00 | 37.24 |
| ATOM | 1360 | O | ALA | 379 | 40.968 | 49.243 | 24.339 | 1.00 | 38.17 |
| ATOM | 1361 | N | LYS | 380 | 40.146 | 48.741 | 22.303 | 1.00 | 38.24 |
| ATOM | 1362 | CA | LYS | 380 | 39.880 | 50.125 | 21.935 | 1.00 | 39.63 |
| ATOM | 1363 | CB | LYS | 380 | 39.184 | 50.196 | 20.565 | 1.00 | 39.82 |
| ATOM | 1364 | CG | LYS | 380 | 39.223 | 51.577 | 19.904 | 1.00 | 40.69 |
| ATOM | 1365 | CD | LYS | 380 | 38.828 | 51.510 | 18.434 | 1.00 | 40.39 |
| ATOM | 1366 | CE | LYS | 380 | 39.265 | 52.757 | 17.654 | 1.00 | 41.28 |
| ATOM | 1367 | NZ | LYS | 380 | 38.608 | 54.040 | 18.063 | 1.00 | 40.83 |
| ATOM | 1368 | C | LYS | 380 | 39.005 | 50.782 | 22.997 | 1.00 | 40.87 |
| ATOM | 1369 | O | LYS | 380 | 39.405 | 51.768 | 23.619 | 1.00 | 42.50 |
| ATOM | 1370 | N | LEU | 381 | 37.843 | 50.187 | 23.250 | 1.00 | 40.55 |
| ATOM | 1371 | CA | LEU | 381 | 36.891 | 50.711 | 24.226 | 1.00 | 40.18 |
| ATOM | 1372 | CB | LEU | 381 | 35.632 | 49.842 | 24.243 | 1.00 | 38.99 |
| ATOM | 1373 | CG | LEU | 381 | 34.870 | 49.610 | 22.940 | 1.00 | 37.56 |
| ATOM | 1374 | CD1 | LEU | 381 | 33.654 | 48.758 | 23.223 | 1.00 | 35.03 |
| ATOM | 1375 | CD2 | LEU | 381 | 34.464 | 50.938 | 22.331 | 1.00 | 38.01 |
| ATOM | 1376 | C | LEU | 381 | 37.458 | 50.801 | 25.642 | 1.00 | 40.57 |
| ATOM | 1377 | O | LEU | 381 | 37.302 | 51.822 | 26.323 | 1.00 | 39.48 |
| ATOM | 1378 | N | VAL | 382 | 38.096 | 49.721 | 26.083 | 1.00 | 42.00 |
| ATOM | 1379 | CA | VAL | 382 | 38.681 | 49.650 | 27.419 | 1.00 | 42.99 |
| ATOM | 1380 | CB | VAL | 382 | 39.322 | 48.252 | 27.692 | 1.00 | 42.81 |
| ATOM | 1381 | CG1 | VAL | 382 | 40.811 | 48.255 | 27.390 | 1.00 | 42.57 |
| ATOM | 1382 | CG2 | VAL | 382 | 39.040 | 47.810 | 29.113 | 1.00 | 40.95 |
| ATOM | 1383 | C | VAL | 382 | 39.699 | 50.775 | 27.575 | 1.00 | 44.23 |
| ATOM | 1384 | O | VAL | 382 | 39.878 | 51.315 | 28.670 | 1.00 | 45.11 |
| ATOM | 1385 | N | ALA | 383 | 40.322 | 51.158 | 26.462 | 1.00 | 44.34 |
| ATOM | 1386 | CA | ALA | 383 | 41.293 | 52.244 | 26.468 | 1.00 | 44.39 |
| ATOM | 1387 | CB | ALA | 383 | 42.115 | 52.238 | 25.181 | 1.00 | 44.85 |

FIGURE 1 (cont.)

| ATOM | 1388 | C   | ALA | 383 | 40.556 | 53.574 | 26.626 | 1.00 | 43.71 |
|------|------|-----|-----|-----|--------|--------|--------|------|-------|
| ATOM | 1389 | O   | ALA | 383 | 41.035 | 54.481 | 27.312 | 1.00 | 46.22 |
| ATOM | 1390 | N   | LEU | 384 | 39.378 | 53.679 | 26.018 | 1.00 | 40.83 |
| ATOM | 1391 | CA  | LEU | 384 | 38.578 | 54.895 | 26.099 | 1.00 | 38.30 |
| ATOM | 1392 | CB  | LEU | 384 | 37.633 | 54.988 | 24.899 | 1.00 | 39.47 |
| ATOM | 1393 | CG  | LEU | 384 | 38.227 | 54.865 | 23.491 | 1.00 | 41.58 |
| ATOM | 1394 | CD1 | LEU | 384 | 37.102 | 54.745 | 22.468 | 1.00 | 42.20 |
| ATOM | 1395 | CD2 | LEU | 384 | 39.130 | 56.052 | 23.168 | 1.00 | 42.42 |
| ATOM | 1396 | C   | LEU | 384 | 37.771 | 54.952 | 27.404 | 1.00 | 36.79 |
| ATOM | 1397 | O   | LEU | 384 | 36.787 | 55.688 | 27.505 | 1.00 | 36.24 |
| ATOM | 1398 | N   | GLY | 385 | 38.164 | 54.147 | 28.385 | 1.00 | 35.50 |
| ATOM | 1399 | CA  | GLY | 385 | 37.475 | 54.145 | 29.664 | 1.00 | 33.80 |
| ATOM | 1400 | C   | GLY | 385 | 36.171 | 53.364 | 29.713 | 1.00 | 33.33 |
| ATOM | 1401 | O   | GLY | 385 | 35.474 | 53.391 | 30.728 | 1.00 | 34.28 |
| ATOM | 1402 | N   | ILE | 386 | 35.825 | 52.668 | 28.633 | 1.00 | 31.60 |
| ATOM | 1403 | CA  | ILE | 386 | 34.590 | 51.890 | 28.604 | 1.00 | 28.68 |
| ATOM | 1404 | CB  | ILE | 386 | 34.121 | 51.649 | 27.152 | 1.00 | 27.72 |
| ATOM | 1405 | CG2 | ILE | 386 | 32.933 | 50.698 | 27.124 | 1.00 | 28.20 |
| ATOM | 1406 | CG1 | ILE | 386 | 33.749 | 52.967 | 26.486 | 1.00 | 25.89 |
| ATOM | 1407 | CD1 | ILE | 386 | 32.566 | 53.650 | 27.126 | 1.00 | 27.25 |
| ATOM | 1408 | C   | ILE | 386 | 34.810 | 50.535 | 29.282 | 1.00 | 28.13 |
| ATOM | 1409 | O   | ILE | 386 | 35.838 | 49.890 | 29.061 | 1.00 | 26.54 |
| ATOM | 1410 | N   | ASN | 387 | 33.844 | 50.098 | 30.092 | 1.00 | 27.35 |
| ATOM | 1411 | CA  | ASN | 387 | 33.944 | 48.800 | 30.771 | 1.00 | 26.98 |
| ATOM | 1412 | CB  | ASN | 387 | 33.020 | 48.745 | 31.997 | 1.00 | 26.31 |
| ATOM | 1413 | CG  | ASN | 387 | 33.080 | 47.404 | 32.715 | 1.00 | 26.76 |
| ATOM | 1414 | OD1 | ASN | 387 | 34.130 | 46.749 | 32.741 | 1.00 | 27.49 |
| ATOM | 1415 | ND2 | ASN | 387 | 31.960 | 46.993 | 33.306 | 1.00 | 23.98 |
| ATOM | 1416 | C   | ASN | 387 | 33.579 | 47.697 | 29.780 | 1.00 | 25.60 |
| ATOM | 1417 | O   | ASN | 387 | 32.509 | 47.090 | 29.867 | 1.00 | 25.99 |
| ATOM | 1418 | N   | ALA | 388 | 34.465 | 47.470 | 28.817 | 1.00 | 24.50 |
| ATOM | 1419 | CA  | ALA | 388 | 34.241 | 46.474 | 27.780 | 1.00 | 24.38 |
| ATOM | 1420 | CB  | ALA | 388 | 34.692 | 47.012 | 26.430 | 1.00 | 20.14 |
| ATOM | 1421 | C   | ALA | 388 | 34.945 | 45.167 | 28.088 | 1.00 | 24.87 |
| ATOM | 1422 | O   | ALA | 388 | 36.080 | 45.156 | 28.559 | 1.00 | 27.09 |
| ATOM | 1423 | N   | VAL | 389 | 34.269 | 44.059 | 27.829 | 1.00 | 25.51 |
| ATOM | 1424 | CA  | VAL | 389 | 34.842 | 42.750 | 28.076 | 1.00 | 25.75 |
| ATOM | 1425 | CB  | VAL | 389 | 34.277 | 42.094 | 29.368 | 1.00 | 27.61 |
| ATOM | 1426 | CG1 | VAL | 389 | 34.659 | 42.918 | 30.586 | 1.00 | 27.58 |
| ATOM | 1427 | CG2 | VAL | 389 | 32.772 | 41.946 | 29.293 | 1.00 | 30.47 |
| ATOM | 1428 | C   | VAL | 389 | 34.540 | 41.896 | 26.873 | 1.00 | 24.33 |
| ATOM | 1429 | O   | VAL | 389 | 33.464 | 41.989 | 26.300 | 1.00 | 24.05 |
| ATOM | 1430 | N   | ALA | 390 | 35.520 | 41.119 | 26.444 | 1.00 | 25.42 |
| ATOM | 1431 | CA  | ALA | 390 | 35.345 | 40.253 | 25.285 | 1.00 | 26.04 |
| ATOM | 1432 | CB  | ALA | 390 | 36.674 | 40.083 | 24.531 | 1.00 | 23.07 |
| ATOM | 1433 | C   | ALA | 390 | 34.794 | 38.888 | 25.667 | 1.00 | 26.03 |
| ATOM | 1434 | O   | ALA | 390 | 34.959 | 38.416 | 26.799 | 1.00 | 25.70 |
| ATOM | 1435 | N   | TYR | 391 | 34.076 | 38.286 | 24.732 | 1.00 | 26.60 |
| ATOM | 1436 | CA  | TYR | 391 | 33.565 | 36.952 | 24.940 | 1.00 | 26.52 |
| ATOM | 1437 | CB  | TYR | 391 | 32.235 | 36.903 | 25.691 | 1.00 | 25.87 |
| ATOM | 1438 | CG  | TYR | 391 | 31.857 | 35.459 | 25.965 | 1.00 | 27.47 |
| ATOM | 1439 | CD1 | TYR | 391 | 32.555 | 34.713 | 26.915 | 1.00 | 28.87 |
| ATOM | 1440 | CE1 | TYR | 391 | 32.306 | 33.360 | 27.087 | 1.00 | 29.43 |
| ATOM | 1441 | CD2 | TYR | 391 | 30.886 | 34.802 | 25.199 | 1.00 | 27.70 |
| ATOM | 1442 | CE2 | TYR | 391 | 30.630 | 33.446 | 25.368 | 1.00 | 26.82 |
| ATOM | 1443 | CZ  | TYR | 391 | 31.344 | 32.737 | 26.312 | 1.00 | 28.58 |
| ATOM | 1444 | OH  | TYR | 391 | 31.097 | 31.405 | 26.511 | 1.00 | 30.59 |
| ATOM | 1445 | C   | TYR | 391 | 33.422 | 36.195 | 23.645 | 1.00 | 26.74 |

FIGURE 1 (cont.)

| ATOM | 1446 | O   | TYR | 391 | 32.853 | 36.685 | 22.675 | 1.00 | 25.62 |
|------|------|-----|-----|-----|--------|--------|--------|------|-------|
| ATOM | 1447 | N   | TYR | 392 | 33.981 | 34.997 | 23.646 | 1.00 | 28.03 |
| ATOM | 1448 | CA  | TYR | 392 | 33.906 | 34.095 | 22.522 | 1.00 | 30.93 |
| ATOM | 1449 | CB  | TYR | 392 | 34.803 | 34.551 | 21.377 | 1.00 | 31.00 |
| ATOM | 1450 | CG  | TYR | 392 | 36.167 | 35.043 | 21.778 | 1.00 | 30.91 |
| ATOM | 1451 | CD1 | TYR | 392 | 37.158 | 34.157 | 22.202 | 1.00 | 30.94 |
| ATOM | 1452 | CE1 | TYR | 392 | 38.436 | 34.609 | 22.509 | 1.00 | 29.59 |
| ATOM | 1453 | CD2 | TYR | 392 | 36.492 | 36.394 | 21.678 | 1.00 | 29.43 |
| ATOM | 1454 | CE2 | TYR | 392 | 37.757 | 36.846 | 21.982 | 1.00 | 29.05 |
| ATOM | 1455 | CZ  | TYR | 392 | 38.720 | 35.949 | 22.396 | 1.00 | 27.90 |
| ATOM | 1456 | OH  | TYR | 392 | 39.964 | 36.401 | 22.718 | 1.00 | 29.68 |
| ATOM | 1457 | C   | TYR | 392 | 34.262 | 32.706 | 23.026 | 1.00 | 33.17 |
| ATOM | 1458 | O   | TYR | 392 | 34.577 | 32.547 | 24.204 | 1.00 | 33.99 |
| ATOM | 1459 | N   | ARG | 393 | 34.163 | 31.706 | 22.154 | 1.00 | 35.69 |
| ATOM | 1460 | CA  | ARG | 393 | 34.450 | 30.324 | 22.528 | 1.00 | 36.12 |
| ATOM | 1461 | CB  | ARG | 393 | 34.221 | 29.383 | 21.344 | 1.00 | 40.66 |
| ATOM | 1462 | CG  | ARG | 393 | 34.624 | 27.931 | 21.595 | 1.00 | 45.96 |
| ATOM | 1463 | CD  | ARG | 393 | 34.246 | 27.040 | 20.406 | 1.00 | 50.06 |
| ATOM | 1464 | NE  | ARG | 393 | 32.903 | 26.481 | 20.602 | 1.00 | 53.83 |
| ATOM | 1465 | CZ  | ARG | 393 | 32.668 | 25.370 | 21.300 | 1.00 | 55.97 |
| ATOM | 1466 | NH1 | ARG | 393 | 31.415 | 24.957 | 21.475 | 1.00 | 57.63 |
| ATOM | 1467 | NH2 | ARG | 393 | 33.682 | 24.619 | 21.738 | 1.00 | 57.66 |
| ATOM | 1468 | C   | ARG | 393 | 35.862 | 30.178 | 23.071 | 1.00 | 34.84 |
| ATOM | 1469 | O   | ARG | 393 | 36.833 | 30.615 | 22.448 | 1.00 | 33.70 |
| ATOM | 1470 | N   | GLY | 394 | 35.946 | 29.572 | 24.253 | 1.00 | 33.32 |
| ATOM | 1471 | CA  | GLY | 394 | 37.211 | 29.374 | 24.929 | 1.00 | 32.50 |
| ATOM | 1472 | C   | GLY | 394 | 37.360 | 30.280 | 26.141 | 1.00 | 31.93 |
| ATOM | 1473 | O   | GLY | 394 | 38.203 | 30.031 | 27.005 | 1.00 | 33.23 |
| ATOM | 1474 | N   | LEU | 395 | 36.552 | 31.336 | 26.205 | 1.00 | 30.71 |
| ATOM | 1475 | CA  | LEU | 395 | 36.601 | 32.281 | 27.317 | 1.00 | 29.49 |
| ATOM | 1476 | CB  | LEU | 395 | 36.238 | 33.695 | 26.869 | 1.00 | 26.83 |
| ATOM | 1477 | CG  | LEU | 395 | 37.160 | 34.324 | 25.830 | 1.00 | 25.83 |
| ATOM | 1478 | CD1 | LEU | 395 | 37.126 | 35.822 | 26.000 | 1.00 | 25.35 |
| ATOM | 1479 | CD2 | LEU | 395 | 38.586 | 33.824 | 25.988 | 1.00 | 25.20 |
| ATOM | 1480 | C   | LEU | 395 | 35.712 | 31.868 | 28.470 | 1.00 | 29.64 |
| ATOM | 1481 | O   | LEU | 395 | 35.046 | 30.833 | 28.415 | 1.00 | 30.33 |
| ATOM | 1482 | N   | ASP | 396 | 35.700 | 32.691 | 29.510 | 1.00 | 30.84 |
| ATOM | 1483 | CA  | ASP | 396 | 34.912 | 32.411 | 30.697 | 1.00 | 32.76 |
| ATOM | 1484 | CB  | ASP | 396 | 35.813 | 32.527 | 31.936 | 1.00 | 33.42 |
| ATOM | 1485 | CG  | ASP | 396 | 35.194 | 31.932 | 33.187 | 1.00 | 32.63 |
| ATOM | 1486 | OD1 | ASP | 396 | 33.996 | 31.567 | 33.191 | 1.00 | 32.81 |
| ATOM | 1487 | OD2 | ASP | 396 | 35.932 | 31.823 | 34.180 | 1.00 | 34.06 |
| ATOM | 1488 | C   | ASP | 396 | 33.731 | 33.376 | 30.790 | 1.00 | 33.30 |
| ATOM | 1489 | O   | ASP | 396 | 33.900 | 34.569 | 31.070 | 1.00 | 33.42 |
| ATOM | 1490 | N   | VAL | 397 | 32.529 | 32.842 | 30.605 | 1.00 | 33.00 |
| ATOM | 1491 | CA  | VAL | 397 | 31.327 | 33.658 | 30.650 | 1.00 | 33.17 |
| ATOM | 1492 | CB  | VAL | 397 | 30.145 | 32.937 | 29.985 | 1.00 | 34.45 |
| ATOM | 1493 | CG1 | VAL | 397 | 29.618 | 31.827 | 30.898 | 1.00 | 34.59 |
| ATOM | 1494 | CG2 | VAL | 397 | 29.052 | 33.945 | 29.604 | 1.00 | 33.81 |
| ATOM | 1495 | C   | VAL | 397 | 30.913 | 34.130 | 32.047 | 1.00 | 32.83 |
| ATOM | 1496 | O   | VAL | 397 | 30.157 | 35.099 | 32.176 | 1.00 | 33.92 |
| ATOM | 1497 | N   | SER | 398 | 31.419 | 33.478 | 33.089 | 1.00 | 31.28 |
| ATOM | 1498 | CA  | SER | 398 | 31.060 | 33.865 | 34.445 | 1.00 | 30.65 |
| ATOM | 1499 | CB  | SER | 398 | 31.390 | 32.741 | 35.424 | 1.00 | 31.52 |
| ATOM | 1500 | OG  | SER | 398 | 32.755 | 32.370 | 35.345 | 1.00 | 33.10 |
| ATOM | 1501 | C   | SER | 398 | 31.714 | 35.166 | 34.910 | 1.00 | 30.89 |
| ATOM | 1502 | O   | SER | 398 | 31.368 | 35.702 | 35.966 | 1.00 | 31.87 |
| ATOM | 1503 | N   | VAL | 399 | 32.668 | 35.673 | 34.140 | 1.00 | 30.49 |

FIGURE 1 (cont.)

| | | | | | | | | | |
|---|---|---|---|---|---|---|---|---|---|
| ATOM | 1504 | CA | VAL | 399 | 33.326 | 36.907 | 34.529 | 1.00 | 29.65 |
| ATOM | 1505 | CB | VAL | 399 | 34.793 | 36.976 | 34.008 | 1.00 | 29.94 |
| ATOM | 1506 | CG1 | VAL | 399 | 35.501 | 35.636 | 34.242 | 1.00 | 29.09 |
| ATOM | 1507 | CG2 | VAL | 399 | 34.841 | 37.372 | 32.552 | 1.00 | 29.84 |
| ATOM | 1508 | C | VAL | 399 | 32.512 | 38.122 | 34.076 | 1.00 | 29.51 |
| ATOM | 1509 | O | VAL | 399 | 32.753 | 39.245 | 34.530 | 1.00 | 30.22 |
| ATOM | 1510 | N | ILE | 400 | 31.534 | 37.889 | 33.202 | 1.00 | 27.63 |
| ATOM | 1511 | CA | ILE | 400 | 30.682 | 38.961 | 32.695 | 1.00 | 26.65 |
| ATOM | 1512 | CB | ILE | 400 | 29.877 | 38.489 | 31.457 | 1.00 | 26.73 |
| ATOM | 1513 | CG2 | ILE | 400 | 29.017 | 39.627 | 30.912 | 1.00 | 24.30 |
| ATOM | 1514 | CG1 | ILE | 400 | 30.836 | 37.966 | 30.381 | 1.00 | 27.93 |
| ATOM | 1515 | CD1 | ILE | 400 | 30.161 | 37.431 | 29.132 | 1.00 | 27.24 |
| ATOM | 1516 | C | ILE | 400 | 29.717 | 39.357 | 33.808 | 1.00 | 26.54 |
| ATOM | 1517 | O | ILE | 400 | 28.987 | 38.521 | 34.320 | 1.00 | 25.84 |
| ATOM | 1518 | N | PRO | 401 | 29.720 | 40.637 | 34.213 | 1.00 | 27.05 |
| ATOM | 1519 | CD | PRO | 401 | 30.441 | 41.786 | 33.632 | 1.00 | 26.21 |
| ATOM | 1520 | CA | PRO | 401 | 28.816 | 41.069 | 35.281 | 1.00 | 27.20 |
| ATOM | 1521 | CB | PRO | 401 | 29.191 | 42.537 | 35.469 | 1.00 | 26.22 |
| ATOM | 1522 | CG | PRO | 401 | 29.597 | 42.959 | 34.085 | 1.00 | 25.90 |
| ATOM | 1523 | C | PRO | 401 | 27.339 | 40.903 | 34.906 | 1.00 | 29.40 |
| ATOM | 1524 | O | PRO | 401 | 26.945 | 41.134 | 33.773 | 1.00 | 29.57 |
| ATOM | 1525 | N | THR | 402 | 26.551 | 40.447 | 35.871 | 1.00 | 30.54 |
| ATOM | 1526 | CA | THR | 402 | 25.123 | 40.231 | 35.727 | 1.00 | 30.29 |
| ATOM | 1527 | CB | THR | 402 | 24.663 | 39.255 | 36.825 | 1.00 | 31.76 |
| ATOM | 1528 | OG1 | THR | 402 | 25.063 | 37.929 | 36.462 | 1.00 | 35.36 |
| ATOM | 1529 | CG2 | THR | 402 | 23.168 | 39.308 | 37.059 | 1.00 | 34.23 |
| ATOM | 1530 | C | THR | 402 | 24.373 | 41.557 | 35.835 | 1.00 | 29.90 |
| ATOM | 1531 | O | THR | 402 | 23.246 | 41.695 | 35.357 | 1.00 | 29.95 |
| ATOM | 1532 | N | SER | 403 | 24.997 | 42.532 | 36.474 | 1.00 | 29.98 |
| ATOM | 1533 | CA | SER | 403 | 24.385 | 43.839 | 36.624 | 1.00 | 30.57 |
| ATOM | 1534 | CB | SER | 403 | 23.655 | 43.927 | 37.961 | 1.00 | 30.45 |
| ATOM | 1535 | OG | SER | 403 | 24.372 | 43.219 | 38.954 | 1.00 | 34.50 |
| ATOM | 1536 | C | SER | 403 | 25.451 | 44.917 | 36.499 | 1.00 | 30.16 |
| ATOM | 1537 | O | SER | 403 | 26.650 | 44.628 | 36.581 | 1.00 | 30.53 |
| ATOM | 1538 | N | GLY | 404 | 25.008 | 46.146 | 36.265 | 1.00 | 29.14 |
| ATOM | 1539 | CA | GLY | 404 | 25.924 | 47.257 | 36.119 | 1.00 | 27.59 |
| ATOM | 1540 | C | GLY | 404 | 26.336 | 47.472 | 34.675 | 1.00 | 26.53 |
| ATOM | 1541 | O | GLY | 404 | 26.237 | 46.563 | 33.852 | 1.00 | 26.16 |
| ATOM | 1542 | N | ASP | 405 | 26.796 | 48.685 | 34.381 | 1.00 | 25.54 |
| ATOM | 1543 | CA | ASP | 405 | 27.241 | 49.067 | 33.049 | 1.00 | 23.74 |
| ATOM | 1544 | CB | ASP | 405 | 27.837 | 50.468 | 33.062 | 1.00 | 23.03 |
| ATOM | 1545 | CG | ASP | 405 | 26.838 | 51.530 | 33.392 | 1.00 | 24.18 |
| ATOM | 1546 | OD1 | ASP | 405 | 25.636 | 51.217 | 33.568 | 1.00 | 22.99 |
| ATOM | 1547 | OD2 | ASP | 405 | 27.277 | 52.698 | 33.480 | 1.00 | 24.90 |
| ATOM | 1548 | C | ASP | 405 | 28.324 | 48.156 | 32.543 | 1.00 | 23.67 |
| ATOM | 1549 | O | ASP | 405 | 29.292 | 47.873 | 33.259 | 1.00 | 25.75 |
| ATOM | 1550 | N | VAL | 406 | 28.211 | 47.774 | 31.279 | 1.00 | 23.25 |
| ATOM | 1551 | CA | VAL | 406 | 29.210 | 46.926 | 30.656 | 1.00 | 22.78 |
| ATOM | 1552 | CB | VAL | 406 | 29.259 | 45.506 | 31.291 | 1.00 | 23.65 |
| ATOM | 1553 | CG1 | VAL | 406 | 27.978 | 44.730 | 30.983 | 1.00 | 25.24 |
| ATOM | 1554 | CG2 | VAL | 406 | 30.505 | 44.741 | 30.809 | 1.00 | 23.18 |
| ATOM | 1555 | C | VAL | 406 | 28.916 | 46.807 | 29.181 | 1.00 | 21.61 |
| ATOM | 1556 | O | VAL | 406 | 27.767 | 46.920 | 28.760 | 1.00 | 23.02 |
| ATOM | 1557 | N | VAL | 407 | 29.973 | 46.672 | 28.392 | 1.00 | 20.28 |
| ATOM | 1558 | CA | VAL | 407 | 29.842 | 46.490 | 26.960 | 1.00 | 17.52 |
| ATOM | 1559 | CB | VAL | 407 | 30.487 | 47.639 | 26.159 | 1.00 | 15.18 |
| ATOM | 1560 | CG1 | VAL | 407 | 30.314 | 47.406 | 24.675 | 1.00 | 11.58 |
| ATOM | 1561 | CG2 | VAL | 407 | 29.852 | 48.966 | 26.549 | 1.00 | 15.21 |

FIGURE 1 (cont.)

| ATOM | 1562 | C   | VAL | 407 | 30.548 | 45.178 | 26.659 | 1.00 | 17.42 |
|------|------|-----|-----|-----|--------|--------|--------|------|-------|
| ATOM | 1563 | O   | VAL | 407 | 31.753 | 45.060 | 26.806 | 1.00 | 18.03 |
| ATOM | 1564 | N   | VAL | 408 | 29.773 | 44.155 | 26.351 | 1.00 | 17.67 |
| ATOM | 1565 | CA  | VAL | 408 | 30.340 | 42.868 | 26.025 | 1.00 | 18.23 |
| ATOM | 1566 | CB  | VAL | 408 | 29.371 | 41.733 | 26.449 | 1.00 | 19.02 |
| ATOM | 1567 | CG1 | VAL | 408 | 29.885 | 40.373 | 26.012 | 1.00 | 18.33 |
| ATOM | 1568 | CG2 | VAL | 408 | 29.178 | 41.757 | 27.947 | 1.00 | 17.66 |
| ATOM | 1569 | C   | VAL | 408 | 30.572 | 42.860 | 24.509 | 1.00 | 18.78 |
| ATOM | 1570 | O   | VAL | 408 | 29.686 | 43.231 | 23.742 | 1.00 | 18.45 |
| ATOM | 1571 | N   | VAL | 409 | 31.800 | 42.568 | 24.093 | 1.00 | 17.88 |
| ATOM | 1572 | CA  | VAL | 409 | 32.137 | 42.483 | 22.679 | 1.00 | 17.88 |
| ATOM | 1573 | CB  | VAL | 409 | 33.418 | 43.249 | 22.359 | 1.00 | 17.72 |
| ATOM | 1574 | CG1 | VAL | 409 | 33.718 | 43.135 | 20.884 | 1.00 | 19.24 |
| ATOM | 1575 | CG2 | VAL | 409 | 33.264 | 44.719 | 22.749 | 1.00 | 17.08 |
| ATOM | 1576 | C   | VAL | 409 | 32.308 | 40.978 | 22.435 | 1.00 | 18.24 |
| ATOM | 1577 | O   | VAL | 409 | 33.267 | 40.360 | 22.909 | 1.00 | 16.84 |
| ATOM | 1578 | N   | ALA | 410 | 31.392 | 40.397 | 21.668 | 1.00 | 18.77 |
| ATOM | 1579 | CA  | ALA | 410 | 31.400 | 38.958 | 21.473 | 1.00 | 18.14 |
| ATOM | 1580 | CB  | ALA | 410 | 30.431 | 38.351 | 22.486 | 1.00 | 18.34 |
| ATOM | 1581 | C   | ALA | 410 | 31.054 | 38.426 | 20.089 | 1.00 | 17.88 |
| ATOM | 1582 | O   | ALA | 410 | 30.686 | 39.176 | 19.181 | 1.00 | 18.45 |
| ATOM | 1583 | N   | THR | 411 | 31.194 | 37.109 | 19.950 | 1.00 | 16.99 |
| ATOM | 1584 | CA  | THR | 411 | 30.827 | 36.404 | 18.738 | 1.00 | 17.24 |
| ATOM | 1585 | CB  | THR | 411 | 31.821 | 35.299 | 18.361 | 1.00 | 16.51 |
| ATOM | 1586 | OG1 | THR | 411 | 31.863 | 34.331 | 19.409 | 1.00 | 18.59 |
| ATOM | 1587 | CG2 | THR | 411 | 33.204 | 35.852 | 18.101 | 1.00 | 18.00 |
| ATOM | 1588 | C   | THR | 411 | 29.504 | 35.711 | 19.103 | 1.00 | 19.33 |
| ATOM | 1589 | O   | THR | 411 | 28.972 | 35.889 | 20.204 | 1.00 | 20.25 |
| ATOM | 1590 | N   | ASP | 412 | 29.016 | 34.851 | 18.221 | 1.00 | 21.45 |
| ATOM | 1591 | CA  | ASP | 412 | 27.768 | 34.145 | 18.473 | 1.00 | 22.15 |
| ATOM | 1592 | CB  | ASP | 412 | 27.239 | 33.567 | 17.166 | 1.00 | 19.65 |
| ATOM | 1593 | CG  | ASP | 412 | 26.783 | 34.635 | 16.221 | 1.00 | 15.73 |
| ATOM | 1594 | OD1 | ASP | 412 | 26.071 | 35.534 | 16.684 | 1.00 | 16.40 |
| ATOM | 1595 | OD2 | ASP | 412 | 27.137 | 34.591 | 15.031 | 1.00 | 16.44 |
| ATOM | 1596 | C   | ASP | 412 | 27.868 | 33.064 | 19.549 | 1.00 | 24.32 |
| ATOM | 1597 | O   | ASP | 412 | 26.888 | 32.380 | 19.848 | 1.00 | 23.10 |
| ATOM | 1598 | N   | ALA | 413 | 29.055 | 32.920 | 20.125 | 1.00 | 28.20 |
| ATOM | 1599 | CA  | ALA | 413 | 29.284 | 31.937 | 21.168 | 1.00 | 31.95 |
| ATOM | 1600 | CB  | ALA | 413 | 30.724 | 31.974 | 21.611 | 1.00 | 31.34 |
| ATOM | 1601 | C   | ALA | 413 | 28.371 | 32.172 | 22.360 | 1.00 | 35.40 |
| ATOM | 1602 | O   | ALA | 413 | 27.812 | 31.222 | 22.905 | 1.00 | 38.88 |
| ATOM | 1603 | N   | LEU | 414 | 28.207 | 33.434 | 22.755 | 1.00 | 38.48 |
| ATOM | 1604 | CA  | LEU | 414 | 27.368 | 33.772 | 23.911 | 1.00 | 40.49 |
| ATOM | 1605 | CB  | LEU | 414 | 27.411 | 35.292 | 24.203 | 1.00 | 40.58 |
| ATOM | 1606 | CG  | LEU | 414 | 26.880 | 35.779 | 25.570 | 1.00 | 39.61 |
| ATOM | 1607 | CD1 | LEU | 414 | 27.734 | 35.225 | 26.691 | 1.00 | 39.02 |
| ATOM | 1608 | CD2 | LEU | 414 | 26.855 | 37.290 | 25.652 | 1.00 | 38.26 |
| ATOM | 1609 | C   | LEU | 414 | 25.923 | 33.298 | 23.721 | 1.00 | 41.04 |
| ATOM | 1610 | O   | LEU | 414 | 25.586 | 32.246 | 24.309 | 1.00 | 41.21 |
| ATOM | 1611 | CB  | PHE | 418 | 23.962 | 34.889 | 28.719 | 1.00 | 49.92 |
| ATOM | 1612 | CG  | PHE | 418 | 24.665 | 35.936 | 29.554 | 1.00 | 49.95 |
| ATOM | 1613 | CD1 | PHE | 418 | 25.107 | 35.639 | 30.844 | 1.00 | 48.64 |
| ATOM | 1614 | CD2 | PHE | 418 | 24.847 | 37.228 | 29.063 | 1.00 | 49.25 |
| ATOM | 1615 | CE1 | PHE | 418 | 25.716 | 36.613 | 31.632 | 1.00 | 48.52 |
| ATOM | 1616 | CE2 | PHE | 418 | 25.457 | 38.212 | 29.846 | 1.00 | 49.33 |
| ATOM | 1617 | CZ  | PHE | 418 | 25.890 | 37.905 | 31.131 | 1.00 | 48.87 |
| ATOM | 1618 | C   | PHE | 418 | 21.732 | 35.511 | 29.710 | 1.00 | 48.72 |
| ATOM | 1619 | O   | PHE | 418 | 21.041 | 36.066 | 28.842 | 1.00 | 48.37 |

FIGURE 1 (cont.)

| | | | | | | | | |
|---|---|---|---|---|---|---|---|---|
| ATOM | 1620 | N   | PHE | 418 | 22.021 | 33.365 | 28.442 | 1.00 50.78 |
| ATOM | 1621 | CA  | PHE | 418 | 22.670 | 34.351 | 29.353 | 1.00 49.76 |
| ATOM | 1622 | N   | THR | 419 | 21.697 | 35.856 | 30.994 | 1.00 46.61 |
| ATOM | 1623 | CA  | THR | 419 | 20.872 | 36.956 | 31.471 | 1.00 45.71 |
| ATOM | 1624 | CB  | THR | 419 | 20.577 | 36.801 | 32.970 | 1.00 48.47 |
| ATOM | 1625 | OG1 | THR | 419 | 21.767 | 36.364 | 33.654 | 1.00 51.07 |
| ATOM | 1626 | CG2 | THR | 419 | 19.463 | 35.785 | 33.182 | 1.00 48.87 |
| ATOM | 1627 | C   | THR | 419 | 21.628 | 38.257 | 31.213 | 1.00 43.14 |
| ATOM | 1628 | O   | THR | 419 | 22.191 | 38.865 | 32.124 | 1.00 42.27 |
| ATOM | 1629 | N   | GLY | 420 | 21.651 | 38.662 | 29.950 | 1.00 41.16 |
| ATOM | 1630 | CA  | GLY | 420 | 22.362 | 39.862 | 29.568 | 1.00 37.36 |
| ATOM | 1631 | C   | GLY | 420 | 21.732 | 41.160 | 30.017 | 1.00 35.27 |
| ATOM | 1632 | O   | GLY | 420 | 22.436 | 42.091 | 30.376 | 1.00 34.05 |
| ATOM | 1633 | N   | ASP | 421 | 20.407 | 41.238 | 29.972 | 1.00 34.00 |
| ATOM | 1634 | CA  | ASP | 421 | 19.705 | 42.454 | 30.365 | 1.00 31.58 |
| ATOM | 1635 | CB  | ASP | 421 | 19.751 | 42.629 | 31.886 | 1.00 33.33 |
| ATOM | 1636 | CG  | ASP | 421 | 18.986 | 43.842 | 32.350 | 1.00 36.90 |
| ATOM | 1637 | OD1 | ASP | 421 | 17.869 | 44.063 | 31.838 | 1.00 37.58 |
| ATOM | 1638 | OD2 | ASP | 421 | 19.510 | 44.586 | 33.212 | 1.00 39.50 |
| ATOM | 1639 | C   | ASP | 421 | 20.376 | 43.626 | 29.654 | 1.00 29.23 |
| ATOM | 1640 | O   | ASP | 421 | 20.784 | 44.614 | 30.274 | 1.00 27.56 |
| ATOM | 1641 | N   | PHE | 422 | 20.510 | 43.480 | 28.340 | 1.00 27.41 |
| ATOM | 1642 | CA  | PHE | 422 | 21.148 | 44.485 | 27.495 | 1.00 25.64 |
| ATOM | 1643 | CB  | PHE | 422 | 21.792 | 43.818 | 26.269 | 1.00 21.10 |
| ATOM | 1644 | CG  | PHE | 422 | 22.973 | 42.955 | 26.601 | 1.00 17.18 |
| ATOM | 1645 | CD1 | PHE | 422 | 22.951 | 41.595 | 26.328 | 1.00 14.50 |
| ATOM | 1646 | CD2 | PHE | 422 | 24.111 | 43.504 | 27.190 | 1.00 15.37 |
| ATOM | 1647 | CE1 | PHE | 422 | 24.049 | 40.787 | 26.638 | 1.00 14.66 |
| ATOM | 1648 | CE2 | PHE | 422 | 25.214 | 42.711 | 27.503 | 1.00 14.24 |
| ATOM | 1649 | CZ  | PHE | 422 | 25.185 | 41.353 | 27.229 | 1.00 12.70 |
| ATOM | 1650 | C   | PHE | 422 | 20.236 | 45.626 | 27.044 | 1.00 24.93 |
| ATOM | 1651 | O   | PHE | 422 | 19.110 | 45.409 | 26.605 | 1.00 24.73 |
| ATOM | 1652 | N   | ASP | 423 | 20.740 | 46.846 | 27.167 | 1.00 24.37 |
| ATOM | 1653 | CA  | ASP | 423 | 20.010 | 48.033 | 26.752 | 1.00 24.05 |
| ATOM | 1654 | CB  | ASP | 423 | 20.607 | 49.285 | 27.398 | 1.00 24.07 |
| ATOM | 1655 | CG  | ASP | 423 | 20.341 | 49.339 | 28.870 | 1.00 23.88 |
| ATOM | 1656 | OD1 | ASP | 423 | 19.159 | 49.417 | 29.246 | 1.00 27.21 |
| ATOM | 1657 | OD2 | ASP | 423 | 21.294 | 49.268 | 29.658 | 1.00 24.16 |
| ATOM | 1658 | C   | ASP | 423 | 20.048 | 48.147 | 25.239 | 1.00 23.57 |
| ATOM | 1659 | O   | ASP | 423 | 19.154 | 48.747 | 24.638 | 1.00 23.30 |
| ATOM | 1660 | N   | SER | 424 | 21.086 | 47.585 | 24.626 | 1.00 21.30 |
| ATOM | 1661 | CA  | SER | 424 | 21.182 | 47.611 | 23.182 | 1.00 20.49 |
| ATOM | 1662 | CB  | SER | 424 | 21.644 | 48.981 | 22.691 | 1.00 21.66 |
| ATOM | 1663 | OG  | SER | 424 | 23.054 | 49.075 | 22.716 | 1.00 22.36 |
| ATOM | 1664 | C   | SER | 424 | 22.110 | 46.538 | 22.633 | 1.00 20.13 |
| ATOM | 1665 | O   | SER | 424 | 22.919 | 45.950 | 23.369 | 1.00 18.98 |
| ATOM | 1666 | N   | VAL | 425 | 21.940 | 46.272 | 21.339 | 1.00 18.97 |
| ATOM | 1667 | CA  | VAL | 425 | 22.751 | 45.319 | 20.588 | 1.00 16.27 |
| ATOM | 1668 | CB  | VAL | 425 | 21.916 | 44.096 | 20.052 | 1.00 15.46 |
| ATOM | 1669 | CG1 | VAL | 425 | 22.703 | 43.332 | 18.999 | 1.00 12.48 |
| ATOM | 1670 | CG2 | VAL | 425 | 21.560 | 43.148 | 21.177 | 1.00 11.79 |
| ATOM | 1671 | C   | VAL | 425 | 23.259 | 46.094 | 19.382 | 1.00 15.96 |
| ATOM | 1672 | O   | VAL | 425 | 22.501 | 46.848 | 18.767 | 1.00 15.96 |
| ATOM | 1673 | N   | ILE | 426 | 24.556 | 46.003 | 19.115 | 1.00 15.81 |
| ATOM | 1674 | CA  | ILE | 426 | 25.139 | 46.644 | 17.947 | 1.00 16.74 |
| ATOM | 1675 | CB  | ILE | 426 | 26.251 | 47.640 | 18.304 | 1.00 18.60 |
| ATOM | 1676 | CG2 | ILE | 426 | 26.805 | 48.275 | 17.022 | 1.00 18.26 |
| ATOM | 1677 | CG1 | ILE | 426 | 25.697 | 48.710 | 19.254 | 1.00 17.67 |

FIGURE 1 (cont.)

```
ATOM   1678  CD1  ILE  426    26.635  49.857  19.531  1.00  19.38
ATOM   1679  C    ILE  426    25.669  45.434  17.199  1.00  17.81
ATOM   1680  O    ILE  426    26.385  44.611  17.774  1.00  18.67
ATOM   1681  N    ASP  427    25.295  45.318  15.931  1.00  18.83
ATOM   1682  CA   ASP  427    25.625  44.158  15.110  1.00  18.61
ATOM   1683  CB   ASP  427    24.284  43.525  14.711  1.00  19.39
ATOM   1684  CG   ASP  427    24.405  42.146  14.094  1.00  18.80
ATOM   1685  OD1  ASP  427    25.516  41.611  13.922  1.00  17.99
ATOM   1686  OD2  ASP  427    23.337  41.592  13.774  1.00  19.23
ATOM   1687  C    ASP  427    26.417  44.516  13.870  1.00  18.42
ATOM   1688  O    ASP  427    26.077  45.479  13.185  1.00  19.02
ATOM   1689  N    CYS  428    27.454  43.728  13.570  1.00  17.93
ATOM   1690  CA   CYS  428    28.277  43.944  12.375  1.00  18.18
ATOM   1691  CB   CYS  428    29.628  43.247  12.502  1.00  18.00
ATOM   1692  SG   CYS  428    29.549  41.453  12.475  1.00  19.71
ATOM   1693  C    CYS  428    27.555  43.423  11.135  1.00  18.32
ATOM   1694  O    CYS  428    27.944  43.708  10.011  1.00  21.01
ATOM   1695  N    ASN  429    26.530  42.609  11.351  1.00  18.21
ATOM   1696  CA   ASN  429    25.713  42.055  10.272  1.00  18.70
ATOM   1697  CB   ASN  429    25.054  43.180   9.462  1.00  18.15
ATOM   1698  CG   ASN  429    24.271  44.152  10.336  1.00  18.71
ATOM   1699  OD1  ASN  429    24.504  45.356  10.294  1.00  19.89
ATOM   1700  ND2  ASN  429    23.358  43.633  11.147  1.00  17.96
ATOM   1701  C    ASN  429    26.386  41.043   9.352  1.00  18.76
ATOM   1702  O    ASN  429    25.867  40.732   8.283  1.00  18.71
ATOM   1703  N    THR  430    27.517  40.492   9.781  1.00  19.72
ATOM   1704  CA   THR  430    28.226  39.486   8.996  1.00  19.58
ATOM   1705  CB   THR  430    29.527  40.044   8.377  1.00  18.32
ATOM   1706  OG1  THR  430    30.433  40.441   9.413  1.00  18.44
ATOM   1707  CG2  THR  430    29.215  41.241   7.505  1.00  16.13
ATOM   1708  C    THR  430    28.532  38.291   9.893  1.00  20.27
ATOM   1709  O    THR  430    28.475  38.399  11.112  1.00  20.61
ATOM   1710  N    CME  431    28.829  37.144   9.300  1.00  21.71
ATOM   1711  CA   CME  431    29.118  35.958  10.088  1.00  23.49
ATOM   1712  C    CME  431    30.100  35.064   9.351  1.00  23.26
ATOM   1713  O    CME  431    30.117  35.024   8.124  1.00  24.03
ATOM   1714  CB   CME  431    27.822  35.191  10.390  1.00  24.65
ATOM   1715  SG   CME  431    26.882  34.701   8.908  1.00  28.78
ATOM   1716  2SG  CME  431    25.080  34.061   9.615  1.00  30.80
ATOM   1717  2CB  CME  431    25.261  32.249   9.685  1.00  32.16
ATOM   1718  2CA  CME  431    26.230  31.721  10.742  1.00  34.08
ATOM   1719  OG   CME  431    26.088  32.402  11.978  1.00  36.06
ATOM   1720  N    VAL  432    30.949  34.393  10.112  1.00  23.66
ATOM   1721  CA   VAL  432    31.952  33.489   9.569  1.00  25.04
ATOM   1722  CB   VAL  432    33.212  33.429  10.487  1.00  26.14
ATOM   1723  CG1  VAL  432    34.215  32.412   9.968  1.00  25.89
ATOM   1724  CG2  VAL  432    33.860  34.811  10.587  1.00  26.03
ATOM   1725  C    VAL  432    31.295  32.135   9.552  1.00  24.44
ATOM   1726  O    VAL  432    30.594  31.780  10.493  1.00  24.47
ATOM   1727  N    THR  433    31.486  31.390   8.474  1.00  25.86
ATOM   1728  CA   THR  433    30.890  30.062   8.374  1.00  26.89
ATOM   1729  CB   THR  433    29.443  30.140   7.829  1.00  26.52
ATOM   1730  OG1  THR  433    28.812  28.859   7.968  1.00  28.69
ATOM   1731  CG2  THR  433    29.438  30.564   6.362  1.00  24.41
ATOM   1732  C    THR  433    31.718  29.093   7.527  1.00  26.04
ATOM   1733  O    THR  433    32.543  29.504   6.709  1.00  24.26
ATOM   1734  N    GLN  434    31.519  27.802   7.774  1.00  27.85
ATOM   1735  CA   GLN  434    32.221  26.750   7.052  1.00  28.61
```

FIGURE 1 (cont.)

| ATOM | 1736 | CB  | GLN | 434 | 32.034 | 25.402 | 7.745   | 1.00 | 31.09 |
|------|------|-----|-----|-----|--------|--------|---------|------|-------|
| ATOM | 1737 | CG  | GLN | 434 | 32.787 | 25.245 | 9.044   | 1.00 | 35.42 |
| ATOM | 1738 | CD  | GLN | 434 | 34.249 | 24.893 | 8.853   | 1.00 | 37.94 |
| ATOM | 1739 | OE1 | GLN | 434 | 34.643 | 23.759 | 9.081   | 1.00 | 44.05 |
| ATOM | 1740 | NE2 | GLN | 434 | 35.057 | 25.853 | 8.428   | 1.00 | 37.21 |
| ATOM | 1741 | C   | GLN | 434 | 31.701 | 26.657 | 5.628   | 1.00 | 27.68 |
| ATOM | 1742 | O   | GLN | 434 | 30.494 | 26.673 | 5.387   | 1.00 | 26.87 |
| ATOM | 1743 | N   | THR | 435 | 32.619 | 26.503 | 4.692   | 1.00 | 26.85 |
| ATOM | 1744 | CA  | THR | 435 | 32.246 | 26.416 | 3.305   | 1.00 | 27.23 |
| ATOM | 1745 | CB  | THR | 435 | 32.334 | 27.804 | 2.651   | 1.00 | 29.34 |
| ATOM | 1746 | OG1 | THR | 435 | 31.794 | 27.751 | 1.323   | 1.00 | 33.86 |
| ATOM | 1747 | CG2 | THR | 435 | 33.792 | 28.265 | 2.593   | 1.00 | 29.75 |
| ATOM | 1748 | C   | THR | 435 | 33.184 | 25.433 | 2.609   | 1.00 | 25.74 |
| ATOM | 1749 | O   | THR | 435 | 34.350 | 25.287 | 3.001   | 1.00 | 24.92 |
| ATOM | 1750 | N   | VAL | 436 | 32.658 | 24.734 | 1.608   | 1.00 | 23.49 |
| ATOM | 1751 | CA  | VAL | 436 | 33.447 | 23.774 | 0.858   | 1.00 | 22.57 |
| ATOM | 1752 | CB  | VAL | 436 | 32.712 | 22.391 | 0.684   | 1.00 | 21.11 |
| ATOM | 1753 | CG1 | VAL | 436 | 31.389 | 22.557 | -0.029  | 1.00 | 19.30 |
| ATOM | 1754 | CG2 | VAL | 436 | 33.602 | 21.399 | -0.061  | 1.00 | 17.28 |
| ATOM | 1755 | C   | VAL | 436 | 33.800 | 24.370 | -0.493  | 1.00 | 22.79 |
| ATOM | 1756 | O   | VAL | 436 | 33.029 | 25.129 | -1.071  | 1.00 | 23.69 |
| ATOM | 1757 | N   | ASP | 437 | 35.009 | 24.084 | -0.951  | 1.00 | 23.38 |
| ATOM | 1758 | CA  | ASP | 437 | 35.470 | 24.562 | -2.237  | 1.00 | 23.03 |
| ATOM | 1759 | CB  | ASP | 437 | 36.593 | 25.582 | -2.043  | 1.00 | 25.16 |
| ATOM | 1760 | CG  | ASP | 437 | 37.087 | 26.176 | -3.358  | 1.00 | 27.57 |
| ATOM | 1761 | OD1 | ASP | 437 | 36.421 | 26.006 | -4.408  | 1.00 | 28.15 |
| ATOM | 1762 | OD2 | ASP | 437 | 38.156 | 26.820 | -3.332  | 1.00 | 30.89 |
| ATOM | 1763 | C   | ASP | 437 | 35.976 | 23.344 | -2.991  | 1.00 | 22.31 |
| ATOM | 1764 | O   | ASP | 437 | 36.949 | 22.724 | -2.581  | 1.00 | 23.36 |
| ATOM | 1765 | N   | PHE | 438 | 35.257 | 22.948 | -4.031  | 1.00 | 22.10 |
| ATOM | 1766 | CA  | PHE | 438 | 35.646 | 21.804 | -4.849  | 1.00 | 24.52 |
| ATOM | 1767 | CB  | PHE | 438 | 34.444 | 21.329 | -5.676  | 1.00 | 24.50 |
| ATOM | 1768 | CG  | PHE | 438 | 33.252 | 20.944 | -4.833  | 1.00 | 27.22 |
| ATOM | 1769 | CD1 | PHE | 438 | 32.162 | 21.800 | -4.713  | 1.00 | 27.14 |
| ATOM | 1770 | CD2 | PHE | 438 | 33.242 | 19.739 | -4.123  | 1.00 | 27.35 |
| ATOM | 1771 | CE1 | PHE | 438 | 31.079 | 21.466 | -3.897  | 1.00 | 27.93 |
| ATOM | 1772 | CE2 | PHE | 438 | 32.166 | 19.394 | -3.305  | 1.00 | 26.72 |
| ATOM | 1773 | CZ  | PHE | 438 | 31.084 | 20.257 | -3.191  | 1.00 | 28.20 |
| ATOM | 1774 | C   | PHE | 438 | 36.784 | 22.298 | -5.741  | 1.00 | 25.20 |
| ATOM | 1775 | O   | PHE | 438 | 36.655 | 22.372 | -6.964  | 1.00 | 27.05 |
| ATOM | 1776 | N   | SER | 439 | 37.905 | 22.609 | -5.094  | 1.00 | 25.29 |
| ATOM | 1777 | CA  | SER | 439 | 39.087 | 23.167 | -5.732  | 1.00 | 24.15 |
| ATOM | 1778 | CB  | SER | 439 | 39.928 | 23.886 | -4.682  | 1.00 | 24.18 |
| ATOM | 1779 | OG  | SER | 439 | 39.975 | 23.146 | -3.471  | 1.00 | 24.29 |
| ATOM | 1780 | C   | SER | 439 | 39.978 | 22.302 | -6.614  | 1.00 | 24.46 |
| ATOM | 1781 | O   | SER | 439 | 40.881 | 22.834 | -7.266  | 1.00 | 24.35 |
| ATOM | 1782 | N   | LEU | 440 | 39.766 | 20.988 | -6.615  | 1.00 | 24.35 |
| ATOM | 1783 | CA  | LEU | 440 | 40.553 | 20.083 | -7.460  | 1.00 | 26.08 |
| ATOM | 1784 | CB  | LEU | 440 | 40.122 | 20.254 | -8.923  | 1.00 | 25.16 |
| ATOM | 1785 | CG  | LEU | 440 | 38.607 | 20.230 | -9.120  | 1.00 | 26.05 |
| ATOM | 1786 | CD1 | LEU | 440 | 38.242 | 20.519 | -10.563 | 1.00 | 25.63 |
| ATOM | 1787 | CD2 | LEU | 440 | 38.072 | 18.879 | -8.673  | 1.00 | 26.91 |
| ATOM | 1788 | C   | LEU | 440 | 42.069 | 20.314 | -7.341  | 1.00 | 26.71 |
| ATOM | 1789 | O   | LEU | 440 | 42.786 | 20.331 | -8.341  | 1.00 | 28.25 |
| ATOM | 1790 | N   | ASP | 441 | 42.551 | 20.455 | -6.111  | 1.00 | 26.91 |
| ATOM | 1791 | CA  | ASP | 441 | 43.966 | 20.705 | -5.858  | 1.00 | 25.13 |
| ATOM | 1792 | CB  | ASP | 441 | 44.167 | 22.197 | -5.573  | 1.00 | 25.06 |
| ATOM | 1793 | CG  | ASP | 441 | 43.347 | 22.691 | -4.367  | 1.00 | 27.62 |

FIGURE 1 (cont.)

| | | | | | | | | |
|---|---|---|---|---|---|---|---|---|
| ATOM | 1794 | OD1 | ASP | 441 | 42.462 | 21.954 | -3.863 | 1.00 26.35 |
| ATOM | 1795 | OD2 | ASP | 441 | 43.605 | 23.821 | -3.905 | 1.00 26.72 |
| ATOM | 1796 | C | ASP | 441 | 44.471 | 19.883 | -4.669 | 1.00 24.82 |
| ATOM | 1797 | O | ASP | 441 | 45.123 | 20.420 | -3.781 | 1.00 24.32 |
| ATOM | 1798 | N | PRO | 442 | 44.328 | 18.548 | -4.718 | 1.00 24.11 |
| ATOM | 1799 | CD | PRO | 442 | 44.909 | 17.709 | -3.650 | 1.00 23.78 |
| ATOM | 1800 | CA | PRO | 442 | 43.750 | 17.712 | -5.773 | 1.00 24.26 |
| ATOM | 1801 | CB | PRO | 442 | 44.505 | 16.401 | -5.588 | 1.00 23.48 |
| ATOM | 1802 | CG | PRO | 442 | 44.562 | 16.289 | -4.100 | 1.00 23.95 |
| ATOM | 1803 | C | PRO | 442 | 42.250 | 17.450 | -5.747 | 1.00 24.59 |
| ATOM | 1804 | O | PRO | 442 | 41.674 | 17.082 | -6.778 | 1.00 26.09 |
| ATOM | 1805 | N | THR | 443 | 41.608 | 17.664 | -4.601 | 1.00 25.49 |
| ATOM | 1806 | CA | THR | 443 | 40.183 | 17.360 | -4.465 | 1.00 23.89 |
| ATOM | 1807 | CB | THR | 443 | 40.014 | 16.138 | -3.532 | 1.00 23.42 |
| ATOM | 1808 | OG1 | THR | 443 | 40.674 | 16.405 | -2.291 | 1.00 24.59 |
| ATOM | 1809 | CG2 | THR | 443 | 40.643 | 14.905 | -4.145 | 1.00 22.83 |
| ATOM | 1810 | C | THR | 443 | 39.269 | 18.502 | -3.996 | 1.00 23.35 |
| ATOM | 1811 | O | THR | 443 | 38.669 | 19.197 | -4.818 | 1.00 22.91 |
| ATOM | 1812 | N | PHE | 444 | 39.125 | 18.666 | -2.684 | 1.00 22.01 |
| ATOM | 1813 | CA | PHE | 444 | 38.271 | 19.713 | -2.141 | 1.00 21.72 |
| ATOM | 1814 | CB | PHE | 444 | 36.883 | 19.159 | -1.748 | 1.00 20.61 |
| ATOM | 1815 | CG | PHE | 444 | 36.910 | 18.077 | -0.693 | 1.00 18.78 |
| ATOM | 1816 | CD1 | PHE | 444 | 36.849 | 18.399 | 0.659 | 1.00 19.13 |
| ATOM | 1817 | CD2 | PHE | 444 | 36.954 | 16.731 | -1.053 | 1.00 18.82 |
| ATOM | 1818 | CE1 | PHE | 444 | 36.827 | 17.394 | 1.640 | 1.00 18.38 |
| ATOM | 1819 | CE2 | PHE | 444 | 36.933 | 15.723 | -0.081 | 1.00 16.79 |
| ATOM | 1820 | CZ | PHE | 444 | 36.869 | 16.052 | 1.261 | 1.00 16.58 |
| ATOM | 1821 | C | PHE | 444 | 38.931 | 20.432 | -0.971 | 1.00 21.99 |
| ATOM | 1822 | O | PHE | 444 | 39.983 | 19.998 | -0.481 | 1.00 22.62 |
| ATOM | 1823 | N | THR | 445 | 38.333 | 21.548 | -0.558 | 1.00 22.06 |
| ATOM | 1824 | CA | THR | 445 | 38.834 | 22.353 | 0.552 | 1.00 22.10 |
| ATOM | 1825 | CB | THR | 445 | 39.519 | 23.642 | 0.040 | 1.00 22.17 |
| ATOM | 1826 | OG1 | THR | 445 | 40.542 | 23.311 | -0.903 | 1.00 24.33 |
| ATOM | 1827 | CG2 | THR | 445 | 40.132 | 24.423 | 1.187 | 1.00 20.65 |
| ATOM | 1828 | C | THR | 445 | 37.682 | 22.795 | 1.452 | 1.00 21.98 |
| ATOM | 1829 | O | THR | 445 | 36.674 | 23.298 | 0.971 | 1.00 21.81 |
| ATOM | 1830 | N | ILE | 446 | 37.806 | 22.555 | 2.745 | 1.00 23.22 |
| ATOM | 1831 | CA | ILE | 446 | 36.789 | 22.998 | 3.684 | 1.00 26.55 |
| ATOM | 1832 | CB | ILE | 446 | 36.318 | 21.874 | 4.652 | 1.00 25.92 |
| ATOM | 1833 | CG2 | ILE | 446 | 35.603 | 22.461 | 5.858 | 1.00 25.60 |
| ATOM | 1834 | CG1 | ILE | 446 | 35.346 | 20.939 | 3.929 | 1.00 22.35 |
| ATOM | 1835 | CD1 | ILE | 446 | 35.814 | 19.552 | 3.909 | 1.00 21.01 |
| ATOM | 1836 | C | ILE | 446 | 37.474 | 24.125 | 4.437 | 1.00 28.48 |
| ATOM | 1837 | O | ILE | 446 | 38.516 | 23.921 | 5.065 | 1.00 30.14 |
| ATOM | 1838 | N | GLU | 447 | 36.943 | 25.330 | 4.276 | 1.00 29.02 |
| ATOM | 1839 | CA | GLU | 447 | 37.494 | 26.509 | 4.916 | 1.00 28.87 |
| ATOM | 1840 | CB | GLU | 447 | 38.245 | 27.325 | 3.867 | 1.00 29.79 |
| ATOM | 1841 | CG | GLU | 447 | 37.433 | 27.601 | 2.611 | 1.00 31.68 |
| ATOM | 1842 | CD | GLU | 447 | 38.282 | 28.042 | 1.435 | 1.00 33.86 |
| ATOM | 1843 | OE1 | GLU | 447 | 39.496 | 28.280 | 1.609 | 1.00 35.31 |
| ATOM | 1844 | OE2 | GLU | 447 | 37.733 | 28.133 | 0.317 | 1.00 37.54 |
| ATOM | 1845 | C | GLU | 447 | 36.340 | 27.310 | 5.520 | 1.00 29.27 |
| ATOM | 1846 | O | GLU | 447 | 35.330 | 26.731 | 5.919 | 1.00 29.04 |
| ATOM | 1847 | N | THR | 448 | 36.497 | 28.625 | 5.633 | 1.00 28.51 |
| ATOM | 1848 | CA | THR | 448 | 35.431 | 29.453 | 6.167 | 1.00 29.44 |
| ATOM | 1849 | CB | THR | 448 | 35.720 | 29.947 | 7.596 | 1.00 29.38 |
| ATOM | 1850 | OG1 | THR | 448 | 36.836 | 30.841 | 7.584 | 1.00 30.76 |
| ATOM | 1851 | CG2 | THR | 448 | 36.019 | 28.797 | 8.514 | 1.00 30.09 |

FIGURE 1 (cont.)

| | | | | | | | | | |
|---|---|---|---|---|---|---|---|---|---|
| ATOM | 1852 | C | THR | 448 | 35.267 | 30.657 | 5.261 | 1.00 | 29.41 |
| ATOM | 1853 | O | THR | 448 | 36.198 | 31.027 | 4.549 | 1.00 | 29.33 |
| ATOM | 1854 | N | THR | 449 | 34.059 | 31.213 | 5.228 | 1.00 | 29.92 |
| ATOM | 1855 | CA | THR | 449 | 33.773 | 32.390 | 4.421 | 1.00 | 29.42 |
| ATOM | 1856 | CB | THR | 449 | 32.943 | 32.047 | 3.174 | 1.00 | 28.46 |
| ATOM | 1857 | OG1 | THR | 449 | 33.623 | 31.047 | 2.417 | 1.00 | 29.99 |
| ATOM | 1858 | CG2 | THR | 449 | 32.770 | 33.272 | 2.294 | 1.00 | 28.99 |
| ATOM | 1859 | C | THR | 449 | 32.976 | 33.363 | 5.276 | 1.00 | 29.18 |
| ATOM | 1860 | O | THR | 449 | 32.068 | 32.953 | 6.006 | 1.00 | 28.97 |
| ATOM | 1861 | N | THR | 450 | 33.380 | 34.628 | 5.256 | 1.00 | 27.76 |
| ATOM | 1862 | CA | THR | 450 | 32.668 | 35.638 | 6.008 | 1.00 | 26.60 |
| ATOM | 1863 | CB | THR | 450 | 33.600 | 36.759 | 6.469 | 1.00 | 27.00 |
| ATOM | 1864 | OG1 | THR | 450 | 34.613 | 36.202 | 7.324 | 1.00 | 26.73 |
| ATOM | 1865 | CG2 | THR | 450 | 32.812 | 37.819 | 7.247 | 1.00 | 25.31 |
| ATOM | 1866 | C | THR | 450 | 31.578 | 36.145 | 5.076 | 1.00 | 26.94 |
| ATOM | 1867 | O | THR | 450 | 31.856 | 36.685 | 4.003 | 1.00 | 26.91 |
| ATOM | 1868 | N | LEU | 451 | 30.333 | 35.896 | 5.464 | 1.00 | 26.50 |
| ATOM | 1869 | CA | LEU | 451 | 29.184 | 36.267 | 4.661 | 1.00 | 25.37 |
| ATOM | 1870 | CB | LEU | 451 | 28.401 | 35.007 | 4.294 | 1.00 | 25.61 |
| ATOM | 1871 | CG | LEU | 451 | 29.076 | 33.801 | 3.662 | 1.00 | 26.81 |
| ATOM | 1872 | CD1 | LEU | 451 | 28.101 | 32.649 | 3.739 | 1.00 | 27.81 |
| ATOM | 1873 | CD2 | LEU | 451 | 29.459 | 34.096 | 2.220 | 1.00 | 26.32 |
| ATOM | 1874 | C | LEU | 451 | 28.215 | 37.168 | 5.399 | 1.00 | 24.26 |
| ATOM | 1875 | O | LEU | 451 | 28.287 | 37.313 | 6.622 | 1.00 | 23.50 |
| ATOM | 1876 | N | PRO | 452 | 27.324 | 37.834 | 4.646 | 1.00 | 22.96 |
| ATOM | 1877 | CD | PRO | 452 | 27.281 | 37.930 | 3.174 | 1.00 | 23.01 |
| ATOM | 1878 | CA | PRO | 452 | 26.328 | 38.707 | 5.252 | 1.00 | 21.34 |
| ATOM | 1879 | CB | PRO | 452 | 25.528 | 39.189 | 4.045 | 1.00 | 22.18 |
| ATOM | 1880 | CG | PRO | 452 | 26.545 | 39.213 | 2.957 | 1.00 | 23.73 |
| ATOM | 1881 | C | PRO | 452 | 25.490 | 37.742 | 6.069 | 1.00 | 20.41 |
| ATOM | 1882 | O | PRO | 452 | 25.315 | 36.587 | 5.674 | 1.00 | 20.81 |
| ATOM | 1883 | N | GLN | 453 | 24.983 | 38.197 | 7.201 | 1.00 | 19.57 |
| ATOM | 1884 | CA | GLN | 453 | 24.179 | 37.334 | 8.053 | 1.00 | 18.59 |
| ATOM | 1885 | CB | GLN | 453 | 23.888 | 38.047 | 9.364 | 1.00 | 18.03 |
| ATOM | 1886 | CG | GLN | 453 | 22.915 | 39.183 | 9.194 | 1.00 | 16.29 |
| ATOM | 1887 | CD | GLN | 453 | 22.857 | 40.088 | 10.384 | 1.00 | 17.25 |
| ATOM | 1888 | OE1 | GLN | 453 | 22.521 | 41.259 | 10.244 | 1.00 | 18.98 |
| ATOM | 1889 | NE2 | GLN | 453 | 23.184 | 39.565 | 11.571 | 1.00 | 12.28 |
| ATOM | 1890 | C | GLN | 453 | 22.861 | 37.023 | 7.368 | 1.00 | 19.31 |
| ATOM | 1891 | O | GLN | 453 | 22.451 | 37.735 | 6.445 | 1.00 | 19.70 |
| ATOM | 1892 | N | ASP | 454 | 22.215 | 35.939 | 7.786 | 1.00 | 19.47 |
| ATOM | 1893 | CA | ASP | 454 | 20.915 | 35.592 | 7.225 | 1.00 | 20.05 |
| ATOM | 1894 | CB | ASP | 454 | 20.831 | 34.095 | 6.866 | 1.00 | 20.04 |
| ATOM | 1895 | CG | ASP | 454 | 20.782 | 33.200 | 8.086 | 1.00 | 22.40 |
| ATOM | 1896 | OD1 | ASP | 454 | 21.568 | 33.406 | 9.032 | 1.00 | 22.31 |
| ATOM | 1897 | OD2 | ASP | 454 | 19.926 | 32.296 | 8.103 | 1.00 | 25.12 |
| ATOM | 1898 | C | ASP | 454 | 19.883 | 36.001 | 8.281 | 1.00 | 19.45 |
| ATOM | 1899 | O | ASP | 454 | 20.250 | 36.566 | 9.309 | 1.00 | 19.72 |
| ATOM | 1900 | N | ALA | 455 | 18.607 | 35.720 | 8.041 | 1.00 | 20.44 |
| ATOM | 1901 | CA | ALA | 455 | 17.544 | 36.083 | 8.986 | 1.00 | 20.48 |
| ATOM | 1902 | CB | ALA | 455 | 16.178 | 35.765 | 8.390 | 1.00 | 17.68 |
| ATOM | 1903 | C | ALA | 455 | 17.662 | 35.469 | 10.380 | 1.00 | 19.73 |
| ATOM | 1904 | O | ALA | 455 | 17.265 | 36.091 | 11.368 | 1.00 | 22.40 |
| ATOM | 1905 | N | VAL | 456 | 18.147 | 34.234 | 10.462 | 1.00 | 20.09 |
| ATOM | 1906 | CA | VAL | 456 | 18.295 | 33.564 | 11.754 | 1.00 | 19.00 |
| ATOM | 1907 | CB | VAL | 456 | 18.746 | 32.099 | 11.578 | 1.00 | 19.21 |
| ATOM | 1908 | CG1 | VAL | 456 | 19.143 | 31.485 | 12.933 | 1.00 | 17.42 |
| ATOM | 1909 | CG2 | VAL | 456 | 17.636 | 31.293 | 10.917 | 1.00 | 16.27 |

FIGURE 1 (cont.)

| | | | | | | | | | |
|---|---|---|---|---|---|---|---|---|---|
| ATOM | 1910 | C | VAL | 456 | 19.316 | 34.319 | 12.594 | 1.00 | 17.87 |
| ATOM | 1911 | O | VAL | 456 | 19.062 | 34.642 | 13.744 | 1.00 | 18.04 |
| ATOM | 1912 | N | SER | 457 | 20.438 | 34.660 | 11.972 | 1.00 | 19.53 |
| ATOM | 1913 | CA | SER | 457 | 21.517 | 35.392 | 12.630 | 1.00 | 19.10 |
| ATOM | 1914 | CB | SER | 457 | 22.673 | 35.589 | 11.644 | 1.00 | 17.70 |
| ATOM | 1915 | OG | SER | 457 | 23.631 | 36.508 | 12.143 | 1.00 | 20.26 |
| ATOM | 1916 | C | SER | 457 | 21.049 | 36.745 | 13.157 | 1.00 | 18.37 |
| ATOM | 1917 | O | SER | 457 | 21.246 | 37.063 | 14.324 | 1.00 | 18.88 |
| ATOM | 1918 | N | ARG | 458 | 20.402 | 37.519 | 12.292 | 1.00 | 18.67 |
| ATOM | 1919 | CA | ARG | 458 | 19.916 | 38.851 | 12.636 | 1.00 | 18.34 |
| ATOM | 1920 | CB | ARG | 458 | 19.356 | 39.551 | 11.389 | 1.00 | 15.93 |
| ATOM | 1921 | CG | ARG | 458 | 19.049 | 41.042 | 11.573 | 1.00 | 15.45 |
| ATOM | 1922 | CD | ARG | 458 | 18.892 | 41.721 | 10.220 | 1.00 | 13.63 |
| ATOM | 1923 | NE | ARG | 458 | 18.931 | 43.176 | 10.303 | 1.00 | 14.59 |
| ATOM | 1924 | CZ | ARG | 458 | 19.865 | 43.935 | 9.733 | 1.00 | 16.49 |
| ATOM | 1925 | NH1 | ARG | 458 | 19.816 | 45.257 | 9.859 | 1.00 | 18.89 |
| ATOM | 1926 | NH2 | ARG | 458 | 20.871 | 43.377 | 9.062 | 1.00 | 17.85 |
| ATOM | 1927 | C | ARG | 458 | 18.863 | 38.798 | 13.723 | 1.00 | 18.62 |
| ATOM | 1928 | O | ARG | 458 | 18.924 | 39.562 | 14.674 | 1.00 | 18.82 |
| ATOM | 1929 | N | THR | 459 | 17.900 | 37.896 | 13.580 | 1.00 | 20.47 |
| ATOM | 1930 | CA | THR | 459 | 16.831 | 37.759 | 14.571 | 1.00 | 22.62 |
| ATOM | 1931 | CB | THR | 459 | 15.759 | 36.708 | 14.120 | 1.00 | 23.54 |
| ATOM | 1932 | OG1 | THR | 459 | 15.175 | 37.109 | 12.872 | 1.00 | 23.92 |
| ATOM | 1933 | CG2 | THR | 459 | 14.655 | 36.566 | 15.168 | 1.00 | 23.27 |
| ATOM | 1934 | C | THR | 459 | 17.395 | 37.354 | 15.939 | 1.00 | 22.25 |
| ATOM | 1935 | O | THR | 459 | 16.988 | 37.896 | 16.974 | 1.00 | 22.42 |
| ATOM | 1936 | N | GLN | 460 | 18.324 | 36.400 | 15.945 | 1.00 | 21.83 |
| ATOM | 1937 | CA | GLN | 460 | 18.913 | 35.943 | 17.196 | 1.00 | 23.58 |
| ATOM | 1938 | CB | GLN | 460 | 19.575 | 34.574 | 17.022 | 1.00 | 28.20 |
| ATOM | 1939 | CG | GLN | 460 | 18.532 | 33.481 | 16.700 | 1.00 | 34.19 |
| ATOM | 1940 | CD | GLN | 460 | 19.106 | 32.076 | 16.567 | 1.00 | 38.92 |
| ATOM | 1941 | OE1 | GLN | 460 | 18.389 | 31.140 | 16.174 | 1.00 | 41.47 |
| ATOM | 1942 | NE2 | GLN | 460 | 20.386 | 31.910 | 16.903 | 1.00 | 41.20 |
| ATOM | 1943 | C | GLN | 460 | 19.847 | 36.972 | 17.814 | 1.00 | 21.76 |
| ATOM | 1944 | O | GLN | 460 | 19.841 | 37.167 | 19.024 | 1.00 | 22.18 |
| ATOM | 1945 | N | ARG | 461 | 20.601 | 37.677 | 16.983 | 1.00 | 20.55 |
| ATOM | 1946 | CA | ARG | 461 | 21.490 | 38.710 | 17.485 | 1.00 | 19.90 |
| ATOM | 1947 | CB | ARG | 461 | 22.460 | 39.178 | 16.398 | 1.00 | 18.96 |
| ATOM | 1948 | CG | ARG | 461 | 23.810 | 38.533 | 16.562 | 1.00 | 18.17 |
| ATOM | 1949 | CD | ARG | 461 | 24.341 | 37.840 | 15.337 | 1.00 | 20.30 |
| ATOM | 1950 | NE | ARG | 461 | 25.088 | 38.742 | 14.479 | 1.00 | 21.22 |
| ATOM | 1951 | CZ | ARG | 461 | 26.196 | 38.426 | 13.812 | 1.00 | 20.58 |
| ATOM | 1952 | NH1 | ARG | 461 | 26.740 | 37.220 | 13.886 | 1.00 | 18.60 |
| ATOM | 1953 | NH2 | ARG | 461 | 26.716 | 39.316 | 12.992 | 1.00 | 23.17 |
| ATOM | 1954 | C | ARG | 461 | 20.661 | 39.855 | 18.042 | 1.00 | 20.36 |
| ATOM | 1955 | O | ARG | 461 | 20.824 | 40.229 | 19.201 | 1.00 | 21.32 |
| ATOM | 1956 | N | ARG | 462 | 19.724 | 40.366 | 17.247 | 1.00 | 20.67 |
| ATOM | 1957 | CA | ARG | 462 | 18.847 | 41.453 | 17.685 | 1.00 | 20.84 |
| ATOM | 1958 | CB | ARG | 462 | 17.857 | 41.820 | 16.574 | 1.00 | 21.40 |
| ATOM | 1959 | CG | ARG | 462 | 16.931 | 42.969 | 16.941 | 1.00 | 22.08 |
| ATOM | 1960 | CD | ARG | 462 | 15.792 | 43.156 | 15.944 | 1.00 | 21.34 |
| ATOM | 1961 | NE | ARG | 462 | 14.830 | 42.062 | 16.007 | 1.00 | 21.80 |
| ATOM | 1962 | CZ | ARG | 462 | 13.742 | 41.978 | 15.247 | 1.00 | 21.21 |
| ATOM | 1963 | NH1 | ARG | 462 | 12.935 | 40.937 | 15.371 | 1.00 | 22.57 |
| ATOM | 1964 | NH2 | ARG | 462 | 13.459 | 42.929 | 14.367 | 1.00 | 18.74 |
| ATOM | 1965 | C | ARG | 462 | 18.056 | 41.018 | 18.926 | 1.00 | 21.55 |
| ATOM | 1966 | O | ARG | 462 | 17.801 | 41.822 | 19.833 | 1.00 | 21.69 |
| ATOM | 1967 | N | GLY | 463 | 17.711 | 39.731 | 18.965 | 1.00 | 21.00 |

FIGURE 1 (cont.)

| | | | | | | | | |
|---|---|---|---|---|---|---|---|---|
| ATOM | 1968 | CA | GLY | 463 | 16.950 | 39.173 | 20.064 | 1.00 21.40 |
| ATOM | 1969 | C | GLY | 463 | 17.594 | 39.194 | 21.434 | 1.00 23.27 |
| ATOM | 1970 | O | GLY | 463 | 16.951 | 38.847 | 22.420 | 1.00 25.42 |
| ATOM | 1971 | N | ARG | 464 | 18.856 | 39.586 | 21.522 | 1.00 24.33 |
| ATOM | 1972 | CA | ARG | 464 | 19.530 | 39.644 | 22.814 | 1.00 25.08 |
| ATOM | 1973 | CB | ARG | 464 | 21.044 | 39.714 | 22.620 | 1.00 25.94 |
| ATOM | 1974 | CG | ARG | 464 | 21.632 | 38.564 | 21.823 | 1.00 28.27 |
| ATOM | 1975 | CD | ARG | 464 | 21.511 | 37.237 | 22.554 | 1.00 31.16 |
| ATOM | 1976 | NE | ARG | 464 | 22.670 | 36.393 | 22.274 | 1.00 35.52 |
| ATOM | 1977 | CZ | ARG | 464 | 22.887 | 35.766 | 21.119 | 1.00 39.25 |
| ATOM | 1978 | NH1 | ARG | 464 | 23.987 | 35.031 | 20.963 | 1.00 40.53 |
| ATOM | 1979 | NH2 | ARG | 464 | 21.991 | 35.828 | 20.132 | 1.00 39.41 |
| ATOM | 1980 | C | ARG | 464 | 19.042 | 40.848 | 23.634 | 1.00 25.24 |
| ATOM | 1981 | O | ARG | 464 | 19.297 | 40.933 | 24.843 | 1.00 24.97 |
| ATOM | 1982 | N | THR | 465 | 18.360 | 41.784 | 22.975 | 1.00 25.46 |
| ATOM | 1983 | CA | THR | 465 | 17.821 | 42.970 | 23.651 | 1.00 25.46 |
| ATOM | 1984 | CB | THR | 465 | 18.428 | 44.286 | 23.081 | 1.00 22.61 |
| ATOM | 1985 | OG1 | THR | 465 | 18.181 | 45.357 | 23.993 | 1.00 21.95 |
| ATOM | 1986 | CG2 | THR | 465 | 17.831 | 44.644 | 21.731 | 1.00 19.47 |
| ATOM | 1987 | C | THR | 465 | 16.285 | 42.987 | 23.545 | 1.00 27.08 |
| ATOM | 1988 | O | THR | 465 | 15.697 | 42.133 | 22.874 | 1.00 27.65 |
| ATOM | 1989 | N | GLY | 466 | 15.644 | 43.931 | 24.230 | 1.00 28.70 |
| ATOM | 1990 | CA | GLY | 466 | 14.194 | 44.025 | 24.192 | 1.00 30.14 |
| ATOM | 1991 | C | GLY | 466 | 13.486 | 42.861 | 24.871 | 1.00 31.44 |
| ATOM | 1992 | O | GLY | 466 | 12.354 | 42.508 | 24.512 | 1.00 32.18 |
| ATOM | 1993 | N | ARG | 467 | 14.135 | 42.280 | 25.875 | 1.00 32.23 |
| ATOM | 1994 | CA | ARG | 467 | 13.578 | 41.143 | 26.600 | 1.00 32.05 |
| ATOM | 1995 | CB | ARG | 467 | 14.679 | 40.144 | 26.937 | 1.00 29.85 |
| ATOM | 1996 | CG | ARG | 467 | 15.369 | 39.574 | 25.734 | 1.00 28.91 |
| ATOM | 1997 | CD | ARG | 467 | 16.432 | 38.620 | 26.174 | 1.00 30.63 |
| ATOM | 1998 | NE | ARG | 467 | 17.122 | 38.018 | 25.044 | 1.00 33.36 |
| ATOM | 1999 | CZ | ARG | 467 | 17.549 | 36.760 | 25.027 | 1.00 35.37 |
| ATOM | 2000 | NH1 | ARG | 467 | 18.173 | 36.275 | 23.959 | 1.00 36.51 |
| ATOM | 2001 | NH2 | ARG | 467 | 17.370 | 35.987 | 26.088 | 1.00 36.08 |
| ATOM | 2002 | C | ARG | 467 | 12.858 | 41.567 | 27.873 | 1.00 33.30 |
| ATOM | 2003 | O | ARG | 467 | 13.431 | 41.573 | 28.963 | 1.00 34.17 |
| ATOM | 2004 | N | GLY | 468 | 11.583 | 41.898 | 27.732 | 1.00 34.55 |
| ATOM | 2005 | CA | GLY | 468 | 10.808 | 42.314 | 28.882 | 1.00 34.38 |
| ATOM | 2006 | C | GLY | 468 | 10.967 | 43.791 | 29.163 | 1.00 34.53 |
| ATOM | 2007 | O | GLY | 468 | 10.558 | 44.274 | 30.213 | 1.00 36.37 |
| ATOM | 2008 | N | LYS | 469 | 11.590 | 44.503 | 28.237 | 1.00 33.19 |
| ATOM | 2009 | CA | LYS | 469 | 11.787 | 45.932 | 28.379 | 1.00 32.67 |
| ATOM | 2010 | CB | LYS | 469 | 12.797 | 46.258 | 29.491 | 1.00 34.53 |
| ATOM | 2011 | CG | LYS | 469 | 14.257 | 45.905 | 29.206 | 1.00 35.53 |
| ATOM | 2012 | CD | LYS | 469 | 15.157 | 46.408 | 30.336 | 1.00 35.50 |
| ATOM | 2013 | CE | LYS | 469 | 16.634 | 46.384 | 29.961 | 1.00 36.18 |
| ATOM | 2014 | NZ | LYS | 469 | 17.508 | 46.793 | 31.106 | 1.00 33.86 |
| ATOM | 2015 | C | LYS | 469 | 12.291 | 46.417 | 27.045 | 1.00 31.65 |
| ATOM | 2016 | O | LYS | 469 | 12.765 | 45.627 | 26.234 | 1.00 32.31 |
| ATOM | 2017 | N | PRO | 470 | 12.164 | 47.717 | 26.778 | 1.00 30.75 |
| ATOM | 2018 | CD | PRO | 470 | 11.491 | 48.754 | 27.580 | 1.00 30.88 |
| ATOM | 2019 | CA | PRO | 470 | 12.626 | 48.255 | 25.500 | 1.00 28.89 |
| ATOM | 2020 | CB | PRO | 470 | 12.238 | 49.731 | 25.597 | 1.00 29.64 |
| ATOM | 2021 | CG | PRO | 470 | 11.044 | 49.721 | 26.519 | 1.00 30.22 |
| ATOM | 2022 | C | PRO | 470 | 14.130 | 48.089 | 25.298 | 1.00 27.83 |
| ATOM | 2023 | O | PRO | 470 | 14.910 | 48.069 | 26.256 | 1.00 28.38 |
| ATOM | 2024 | N | GLY | 471 | 14.525 | 47.975 | 24.040 | 1.00 25.46 |
| ATOM | 2025 | CA | GLY | 471 | 15.923 | 47.834 | 23.701 | 1.00 22.38 |

FIGURE 1 (cont.)

```
ATOM   2026  C    GLY  471      16.164  48.513  22.373  1.00 20.97
ATOM   2027  O    GLY  471      15.216  48.887  21.668  1.00 20.48
ATOM   2028  N    ILE  472      17.431  48.715  22.043  1.00 20.35
ATOM   2029  CA   ILE  472      17.803  49.344  20.792  1.00 19.19
ATOM   2030  CB   ILE  472      18.500  50.710  21.018  1.00 19.31
ATOM   2031  CG2  ILE  472      18.916  51.317  19.697  1.00 19.60
ATOM   2032  CG1  ILE  472      17.534  51.680  21.706  1.00 20.42
ATOM   2033  CD1  ILE  472      18.101  53.048  21.989  1.00 20.47
ATOM   2034  C    ILE  472      18.727  48.400  20.045  1.00 20.13
ATOM   2035  O    ILE  472      19.509  47.650  20.651  1.00 18.96
ATOM   2036  N    TYR  473      18.593  48.402  18.726  1.00 20.53
ATOM   2037  CA   TYR  473      19.406  47.562  17.865  1.00 20.24
ATOM   2038  CB   TYR  473      18.527  46.504  17.184  1.00 17.07
ATOM   2039  CG   TYR  473      19.236  45.657  16.154  1.00 16.23
ATOM   2040  CD1  TYR  473      20.183  44.704  16.537  1.00 16.38
ATOM   2041  CE1  TYR  473      20.844  43.918  15.594  1.00 15.97
ATOM   2042  CD2  TYR  473      18.961  45.809  14.792  1.00 15.90
ATOM   2043  CE2  TYR  473      19.615  45.033  13.830  1.00 17.92
ATOM   2044  CZ   TYR  473      20.561  44.085  14.236  1.00 19.05
ATOM   2045  OH   TYR  473      21.232  43.322  13.292  1.00 16.03
ATOM   2046  C    TYR  473      20.054  48.481  16.839  1.00 20.38
ATOM   2047  O    TYR  473      19.372  49.235  16.156  1.00 21.81
ATOM   2048  N    ARG  474      21.377  48.486  16.795  1.00 21.07
ATOM   2049  CA   ARG  474      22.087  49.311  15.833  1.00 21.12
ATOM   2050  CB   ARG  474      23.092  50.217  16.535  1.00 22.36
ATOM   2051  CG   ARG  474      22.454  51.054  17.627  1.00 24.18
ATOM   2052  CD   ARG  474      23.444  51.980  18.304  1.00 25.34
ATOM   2053  NE   ARG  474      22.844  52.571  19.493  1.00 26.57
ATOM   2054  CZ   ARG  474      21.960  53.562  19.476  1.00 26.60
ATOM   2055  NH1  ARG  474      21.468  54.026  20.615  1.00 25.83
ATOM   2056  NH2  ARG  474      21.580  54.105  18.327  1.00 27.33
ATOM   2057  C    ARG  474      22.766  48.354  14.876  1.00 21.22
ATOM   2058  O    ARG  474      23.282  47.310  15.281  1.00 21.04
ATOM   2059  N    PHE  475      22.740  48.699  13.599  1.00 22.21
ATOM   2060  CA   PHE  475      23.306  47.849  12.575  1.00 23.28
ATOM   2061  CB   PHE  475      22.170  47.148  11.815  1.00 25.19
ATOM   2062  CG   PHE  475      21.164  48.103  11.199  1.00 26.26
ATOM   2063  CD1  PHE  475      20.079  48.570  11.941  1.00 25.75
ATOM   2064  CD2  PHE  475      21.307  48.537   9.878  1.00 26.21
ATOM   2065  CE1  PHE  475      19.156  49.452  11.374  1.00 24.75
ATOM   2066  CE2  PHE  475      20.390  49.417   9.306  1.00 24.17
ATOM   2067  CZ   PHE  475      19.314  49.873  10.060  1.00 23.51
ATOM   2068  C    PHE  475      24.151  48.638  11.598  1.00 23.82
ATOM   2069  O    PHE  475      23.960  49.843  11.428  1.00 25.90
ATOM   2070  N    VAL  476      25.082  47.946  10.955  1.00 23.60
ATOM   2071  CA   VAL  476      25.957  48.545   9.959  1.00 22.75
ATOM   2072  CB   VAL  476      27.299  47.772   9.898  1.00 23.15
ATOM   2073  CG1  VAL  476      28.178  48.292   8.773  1.00 22.36
ATOM   2074  CG2  VAL  476      28.019  47.881  11.227  1.00 23.76
ATOM   2075  C    VAL  476      25.263  48.440   8.594  1.00 21.91
ATOM   2076  O    VAL  476      25.323  49.353   7.774  1.00 22.30
ATOM   2077  N    ALA  477      24.590  47.320   8.371  1.00 21.29
ATOM   2078  CA   ALA  477      23.919  47.066   7.111  1.00 21.64
ATOM   2079  CB   ALA  477      24.658  45.974   6.328  1.00 21.38
ATOM   2080  C    ALA  477      22.454  46.696   7.301  1.00 21.13
ATOM   2081  O    ALA  477      22.091  45.962   8.218  1.00 20.40
ATOM   2082  N    PRO  478      21.598  47.195   6.403  1.00 21.02
ATOM   2083  CD   PRO  478      21.990  48.162   5.360  1.00 21.21
```

FIGURE 1 (cont.)

| ATOM | 2084 | CA  | PRO | 478 | 20.152 | 46.976 | 6.400  | 1.00 | 23.06 |
|------|------|-----|-----|-----|--------|--------|--------|------|-------|
| ATOM | 2085 | CB  | PRO | 478 | 19.648 | 48.180 | 5.601  | 1.00 | 23.71 |
| ATOM | 2086 | CG  | PRO | 478 | 20.722 | 48.326 | 4.561  | 1.00 | 23.74 |
| ATOM | 2087 | C   | PRO | 478 | 19.669 | 45.653 | 5.791  | 1.00 | 21.67 |
| ATOM | 2088 | O   | PRO | 478 | 18.532 | 45.226 | 6.028  | 1.00 | 21.26 |
| ATOM | 2089 | N   | GLY | 479 | 20.515 | 45.021 | 4.992  | 1.00 | 19.99 |
| ATOM | 2090 | CA  | GLY | 479 | 20.118 | 43.779 | 4.368  | 1.00 | 19.25 |
| ATOM | 2091 | C   | GLY | 479 | 20.473 | 42.550 | 5.166  | 1.00 | 19.67 |
| ATOM | 2092 | O   | GLY | 479 | 21.255 | 42.611 | 6.117  | 1.00 | 19.75 |
| ATOM | 2093 | N   | GLU | 480 | 19.892 | 41.430 | 4.762  | 1.00 | 18.74 |
| ATOM | 2094 | CA  | GLU | 480 | 20.135 | 40.145 | 5.395  | 1.00 | 19.62 |
| ATOM | 2095 | CB  | GLU | 480 | 19.266 | 39.994 | 6.641  | 1.00 | 19.51 |
| ATOM | 2096 | CG  | GLU | 480 | 17.798 | 39.867 | 6.293  | 1.00 | 20.84 |
| ATOM | 2097 | CD  | GLU | 480 | 16.907 | 39.754 | 7.487  | 1.00 | 20.69 |
| ATOM | 2098 | OE1 | GLU | 480 | 15.720 | 40.123 | 7.353  | 1.00 | 21.54 |
| ATOM | 2099 | OE2 | GLU | 480 | 17.383 | 39.300 | 8.547  | 1.00 | 20.24 |
| ATOM | 2100 | C   | GLU | 480 | 19.713 | 39.095 | 4.373  | 1.00 | 20.25 |
| ATOM | 2101 | O   | GLU | 480 | 18.875 | 39.368 | 3.508  | 1.00 | 21.34 |
| ATOM | 2102 | N   | ARG | 481 | 20.297 | 37.908 | 4.442  | 1.00 | 19.33 |
| ATOM | 2103 | CA  | ARG | 481 | 19.916 | 36.858 | 3.515  | 1.00 | 18.50 |
| ATOM | 2104 | CB  | ARG | 481 | 21.063 | 35.868 | 3.302  | 1.00 | 18.20 |
| ATOM | 2105 | CG  | ARG | 481 | 22.241 | 36.404 | 2.523  | 1.00 | 15.86 |
| ATOM | 2106 | CD  | ARG | 481 | 23.287 | 35.325 | 2.421  | 1.00 | 15.43 |
| ATOM | 2107 | NE  | ARG | 481 | 23.964 | 35.096 | 3.694  | 1.00 | 14.91 |
| ATOM | 2108 | CZ  | ARG | 481 | 23.950 | 33.946 | 4.367  | 1.00 | 15.54 |
| ATOM | 2109 | NH1 | ARG | 481 | 23.279 | 32.903 | 3.897  | 1.00 | 15.94 |
| ATOM | 2110 | NH2 | ARG | 481 | 24.642 | 33.826 | 5.495  | 1.00 | 11.48 |
| ATOM | 2111 | C   | ARG | 481 | 18.744 | 36.118 | 4.118  | 1.00 | 19.75 |
| ATOM | 2112 | O   | ARG | 481 | 18.698 | 35.898 | 5.332  | 1.00 | 19.19 |
| ATOM | 2113 | N   | PRO | 482 | 17.726 | 35.814 | 3.303  | 1.00 | 21.15 |
| ATOM | 2114 | CD  | PRO | 482 | 17.480 | 36.254 | 1.914  | 1.00 | 21.49 |
| ATOM | 2115 | CA  | PRO | 482 | 16.577 | 35.081 | 3.848  | 1.00 | 21.68 |
| ATOM | 2116 | CB  | PRO | 482 | 15.704 | 34.858 | 2.611  | 1.00 | 21.74 |
| ATOM | 2117 | CG  | PRO | 482 | 15.976 | 36.100 | 1.785  | 1.00 | 22.13 |
| ATOM | 2118 | C   | PRO | 482 | 17.096 | 33.749 | 4.422  | 1.00 | 21.37 |
| ATOM | 2119 | O   | PRO | 482 | 18.049 | 33.166 | 3.896  | 1.00 | 21.05 |
| ATOM | 2120 | N   | SER | 483 | 16.502 | 33.288 | 5.513  | 1.00 | 21.11 |
| ATOM | 2121 | CA  | SER | 483 | 16.942 | 32.048 | 6.133  | 1.00 | 21.78 |
| ATOM | 2122 | CB  | SER | 483 | 16.247 | 31.868 | 7.487  | 1.00 | 21.27 |
| ATOM | 2123 | OG  | SER | 483 | 14.868 | 31.562 | 7.331  | 1.00 | 19.02 |
| ATOM | 2124 | C   | SER | 483 | 16.591 | 30.860 | 5.251  | 1.00 | 22.57 |
| ATOM | 2125 | O   | SER | 483 | 15.780 | 30.983 | 4.343  | 1.00 | 22.97 |
| ATOM | 2126 | N   | GLY | 484 | 17.213 | 29.714 | 5.502  | 1.00 | 24.13 |
| ATOM | 2127 | CA  | GLY | 484 | 16.835 | 28.539 | 4.747  | 1.00 | 26.14 |
| ATOM | 2128 | C   | GLY | 484 | 17.833 | 27.793 | 3.904  | 1.00 | 27.18 |
| ATOM | 2129 | O   | GLY | 484 | 17.500 | 26.727 | 3.387  | 1.00 | 28.70 |
| ATOM | 2130 | N   | MET | 485 | 19.028 | 28.337 | 3.722  | 1.00 | 27.71 |
| ATOM | 2131 | CA  | MET | 485 | 20.027 | 27.653 | 2.913  | 1.00 | 27.75 |
| ATOM | 2132 | CB  | MET | 485 | 20.517 | 28.557 | 1.782  | 1.00 | 30.73 |
| ATOM | 2133 | CG  | MET | 485 | 19.436 | 29.106 | 0.850  | 1.00 | 36.02 |
| ATOM | 2134 | SD  | MET | 485 | 18.683 | 27.861 | -0.207 | 1.00 | 42.25 |
| ATOM | 2135 | CE  | MET | 485 | 20.139 | 26.751 | -0.591 | 1.00 | 41.08 |
| ATOM | 2136 | C   | MET | 485 | 21.221 | 27.259 | 3.759  | 1.00 | 25.81 |
| ATOM | 2137 | O   | MET | 485 | 21.559 | 27.941 | 4.726  | 1.00 | 23.50 |
| ATOM | 2138 | N   | PHE | 486 | 21.812 | 26.116 | 3.443  | 1.00 | 25.36 |
| ATOM | 2139 | CA  | PHE | 486 | 23.018 | 25.693 | 4.138  | 1.00 | 25.36 |
| ATOM | 2140 | CB  | PHE | 486 | 22.746 | 24.797 | 5.359  | 1.00 | 23.40 |
| ATOM | 2141 | CG  | PHE | 486 | 22.193 | 23.445 | 5.035  | 1.00 | 24.70 |

FIGURE 1 (cont.)

| | | | | | | | | |
|---|---|---|---|---|---|---|---|---|
| ATOM | 2142 | CD1 | PHE | 486 | 23.048 | 22.371 | 4.795 | 1.00 25.53 |
| ATOM | 2143 | CD2 | PHE | 486 | 20.822 | 23.226 | 5.034 | 1.00 23.72 |
| ATOM | 2144 | CE1 | PHE | 486 | 22.549 | 21.098 | 4.564 | 1.00 25.73 |
| ATOM | 2145 | CE2 | PHE | 486 | 20.311 | 21.959 | 4.804 | 1.00 25.05 |
| ATOM | 2146 | CZ | PHE | 486 | 21.174 | 20.887 | 4.569 | 1.00 25.77 |
| ATOM | 2147 | C | PHE | 486 | 24.004 | 25.089 | 3.141 | 1.00 24.60 |
| ATOM | 2148 | O | PHE | 486 | 23.616 | 24.599 | 2.075 | 1.00 22.55 |
| ATOM | 2149 | N | ASP | 487 | 25.282 | 25.232 | 3.465 | 1.00 25.33 |
| ATOM | 2150 | CA | ASP | 487 | 26.392 | 24.769 | 2.639 | 1.00 25.56 |
| ATOM | 2151 | CB | ASP | 487 | 27.674 | 25.435 | 3.150 | 1.00 25.82 |
| ATOM | 2152 | CG | ASP | 487 | 28.810 | 25.337 | 2.174 | 1.00 25.43 |
| ATOM | 2153 | OD1 | ASP | 487 | 28.767 | 26.041 | 1.155 | 1.00 26.83 |
| ATOM | 2154 | OD2 | ASP | 487 | 29.752 | 24.568 | 2.421 | 1.00 26.93 |
| ATOM | 2155 | C | ASP | 487 | 26.590 | 23.244 | 2.582 | 1.00 26.12 |
| ATOM | 2156 | O | ASP | 487 | 26.323 | 22.518 | 3.548 | 1.00 26.16 |
| ATOM | 2157 | N | SER | 488 | 27.134 | 22.781 | 1.462 | 1.00 26.57 |
| ATOM | 2158 | CA | SER | 488 | 27.421 | 21.365 | 1.244 | 1.00 26.60 |
| ATOM | 2159 | CB | SER | 488 | 27.972 | 21.165 | -0.173 | 1.00 28.61 |
| ATOM | 2160 | OG | SER | 488 | 28.173 | 19.795 | -0.481 | 1.00 31.93 |
| ATOM | 2161 | C | SER | 488 | 28.421 | 20.838 | 2.286 | 1.00 26.05 |
| ATOM | 2162 | O | SER | 488 | 28.447 | 19.639 | 2.583 | 1.00 26.13 |
| ATOM | 2163 | N | SER | 489 | 29.227 | 21.728 | 2.861 | 1.00 24.66 |
| ATOM | 2164 | CA | SER | 489 | 30.185 | 21.301 | 3.864 | 1.00 22.91 |
| ATOM | 2165 | CB | SER | 489 | 31.078 | 22.459 | 4.300 | 1.00 21.25 |
| ATOM | 2166 | OG | SER | 489 | 30.310 | 23.551 | 4.768 | 1.00 21.37 |
| ATOM | 2167 | C | SER | 489 | 29.422 | 20.737 | 5.062 | 1.00 23.17 |
| ATOM | 2168 | O | SER | 489 | 29.978 | 19.963 | 5.846 | 1.00 24.42 |
| ATOM | 2169 | N | VAL | 490 | 28.156 | 21.129 | 5.216 | 1.00 21.89 |
| ATOM | 2170 | CA | VAL | 490 | 27.363 | 20.620 | 6.324 | 1.00 21.05 |
| ATOM | 2171 | CB | VAL | 490 | 26.038 | 21.396 | 6.522 | 1.00 21.77 |
| ATOM | 2172 | CG1 | VAL | 490 | 25.220 | 20.725 | 7.598 | 1.00 20.51 |
| ATOM | 2173 | CG2 | VAL | 490 | 26.314 | 22.853 | 6.931 | 1.00 20.48 |
| ATOM | 2174 | C | VAL | 490 | 27.088 | 19.147 | 6.051 | 1.00 20.91 |
| ATOM | 2175 | O | VAL | 490 | 27.114 | 18.341 | 6.973 | 1.00 22.47 |
| ATOM | 2176 | N | LEU | 491 | 26.879 | 18.793 | 4.779 | 1.00 21.01 |
| ATOM | 2177 | CA | LEU | 491 | 26.636 | 17.397 | 4.390 | 1.00 21.10 |
| ATOM | 2178 | CB | LEU | 491 | 26.283 | 17.289 | 2.909 | 1.00 20.22 |
| ATOM | 2179 | CG | LEU | 491 | 25.006 | 18.026 | 2.505 | 1.00 22.49 |
| ATOM | 2180 | CD1 | LEU | 491 | 24.743 | 17.853 | 1.014 | 1.00 20.45 |
| ATOM | 2181 | CD2 | LEU | 491 | 23.829 | 17.495 | 3.329 | 1.00 21.46 |
| ATOM | 2182 | C | LEU | 491 | 27.900 | 16.594 | 4.686 | 1.00 20.78 |
| ATOM | 2183 | O | LEU | 491 | 27.843 | 15.522 | 5.292 | 1.00 22.36 |
| ATOM | 2184 | N | CYS | 492 | 29.046 | 17.138 | 4.291 | 1.00 19.79 |
| ATOM | 2185 | CA | CYS | 492 | 30.317 | 16.491 | 4.556 | 1.00 19.65 |
| ATOM | 2186 | CB | CYS | 492 | 31.468 | 17.390 | 4.092 | 1.00 18.82 |
| ATOM | 2187 | SG | CYS | 492 | 33.106 | 16.704 | 4.401 | 1.00 20.38 |
| ATOM | 2188 | C | CYS | 492 | 30.413 | 16.274 | 6.067 | 1.00 19.87 |
| ATOM | 2189 | O | CYS | 492 | 30.801 | 15.205 | 6.537 | 1.00 20.08 |
| ATOM | 2190 | N | GLU | 493 | 29.997 | 17.289 | 6.817 | 1.00 21.33 |
| ATOM | 2191 | CA | GLU | 493 | 30.028 | 17.262 | 8.274 | 1.00 22.71 |
| ATOM | 2192 | CB | GLU | 493 | 29.724 | 18.648 | 8.830 | 1.00 24.31 |
| ATOM | 2193 | CG | GLU | 493 | 30.165 | 18.820 | 10.269 | 1.00 28.02 |
| ATOM | 2194 | CD | GLU | 493 | 30.042 | 20.247 | 10.763 | 1.00 29.49 |
| ATOM | 2195 | OE1 | GLU | 493 | 29.269 | 21.030 | 10.166 | 1.00 31.62 |
| ATOM | 2196 | OE2 | GLU | 493 | 30.720 | 20.585 | 11.758 | 1.00 32.33 |
| ATOM | 2197 | C | GLU | 493 | 29.074 | 16.229 | 8.862 | 1.00 21.21 |
| ATOM | 2198 | O | GLU | 493 | 29.344 | 15.663 | 9.925 | 1.00 21.52 |
| ATOM | 2199 | N | CYS | 494 | 27.975 | 15.969 | 8.161 | 1.00 20.48 |

FIGURE 1 (cont.)

| | | | | | | | | |
|---|---|---|---|---|---|---|---|---|
| ATOM | 2200 | CA | CYS | 494 | 27.008 | 14.970 | 8.611 | 1.00 20.92 |
| ATOM | 2201 | CB | CYS | 494 | 25.690 | 15.097 | 7.830 | 1.00 20.47 |
| ATOM | 2202 | SG | CYS | 494 | 24.630 | 16.512 | 8.329 | 1.00 19.52 |
| ATOM | 2203 | C | CYS | 494 | 27.616 | 13.565 | 8.471 | 1.00 20.64 |
| ATOM | 2204 | O | CYS | 494 | 27.548 | 12.750 | 9.404 | 1.00 21.39 |
| ATOM | 2205 | N | TYR | 495 | 28.240 | 13.296 | 7.324 | 1.00 18.97 |
| ATOM | 2206 | CA | TYR | 495 | 28.886 | 12.008 | 7.092 | 1.00 20.35 |
| ATOM | 2207 | CB | TYR | 495 | 29.372 | 11.918 | 5.645 | 1.00 19.37 |
| ATOM | 2208 | CG | TYR | 495 | 28.260 | 11.676 | 4.653 | 1.00 19.50 |
| ATOM | 2209 | CD1 | TYR | 495 | 27.606 | 12.740 | 4.038 | 1.00 19.12 |
| ATOM | 2210 | CE1 | TYR | 495 | 26.557 | 12.524 | 3.146 | 1.00 18.63 |
| ATOM | 2211 | CD2 | TYR | 495 | 27.840 | 10.378 | 4.348 | 1.00 18.29 |
| ATOM | 2212 | CE2 | TYR | 495 | 26.794 | 10.154 | 3.461 | 1.00 18.31 |
| ATOM | 2213 | CZ | TYR | 495 | 26.158 | 11.229 | 2.866 | 1.00 18.52 |
| ATOM | 2214 | OH | TYR | 495 | 25.114 | 11.014 | 1.997 | 1.00 22.20 |
| ATOM | 2215 | C | TYR | 495 | 30.060 | 11.804 | 8.059 | 1.00 20.52 |
| ATOM | 2216 | O | TYR | 495 | 30.287 | 10.708 | 8.572 | 1.00 20.61 |
| ATOM | 2217 | N | ASP | 496 | 30.804 | 12.874 | 8.302 | 1.00 21.88 |
| ATOM | 2218 | CA | ASP | 496 | 31.934 | 12.834 | 9.212 | 1.00 23.32 |
| ATOM | 2219 | CB | ASP | 496 | 32.631 | 14.204 | 9.212 | 1.00 25.74 |
| ATOM | 2220 | CG | ASP | 496 | 33.981 | 14.190 | 9.928 | 1.00 28.22 |
| ATOM | 2221 | OD1 | ASP | 496 | 35.028 | 14.310 | 9.252 | 1.00 27.49 |
| ATOM | 2222 | OD2 | ASP | 496 | 33.995 | 14.083 | 11.172 | 1.00 29.66 |
| ATOM | 2223 | C | ASP | 496 | 31.433 | 12.459 | 10.613 | 1.00 24.14 |
| ATOM | 2224 | O | ASP | 496 | 32.051 | 11.639 | 11.302 | 1.00 24.65 |
| ATOM | 2225 | N | ALA | 497 | 30.291 | 13.023 | 11.007 | 1.00 25.27 |
| ATOM | 2226 | CA | ALA | 497 | 29.685 | 12.758 | 12.322 | 1.00 25.04 |
| ATOM | 2227 | CB | ALA | 497 | 28.555 | 13.746 | 12.592 | 1.00 26.49 |
| ATOM | 2228 | C | ALA | 497 | 29.169 | 11.327 | 12.464 | 1.00 25.23 |
| ATOM | 2229 | O | ALA | 497 | 29.274 | 10.718 | 13.540 | 1.00 24.69 |
| ATOM | 2230 | N | GLY | 498 | 28.571 | 10.807 | 11.397 | 1.00 24.53 |
| ATOM | 2231 | CA | GLY | 498 | 28.077 | 9.443 | 11.433 | 1.00 25.39 |
| ATOM | 2232 | C | GLY | 498 | 29.231 | 8.490 | 11.695 | 1.00 25.40 |
| ATOM | 2233 | O | GLY | 498 | 29.164 | 7.619 | 12.567 | 1.00 24.85 |
| ATOM | 2234 | N | CME | 499 | 30.314 | 8.708 | 10.960 | 1.00 25.32 |
| ATOM | 2235 | CA | CME | 499 | 31.527 | 7.908 | 11.068 | 1.00 25.32 |
| ATOM | 2236 | C | CME | 499 | 32.278 | 8.088 | 12.377 | 1.00 23.75 |
| ATOM | 2237 | O | CME | 499 | 32.746 | 7.116 | 12.958 | 1.00 23.80 |
| ATOM | 2238 | CB | CME | 499 | 32.475 | 8.244 | 9.917 | 1.00 25.58 |
| ATOM | 2239 | SG | CME | 499 | 31.828 | 7.806 | 8.284 | 1.00 25.23 |
| ATOM | 2240 | 2SG | CME | 499 | 31.898 | 5.788 | 8.347 | 1.00 25.26 |
| ATOM | 2241 | 2CB | CME | 499 | 33.623 | 5.432 | 7.900 | 1.00 22.20 |
| ATOM | 2242 | 2CA | CME | 499 | 33.954 | 5.815 | 6.487 | 1.00 20.21 |
| ATOM | 2243 | OG | CME | 499 | 33.382 | 4.900 | 5.576 | 1.00 20.89 |
| ATOM | 2244 | N | ALA | 500 | 32.397 | 9.329 | 12.835 | 1.00 23.46 |
| ATOM | 2245 | CA | ALA | 500 | 33.126 | 9.619 | 14.068 | 1.00 23.38 |
| ATOM | 2246 | CB | ALA | 500 | 33.626 | 11.066 | 14.060 | 1.00 22.52 |
| ATOM | 2247 | C | ALA | 500 | 32.359 | 9.351 | 15.349 | 1.00 25.43 |
| ATOM | 2248 | O | ALA | 500 | 32.889 | 8.739 | 16.279 | 1.00 25.86 |
| ATOM | 2249 | N | TRP | 501 | 31.102 | 9.781 | 15.392 | 1.00 27.22 |
| ATOM | 2250 | CA | TRP | 501 | 30.303 | 9.623 | 16.601 | 1.00 28.60 |
| ATOM | 2251 | CB | TRP | 501 | 29.788 | 10.983 | 17.057 | 1.00 27.51 |
| ATOM | 2252 | CG | TRP | 501 | 30.851 | 11.978 | 17.305 | 1.00 25.74 |
| ATOM | 2253 | CD2 | TRP | 501 | 31.598 | 12.149 | 18.510 | 1.00 23.93 |
| ATOM | 2254 | CE2 | TRP | 501 | 32.450 | 13.254 | 18.319 | 1.00 24.45 |
| ATOM | 2255 | CE3 | TRP | 501 | 31.631 | 11.477 | 19.732 | 1.00 23.70 |
| ATOM | 2256 | CD1 | TRP | 501 | 31.270 | 12.947 | 16.450 | 1.00 25.45 |
| ATOM | 2257 | NE1 | TRP | 501 | 32.230 | 13.725 | 17.052 | 1.00 26.50 |

FIGURE 1 (cont.)

| ATOM | 2258 | CZ2 | TRP | 501 | 33.319 | 13.706 | 19.304 | 1.00 | 24.88 |
|---|---|---|---|---|---|---|---|---|---|
| ATOM | 2259 | CZ3 | TRP | 501 | 32.498 | 11.924 | 20.712 | 1.00 | 24.31 |
| ATOM | 2260 | CH2 | TRP | 501 | 33.331 | 13.028 | 20.493 | 1.00 | 25.27 |
| ATOM | 2261 | C | TRP | 501 | 29.116 | 8.675 | 16.639 | 1.00 | 29.45 |
| ATOM | 2262 | O | TRP | 501 | 28.799 | 8.155 | 17.708 | 1.00 | 31.24 |
| ATOM | 2263 | N | TYR | 502 | 28.452 | 8.442 | 15.512 | 1.00 | 29.45 |
| ATOM | 2264 | CA | TYR | 502 | 27.244 | 7.623 | 15.556 | 1.00 | 28.83 |
| ATOM | 2265 | CB | TYR | 502 | 26.064 | 8.418 | 14.987 | 1.00 | 26.77 |
| ATOM | 2266 | CG | TYR | 502 | 25.962 | 9.775 | 15.638 | 1.00 | 26.30 |
| ATOM | 2267 | CD1 | TYR | 502 | 26.177 | 10.940 | 14.907 | 1.00 | 25.61 |
| ATOM | 2268 | CE1 | TYR | 502 | 26.215 | 12.178 | 15.534 | 1.00 | 26.43 |
| ATOM | 2269 | CD2 | TYR | 502 | 25.768 | 9.888 | 17.019 | 1.00 | 25.72 |
| ATOM | 2270 | CE2 | TYR | 502 | 25.804 | 11.118 | 17.655 | 1.00 | 26.34 |
| ATOM | 2271 | CZ | TYR | 502 | 26.031 | 12.258 | 16.908 | 1.00 | 26.72 |
| ATOM | 2272 | OH | TYR | 502 | 26.103 | 13.475 | 17.541 | 1.00 | 29.21 |
| ATOM | 2273 | C | TYR | 502 | 27.268 | 6.226 | 15.004 | 1.00 | 29.90 |
| ATOM | 2274 | O | TYR | 502 | 26.218 | 5.623 | 14.808 | 1.00 | 30.51 |
| ATOM | 2275 | N | GLU | 503 | 28.459 | 5.688 | 14.795 | 1.00 | 30.61 |
| ATOM | 2276 | CA | GLU | 503 | 28.585 | 4.337 | 14.272 | 1.00 | 31.76 |
| ATOM | 2277 | CB | GLU | 503 | 28.115 | 3.320 | 15.300 | 1.00 | 33.16 |
| ATOM | 2278 | CG | GLU | 503 | 28.959 | 3.248 | 16.531 | 1.00 | 37.65 |
| ATOM | 2279 | CD | GLU | 503 | 28.810 | 1.913 | 17.218 | 1.00 | 42.70 |
| ATOM | 2280 | OE1 | GLU | 503 | 27.654 | 1.459 | 17.415 | 1.00 | 44.39 |
| ATOM | 2281 | OE2 | GLU | 503 | 29.854 | 1.304 | 17.541 | 1.00 | 46.49 |
| ATOM | 2282 | C | GLU | 503 | 27.781 | 4.150 | 13.008 | 1.00 | 30.99 |
| ATOM | 2283 | O | GLU | 503 | 27.274 | 3.062 | 12.740 | 1.00 | 32.02 |
| ATOM | 2284 | N | LEU | 504 | 27.670 | 5.212 | 12.224 | 1.00 | 31.39 |
| ATOM | 2285 | CA | LEU | 504 | 26.905 | 5.147 | 10.992 | 1.00 | 29.95 |
| ATOM | 2286 | CB | LEU | 504 | 25.963 | 6.351 | 10.864 | 1.00 | 26.33 |
| ATOM | 2287 | CG | LEU | 504 | 24.920 | 6.570 | 11.959 | 1.00 | 24.35 |
| ATOM | 2288 | CD1 | LEU | 504 | 24.128 | 7.804 | 11.624 | 1.00 | 24.54 |
| ATOM | 2289 | CD2 | LEU | 504 | 24.006 | 5.375 | 12.084 | 1.00 | 22.44 |
| ATOM | 2290 | C | LEU | 504 | 27.752 | 5.034 | 9.736 | 1.00 | 31.09 |
| ATOM | 2291 | O | LEU | 504 | 28.750 | 5.747 | 9.556 | 1.00 | 32.06 |
| ATOM | 2292 | N | THR | 505 | 27.323 | 4.116 | 8.883 | 1.00 | 29.82 |
| ATOM | 2293 | CA | THR | 505 | 27.918 | 3.847 | 7.590 | 1.00 | 28.87 |
| ATOM | 2294 | CB | THR | 505 | 27.336 | 2.520 | 7.067 | 1.00 | 29.51 |
| ATOM | 2295 | OG1 | THR | 505 | 27.897 | 1.429 | 7.806 | 1.00 | 32.11 |
| ATOM | 2296 | CG2 | THR | 505 | 27.595 | 2.337 | 5.612 | 1.00 | 31.82 |
| ATOM | 2297 | C | THR | 505 | 27.475 | 4.989 | 6.672 | 1.00 | 27.43 |
| ATOM | 2298 | O | THR | 505 | 26.390 | 5.542 | 6.857 | 1.00 | 28.06 |
| ATOM | 2299 | N | PRO | 506 | 28.302 | 5.367 | 5.680 | 1.00 | 26.19 |
| ATOM | 2300 | CD | PRO | 506 | 29.680 | 4.930 | 5.378 | 1.00 | 25.34 |
| ATOM | 2301 | CA | PRO | 506 | 27.895 | 6.456 | 4.784 | 1.00 | 24.28 |
| ATOM | 2302 | CB | PRO | 506 | 29.007 | 6.460 | 3.734 | 1.00 | 24.62 |
| ATOM | 2303 | CG | PRO | 506 | 30.212 | 6.083 | 4.533 | 1.00 | 23.11 |
| ATOM | 2304 | C | PRO | 506 | 26.529 | 6.153 | 4.165 | 1.00 | 24.09 |
| ATOM | 2305 | O | PRO | 506 | 25.705 | 7.046 | 3.990 | 1.00 | 22.93 |
| ATOM | 2306 | N | ALA | 507 | 26.291 | 4.880 | 3.855 | 1.00 | 24.47 |
| ATOM | 2307 | CA | ALA | 507 | 25.018 | 4.448 | 3.283 | 1.00 | 23.40 |
| ATOM | 2308 | CB | ALA | 507 | 25.079 | 2.968 | 2.912 | 1.00 | 22.03 |
| ATOM | 2309 | C | ALA | 507 | 23.871 | 4.715 | 4.269 | 1.00 | 23.01 |
| ATOM | 2310 | O | ALA | 507 | 22.786 | 5.133 | 3.866 | 1.00 | 22.45 |
| ATOM | 2311 | N | GLU | 508 | 24.123 | 4.488 | 5.555 | 1.00 | 22.85 |
| ATOM | 2312 | CA | GLU | 508 | 23.125 | 4.724 | 6.596 | 1.00 | 25.62 |
| ATOM | 2313 | CB | GLU | 508 | 23.593 | 4.149 | 7.936 | 1.00 | 26.13 |
| ATOM | 2314 | CG | GLU | 508 | 23.710 | 2.638 | 7.941 | 1.00 | 30.10 |
| ATOM | 2315 | CD | GLU | 508 | 24.322 | 2.069 | 9.217 | 1.00 | 32.11 |

FIGURE 1 (cont.)

| ATOM | 2316 | OE1 | GLU | 508 | 24.722 | 2.840 | 10.110 | 1.00 | 34.14 |
|---|---|---|---|---|---|---|---|---|---|
| ATOM | 2317 | OE2 | GLU | 508 | 24.406 | 0.828 | 9.323 | 1.00 | 35.16 |
| ATOM | 2318 | C | GLU | 508 | 22.849 | 6.222 | 6.743 | 1.00 | 26.03 |
| ATOM | 2319 | O | GLU | 508 | 21.694 | 6.635 | 6.843 | 1.00 | 26.78 |
| ATOM | 2320 | N | THR | 509 | 23.912 | 7.025 | 6.773 | 1.00 | 25.74 |
| ATOM | 2321 | CA | THR | 509 | 23.785 | 8.474 | 6.882 | 1.00 | 24.39 |
| ATOM | 2322 | CB | THR | 509 | 25.168 | 9.148 | 6.907 | 1.00 | 23.11 |
| ATOM | 2323 | OG1 | THR | 509 | 25.853 | 8.790 | 8.113 | 1.00 | 20.57 |
| ATOM | 2324 | CG2 | THR | 509 | 25.035 | 10.659 | 6.828 | 1.00 | 22.40 |
| ATOM | 2325 | C | THR | 509 | 22.973 | 9.000 | 5.692 | 1.00 | 25.46 |
| ATOM | 2326 | O | THR | 509 | 22.129 | 9.886 | 5.853 | 1.00 | 27.07 |
| ATOM | 2327 | N | THR | 510 | 23.193 | 8.421 | 4.513 | 1.00 | 24.22 |
| ATOM | 2328 | CA | THR | 510 | 22.471 | 8.825 | 3.314 | 1.00 | 23.80 |
| ATOM | 2329 | CB | THR | 510 | 22.992 | 8.074 | 2.087 | 1.00 | 23.34 |
| ATOM | 2330 | OG1 | THR | 510 | 24.355 | 8.443 | 1.855 | 1.00 | 26.59 |
| ATOM | 2331 | CG2 | THR | 510 | 22.193 | 8.429 | 0.870 | 1.00 | 22.93 |
| ATOM | 2332 | C | THR | 510 | 20.961 | 8.624 | 3.457 | 1.00 | 23.48 |
| ATOM | 2333 | O | THR | 510 | 20.174 | 9.456 | 3.013 | 1.00 | 23.82 |
| ATOM | 2334 | N | VAL | 511 | 20.565 | 7.529 | 4.098 | 1.00 | 24.04 |
| ATOM | 2335 | CA | VAL | 511 | 19.157 | 7.216 | 4.321 | 1.00 | 23.83 |
| ATOM | 2336 | CB | VAL | 511 | 19.019 | 5.872 | 5.072 | 1.00 | 25.13 |
| ATOM | 2337 | CG1 | VAL | 511 | 17.577 | 5.644 | 5.509 | 1.00 | 24.67 |
| ATOM | 2338 | CG2 | VAL | 511 | 19.480 | 4.729 | 4.168 | 1.00 | 24.94 |
| ATOM | 2339 | C | VAL | 511 | 18.482 | 8.329 | 5.122 | 1.00 | 22.86 |
| ATOM | 2340 | O | VAL | 511 | 17.391 | 8.783 | 4.783 | 1.00 | 23.35 |
| ATOM | 2341 | N | ARG | 512 | 19.160 | 8.779 | 6.168 | 1.00 | 22.63 |
| ATOM | 2342 | CA | ARG | 512 | 18.663 | 9.843 | 7.028 | 1.00 | 22.06 |
| ATOM | 2343 | CB | ARG | 512 | 19.465 | 9.846 | 8.325 | 1.00 | 20.58 |
| ATOM | 2344 | CG | ARG | 512 | 19.312 | 8.538 | 9.080 | 1.00 | 21.48 |
| ATOM | 2345 | CD | ARG | 512 | 20.435 | 8.307 | 10.076 | 1.00 | 22.08 |
| ATOM | 2346 | NE | ARG | 512 | 20.375 | 6.949 | 10.602 | 1.00 | 22.43 |
| ATOM | 2347 | CZ | ARG | 512 | 20.475 | 6.631 | 11.889 | 1.00 | 24.44 |
| ATOM | 2348 | NH1 | ARG | 512 | 20.401 | 5.361 | 12.262 | 1.00 | 24.03 |
| ATOM | 2349 | NH2 | ARG | 512 | 20.666 | 7.574 | 12.804 | 1.00 | 26.08 |
| ATOM | 2350 | C | ARG | 512 | 18.693 | 11.222 | 6.348 | 1.00 | 22.38 |
| ATOM | 2351 | O | ARG | 512 | 17.727 | 11.990 | 6.424 | 1.00 | 20.41 |
| ATOM | 2352 | N | LEU | 513 | 19.788 | 11.524 | 5.657 | 1.00 | 23.97 |
| ATOM | 2353 | CA | LEU | 513 | 19.907 | 12.802 | 4.970 | 1.00 | 23.82 |
| ATOM | 2354 | CB | LEU | 513 | 21.351 | 13.042 | 4.511 | 1.00 | 23.01 |
| ATOM | 2355 | CG | LEU | 513 | 22.412 | 13.142 | 5.619 | 1.00 | 22.43 |
| ATOM | 2356 | CD1 | LEU | 513 | 23.758 | 13.482 | 5.030 | 1.00 | 20.55 |
| ATOM | 2357 | CD2 | LEU | 513 | 22.027 | 14.191 | 6.637 | 1.00 | 21.42 |
| ATOM | 2358 | C | LEU | 513 | 18.923 | 12.860 | 3.800 | 1.00 | 23.93 |
| ATOM | 2359 | O | LEU | 513 | 18.388 | 13.917 | 3.481 | 1.00 | 26.02 |
| ATOM | 2360 | N | ARG | 514 | 18.641 | 11.714 | 3.196 | 1.00 | 23.65 |
| ATOM | 2361 | CA | ARG | 514 | 17.697 | 11.653 | 2.086 | 1.00 | 23.31 |
| ATOM | 2362 | CB | ARG | 514 | 17.726 | 10.259 | 1.461 | 1.00 | 24.64 |
| ATOM | 2363 | CG | ARG | 514 | 16.779 | 10.063 | 0.294 | 1.00 | 27.95 |
| ATOM | 2364 | CD | ARG | 514 | 17.055 | 11.033 | -0.848 | 1.00 | 31.79 |
| ATOM | 2365 | NE | ARG | 514 | 18.388 | 10.876 | -1.430 | 1.00 | 34.83 |
| ATOM | 2366 | CZ | ARG | 514 | 19.048 | 11.847 | -2.057 | 1.00 | 35.11 |
| ATOM | 2367 | NH1 | ARG | 514 | 20.251 | 11.608 | -2.561 | 1.00 | 36.73 |
| ATOM | 2368 | NH2 | ARG | 514 | 18.523 | 13.067 | -2.154 | 1.00 | 34.98 |
| ATOM | 2369 | C | ARG | 514 | 16.289 | 11.997 | 2.595 | 1.00 | 23.18 |
| ATOM | 2370 | O | ARG | 514 | 15.598 | 12.822 | 2.010 | 1.00 | 23.43 |
| ATOM | 2371 | N | ALA | 515 | 15.892 | 11.396 | 3.714 | 1.00 | 22.98 |
| ATOM | 2372 | CA | ALA | 515 | 14.585 | 11.648 | 4.319 | 1.00 | 23.14 |
| ATOM | 2373 | CB | ALA | 515 | 14.434 | 10.836 | 5.587 | 1.00 | 22.55 |

FIGURE 1 (cont.)

| | | | | | | | | | |
|---|---|---|---|---|---|---|---|---|---|
| ATOM | 2374 | C   | ALA | 515 | 14.430 | 13.135 | 4.630  | 1.00 | 23.92 |
| ATOM | 2375 | O   | ALA | 515 | 13.382 | 13.721 | 4.379  | 1.00 | 23.30 |
| ATOM | 2376 | N   | TYR | 516 | 15.483 | 13.734 | 5.181  | 1.00 | 24.72 |
| ATOM | 2377 | CA  | TYR | 516 | 15.493 | 15.157 | 5.505  | 1.00 | 24.73 |
| ATOM | 2378 | CB  | TYR | 516 | 16.860 | 15.537 | 6.077  | 1.00 | 20.83 |
| ATOM | 2379 | CG  | TYR | 516 | 16.997 | 16.989 | 6.481  | 1.00 | 21.19 |
| ATOM | 2380 | CD1 | TYR | 516 | 16.811 | 17.385 | 7.805  | 1.00 | 19.78 |
| ATOM | 2381 | CE1 | TYR | 516 | 16.966 | 18.717 | 8.189  | 1.00 | 18.78 |
| ATOM | 2382 | CD2 | TYR | 516 | 17.340 | 17.971 | 5.545  | 1.00 | 20.90 |
| ATOM | 2383 | CE2 | TYR | 516 | 17.493 | 19.308 | 5.924  | 1.00 | 20.29 |
| ATOM | 2384 | CZ  | TYR | 516 | 17.305 | 19.662 | 7.246  | 1.00 | 18.46 |
| ATOM | 2385 | OH  | TYR | 516 | 17.473 | 20.960 | 7.626  | 1.00 | 21.53 |
| ATOM | 2386 | C   | TYR | 516 | 15.213 | 15.963 | 4.226  | 1.00 | 26.41 |
| ATOM | 2387 | O   | TYR | 516 | 14.390 | 16.883 | 4.218  | 1.00 | 26.36 |
| ATOM | 2388 | N   | MET | 517 | 15.893 | 15.594 | 3.146  | 1.00 | 27.82 |
| ATOM | 2389 | CA  | MET | 517 | 15.736 | 16.268 | 1.868  | 1.00 | 29.62 |
| ATOM | 2390 | CB  | MET | 517 | 16.897 | 15.910 | 0.929  | 1.00 | 32.52 |
| ATOM | 2391 | CG  | MET | 517 | 18.257 | 16.449 | 1.415  | 1.00 | 36.99 |
| ATOM | 2392 | SD  | MET | 517 | 19.641 | 16.357 | 0.240  | 1.00 | 42.11 |
| ATOM | 2393 | CE  | MET | 517 | 19.692 | 18.060 | -0.335 | 1.00 | 41.79 |
| ATOM | 2394 | C   | MET | 517 | 14.394 | 15.971 | 1.215  | 1.00 | 30.17 |
| ATOM | 2395 | O   | MET | 517 | 13.863 | 16.793 | 0.484  | 1.00 | 31.65 |
| ATOM | 2396 | N   | ASN | 518 | 13.824 | 14.813 | 1.507  | 1.00 | 30.49 |
| ATOM | 2397 | CA  | ASN | 518 | 12.543 | 14.455 | 0.926  | 1.00 | 31.49 |
| ATOM | 2398 | CB  | ASN | 518 | 12.338 | 12.941 | 0.965  | 1.00 | 33.77 |
| ATOM | 2399 | CG  | ASN | 518 | 12.983 | 12.236 | -0.210 | 1.00 | 35.89 |
| ATOM | 2400 | OD1 | ASN | 518 | 13.269 | 12.852 | -1.245 | 1.00 | 36.28 |
| ATOM | 2401 | ND2 | ASN | 518 | 13.204 | 10.929 | -0.065 | 1.00 | 35.87 |
| ATOM | 2402 | C   | ASN | 518 | 11.359 | 15.146 | 1.585  | 1.00 | 32.06 |
| ATOM | 2403 | O   | ASN | 518 | 10.242 | 15.100 | 1.059  | 1.00 | 33.11 |
| ATOM | 2404 | N   | THR | 519 | 11.568 | 15.770 | 2.740  | 1.00 | 31.41 |
| ATOM | 2405 | CA  | THR | 519 | 10.453 | 16.441 | 3.389  | 1.00 | 29.95 |
| ATOM | 2406 | CB  | THR | 519 | 10.353 | 16.087 | 4.881  | 1.00 | 30.80 |
| ATOM | 2407 | OG1 | THR | 519 | 11.403 | 16.723 | 5.606  | 1.00 | 36.48 |
| ATOM | 2408 | CG2 | THR | 519 | 10.477 | 14.588 | 5.069  | 1.00 | 32.01 |
| ATOM | 2409 | C   | THR | 519 | 10.435 | 17.955 | 3.166  | 1.00 | 28.51 |
| ATOM | 2410 | O   | THR | 519 | 11.380 | 18.678 | 3.509  | 1.00 | 27.20 |
| ATOM | 2411 | N   | PRO | 520 | 9.361  | 18.447 | 2.528  | 1.00 | 27.84 |
| ATOM | 2412 | CD  | PRO | 520 | 8.275  | 17.657 | 1.919  | 1.00 | 27.48 |
| ATOM | 2413 | CA  | PRO | 520 | 9.185  | 19.869 | 2.236  | 1.00 | 25.32 |
| ATOM | 2414 | CB  | PRO | 520 | 7.850  | 19.891 | 1.491  | 1.00 | 25.57 |
| ATOM | 2415 | CG  | PRO | 520 | 7.812  | 18.568 | 0.806  | 1.00 | 25.28 |
| ATOM | 2416 | C   | PRO | 520 | 9.117  | 20.740 | 3.482  | 1.00 | 24.11 |
| ATOM | 2417 | O   | PRO | 520 | 8.695  | 20.294 | 4.544  | 1.00 | 24.19 |
| ATOM | 2418 | N   | GLY | 521 | 9.553  | 21.985 | 3.341  | 1.00 | 23.43 |
| ATOM | 2419 | CA  | GLY | 521 | 9.491  | 22.931 | 4.437  | 1.00 | 23.18 |
| ATOM | 2420 | C   | GLY | 521 | 10.708 | 23.045 | 5.313  | 1.00 | 23.53 |
| ATOM | 2421 | O   | GLY | 521 | 10.690 | 23.813 | 6.279  | 1.00 | 23.92 |
| ATOM | 2422 | N   | LEU | 522 | 11.744 | 22.267 | 5.010  | 1.00 | 23.75 |
| ATOM | 2423 | CA  | LEU | 522 | 12.985 | 22.293 | 5.783  | 1.00 | 21.75 |
| ATOM | 2424 | CB  | LEU | 522 | 13.448 | 20.860 | 6.099  | 1.00 | 20.22 |
| ATOM | 2425 | CG  | LEU | 522 | 12.696 | 20.053 | 7.166  | 1.00 | 19.37 |
| ATOM | 2426 | CD1 | LEU | 522 | 13.320 | 18.681 | 7.255  | 1.00 | 18.45 |
| ATOM | 2427 | CD2 | LEU | 522 | 12.754 | 20.739 | 8.521  | 1.00 | 17.70 |
| ATOM | 2428 | C   | LEU | 522 | 14.076 | 23.051 | 5.029  | 1.00 | 19.66 |
| ATOM | 2429 | O   | LEU | 522 | 13.898 | 23.398 | 3.867  | 1.00 | 19.67 |
| ATOM | 2430 | N   | PRO | 523 | 15.157 | 23.439 | 5.725  | 1.00 | 18.95 |
| ATOM | 2431 | CD  | PRO | 523 | 15.328 | 23.445 | 7.187  | 1.00 | 16.62 |

FIGURE 1 (cont.)

```
ATOM   2432  CA   PRO  523      16.255   24.159    5.073  1.00 20.39
ATOM   2433  CB   PRO  523      17.270   24.305    6.208  1.00 19.00
ATOM   2434  CG   PRO  523      16.387   24.512    7.380  1.00 19.06
ATOM   2435  C    PRO  523      16.814   23.317    3.912  1.00 22.86
ATOM   2436  O    PRO  523      16.822   22.083    3.981  1.00 23.38
ATOM   2437  N    VAL  524      17.302   23.973    2.862  1.00 25.30
ATOM   2438  CA   VAL  524      17.819   23.250    1.707  1.00 27.02
ATOM   2439  CB   VAL  524      16.986   23.556    0.438  1.00 27.40
ATOM   2440  CG1  VAL  524      15.537   23.193    0.671  1.00 26.10
ATOM   2441  CG2  VAL  524      17.098   25.016    0.066  1.00 29.26
ATOM   2442  C    VAL  524      19.302   23.426    1.391  1.00 27.30
ATOM   2443  O    VAL  524      19.912   24.461    1.674  1.00 27.05
ATOM   2444  N    CYS  525      19.866   22.377    0.809  1.00 28.81
ATOM   2445  CA   CYS  525      21.260   22.331    0.397  1.00 30.97
ATOM   2446  CB   CYS  525      22.095   21.541    1.401  1.00 32.28
ATOM   2447  SG   CYS  525      21.430   19.886    1.803  1.00 38.03
ATOM   2448  C    CYS  525      21.285   21.617   -0.948  1.00 31.93
ATOM   2449  O    CYS  525      20.280   21.019   -1.365  1.00 31.91
ATOM   2450  N    GLN  526      22.416   21.699   -1.639  1.00 32.52
ATOM   2451  CA   GLN  526      22.557   21.053   -2.932  1.00 33.47
ATOM   2452  CB   GLN  526      23.831   21.525   -3.622  1.00 36.06
ATOM   2453  CG   GLN  526      23.797   22.989   -4.028  1.00 39.05
ATOM   2454  CD   GLN  526      25.143   23.497   -4.519  1.00 43.09
ATOM   2455  OE1  GLN  526      26.181   22.863   -4.302  1.00 44.20
ATOM   2456  NE2  GLN  526      25.134   24.648   -5.181  1.00 45.25
ATOM   2457  C    GLN  526      22.588   19.553   -2.709  1.00 32.95
ATOM   2458  O    GLN  526      23.203   19.070   -1.757  1.00 33.73
ATOM   2459  N    ASP  527      21.915   18.816   -3.580  1.00 32.09
ATOM   2460  CA   ASP  527      21.857   17.372   -3.459  1.00 31.50
ATOM   2461  CB   ASP  527      20.800   16.819   -4.421  1.00 33.07
ATOM   2462  CG   ASP  527      20.444   15.364   -4.145  1.00 34.64
ATOM   2463  OD1  ASP  527      19.441   14.898   -4.729  1.00 37.28
ATOM   2464  OD2  ASP  527      21.152   14.684   -3.363  1.00 36.58
ATOM   2465  C    ASP  527      23.220   16.747   -3.740  1.00 30.96
ATOM   2466  O    ASP  527      23.507   16.370   -4.877  1.00 30.98
ATOM   2467  N    HIS  528      24.070   16.673   -2.716  1.00 29.78
ATOM   2468  CA   HIS  528      25.408   16.079   -2.856  1.00 28.64
ATOM   2469  CB   HIS  528      26.500   17.060   -2.445  1.00 26.18
ATOM   2470  CG   HIS  528      26.610   18.248   -3.333  1.00 23.97
ATOM   2471  CD2  HIS  528      25.951   18.579   -4.468  1.00 23.60
ATOM   2472  ND1  HIS  528      27.483   19.281   -3.077  1.00 23.80
ATOM   2473  CE1  HIS  528      27.357   20.202   -4.015  1.00 24.23
ATOM   2474  NE2  HIS  528      26.433   19.801   -4.870  1.00 25.47
ATOM   2475  C    HIS  528      25.556   14.840   -1.997  1.00 28.65
ATOM   2476  O    HIS  528      26.657   14.516   -1.557  1.00 28.39
ATOM   2477  N    LEU  529      24.453   14.137   -1.776  1.00 29.34
ATOM   2478  CA   LEU  529      24.478   12.947   -0.942  1.00 29.62
ATOM   2479  CB   LEU  529      23.047   12.479   -0.645  1.00 29.60
ATOM   2480  CG   LEU  529      22.188   13.506    0.109  1.00 27.75
ATOM   2481  CD1  LEU  529      20.849   12.898    0.483  1.00 26.93
ATOM   2482  CD2  LEU  529      22.917   13.973    1.356  1.00 24.19
ATOM   2483  C    LEU  529      25.326   11.827   -1.540  1.00 29.38
ATOM   2484  O    LEU  529      26.158   11.237   -0.847  1.00 28.82
ATOM   2485  N    ALA  530      25.140   11.564   -2.830  1.00 29.06
ATOM   2486  CA   ALA  530      25.904   10.519   -3.508  1.00 29.34
ATOM   2487  CB   ALA  530      25.415   10.343   -4.951  1.00 29.19
ATOM   2488  C    ALA  530      27.394   10.856   -3.489  1.00 28.63
ATOM   2489  O    ALA  530      28.236    9.991   -3.217  1.00 29.57
```

FIGURE 1 (cont.)

| | | | | | | | | |
|---|---|---|---|---|---|---|---|---|
| ATOM | 2490 | N | PHE | 531 | 27.709 | 12.125 | -3.731 | 1.00 26.99 |
| ATOM | 2491 | CA | PHE | 531 | 29.094 | 12.553 | -3.735 | 1.00 25.83 |
| ATOM | 2492 | CB | PHE | 531 | 29.232 | 14.024 | -4.124 | 1.00 25.62 |
| ATOM | 2493 | CG | PHE | 531 | 30.621 | 14.553 | -3.938 | 1.00 26.14 |
| ATOM | 2494 | CD1 | PHE | 531 | 31.652 | 14.139 | -4.778 | 1.00 26.59 |
| ATOM | 2495 | CD2 | PHE | 531 | 30.918 | 15.398 | -2.883 | 1.00 25.50 |
| ATOM | 2496 | CE1 | PHE | 531 | 32.962 | 14.556 | -4.564 | 1.00 25.76 |
| ATOM | 2497 | CE2 | PHE | 531 | 32.222 | 15.820 | -2.659 | 1.00 27.06 |
| ATOM | 2498 | CZ | PHE | 531 | 33.249 | 15.396 | -3.502 | 1.00 26.12 |
| ATOM | 2499 | C | PHE | 531 | 29.769 | 12.325 | -2.395 | 1.00 24.62 |
| ATOM | 2500 | O | PHE | 531 | 30.763 | 11.617 | -2.328 | 1.00 26.66 |
| ATOM | 2501 | N | TRP | 532 | 29.222 | 12.900 | -1.327 | 1.00 22.70 |
| ATOM | 2502 | CA | TRP | 532 | 29.824 | 12.758 | -0.002 | 1.00 21.65 |
| ATOM | 2503 | CB | TRP | 532 | 29.145 | 13.682 | 1.006 | 1.00 20.94 |
| ATOM | 2504 | CG | TRP | 532 | 29.451 | 15.121 | 0.742 | 1.00 20.29 |
| ATOM | 2505 | CD2 | TRP | 532 | 30.739 | 15.758 | 0.824 | 1.00 21.51 |
| ATOM | 2506 | CE2 | TRP | 532 | 30.557 | 17.112 | 0.462 | 1.00 21.80 |
| ATOM | 2507 | CE3 | TRP | 532 | 32.027 | 15.315 | 1.162 | 1.00 20.31 |
| ATOM | 2508 | CD1 | TRP | 532 | 28.573 | 16.082 | 0.351 | 1.00 20.68 |
| ATOM | 2509 | NE1 | TRP | 532 | 29.228 | 17.281 | 0.180 | 1.00 21.58 |
| ATOM | 2510 | CZ2 | TRP | 532 | 31.618 | 18.037 | 0.428 | 1.00 21.77 |
| ATOM | 2511 | CZ3 | TRP | 532 | 33.080 | 16.230 | 1.130 | 1.00 22.10 |
| ATOM | 2512 | CH2 | TRP | 532 | 32.866 | 17.579 | 0.763 | 1.00 21.20 |
| ATOM | 2513 | C | TRP | 532 | 29.865 | 11.328 | 0.496 | 1.00 21.68 |
| ATOM | 2514 | O | TRP | 532 | 30.800 | 10.925 | 1.206 | 1.00 20.01 |
| ATOM | 2515 | N | GLU | 533 | 28.848 | 10.561 | 0.122 | 1.00 22.69 |
| ATOM | 2516 | CA | GLU | 533 | 28.787 | 9.159 | 0.488 | 1.00 23.84 |
| ATOM | 2517 | CB | GLU | 533 | 27.455 | 8.553 | 0.058 | 1.00 26.03 |
| ATOM | 2518 | CG | GLU | 533 | 27.279 | 7.129 | 0.543 | 1.00 26.87 |
| ATOM | 2519 | CD | GLU | 533 | 26.055 | 6.468 | -0.018 | 1.00 27.26 |
| ATOM | 2520 | OE1 | GLU | 533 | 25.058 | 7.165 | -0.302 | 1.00 26.87 |
| ATOM | 2521 | OE2 | GLU - | 533 | 26.103 | 5.238 | -0.185 | 1.00 30.58 |
| ATOM | 2522 | C | GLU | 533 | 29.926 | 8.450 | -0.245 | 1.00 23.94 |
| ATOM | 2523 | O | GLU | 533 | 30.584 | 7.569 | 0.319 | 1.00 24.95 |
| ATOM | 2524 | N | GLY | 534 | 30.149 | 8.832 | -1.502 | 1.00 23.38 |
| ATOM | 2525 | CA | GLY | 534 | 31.227 | 8.236 | -2.277 | 1.00 23.87 |
| ATOM | 2526 | C | GLY | 534 | 32.555 | 8.469 | -1.569 | 1.00 23.44 |
| ATOM | 2527 | O | GLY | 534 | 33.263 | 7.517 | -1.214 | 1.00 22.74 |
| ATOM | 2528 | N | VAL | 535 | 32.829 | 9.739 | -1.269 | 1.00 22.38 |
| ATOM | 2529 | CA | VAL | 535 | 34.050 | 10.147 | -0.584 | 1.00 22.30 |
| ATOM | 2530 | CB | VAL | 535 | 34.037 | 11.674 | -0.254 | 1.00 21.82 |
| ATOM | 2531 | CG1 | VAL | 535 | 35.184 | 12.033 | 0.702 | 1.00 17.86 |
| ATOM | 2532 | CG2 | VAL | 535 | 34.124 | 12.491 | -1.541 | 1.00 17.05 |
| ATOM | 2533 | C | VAL | 535 | 34.312 | 9.351 | 0.696 | 1.00 22.60 |
| ATOM | 2534 | O | VAL | 535 | 35.324 | 8.655 | 0.799 | 1.00 23.81 |
| ATOM | 2535 | N | PHE | 536 | 33.381 | 9.411 | 1.645 | 1.00 22.80 |
| ATOM | 2536 | CA | PHE | 536 | 33.548 | 8.710 | 2.916 | 1.00 21.82 |
| ATOM | 2537 | CB | PHE | 536 | 32.496 | 9.169 | 3.931 | 1.00 21.01 |
| ATOM | 2538 | CG | PHE | 536 | 32.793 | 10.514 | 4.529 | 1.00 18.99 |
| ATOM | 2539 | CD1 | PHE | 536 | 32.371 | 11.677 | 3.901 | 1.00 15.68 |
| ATOM | 2540 | CD2 | PHE | 536 | 33.555 | 10.616 | 5.687 | 1.00 16.90 |
| ATOM | 2541 | CE1 | PHE | 536 | 32.708 | 12.921 | 4.410 | 1.00 16.35 |
| ATOM | 2542 | CE2 | PHE | 536 | 33.893 | 11.861 | 6.204 | 1.00 17.77 |
| ATOM | 2543 | CZ | PHE | 536 | 33.469 | 13.019 | 5.561 | 1.00 14.57 |
| ATOM | 2544 | C | PHE | 536 | 33.598 | 7.192 | 2.817 | 1.00 23.73 |
| ATOM | 2545 | O | PHE | 536 | 34.253 | 6.535 | 3.632 | 1.00 22.08 |
| ATOM | 2546 | N | THR | 537 | 32.941 | 6.633 | 1.805 | 1.00 26.19 |
| ATOM | 2547 | CA | THR | 537 | 32.952 | 5.189 | 1.619 | 1.00 28.54 |

FIGURE 1 (cont.)

| | | | | | | | | |
|---|---|---|---|---|---|---|---|---|
| ATOM | 2548 | CB  | THR | 537 | 31.998 | 4.771  | 0.490  | 1.00 29.40 |
| ATOM | 2549 | OG1 | THR | 537 | 30.649 | 5.019  | 0.905  | 1.00 31.40 |
| ATOM | 2550 | CG2 | THR | 537 | 32.148 | 3.287  | 0.174  | 1.00 29.35 |
| ATOM | 2551 | C   | THR | 537 | 34.380 | 4.686  | 1.342  | 1.00 29.80 |
| ATOM | 2552 | O   | THR | 537 | 34.741 | 3.566  | 1.722  | 1.00 30.70 |
| ATOM | 2553 | N   | GLY | 538 | 35.201 | 5.537  | 0.733  | 1.00 29.84 |
| ATOM | 2554 | CA  | GLY | 538 | 36.567 | 5.151  | 0.437  | 1.00 28.99 |
| ATOM | 2555 | C   | GLY | 538 | 37.549 | 5.377  | 1.573  | 1.00 28.25 |
| ATOM | 2556 | O   | GLY | 538 | 38.678 | 4.892  | 1.523  | 1.00 28.81 |
| ATOM | 2557 | N   | LEU | 539 | 37.132 | 6.094  | 2.606  | 1.00 27.46 |
| ATOM | 2558 | CA  | LEU | 539 | 38.020 | 6.375  | 3.720  | 1.00 27.32 |
| ATOM | 2559 | CB  | LEU | 539 | 37.655 | 7.707  | 4.378  | 1.00 26.09 |
| ATOM | 2560 | CG  | LEU | 539 | 37.583 | 8.951  | 3.481  | 1.00 24.55 |
| ATOM | 2561 | CD1 | LEU | 539 | 37.394 | 10.159 | 4.367  | 1.00 23.67 |
| ATOM | 2562 | CD2 | LEU | 539 | 38.843 | 9.108  | 2.645  | 1.00 24.83 |
| ATOM | 2563 | C   | LEU | 539 | 37.963 | 5.248  | 4.725  | 1.00 28.87 |
| ATOM | 2564 | O   | LEU | 539 | 37.689 | 5.458  | 5.909  | 1.00 30.15 |
| ATOM | 2565 | N   | THR | 540 | 38.259 | 4.047  | 4.250  | 1.00 29.75 |
| ATOM | 2566 | CA  | THR | 540 | 38.224 | 2.872  | 5.098  | 1.00 30.28 |
| ATOM | 2567 | CB  | THR | 540 | 37.875 | 1.625  | 4.277  | 1.00 30.11 |
| ATOM | 2568 | OG1 | THR | 540 | 38.931 | 1.351  | 3.352  | 1.00 30.87 |
| ATOM | 2569 | CG2 | THR | 540 | 36.591 | 1.858  | 3.492  | 1.00 31.21 |
| ATOM | 2570 | C   | THR | 540 | 39.533 | 2.652  | 5.857  | 1.00 30.76 |
| ATOM | 2571 | O   | THR | 540 | 40.573 | 3.203  | 5.509  | 1.00 30.52 |
| ATOM | 2572 | N   | HIS | 541 | 39.452 | 1.859  | 6.921  | 1.00 31.78 |
| ATOM | 2573 | CA  | HIS | 541 | 40.603 | 1.524  | 7.757  | 1.00 31.88 |
| ATOM | 2574 | CB  | HIS | 541 | 41.605 | 0.652  | 6.969  | 1.00 31.23 |
| ATOM | 2575 | C   | HIS | 541 | 41.295 | 2.741  | 8.365  | 1.00 30.69 |
| ATOM | 2576 | O   | HIS | 541 | 42.461 | 2.992  | 8.097  | 1.00 33.64 |
| ATOM | 2577 | N   | ILE | 542 | 40.581 | 3.483  | 9.202  | 1.00 29.88 |
| ATOM | 2578 | CA  | ILE | 542 | 41.149 | 4.661  | 9.852  | 1.00 29.84 |
| ATOM | 2579 | CB  | ILE | 542 | 40.032 | 5.650  | 10.323 | 1.00 28.82 |
| ATOM | 2580 | CG2 | ILE | 542 | 39.306 | 5.107  | 11.560 | 1.00 27.39 |
| ATOM | 2581 | CG1 | ILE | 542 | 40.622 | 7.021  | 10.661 | 1.00 26.39 |
| ATOM | 2582 | CD1 | ILE | 542 | 39.573 | 8.090  | 10.915 | 1.00 22.88 |
| ATOM | 2583 | C   | ILE | 542 | 41.912 | 4.172  | 11.068 | 1.00 31.23 |
| ATOM | 2584 | O   | ILE | 542 | 41.687 | 3.052  | 11.523 | 1.00 32.59 |
| ATOM | 2585 | N   | ASP | 543 | 42.833 | 4.978  | 11.583 | 1.00 32.70 |
| ATOM | 2586 | CA  | ASP | 543 | 43.558 | 4.580  | 12.778 | 1.00 33.07 |
| ATOM | 2587 | CB  | ASP | 543 | 44.882 | 5.326  | 12.906 | 1.00 32.63 |
| ATOM | 2588 | CG  | ASP | 543 | 45.667 | 4.909  | 14.136 | 1.00 34.41 |
| ATOM | 2589 | OD1 | ASP | 543 | 46.261 | 3.815  | 14.106 | 1.00 37.12 |
| ATOM | 2590 | OD2 | ASP | 543 | 45.698 | 5.666  | 15.135 | 1.00 35.50 |
| ATOM | 2591 | C   | ASP | 543 | 42.636 | 4.978  | 13.914 | 1.00 34.38 |
| ATOM | 2592 | O   | ASP | 543 | 42.306 | 6.160  | 14.067 | 1.00 34.89 |
| ATOM | 2593 | N   | ALA | 544 | 42.206 | 3.997  | 14.702 | 1.00 34.33 |
| ATOM | 2594 | CA  | ALA | 544 | 41.307 | 4.260  | 15.820 | 1.00 34.13 |
| ATOM | 2595 | CB  | ALA | 544 | 40.876 | 2.956  | 16.460 | 1.00 34.20 |
| ATOM | 2596 | C   | ALA | 544 | 41.873 | 5.212  | 16.876 | 1.00 34.61 |
| ATOM | 2597 | O   | ALA | 544 | 41.133 | 5.998  | 17.463 | 1.00 34.47 |
| ATOM | 2598 | N   | HIS | 545 | 43.180 | 5.159  | 17.113 | 1.00 36.16 |
| ATOM | 2599 | CA  | HIS | 545 | 43.782 | 6.035  | 18.111 | 1.00 36.63 |
| ATOM | 2600 | CB  | HIS | 545 | 45.216 | 5.635  | 18.445 | 1.00 38.84 |
| ATOM | 2601 | CG  | HIS | 545 | 45.902 | 6.604  | 19.362 | 1.00 41.47 |
| ATOM | 2602 | CD2 | HIS | 545 | 47.105 | 7.221  | 19.272 | 1.00 41.80 |
| ATOM | 2603 | ND1 | HIS | 545 | 45.320 | 7.068  | 20.523 | 1.00 42.23 |
| ATOM | 2604 | CE1 | HIS | 545 | 46.136 | 7.927  | 21.110 | 1.00 42.36 |
| ATOM | 2605 | NE2 | HIS | 545 | 47.225 | 8.039  | 20.371 | 1.00 42.08 |

FIGURE 1 (cont.)

| ATOM | 2606 | C   | HIS | 545 | 43.773 | 7.491  | 17.709 | 1.00 | 36.37 |
|------|------|-----|-----|-----|--------|--------|--------|------|-------|
| ATOM | 2607 | O   | HIS | 545 | 43.606 | 8.358  | 18.561 | 1.00 | 37.33 |
| ATOM | 2608 | N   | PHE | 546 | 44.043 | 7.767  | 16.437 | 1.00 | 35.97 |
| ATOM | 2609 | CA  | PHE | 546 | 44.044 | 9.148  | 15.958 | 1.00 | 36.04 |
| ATOM | 2610 | CB  | PHE | 546 | 44.565 | 9.232  | 14.520 | 1.00 | 35.63 |
| ATOM | 2611 | CG  | PHE | 546 | 46.052 | 9.084  | 14.405 | 1.00 | 35.41 |
| ATOM | 2612 | CD1 | PHE | 546 | 46.890 | 9.545  | 15.411 | 1.00 | 35.87 |
| ATOM | 2613 | CD2 | PHE | 546 | 46.618 | 8.471  | 13.292 | 1.00 | 36.70 |
| ATOM | 2614 | CE1 | PHE | 546 | 48.264 | 9.397  | 15.310 | 1.00 | 35.65 |
| ATOM | 2615 | CE2 | PHE | 546 | 47.996 | 8.317  | 13.183 | 1.00 | 34.51 |
| ATOM | 2616 | CZ  | PHE | 546 | 48.817 | 8.779  | 14.192 | 1.00 | 35.18 |
| ATOM | 2617 | C   | PHE | 546 | 42.632 | 9.713  | 16.041 | 1.00 | 35.77 |
| ATOM | 2618 | O   | PHE | 546 | 42.435 | 10.845 | 16.486 | 1.00 | 34.76 |
| ATOM | 2619 | N   | LEU | 547 | 41.655 | 8.898  | 15.643 | 1.00 | 36.27 |
| ATOM | 2620 | CA  | LEU | 547 | 40.244 | 9.287  | 15.673 | 1.00 | 36.99 |
| ATOM | 2621 | CB  | LEU | 547 | 39.365 | 8.134  | 15.188 | 1.00 | 35.89 |
| ATOM | 2622 | CG  | LEU | 547 | 37.856 | 8.399  | 15.168 | 1.00 | 35.86 |
| ATOM | 2623 | CD1 | LEU | 547 | 37.535 | 9.650  | 14.342 | 1.00 | 34.64 |
| ATOM | 2624 | CD2 | LEU | 547 | 37.143 | 7.178  | 14.609 | 1.00 | 35.41 |
| ATOM | 2625 | C   | LEU | 547 | 39.824 | 9.718  | 17.075 | 1.00 | 37.45 |
| ATOM | 2626 | O   | LEU | 547 | 39.218 | 10.776 | 17.253 | 1.00 | 36.59 |
| ATOM | 2627 | N   | SER | 548 | 40.176 | 8.906  | 18.066 | 1.00 | 38.91 |
| ATOM | 2628 | CA  | SER | 548 | 39.855 | 9.212  | 19.454 | 1.00 | 40.88 |
| ATOM | 2629 | CB  | SER | 548 | 40.258 | 8.050  | 20.375 | 1.00 | 42.68 |
| ATOM | 2630 | OG  | SER | 548 | 41.228 | 7.208  | 19.763 | 1.00 | 46.74 |
| ATOM | 2631 | C   | SER | 548 | 40.534 | 10.505 | 19.902 | 1.00 | 40.49 |
| ATOM | 2632 | O   | SER | 548 | 40.013 | 11.231 | 20.747 | 1.00 | 41.69 |
| ATOM | 2633 | N   | GLN | 549 | 41.691 | 10.802 | 19.328 | 1.00 | 39.68 |
| ATOM | 2634 | CA  | GLN | 549 | 42.395 | 12.015 | 19.686 | 1.00 | 39.49 |
| ATOM | 2635 | CB  | GLN | 549 | 43.845 | 11.956 | 19.218 | 1.00 | 41.25 |
| ATOM | 2636 | CG  | GLN | 549 | 44.736 | 11.018 | 20.006 | 1.00 | 42.18 |
| ATOM | 2637 | CD  | GLN | 549 | 46.209 | 11.238 | 19.706 | 1.00 | 42.98 |
| ATOM | 2638 | OE1 | GLN | 549 | 46.922 | 10.300 | 19.363 | 1.00 | 44.07 |
| ATOM | 2639 | NE2 | GLN | 549 | 46.674 | 12.479 | 19.847 | 1.00 | 42.49 |
| ATOM | 2640 | C   | GLN | 549 | 41.723 | 13.222 | 19.063 | 1.00 | 40.07 |
| ATOM | 2641 | O   | GLN | 549 | 41.451 | 14.213 | 19.741 | 1.00 | 39.72 |
| ATOM | 2642 | N   | THR | 550 | 41.437 | 13.124 | 17.770 | 1.00 | 41.21 |
| ATOM | 2643 | CA  | THR | 550 | 40.824 | 14.222 | 17.036 | 1.00 | 43.02 |
| ATOM | 2644 | CB  | THR | 550 | 40.714 | 13.920 | 15.515 | 1.00 | 43.79 |
| ATOM | 2645 | OG1 | THR | 550 | 40.200 | 12.595 | 15.307 | 1.00 | 44.92 |
| ATOM | 2646 | CG2 | THR | 550 | 42.069 | 14.041 | 14.857 | 1.00 | 43.92 |
| ATOM | 2647 | C   | THR | 550 | 39.469 | 14.641 | 17.575 | 1.00 | 43.65 |
| ATOM | 2648 | O   | THR | 550 | 39.197 | 15.836 | 17.716 | 1.00 | 43.09 |
| ATOM | 2649 | N   | LYS | 551 | 38.611 | 13.671 | 17.871 | 1.00 | 45.05 |
| ATOM | 2650 | CA  | LYS | 551 | 37.301 | 14.027 | 18.391 | 1.00 | 46.81 |
| ATOM | 2651 | CB  | LYS | 551 | 36.265 | 12.922 | 18.145 | 1.00 | 45.60 |
| ATOM | 2652 | CG  | LYS | 551 | 36.584 | 11.534 | 18.617 | 1.00 | 44.11 |
| ATOM | 2653 | CD  | LYS | 551 | 35.523 | 10.578 | 18.052 | 1.00 | 42.52 |
| ATOM | 2654 | CE  | LYS | 551 | 35.569 | 9.206  | 18.706 | 1.00 | 41.73 |
| ATOM | 2655 | NZ  | LYS | 551 | 34.474 | 8.315  | 18.244 | 1.00 | 39.62 |
| ATOM | 2656 | C   | LYS | 551 | 37.345 | 14.523 | 19.837 | 1.00 | 47.87 |
| ATOM | 2657 | O   | LYS | 551 | 36.420 | 15.198 | 20.304 | 1.00 | 48.23 |
| ATOM | 2658 | N   | GLN | 552 | 38.473 | 14.275 | 20.499 | 1.00 | 49.00 |
| ATOM | 2659 | CA  | GLN | 552 | 38.699 | 14.719 | 21.870 | 1.00 | 49.66 |
| ATOM | 2660 | CB  | GLN | 552 | 39.705 | 13.800 | 22.555 | 1.00 | 51.22 |
| ATOM | 2661 | CG  | GLN | 552 | 40.070 | 14.232 | 23.961 | 1.00 | 55.29 |
| ATOM | 2662 | CD  | GLN | 552 | 41.365 | 13.612 | 24.435 | 1.00 | 57.87 |
| ATOM | 2663 | OE1 | GLN | 552 | 41.518 | 12.388 | 24.443 | 1.00 | 59.24 |

FIGURE 1 (cont.)

| ATOM | 2664 | NE2 | GLN | 552 | 42.315 | 14.457 | 24.827 | 1.00 | 59.52 |
|---|---|---|---|---|---|---|---|---|---|
| ATOM | 2665 | C | GLN | 552 | 39.250 | 16.150 | 21.837 | 1.00 | 50.06 |
| ATOM | 2666 | O | GLN | 552 | 39.060 | 16.930 | 22.776 | 1.00 | 49.38 |
| ATOM | 2667 | N | SER | 553 | 39.944 | 16.479 | 20.748 | 1.00 | 50.55 |
| ATOM | 2668 | CA | SER | 553 | 40.532 | 17.802 | 20.560 | 1.00 | 50.62 |
| ATOM | 2669 | CB | SER | 553 | 41.660 | 17.742 | 19.514 | 1.00 | 50.03 |
| ATOM | 2670 | OG | SER | 553 | 41.169 | 17.575 | 18.189 | 1.00 | 47.69 |
| ATOM | 2671 | C | SER | 553 | 39.494 | 18.833 | 20.129 | 1.00 | 51.44 |
| ATOM | 2672 | O | SER | 553 | 39.792 | 20.024 | 20.048 | 1.00 | 52.81 |
| ATOM | 2673 | N | GLY | 554 | 38.282 | 18.375 | 19.840 | 1.00 | 52.03 |
| ATOM | 2674 | CA | GLY | 554 | 37.240 | 19.282 | 19.397 | 1.00 | 52.43 |
| ATOM | 2675 | C | GLY | 554 | 37.401 | 19.638 | 17.924 | 1.00 | 52.57 |
| ATOM | 2676 | O | GLY | 554 | 36.778 | 20.581 | 17.426 | 1.00 | 53.51 |
| ATOM | 2677 | N | GLU | 555 | 38.231 | 18.874 | 17.221 | 1.00 | 51.69 |
| ATOM | 2678 | CA | GLU | 555 | 38.470 | 19.103 | 15.802 | 1.00 | 50.16 |
| ATOM | 2679 | CB | GLU | 555 | 39.399 | 18.011 | 15.259 | 1.00 | 51.56 |
| ATOM | 2680 | CG | GLU | 555 | 40.415 | 18.498 | 14.237 | 1.00 | 53.15 |
| ATOM | 2681 | CD | GLU | 555 | 41.455 | 19.438 | 14.830 | 1.00 | 53.99 |
| ATOM | 2682 | OE1 | GLU | 555 | 42.325 | 18.955 | 15.595 | 1.00 | 54.91 |
| ATOM | 2683 | OE2 | GLU | 555 | 41.406 | 20.652 | 14.521 | 1.00 | 53.02 |
| ATOM | 2684 | C | GLU | 555 | 37.136 | 19.099 | 15.047 | 1.00 | 47.60 |
| ATOM | 2685 | O | GLU | 555 | 36.346 | 18.171 | 15.193 | 1.00 | 48.20 |
| ATOM | 2686 | N | ASN | 556 | 36.916 | 20.125 | 14.226 | 1.00 | 45.50 |
| ATOM | 2687 | CA | ASN | 556 | 35.683 | 20.303 | 13.439 | 1.00 | 42.96 |
| ATOM | 2688 | CB | ASN | 556 | 35.796 | 21.560 | 12.573 | 1.00 | 44.24 |
| ATOM | 2689 | CG | ASN | 556 | 34.507 | 22.366 | 12.529 | 1.00 | 45.63 |
| ATOM | 2690 | OD1 | ASN | 556 | 34.544 | 23.589 | 12.485 | 1.00 | 46.71 |
| ATOM | 2691 | ND2 | ASN | 556 | 33.366 | 21.687 | 12.533 | 1.00 | 46.27 |
| ATOM | 2692 | C | ASN | 556 | 35.240 | 19.117 | 12.564 | 1.00 | 40.45 |
| ATOM | 2693 | O | ASN | 556 | 34.038 | 18.830 | 12.448 | 1.00 | 41.36 |
| ATOM | 2694 | N | PHE | 557 | 36.188 | 18.477 | 11.894 | 1.00 | 35.01 |
| ATOM | 2695 | CA | PHE | 557 | 35.874 | 17.321 | 11.056 | 1.00 | 30.51 |
| ATOM | 2696 | CB | PHE | 557 | 36.141 | 17.617 | 9.575 | 1.00 | 26.25 |
| ATOM | 2697 | CG | PHE | 557 | 35.119 | 18.516 | 8.936 | 1.00 | 24.10 |
| ATOM | 2698 | CD1 | PHE | 557 | 35.093 | 19.878 | 9.212 | 1.00 | 23.27 |
| ATOM | 2699 | CD2 | PHE | 557 | 34.184 | 18.001 | 8.050 | 1.00 | 21.00 |
| ATOM | 2700 | CE1 | PHE | 557 | 34.150 | 20.710 | 8.612 | 1.00 | 20.85 |
| ATOM | 2701 | CE2 | PHE | 557 | 33.243 | 18.825 | 7.450 | 1.00 | 18.34 |
| ATOM | 2702 | CZ | PHE | 557 | 33.225 | 20.174 | 7.731 | 1.00 | 20.74 |
| ATOM | 2703 | C | PHE | 557 | 36.809 | 16.228 | 11.535 | 1.00 | 29.61 |
| ATOM | 2704 | O | PHE | 557 | 37.739 | 15.845 | 10.825 | 1.00 | 30.80 |
| ATOM | 2705 | N | PRO | 558 | 36.557 | 15.687 | 12.738 | 1.00 | 28.44 |
| ATOM | 2706 | CD | PRO | 558 | 35.338 | 15.899 | 13.535 | 1.00 | 27.55 |
| ATOM | 2707 | CA | PRO | 558 | 37.378 | 14.633 | 13.341 | 1.00 | 27.40 |
| ATOM | 2708 | CB | PRO | 558 | 36.580 | 14.244 | 14.586 | 1.00 | 27.92 |
| ATOM | 2709 | CG | PRO | 558 | 35.178 | 14.573 | 14.212 | 1.00 | 28.58 |
| ATOM | 2710 | C | PRO | 558 | 37.715 | 13.434 | 12.459 | 1.00 | 25.97 |
| ATOM | 2711 | O | PRO | 558 | 38.848 | 12.948 | 12.490 | 1.00 | 25.27 |
| ATOM | 2712 | N | TYR | 559 | 36.763 | 12.977 | 11.652 | 1.00 | 23.97 |
| ATOM | 2713 | CA | TYR | 559 | 37.039 | 11.836 | 10.796 | 1.00 | 23.89 |
| ATOM | 2714 | CB | TYR | 559 | 35.753 | 11.193 | 10.258 | 1.00 | 21.95 |
| ATOM | 2715 | CG | TYR | 559 | 35.984 | 9.781 | 9.769 | 1.00 | 21.57 |
| ATOM | 2716 | CD1 | TYR | 559 | 35.891 | 8.685 | 10.639 | 1.00 | 24.12 |
| ATOM | 2717 | CE1 | TYR | 559 | 36.204 | 7.389 | 10.207 | 1.00 | 22.12 |
| ATOM | 2718 | CD2 | TYR | 559 | 36.382 | 9.541 | 8.461 | 1.00 | 22.30 |
| ATOM | 2719 | CE2 | TYR | 559 | 36.696 | 8.261 | 8.024 | 1.00 | 22.08 |
| ATOM | 2720 | CZ | TYR | 559 | 36.610 | 7.199 | 8.895 | 1.00 | 22.68 |
| ATOM | 2721 | OH | TYR | 559 | 36.966 | 5.958 | 8.437 | 1.00 | 28.01 |

FIGURE 1 (cont.)

| ATOM | 2722 | C   | TYR  | 559 | 38.002 | 12.202 | 9.661  | 1.00 | 23.70 |
|------|------|-----|------|-----|--------|--------|--------|------|-------|
| ATOM | 2723 | O   | TYR  | 559 | 38.932 | 11.451 | 9.360  | 1.00 | 25.56 |
| ATOM | 2724 | N   | LEU  | 560 | 37.819 | 13.366 | 9.053  | 1.00 | 23.40 |
| ATOM | 2725 | CA  | LEU  | 560 | 38.716 | 13.756 | 7.965  | 1.00 | 22.40 |
| ATOM | 2726 | CB  | LEU  | 560 | 38.184 | 14.979 | 7.203  | 1.00 | 19.29 |
| ATOM | 2727 | CG  | LEU  | 560 | 36.905 | 14.744 | 6.387  | 1.00 | 19.21 |
| ATOM | 2728 | CD1 | LEU  | 560 | 36.621 | 15.965 | 5.524  | 1.00 | 17.94 |
| ATOM | 2729 | CD2 | LEU  | 560 | 37.023 | 13.499 | 5.508  | 1.00 | 16.77 |
| ATOM | 2730 | C   | LEU  | 560 | 40.133 | 14.007 | 8.475  | 1.00 | 21.57 |
| ATOM | 2731 | O   | LEU  | 560 | 41.096 | 13.511 | 7.896  | 1.00 | 22.32 |
| ATOM | 2732 | N   | VAL  | 561 | 40.247 | 14.730 | 9.587  | 1.00 | 21.43 |
| ATOM | 2733 | CA  | VAL  | 561 | 41.543 | 15.049 | 10.175 | 1.00 | 20.86 |
| ATOM | 2734 | CB  | VAL  | 561 | 41.404 | 15.990 | 11.397 | 1.00 | 20.24 |
| ATOM | 2735 | CG1 | VAL  | 561 | 42.761 | 16.265 | 12.011 | 1.00 | 22.08 |
| ATOM | 2736 | CG2 | VAL  | 561 | 40.789 | 17.309 | 10.972 | 1.00 | 20.07 |
| ATOM | 2737 | C   | VAL  | 561 | 42.276 | 13.774 | 10.566 | 1.00 | 21.69 |
| ATOM | 2738 | O   | VAL  | 561 | 43.384 | 13.537 | 10.103 | 1.00 | 22.16 |
| ATOM | 2739 | N   | ALA  | 562 | 41.634 | 12.936 | 11.379 | 1.00 | 22.88 |
| ATOM | 2740 | CA  | ALA  | 562 | 42.210 | 11.672 | 11.831 | 1.00 | 22.13 |
| ATOM | 2741 | CB  | ALA  | 562 | 41.248 | 10.966 | 12.728 | 1.00 | 20.52 |
| ATOM | 2742 | C   | ALA  | 562 | 42.580 | 10.763 | 10.663 | 1.00 | 23.28 |
| ATOM | 2743 | O   | ALA  | 562 | 43.571 | 10.031 | 10.728 | 1.00 | 24.95 |
| ATOM | 2744 | N   | TYR  | 563 | 41.787 | 10.792 | 9.596  | 1.00 | 23.47 |
| ATOM | 2745 | CA  | TYR  | 563 | 42.083 | 9.952  | 8.443  | 1.00 | 24.18 |
| ATOM | 2746 | CB  | TYR  | 563 | 40.887 | 9.861  | 7.496  | 1.00 | 24.43 |
| ATOM | 2747 | CG  | TYR  | 563 | 40.962 | 8.633  | 6.631  | 1.00 | 25.76 |
| ATOM | 2748 | CD1 | TYR  | 563 | 40.645 | 7.376  | 7.151  | 1.00 | 26.28 |
| ATOM | 2749 | CE1 | TYR  | 563 | 40.789 | 6.222  | 6.386  | 1.00 | 27.58 |
| ATOM | 2750 | CD2 | TYR  | 563 | 41.418 | 8.708  | 5.315  | 1.00 | 26.40 |
| ATOM | 2751 | CE2 | TYR  | 563 | 41.566 | 7.560  | 4.538  | 1.00 | 27.19 |
| ATOM | 2752 | CZ  | TYR  | 563 | 41.251 | 6.322  | 5.081  | 1.00 | 27.76 |
| ATOM | 2753 | OH  | TYR- | 563 | 41.391 | 5.193  | 4.314  | 1.00 | 29.58 |
| ATOM | 2754 | C   | TYR  | 563 | 43.345 | 10.426 | 7.701  | 1.00 | 23.93 |
| ATOM | 2755 | O   | TYR  | 563 | 44.206 | 9.612  | 7.341  | 1.00 | 23.21 |
| ATOM | 2756 | N   | GLN  | 564 | 43.452 | 11.736 | 7.478  | 1.00 | 23.24 |
| ATOM | 2757 | CA  | GLN  | 564 | 44.631 | 12.298 | 6.825  | 1.00 | 22.78 |
| ATOM | 2758 | CB  | GLN  | 564 | 44.510 | 13.825 | 6.675  | 1.00 | 21.93 |
| ATOM | 2759 | CG  | GLN  | 564 | 45.804 | 14.539 | 6.222  | 1.00 | 21.73 |
| ATOM | 2760 | CD  | GLN  | 564 | 46.209 | 14.241 | 4.781  | 1.00 | 21.45 |
| ATOM | 2761 | OE1 | GLN  | 564 | 45.773 | 14.928 | 3.846  | 1.00 | 21.98 |
| ATOM | 2762 | NE2 | GLN  | 564 | 47.055 | 13.231 | 4.595  | 1.00 | 18.62 |
| ATOM | 2763 | C   | GLN  | 564 | 45.843 | 11.951 | 7.689  | 1.00 | 22.24 |
| ATOM | 2764 | O   | GLN  | 564 | 46.898 | 11.598 | 7.170  | 1.00 | 22.24 |
| ATOM | 2765 | N   | ALA  | 565 | 45.671 | 12.015 | 9.006  | 1.00 | 22.72 |
| ATOM | 2766 | CA  | ALA  | 565 | 46.749 | 11.700 | 9.938  | 1.00 | 24.32 |
| ATOM | 2767 | CB  | ALA  | 565 | 46.330 | 12.008 | 11.362 | 1.00 | 23.28 |
| ATOM | 2768 | C   | ALA  | 565 | 47.138 | 10.232 | 9.803  | 1.00 | 25.85 |
| ATOM | 2769 | O   | ALA  | 565 | 48.324 | 9.890  | 9.830  | 1.00 | 26.02 |
| ATOM | 2770 | N   | THR  | 566 | 46.138 | 9.377  | 9.607  | 1.00 | 26.56 |
| ATOM | 2771 | CA  | THR  | 566 | 46.359 | 7.939  | 9.446  | 1.00 | 27.00 |
| ATOM | 2772 | CB  | THR  | 566 | 45.007 | 7.215  | 9.330  | 1.00 | 25.94 |
| ATOM | 2773 | OG1 | THR  | 566 | 44.338 | 7.276  | 10.593 | 1.00 | 26.58 |
| ATOM | 2774 | CG2 | THR  | 566 | 45.184 | 5.770  | 8.926  | 1.00 | 25.45 |
| ATOM | 2775 | C   | THR  | 566 | 47.228 | 7.647  | 8.212  | 1.00 | 26.39 |
| ATOM | 2776 | O   | THR  | 566 | 48.239 | 6.951  | 8.288  | 1.00 | 26.71 |
| ATOM | 2777 | N   | VAL  | 567 | 46.823 | 8.205  | 7.082  | 1.00 | 26.66 |
| ATOM | 2778 | CA  | VAL  | 567 | 47.533 | 8.047  | 5.824  | 1.00 | 25.23 |
| ATOM | 2779 | CB  | VAL  | 567 | 46.777 | 8.804  | 4.704  | 1.00 | 24.80 |

FIGURE 1 (cont.)

| ATOM | 2780 | CG1 | VAL | 567 | 47.633 | 8.941  | 3.480  | 1.00 | 24.37 |
|------|------|-----|-----|-----|--------|--------|--------|------|-------|
| ATOM | 2781 | CG2 | VAL | 567 | 45.473 | 8.053  | 4.362  | 1.00 | 24.95 |
| ATOM | 2782 | C   | VAL | 567 | 48.989 | 8.519  | 5.947  | 1.00 | 24.66 |
| ATOM | 2783 | O   | VAL | 567 | 49.903 | 7.867  | 5.438  | 1.00 | 24.50 |
| ATOM | 2784 | N   | CYS | 568 | 49.202 | 9.622  | 6.656  | 1.00 | 24.76 |
| ATOM | 2785 | CA  | CYS | 568 | 50.544 | 10.156 | 6.861  | 1.00 | 25.31 |
| ATOM | 2786 | CB  | CYS | 568 | 50.490 | 11.529 | 7.546  | 1.00 | 24.87 |
| ATOM | 2787 | SG  | CYS | 568 | 49.934 | 12.883 | 6.493  | 1.00 | 23.18 |
| ATOM | 2788 | C   | CYS | 568 | 51.357 | 9.188  | 7.717  | 1.00 | 26.58 |
| ATOM | 2789 | O   | CYS | 568 | 52.460 | 8.797  | 7.351  | 1.00 | 26.47 |
| ATOM | 2790 | N   | ALA | 569 | 50.794 | 8.776  | 8.843  | 1.00 | 27.17 |
| ATOM | 2791 | CA  | ALA | 569 | 51.484 | 7.862  | 9.726  | 1.00 | 28.58 |
| ATOM | 2792 | CB  | ALA | 569 | 50.601 | 7.502  | 10.904 | 1.00 | 28.99 |
| ATOM | 2793 | C   | ALA | 569 | 51.899 | 6.607  | 8.967  | 1.00 | 30.34 |
| ATOM | 2794 | O   | ALA | 569 | 53.086 | 6.270  | 8.921  | 1.00 | 31.47 |
| ATOM | 2795 | N   | ARG | 570 | 50.938 | 5.961  | 8.308  | 1.00 | 30.52 |
| ATOM | 2796 | CA  | ARG | 570 | 51.210 | 4.732  | 7.567  | 1.00 | 30.59 |
| ATOM | 2797 | CB  | ARG | 570 | 49.918 | 4.143  | 6.992  | 1.00 | 30.69 |
| ATOM | 2798 | CG  | ARG | 570 | 48.997 | 3.561  | 8.054  | 1.00 | 30.15 |
| ATOM | 2799 | CD  | ARG | 570 | 47.765 | 2.913  | 7.458  | 1.00 | 29.12 |
| ATOM | 2800 | NE  | ARG | 570 | 46.828 | 2.506  | 8.507  | 1.00 | 30.17 |
| ATOM | 2801 | CZ  | ARG | 570 | 45.516 | 2.374  | 8.336  | 1.00 | 27.42 |
| ATOM | 2802 | NH1 | ARG | 570 | 44.748 | 1.995  | 9.347  | 1.00 | 29.10 |
| ATOM | 2803 | NH2 | ARG | 570 | 44.966 | 2.638  | 7.163  | 1.00 | 27.47 |
| ATOM | 2804 | C   | ARG | 570 | 52.253 | 4.890  | 6.469  | 1.00 | 31.40 |
| ATOM | 2805 | O   | ARG | 570 | 52.902 | 3.923  | 6.084  | 1.00 | 33.32 |
| ATOM | 2806 | N   | ALA | 571 | 52.390 | 6.103  | 5.944  | 1.00 | 31.42 |
| ATOM | 2807 | CA  | ALA | 571 | 53.370 | 6.380  | 4.901  | 1.00 | 29.19 |
| ATOM | 2808 | CB  | ALA | 571 | 52.795 | 7.363  | 3.905  | 1.00 | 26.97 |
| ATOM | 2809 | C   | ALA | 571 | 54.636 | 6.960  | 5.536  | 1.00 | 30.02 |
| ATOM | 2810 | O   | ALA | 571 | 55.630 | 7.179  | 4.859  | 1.00 | 31.04 |
| ATOM | 2811 | N   | GLN | 572 | 54.609 | 7.157  | 6.850  | 1.00 | 31.02 |
| ATOM | 2812 | CA  | GLN | 572 | 55.727 | 7.753  | 7.568  | 1.00 | 31.99 |
| ATOM | 2813 | CB  | GLN | 572 | 56.946 | 6.842  | 7.579  | 1.00 | 35.87 |
| ATOM | 2814 | CG  | GLN | 572 | 56.830 | 5.689  | 8.542  | 1.00 | 41.94 |
| ATOM | 2815 | CD  | GLN | 572 | 58.170 | 5.040  | 8.801  | 1.00 | 45.72 |
| ATOM | 2816 | OE1 | GLN | 572 | 58.562 | 4.819  | 9.954  | 1.00 | 47.02 |
| ATOM | 2817 | NE2 | GLN | 572 | 58.894 | 4.740  | 7.726  | 1.00 | 48.15 |
| ATOM | 2818 | C   | GLN | 572 | 56.071 | 9.093  | 6.935  | 1.00 | 30.48 |
| ATOM | 2819 | O   | GLN | 572 | 57.235 | 9.489  | 6.880  | 1.00 | 30.24 |
| ATOM | 2820 | N   | ALA | 573 | 55.029 | 9.765  | 6.451  | 1.00 | 28.34 |
| ATOM | 2821 | CA  | ALA | 573 | 55.114 | 11.072 | 5.814  | 1.00 | 26.25 |
| ATOM | 2822 | CB  | ALA | 573 | 54.253 | 11.084 | 4.537  | 1.00 | 24.36 |
| ATOM | 2823 | C   | ALA | 573 | 54.601 | 12.113 | 6.822  | 1.00 | 25.50 |
| ATOM | 2824 | O   | ALA | 573 | 53.844 | 11.783 | 7.744  | 1.00 | 24.77 |
| ATOM | 2825 | N   | PRO | 574 | 55.049 | 13.370 | 6.699  | 1.00 | 24.64 |
| ATOM | 2826 | CD  | PRO | 574 | 56.068 | 13.892 | 5.771  | 1.00 | 24.05 |
| ATOM | 2827 | CA  | PRO | 574 | 54.595 | 14.404 | 7.633  | 1.00 | 24.57 |
| ATOM | 2828 | CB  | PRO | 574 | 55.675 | 15.471 | 7.500  | 1.00 | 25.21 |
| ATOM | 2829 | CG  | PRO | 574 | 56.036 | 15.383 | 6.042  | 1.00 | 26.61 |
| ATOM | 2830 | C   | PRO | 574 | 53.227 | 14.957 | 7.253  | 1.00 | 25.52 |
| ATOM | 2831 | O   | PRO | 574 | 52.784 | 14.813 | 6.107  | 1.00 | 25.99 |
| ATOM | 2832 | N   | PRO | 575 | 52.525 | 15.580 | 8.212  | 1.00 | 25.30 |
| ATOM | 2833 | CD  | PRO | 575 | 52.893 | 15.792 | 9.622  | 1.00 | 24.49 |
| ATOM | 2834 | CA  | PRO | 575 | 51.202 | 16.146 | 7.926  | 1.00 | 25.44 |
| ATOM | 2835 | CB  | PRO | 575 | 50.717 | 16.584 | 9.309  | 1.00 | 25.55 |
| ATOM | 2836 | CG  | PRO | 575 | 51.989 | 16.927 | 10.022 | 1.00 | 25.38 |
| ATOM | 2837 | C   | PRO | 575 | 51.327 | 17.324 | 6.955  | 1.00 | 25.27 |

FIGURE 1 (cont.)

```
ATOM   2838  O    PRO  575      52.439   17.751    6.630  1.00 24.04
ATOM   2839  N    PRO  576      50.190   17.827    6.440  1.00 25.82
ATOM   2840  CD   PRO  576      48.829   17.300    6.637  1.00 24.51
ATOM   2841  CA   PRO  576      50.171   18.952    5.501  1.00 26.20
ATOM   2842  CB   PRO  576      48.686   19.236    5.357  1.00 24.96
ATOM   2843  CG   PRO  576      48.099   17.876    5.460  1.00 25.27
ATOM   2844  C    PRO  576      50.935   20.158    6.031  1.00 27.89
ATOM   2845  O    PRO  576      51.529   20.921    5.262  1.00 28.06
ATOM   2846  N    SER  577      50.893   20.333    7.345  1.00 29.44
ATOM   2847  CA   SER  577      51.599   21.415    8.012  1.00 30.58
ATOM   2848  CB   SER  577      50.800   22.720    7.946  1.00 29.32
ATOM   2849  OG   SER  577      49.630   22.650    8.739  1.00 29.45
ATOM   2850  C    SER  577      51.777   20.963    9.452  1.00 32.15
ATOM   2851  O    SER  577      51.410   19.839    9.801  1.00 31.77
ATOM   2852  N    TRP  578      52.371   21.819   10.276  1.00 34.52
ATOM   2853  CA   TRP  578      52.580   21.500   11.680  1.00 35.77
ATOM   2854  CB   TRP  578      54.069   21.540   12.040  1.00 36.18
ATOM   2855  CG   TRP  578      54.784   20.303   11.588  1.00 36.28
ATOM   2856  CD2  TRP  578      54.612   18.983   12.111  1.00 36.36
ATOM   2857  CE2  TRP  578      55.441   18.121   11.353  1.00 35.89
ATOM   2858  CE3  TRP  578      53.835   18.443   13.148  1.00 35.12
ATOM   2859  CD1  TRP  578      55.691   20.196   10.564  1.00 35.71
ATOM   2860  NE1  TRP  578      56.086   18.887   10.418  1.00 35.51
ATOM   2861  CZ2  TRP  578      55.513   16.746   11.599  1.00 35.54
ATOM   2862  CZ3  TRP  578      53.907   17.078   13.391  1.00 35.54
ATOM   2863  CH2  TRP  578      54.741   16.244   12.619  1.00 36.06
ATOM   2864  C    TRP  578      51.761   22.431   12.555  1.00 35.97
ATOM   2865  O    TRP  578      52.179   22.832   13.635  1.00 36.76
ATOM   2866  N    ASP  579      50.595   22.800   12.051  1.00 36.49
ATOM   2867  CA   ASP  579      49.694   23.656   12.786  1.00 38.09
ATOM   2868  CB   ASP  579      48.710   24.314   11.819  1.00 41.72
ATOM   2869  CG   ASP  579      49.409   25.243   10.817  1.00 45.89
ATOM   2870  OD1  ASP  579      49.175   25.102    9.595  1.00 48.85
ATOM   2871  OD2  ASP  579      50.197   26.119   11.248  1.00 48.08
ATOM   2872  C    ASP  579      48.999   22.742   13.792  1.00 37.56
ATOM   2873  O    ASP  579      48.998   21.528   13.606  1.00 38.03
ATOM   2874  N    ALA  580      48.419   23.316   14.847  1.00 36.79
ATOM   2875  CA   ALA  580      47.748   22.552   15.915  1.00 35.50
ATOM   2876  CB   ALA  580      46.956   23.496   16.810  1.00 36.40
ATOM   2877  C    ALA  580      46.856   21.391   15.470  1.00 34.02
ATOM   2878  O    ALA  580      46.700   20.404   16.188  1.00 32.85
ATOM   2879  N    MET  581      46.272   21.520   14.285  1.00 33.63
ATOM   2880  CA   MET  581      45.401   20.492   13.740  1.00 32.54
ATOM   2881  CB   MET  581      44.908   20.902   12.348  1.00 32.51
ATOM   2882  CG   MET  581      44.043   19.857   11.656  1.00 31.86
ATOM   2883  SD   MET  581      43.448   20.404   10.057  1.00 33.21
ATOM   2884  CE   MET  581      42.419   21.765   10.534  1.00 34.37
ATOM   2885  C    MET  581      46.119   19.158   13.636  1.00 32.20
ATOM   2886  O    MET  581      45.470   18.113   13.609  1.00 33.12
ATOM   2887  N    TRP  582      47.450   19.194   13.591  1.00 30.73
ATOM   2888  CA   TRP  582      48.246   17.979   13.455  1.00 29.56
ATOM   2889  CB   TRP  582      49.078   18.060   12.172  1.00 25.83
ATOM   2890  CG   TRP  582      48.252   18.490   10.972  1.00 22.26
ATOM   2891  CD2  TRP  582      47.205   17.743   10.330  1.00 19.39
ATOM   2892  CE2  TRP  582      46.672   18.563    9.319  1.00 18.29
ATOM   2893  CE3  TRP  582      46.666   16.461   10.515  1.00 18.37
ATOM   2894  CD1  TRP  582      48.312   19.690   10.331  1.00 19.79
ATOM   2895  NE1  TRP  582      47.367   19.744    9.345  1.00 19.82
```

FIGURE 1 (cont.)

| ATOM | 2896 | CZ2 | TRP | 582 | 45.620 | 18.148 | 8.490 | 1.00 | 16.85 |
|---|---|---|---|---|---|---|---|---|---|
| ATOM | 2897 | CZ3 | TRP | 582 | 45.623 | 16.047 | 9.693 | 1.00 | 16.11 |
| ATOM | 2898 | CH2 | TRP | 582 | 45.111 | 16.891 | 8.694 | 1.00 | 17.32 |
| ATOM | 2899 | C | TRP | 582 | 49.121 | 17.630 | 14.661 | 1.00 | 31.31 |
| ATOM | 2900 | O | TRP | 582 | 50.215 | 17.097 | 14.519 | 1.00 | 31.41 |
| ATOM | 2901 | N | ALA | 583 | 48.589 | 17.866 | 15.856 | 1.00 | 34.62 |
| ATOM | 2902 | CA | ALA | 583 | 49.285 | 17.575 | 17.107 | 1.00 | 34.61 |
| ATOM | 2903 | CB | ALA | 583 | 48.493 | 18.145 | 18.283 | 1.00 | 34.87 |
| ATOM | 2904 | C | ALA | 583 | 49.496 | 16.075 | 17.295 | 1.00 | 34.99 |
| ATOM | 2905 | O | ALA | 583 | 50.489 | 15.646 | 17.877 | 1.00 | 35.31 |
| ATOM | 2906 | N | CYS | 584 | 48.560 | 15.282 | 16.788 | 1.00 | 37.04 |
| ATOM | 2907 | CA | CYS | 584 | 48.610 | 13.815 | 16.893 | 1.00 | 38.08 |
| ATOM | 2908 | CB | CYS | 584 | 47.396 | 13.199 | 16.182 | 1.00 | 37.55 |
| ATOM | 2909 | SG | CYS | 584 | 47.130 | 13.868 | 14.512 | 1.00 | 40.22 |
| ATOM | 2910 | C | CYS | 584 | 49.886 | 13.200 | 16.317 | 1.00 | 37.89 |
| ATOM | 2911 | O | CYS | 584 | 50.375 | 12.178 | 16.809 | 1.00 | 37.62 |
| ATOM | 2912 | N | LEU | 585 | 50.422 | 13.835 | 15.279 | 1.00 | 37.89 |
| ATOM | 2913 | CA | LEU | 585 | 51.616 | 13.339 | 14.604 | 1.00 | 37.24 |
| ATOM | 2914 | CB | LEU | 585 | 51.506 | 13.590 | 13.099 | 1.00 | 34.72 |
| ATOM | 2915 | CG | LEU | 585 | 50.359 | 12.817 | 12.447 | 1.00 | 33.11 |
| ATOM | 2916 | CD1 | LEU | 585 | 50.194 | 13.205 | 10.994 | 1.00 | 32.42 |
| ATOM | 2917 | CD2 | LEU | 585 | 50.624 | 11.328 | 12.586 | 1.00 | 33.32 |
| ATOM | 2918 | C | LEU | 585 | 52.913 | 13.916 | 15.122 | 1.00 | 37.69 |
| ATOM | 2919 | O | LEU | 585 | 53.967 | 13.659 | 14.549 | 1.00 | 38.68 |
| ATOM | 2920 | N | ILE | 586 | 52.844 | 14.667 | 16.215 | 1.00 | 38.37 |
| ATOM | 2921 | CA | ILE | 586 | 54.033 | 15.286 | 16.776 | 1.00 | 39.55 |
| ATOM | 2922 | CB | ILE | 586 | 53.675 | 16.366 | 17.816 | 1.00 | 38.52 |
| ATOM | 2923 | CG2 | ILE | 586 | 54.915 | 16.799 | 18.593 | 1.00 | 37.57 |
| ATOM | 2924 | CG1 | ILE | 586 | 53.067 | 17.575 | 17.101 | 1.00 | 38.01 |
| ATOM | 2925 | CD1 | ILE | 586 | 52.671 | 18.705 | 18.018 | 1.00 | 37.82 |
| ATOM | 2926 | C | ILE | 586 | 55.015 | 14.277 | 17.355 | 1.00 | 41.37 |
| ATOM | 2927 | O | ILE | 586 | 56.191 | 14.274 | 16.985 | 1.00 | 42.88 |
| ATOM | 2928 | N | ALA | 587 | 54.528 | 13.391 | 18.215 | 1.00 | 41.55 |
| ATOM | 2929 | CA | ALA | 587 | 55.381 | 12.390 | 18.832 | 1.00 | 41.50 |
| ATOM | 2930 | CB | ALA | 587 | 54.544 | 11.442 | 19.665 | 1.00 | 42.38 |
| ATOM | 2931 | C | ALA | 587 | 56.214 | 11.606 | 17.810 | 1.00 | 42.23 |
| ATOM | 2932 | O | ALA | 587 | 57.358 | 11.236 | 18.089 | 1.00 | 43.74 |
| ATOM | 2933 | N | LEU | 588 | 55.644 | 11.375 | 16.628 | 1.00 | 41.27 |
| ATOM | 2934 | CA | LEU | 588 | 56.315 | 10.627 | 15.561 | 1.00 | 39.52 |
| ATOM | 2935 | CB | LEU | 588 | 55.270 | 9.940 | 14.678 | 1.00 | 39.86 |
| ATOM | 2936 | CG | LEU | 588 | 54.315 | 8.889 | 15.240 | 1.00 | 38.47 |
| ATOM | 2937 | CD1 | LEU | 588 | 53.206 | 8.640 | 14.235 | 1.00 | 36.97 |
| ATOM | 2938 | CD2 | LEU | 588 | 55.072 | 7.609 | 15.545 | 1.00 | 37.35 |
| ATOM | 2939 | C | LEU | 588 | 57.190 | 11.497 | 14.656 | 1.00 | 39.04 |
| ATOM | 2940 | O | LEU | 588 | 58.020 | 10.984 | 13.912 | 1.00 | 36.99 |
| ATOM | 2941 | N | LYS | 589 | 56.999 | 12.809 | 14.742 | 1.00 | 40.00 |
| ATOM | 2942 | CA | LYS | 589 | 57.701 | 13.800 | 13.922 | 1.00 | 42.08 |
| ATOM | 2943 | CB | LYS | 589 | 57.711 | 15.158 | 14.635 | 1.00 | 40.84 |
| ATOM | 2944 | CG | LYS | 589 | 58.259 | 16.282 | 13.795 | 1.00 | 41.90 |
| ATOM | 2945 | CD | LYS | 589 | 57.780 | 17.626 | 14.304 | 1.00 | 43.78 |
| ATOM | 2946 | CE | LYS | 589 | 58.264 | 18.756 | 13.414 | 1.00 | 44.18 |
| ATOM | 2947 | NZ | LYS | 589 | 57.675 | 20.058 | 13.824 | 1.00 | 46.71 |
| ATOM | 2948 | C | LYS | 589 | 59.099 | 13.460 | 13.368 | 1.00 | 43.12 |
| ATOM | 2949 | O | LYS | 589 | 59.343 | 13.595 | 12.162 | 1.00 | 43.36 |
| ATOM | 2950 | N | PRO | 590 | 60.026 | 13.013 | 14.230 | 1.00 | 43.51 |
| ATOM | 2951 | CD | PRO | 590 | 59.933 | 12.911 | 15.698 | 1.00 | 44.56 |
| ATOM | 2952 | CA | PRO | 590 | 61.378 | 12.672 | 13.778 | 1.00 | 42.92 |
| ATOM | 2953 | CB | PRO | 590 | 62.039 | 12.177 | 15.059 | 1.00 | 44.20 |

FIGURE 1 (cont.)

| | | | | | | | | |
|---|---|---|---|---|---|---|---|---|
| ATOM | 2954 | CG  | PRO | 590 | 61.380 | 13.008 | 16.112 | 1.00 44.80 |
| ATOM | 2955 | C   | PRO | 590 | 61.432 | 11.598 | 12.700 | 1.00 42.62 |
| ATOM | 2956 | O   | PRO | 590 | 62.368 | 11.558 | 11.901 | 1.00 44.16 |
| ATOM | 2957 | N   | THR | 591 | 60.443 | 10.716 | 12.697 | 1.00 40.90 |
| ATOM | 2958 | CA  | THR | 591 | 60.386 | 9.625  | 11.735 | 1.00 38.82 |
| ATOM | 2959 | CB  | THR | 591 | 59.742 | 8.390  | 12.393 | 1.00 40.84 |
| ATOM | 2960 | OG1 | THR | 591 | 58.390 | 8.691  | 12.775 | 1.00 41.16 |
| ATOM | 2961 | CG2 | THR | 591 | 60.531 | 7.999  | 13.643 | 1.00 40.40 |
| ATOM | 2962 | C   | THR | 591 | 59.637 | 9.953  | 10.441 | 1.00 36.37 |
| ATOM | 2963 | O   | THR | 591 | 59.770 | 9.249  | 9.438  | 1.00 35.64 |
| ATOM | 2964 | N   | LEU | 592 | 58.844 | 11.016 | 10.467 | 1.00 35.52 |
| ATOM | 2965 | CA  | LEU | 592 | 58.054 | 11.415 | 9.308  | 1.00 32.95 |
| ATOM | 2966 | CB  | LEU | 592 | 56.904 | 12.330 | 9.737  | 1.00 31.23 |
| ATOM | 2967 | CG  | LEU | 592 | 55.935 | 11.656 | 10.719 | 1.00 30.46 |
| ATOM | 2968 | CD1 | LEU | 592 | 54.765 | 12.565 | 11.025 | 1.00 30.71 |
| ATOM | 2969 | CD2 | LEU | 592 | 55.438 | 10.341 | 10.145 | 1.00 28.34 |
| ATOM | 2970 | C   | LEU | 592 | 58.945 | 12.090 | 8.293  | 1.00 32.65 |
| ATOM | 2971 | O   | LEU | 592 | 59.561 | 13.116 | 8.579  | 1.00 31.57 |
| ATOM | 2972 | N   | HIS | 593 | 58.998 | 11.508 | 7.100  | 1.00 33.01 |
| ATOM | 2973 | CA  | HIS | 593 | 59.840 | 12.005 | 6.016  | 1.00 33.45 |
| ATOM | 2974 | CB  | HIS | 593 | 61.103 | 11.140 | 5.916  | 1.00 36.56 |
| ATOM | 2975 | CG  | HIS | 593 | 60.814 | 9.677  | 5.743  | 1.00 40.30 |
| ATOM | 2976 | CD2 | HIS | 593 | 60.734 | 8.908  | 4.632  | 1.00 41.91 |
| ATOM | 2977 | ND1 | HIS | 593 | 60.502 | 8.849  | 6.801  | 1.00 42.01 |
| ATOM | 2978 | CE1 | HIS | 593 | 60.239 | 7.634  | 6.351  | 1.00 41.87 |
| ATOM | 2979 | NE2 | HIS | 593 | 60.371 | 7.643  | 5.037  | 1.00 42.34 |
| ATOM | 2980 | C   | HIS | 593 | 59.133 | 11.968 | 4.670  | 1.00 31.17 |
| ATOM | 2981 | O   | HIS | 593 | 58.321 | 11.084 | 4.398  | 1.00 30.16 |
| ATOM | 2982 | N   | GLY | 594 | 59.478 | 12.925 | 3.821  | 1.00 30.14 |
| ATOM | 2983 | CA  | GLY | 594 | 58.907 | 12.975 | 2.490  | 1.00 27.59 |
| ATOM | 2984 | C   | GLY | 594 | 57.747 | 13.918 | 2.282  | 1.00 24.95 |
| ATOM | 2985 | O   | GLY | 594 | 57.465 | 14.775 | 3.123  | 1.00 26.12 |
| ATOM | 2986 | N   | PRO | 595 | 57.093 | 13.815 | 1.119  | 1.00 22.45 |
| ATOM | 2987 | CD  | PRO | 595 | 57.443 | 12.914 | 0.005  | 1.00 21.56 |
| ATOM | 2988 | CA  | PRO | 595 | 55.951 | 14.652 | 0.776  | 1.00 21.39 |
| ATOM | 2989 | CB  | PRO | 595 | 55.888 | 14.516 | -0.739 | 1.00 21.51 |
| ATOM | 2990 | CG  | PRO | 595 | 56.283 | 13.091 | -0.953 | 1.00 21.07 |
| ATOM | 2991 | C   | PRO | 595 | 54.684 | 14.117 | 1.443  | 1.00 21.15 |
| ATOM | 2992 | O   | PRO | 595 | 54.562 | 12.927 | 1.741  | 1.00 21.34 |
| ATOM | 2993 | N   | THR | 596 | 53.752 | 15.017 | 1.695  | 1.00 20.85 |
| ATOM | 2994 | CA  | THR | 596 | 52.489 | 14.685 | 2.314  | 1.00 19.78 |
| ATOM | 2995 | CB  | THR | 596 | 51.855 | 15.958 | 2.914  | 1.00 18.44 |
| ATOM | 2996 | OG1 | THR | 596 | 52.742 | 16.520 | 3.890  | 1.00 18.54 |
| ATOM | 2997 | CG2 | THR | 596 | 50.512 | 15.640 | 3.552  | 1.00 17.29 |
| ATOM | 2998 | C   | THR | 596 | 51.499 | 14.121 | 1.304  | 1.00 19.38 |
| ATOM | 2999 | O   | THR | 596 | 51.308 | 14.712 | 0.233  | 1.00 19.92 |
| ATOM | 3000 | N   | PRO | 597 | 50.977 | 12.901 | 1.551  | 1.00 19.28 |
| ATOM | 3001 | CD  | PRO | 597 | 51.461 | 11.862 | 2.478  | 1.00 18.63 |
| ATOM | 3002 | CA  | PRO | 597 | 49.997 | 12.351 | 0.607  | 1.00 19.90 |
| ATOM | 3003 | CB  | PRO | 597 | 49.972 | 10.863 | 0.970  | 1.00 19.83 |
| ATOM | 3004 | CG  | PRO | 597 | 50.380 | 10.840 | 2.410  | 1.00 19.57 |
| ATOM | 3005 | C   | PRO | 597 | 48.671 | 13.092 | 0.927  | 1.00 20.50 |
| ATOM | 3006 | O   | PRO | 597 | 47.891 | 12.680 | 1.790  | 1.00 20.99 |
| ATOM | 3007 | N   | LEU | 598 | 48.501 | 14.252 | 0.294  | 1.00 18.90 |
| ATOM | 3008 | CA  | LEU | 598 | 47.355 | 15.120 | 0.510  | 1.00 17.83 |
| ATOM | 3009 | CB  | LEU | 598 | 47.514 | 16.493 | -0.128 | 1.00 17.96 |
| ATOM | 3010 | CG  | LEU | 598 | 46.722 | 17.655 | 0.314  | 1.00 18.91 |
| ATOM | 3011 | CD1 | LEU | 598 | 46.948 | 17.896 | 1.792  | 1.00 16.89 |

FIGURE 1 (cont.)

| ATOM | 3012 | CD2 | LEU | 598 | 47.011 | 18.916 | -0.490 | 1.00 | 16.71 |
|---|---|---|---|---|---|---|---|---|---|
| ATOM | 3013 | C | LEU | 598 | 46.037 | 14.542 | 0.010 | 1.00 | 17.19 |
| ATOM | 3014 | O | LEU | 598 | 45.862 | 14.285 | -1.187 | 1.00 | 17.59 |
| ATOM | 3015 | N | LEU | 599 | 45.097 | 14.378 | 0.935 | 1.00 | 15.70 |
| ATOM | 3016 | CA | LEU | 599 | 43.801 | 13.823 | 0.598 | 1.00 | 15.41 |
| ATOM | 3017 | CB | LEU | 599 | 43.236 | 13.034 | 1.782 | 1.00 | 14.25 |
| ATOM | 3018 | CG | LEU | 599 | 44.071 | 11.861 | 2.304 | 1.00 | 14.47 |
| ATOM | 3019 | CD1 | LEU | 599 | 43.268 | 11.092 | 3.331 | 1.00 | 11.46 |
| ATOM | 3020 | CD2 | LEU | 599 | 44.500 | 10.944 | 1.165 | 1.00 | 12.30 |
| ATOM | 3021 | C | LEU | 599 | 42.832 | 14.907 | 0.188 | 1.00 | 15.60 |
| ATOM | 3022 | O | LEU | 599 | 42.063 | 14.739 | -0.743 | 1.00 | 14.98 |
| ATOM | 3023 | N | TYR | 600 | 42.889 | 16.022 | 0.902 | 1.00 | 16.33 |
| ATOM | 3024 | CA | TYR | 600 | 42.025 | 17.178 | 0.675 | 1.00 | 16.87 |
| ATOM | 3025 | CB | TYR | 600 | 40.607 | 16.876 | 1.177 | 1.00 | 16.11 |
| ATOM | 3026 | CG | TYR | 600 | 40.567 | 15.864 | 2.303 | 1.00 | 15.17 |
| ATOM | 3027 | CD1 | TYR | 600 | 41.172 | 16.124 | 3.536 | 1.00 | 15.04 |
| ATOM | 3028 | CE1 | TYR | 600 | 41.198 | 15.163 | 4.546 | 1.00 | 15.31 |
| ATOM | 3029 | CD2 | TYR | 600 | 39.980 | 14.622 | 2.112 | 1.00 | 15.05 |
| ATOM | 3030 | CE2 | TYR | 600 | 39.997 | 13.657 | 3.112 | 1.00 | 16.28 |
| ATOM | 3031 | CZ | TYR | 600 | 40.607 | 13.931 | 4.323 | 1.00 | 15.83 |
| ATOM | 3032 | OH | TYR | 600 | 40.623 | 12.953 | 5.295 | 1.00 | 18.80 |
| ATOM | 3033 | C | TYR | 600 | 42.644 | 18.279 | 1.516 | 1.00 | 16.31 |
| ATOM | 3034 | O | TYR | 600 | 43.624 | 18.025 | 2.212 | 1.00 | 17.03 |
| ATOM | 3035 | N | ARG | 601 | 42.083 | 19.485 | 1.480 | 1.00 | 17.91 |
| ATOM | 3036 | CA | ARG | 601 | 42.623 | 20.578 | 2.287 | 1.00 | 19.15 |
| ATOM | 3037 | CB | ARG | 601 | 42.991 | 21.775 | 1.407 | 1.00 | 19.16 |
| ATOM | 3038 | CG | ARG | 601 | 43.949 | 21.415 | 0.298 | 1.00 | 21.99 |
| ATOM | 3039 | CD | ARG | 601 | 44.411 | 22.615 | -0.487 | 1.00 | 24.32 |
| ATOM | 3040 | NE | ARG | 601 | 45.189 | 22.200 | -1.649 | 1.00 | 27.46 |
| ATOM | 3041 | CZ | ARG | 601 | 46.317 | 22.783 | -2.052 | 1.00 | 29.91 |
| ATOM | 3042 | NH1 | ARG | 601 | 46.954 | 22.328 | -3.127 | 1.00 | 29.79 |
| ATOM | 3043 | NH2 | ARG | 601 | 46.813 | 23.819 | -1.385 | 1.00 | 29.28 |
| ATOM | 3044 | C | ARG | 601 | 41.688 | 21.004 | 3.420 | 1.00 | 20.23 |
| ATOM | 3045 | O | ARG | 601 | 40.501 | 21.273 | 3.208 | 1.00 | 20.27 |
| ATOM | 3046 | N | LEU | 602 | 42.237 | 21.035 | 4.630 | 1.00 | 21.19 |
| ATOM | 3047 | CA | LEU | 602 | 41.496 | 21.427 | 5.821 | 1.00 | 22.38 |
| ATOM | 3048 | CB | LEU | 602 | 41.437 | 20.264 | 6.809 | 1.00 | 22.22 |
| ATOM | 3049 | CG | LEU | 602 | 40.807 | 18.965 | 6.306 | 1.00 | 23.52 |
| ATOM | 3050 | CD1 | LEU | 602 | 40.914 | 17.913 | 7.390 | 1.00 | 22.77 |
| ATOM | 3051 | CD2 | LEU | 602 | 39.349 | 19.186 | 5.895 | 1.00 | 23.14 |
| ATOM | 3052 | C | LEU | 602 | 42.228 | 22.594 | 6.468 | 1.00 | 23.77 |
| ATOM | 3053 | O | LEU | 602 | 41.820 | 23.108 | 7.511 | 1.00 | 24.94 |
| ATOM | 3054 | N | GLY | 603 | 43.318 | 23.003 | 5.830 | 1.00 | 25.45 |
| ATOM | 3055 | CA | GLY | 603 | 44.131 | 24.087 | 6.330 | 1.00 | 25.21 |
| ATOM | 3056 | C | GLY | 603 | 45.240 | 24.352 | 5.339 | 1.00 | 26.57 |
| ATOM | 3057 | O | GLY | 603 | 45.160 | 23.924 | 4.183 | 1.00 | 26.29 |
| ATOM | 3058 | N | ALA | 604 | 46.293 | 25.021 | 5.796 | 1.00 | 27.24 |
| ATOM | 3059 | CA | ALA | 604 | 47.417 | 25.362 | 4.934 | 1.00 | 27.36 |
| ATOM | 3060 | CB | ALA | 604 | 48.215 | 26.499 | 5.554 | 1.00 | 27.18 |
| ATOM | 3061 | C | ALA | 604 | 48.315 | 24.164 | 4.684 | 1.00 | 26.80 |
| ATOM | 3062 | O | ALA | 604 | 48.598 | 23.395 | 5.603 | 1.00 | 26.71 |
| ATOM | 3063 | N | VAL | 605 | 48.728 | 23.990 | 3.431 | 1.00 | 28.18 |
| ATOM | 3064 | CA | VAL | 605 | 49.615 | 22.892 | 3.059 | 1.00 | 29.48 |
| ATOM | 3065 | CB | VAL | 605 | 49.089 | 22.064 | 1.812 | 1.00 | 28.74 |
| ATOM | 3066 | CG1 | VAL | 605 | 47.642 | 21.658 | 2.015 | 1.00 | 28.64 |
| ATOM | 3067 | CG2 | VAL | 605 | 49.221 | 22.825 | 0.518 | 1.00 | 29.95 |
| ATOM | 3068 | C | VAL | 605 | 51.000 | 23.487 | 2.821 | 1.00 | 30.10 |
| ATOM | 3069 | O | VAL | 605 | 51.255 | 24.133 | 1.807 | 1.00 | 30.89 |

FIGURE 1 (cont.)

| ATOM | 3070 | N   | GLN | 606 | 51.863 | 23.357 | 3.818  | 1.00 | 31.14 |
|------|------|-----|-----|-----|--------|--------|--------|------|-------|
| ATOM | 3071 | CA  | GLN | 606 | 53.213 | 23.897 | 3.720  | 1.00 | 32.44 |
| ATOM | 3072 | CB  | GLN | 606 | 53.627 | 24.481 | 5.068  | 1.00 | 34.05 |
| ATOM | 3073 | CG  | GLN | 606 | 52.846 | 25.750 | 5.412  | 1.00 | 38.82 |
| ATOM | 3074 | CD  | GLN | 606 | 52.595 | 25.915 | 6.899  | 1.00 | 41.93 |
| ATOM | 3075 | OE1 | GLN | 606 | 51.501 | 26.294 | 7.316  | 1.00 | 44.45 |
| ATOM | 3076 | NE2 | GLN | 606 | 53.605 | 25.625 | 7.710  | 1.00 | 43.43 |
| ATOM | 3077 | C   | GLN | 606 | 54.249 | 22.900 | 3.200  | 1.00 | 31.71 |
| ATOM | 3078 | O   | GLN | 606 | 55.117 | 23.251 | 2.399  | 1.00 | 32.38 |
| ATOM | 3079 | N   | ASN | 607 | 54.143 | 21.652 | 3.636  | 1.00 | 30.92 |
| ATOM | 3080 | CA  | ASN | 607 | 55.074 | 20.616 | 3.208  | 1.00 | 29.53 |
| ATOM | 3081 | CB  | ASN | 607 | 54.861 | 19.351 | 4.047  | 1.00 | 31.91 |
| ATOM | 3082 | CG  | ASN | 607 | 55.911 | 18.281 | 3.778  | 1.00 | 34.41 |
| ATOM | 3083 | OD1 | ASN | 607 | 57.109 | 18.580 | 3.692  | 1.00 | 35.38 |
| ATOM | 3084 | ND2 | ASN | 607 | 55.471 | 17.035 | 3.626  | 1.00 | 33.25 |
| ATOM | 3085 | C   | ASN | 607 | 54.892 | 20.287 | 1.728  | 1.00 | 28.03 |
| ATOM | 3086 | O   | ASN | 607 | 53.937 | 20.733 | 1.089  | 1.00 | 27.96 |
| ATOM | 3087 | N   | GLU | 608 | 55.852 | 19.566 | 1.164  | 1.00 | 26.45 |
| ATOM | 3088 | CA  | GLU | 608 | 55.755 | 19.146 | -0.227 | 1.00 | 25.62 |
| ATOM | 3089 | CB  | GLU | 608 | 57.023 | 18.420 | -0.663 | 1.00 | 28.49 |
| ATOM | 3090 | CG  | GLU | 608 | 58.214 | 19.314 | -0.845 | 1.00 | 33.96 |
| ATOM | 3091 | CD  | GLU | 608 | 59.497 | 18.528 | -0.996 | 1.00 | 38.84 |
| ATOM | 3092 | OE1 | GLU | 608 | 59.482 | 17.495 | -1.711 | 1.00 | 40.73 |
| ATOM | 3093 | OE2 | GLU | 608 | 60.515 | 18.941 | -0.388 | 1.00 | 40.03 |
| ATOM | 3094 | C   | GLU | 608 | 54.604 | 18.168 | -0.242 | 1.00 | 22.39 |
| ATOM | 3095 | O   | GLU | 608 | 54.364 | 17.499 | 0.754  | 1.00 | 22.12 |
| ATOM | 3096 | N   | VAL | 609 | 53.947 | 18.036 | -1.384 | 1.00 | 21.16 |
| ATOM | 3097 | CA  | VAL | 609 | 52.803 | 17.147 | -1.525 | 1.00 | 19.97 |
| ATOM | 3098 | CB  | VAL | 609 | 51.526 | 17.971 | -1.943 | 1.00 | 18.69 |
| ATOM | 3099 | CG1 | VAL | 609 | 50.343 | 17.049 | -2.263 | 1.00 | 18.90 |
| ATOM | 3100 | CG2 | VAL | 609 | 51.136 | 18.937 | -0.851 | 1.00 | 17.99 |
| ATOM | 3101 | C   | VAL | 609 | 53.020 | 16.099 | -2.607 | 1.00 | 19.62 |
| ATOM | 3102 | O   | VAL | 609 | 53.767 | 16.337 | -3.560 | 1.00 | 19.53 |
| ATOM | 3103 | N   | THR | 610 | 52.413 | 14.926 | -2.419 | 1.00 | 19.46 |
| ATOM | 3104 | CA  | THR | 610 | 52.412 | 13.872 | -3.430 | 1.00 | 20.82 |
| ATOM | 3105 | CB  | THR | 610 | 53.156 | 12.556 | -3.003 | 1.00 | 21.42 |
| ATOM | 3106 | OG1 | THR | 610 | 53.151 | 11.639 | -4.108 | 1.00 | 21.70 |
| ATOM | 3107 | CG2 | THR | 610 | 52.507 | 11.877 | -1.806 | 1.00 | 20.08 |
| ATOM | 3108 | C   | THR | 610 | 50.917 | 13.607 | -3.657 | 1.00 | 21.22 |
| ATOM | 3109 | O   | THR | 610 | 50.105 | 13.807 | -2.743 | 1.00 | 22.98 |
| ATOM | 3110 | N   | LEU | 611 | 50.541 | 13.278 | -4.890 | 1.00 | 21.98 |
| ATOM | 3111 | CA  | LEU | 611 | 49.145 | 12.981 | -5.239 | 1.00 | 21.98 |
| ATOM | 3112 | CB  | LEU | 611 | 48.648 | 13.895 | -6.369 | 1.00 | 20.70 |
| ATOM | 3113 | CG  | LEU | 611 | 48.629 | 15.415 | -6.175 | 1.00 | 22.00 |
| ATOM | 3114 | CD1 | LEU | 611 | 47.817 | 16.058 | -7.299 | 1.00 | 20.18 |
| ATOM | 3115 | CD2 | LEU | 611 | 48.018 | 15.759 | -4.815 | 1.00 | 22.59 |
| ATOM | 3116 | C   | LEU | 611 | 49.030 | 11.528 | -5.700 | 1.00 | 22.41 |
| ATOM | 3117 | O   | LEU | 611 | 48.086 | 11.155 | -6.389 | 1.00 | 24.23 |
| ATOM | 3118 | N   | THR | 612 | 49.997 | 10.709 | -5.321 | 1.00 | 23.19 |
| ATOM | 3119 | CA  | THR | 612 | 50.002 | 9.319  | -5.732 | 1.00 | 25.23 |
| ATOM | 3120 | CB  | THR | 612 | 51.449 | 8.834  | -5.995 | 1.00 | 27.01 |
| ATOM | 3121 | OG1 | THR | 612 | 52.242 | 8.995  | -4.805 | 1.00 | 29.09 |
| ATOM | 3122 | CG2 | THR | 612 | 52.079 | 9.633  | -7.127 | 1.00 | 27.28 |
| ATOM | 3123 | C   | THR | 612 | 49.331 | 8.350  | -4.765 | 1.00 | 24.95 |
| ATOM | 3124 | O   | THR | 612 | 49.217 | 7.168  | -5.072 | 1.00 | 25.66 |
| ATOM | 3125 | N   | HIS | 613 | 48.904 | 8.816  | -3.595 | 1.00 | 24.14 |
| ATOM | 3126 | CA  | HIS | 613 | 48.283 | 7.898  | -2.653 | 1.00 | 23.56 |
| ATOM | 3127 | CB  | HIS | 613 | 48.080 | 8.555  | -1.292 | 1.00 | 21.38 |

FIGURE 1 (cont.)

| | | | | | | | | |
|---|---|---|---|---|---|---|---|---|
| ATOM | 3128 | CG  | HIS | 613 | 47.870 | 7.579  | -0.171  | 1.00 21.58 |
| ATOM | 3129 | CD2 | HIS | 613 | 48.699 | 7.162  | 0.814   | 1.00 21.05 |
| ATOM | 3130 | ND1 | HIS | 613 | 46.680 | 6.909  | 0.026   | 1.00 20.95 |
| ATOM | 3131 | CE1 | HIS | 613 | 46.788 | 6.118  | 1.080   | 1.00 18.99 |
| ATOM | 3132 | NE2 | HIS | 613 | 48.002 | 6.255  | 1.577   | 1.00 19.71 |
| ATOM | 3133 | C   | HIS | 613 | 46.962 | 7.381  | -3.225  | 1.00 24.95 |
| ATOM | 3134 | O   | HIS | 613 | 46.211 | 8.132  | -3.855  | 1.00 24.56 |
| ATOM | 3135 | N   | PRO | 614 | 46.683 | 6.074  | -3.047  | 1.00 25.96 |
| ATOM | 3136 | CD  | PRO | 614 | 47.577 | 5.083  | -2.412  | 1.00 25.46 |
| ATOM | 3137 | CA  | PRO | 614 | 45.455 | 5.430  | -3.537  | 1.00 25.84 |
| ATOM | 3138 | CB  | PRO | 614 | 45.526 | 4.051  | -2.884  | 1.00 25.79 |
| ATOM | 3139 | CG  | PRO | 614 | 46.989 | 3.774  | -2.849  | 1.00 26.21 |
| ATOM | 3140 | C   | PRO | 614 | 44.168 | 6.182  | -3.137  | 1.00 26.01 |
| ATOM | 3141 | O   | PRO | 614 | 43.253 | 6.346  | -3.946  | 1.00 26.99 |
| ATOM | 3142 | N   | ILE | 615 | 44.114 | 6.643  | -1.890  | 1.00 25.62 |
| ATOM | 3143 | CA  | ILE | 615 | 42.959 | 7.379  | -1.383  | 1.00 25.23 |
| ATOM | 3144 | CB  | ILE | 615 | 43.075 | 7.635  | 0.132   | 1.00 26.29 |
| ATOM | 3145 | CG2 | ILE | 615 | 41.823 | 8.358  | 0.644   | 1.00 25.16 |
| ATOM | 3146 | CG1 | ILE | 615 | 43.264 | 6.306  | 0.873   | 1.00 24.79 |
| ATOM | 3147 | CD1 | ILE | 615 | 42.158 | 5.291  | 0.603   | 1.00 25.74 |
| ATOM | 3148 | C   | ILE | 615 | 42.766 | 8.699  | -2.127  | 1.00 25.02 |
| ATOM | 3149 | O   | ILE | 615 | 41.641 | 9.075  | -2.449  | 1.00 24.98 |
| ATOM | 3150 | N   | THR | 616 | 43.870 | 9.388  | -2.409  | 1.00 24.97 |
| ATOM | 3151 | CA  | THR | 616 | 43.838 | 10.654 | -3.142  | 1.00 24.03 |
| ATOM | 3152 | CB  | THR | 616 | 45.268 | 11.208 | -3.307  | 1.00 21.36 |
| ATOM | 3153 | OG1 | THR | 616 | 45.880 | 11.313 | -2.023  | 1.00 19.82 |
| ATOM | 3154 | CG2 | THR | 616 | 45.255 | 12.573 | -3.946  | 1.00 22.30 |
| ATOM | 3155 | C   | THR | 616 | 43.234 | 10.403 | -4.531  | 1.00 25.54 |
| ATOM | 3156 | O   | THR | 616 | 42.312 | 11.107 | -4.970  | 1.00 25.06 |
| ATOM | 3157 | N   | LYS | 617 | 43.745 | 9.374  | -5.205  | 1.00 26.21 |
| ATOM | 3158 | CA  | LYS | 617 | 43.268 | 9.013  | -6.532  | 1.00 26.68 |
| ATOM | 3159 | CB  | LYS | 617 | 44.103 | 7.865  | -7.106  | 1.00 29.57 |
| ATOM | 3160 | CG  | LYS | 617 | 45.601 | 8.150  | -7.174  | 1.00 32.92 |
| ATOM | 3161 | CD  | LYS | 617 | 46.125 | 8.036  | -8.593  | 1.00 36.18 |
| ATOM | 3162 | CE  | LYS | 617 | 45.459 | 9.068  | -9.512  | 1.00 39.50 |
| ATOM | 3163 | NZ  | LYS | 617 | 45.780 | 8.867  | -10.963 | 1.00 39.79 |
| ATOM | 3164 | C   | LYS | 617 | 41.789 | 8.630  | -6.469  | 1.00 25.76 |
| ATOM | 3165 | O   | LYS | 617 | 41.023 | 8.968  | -7.375  | 1.00 23.91 |
| ATOM | 3166 | N   | TYR | 618 | 41.401 | 7.935  | -5.397  | 1.00 25.82 |
| ATOM | 3167 | CA  | TYR | 618 | 40.010 | 7.518  | -5.180  | 1.00 26.33 |
| ATOM | 3168 | CB  | TYR | 618 | 39.884 | 6.701  | -3.883  | 1.00 28.26 |
| ATOM | 3169 | CG  | TYR | 618 | 38.441 | 6.394  | -3.504  | 1.00 32.04 |
| ATOM | 3170 | CD1 | TYR | 618 | 37.768 | 5.307  | -4.081  | 1.00 33.48 |
| ATOM | 3171 | CE1 | TYR | 618 | 36.423 | 5.049  | -3.804  | 1.00 32.78 |
| ATOM | 3172 | CD2 | TYR | 618 | 37.725 | 7.221  | -2.624  | 1.00 31.35 |
| ATOM | 3173 | CE2 | TYR | 618 | 36.372 | 6.971  | -2.339  | 1.00 31.99 |
| ATOM | 3174 | CZ  | TYR | 618 | 35.735 | 5.880  | -2.938  | 1.00 33.67 |
| ATOM | 3175 | OH  | TYR | 618 | 34.421 | 5.588  | -2.668  | 1.00 34.74 |
| ATOM | 3176 | C   | TYR | 618 | 39.091 | 8.740  | -5.086  | 1.00 26.08 |
| ATOM | 3177 | O   | TYR | 618 | 38.135 | 8.871  | -5.850  | 1.00 24.27 |
| ATOM | 3178 | N   | ILE | 619 | 39.395 | 9.637  | -4.148  | 1.00 26.53 |
| ATOM | 3179 | CA  | ILE | 619 | 38.592 | 10.840 | -3.952  | 1.00 26.78 |
| ATOM | 3180 | CB  | ILE | 619 | 39.110 | 11.696 | -2.771  | 1.00 26.09 |
| ATOM | 3181 | CG2 | ILE | 619 | 38.201 | 12.890 | -2.554  | 1.00 27.00 |
| ATOM | 3182 | CG1 | ILE | 619 | 39.114 | 10.868 | -1.484  | 1.00 24.87 |
| ATOM | 3183 | CD1 | ILE | 619 | 39.696 | 11.585 | -0.275  | 1.00 23.06 |
| ATOM | 3184 | C   | ILE | 619 | 38.531 | 11.669 | -5.232  | 1.00 27.63 |
| ATOM | 3185 | O   | ILE | 619 | 37.510 | 12.299 | -5.517  | 1.00 28.56 |

FIGURE 1 (cont.)

| | | | | | | | | |
|---|---|---|---|---|---|---|---|---|
| ATOM | 3186 | N | MET | 620 | 39.603 | 11.635 | -6.020 | 1.00 28.31 |
| ATOM | 3187 | CA | MET | 620 | 39.642 | 12.367 | -7.281 | 1.00 29.16 |
| ATOM | 3188 | CB | MET | 620 | 41.047 | 12.339 | -7.888 | 1.00 30.86 |
| ATOM | 3189 | CG | MET | 620 | 42.068 | 13.180 | -7.133 | 1.00 31.31 |
| ATOM | 3190 | SD | MET | 620 | 43.700 | 13.152 | -7.887 | 1.00 33.66 |
| ATOM | 3191 | CE | MET | 620 | 43.745 | 14.717 | -8.555 | 1.00 34.32 |
| ATOM | 3192 | C | MET | 620 | 38.625 | 11.813 | -8.274 | 1.00 29.85 |
| ATOM | 3193 | O | MET | 620 | 38.040 | 12.563 | -9.048 | 1.00 29.99 |
| ATOM | 3194 | N | THR | 621 | 38.397 | 10.504 | -8.248 | 1.00 31.58 |
| ATOM | 3195 | CA | THR | 621 | 37.412 | 9.909 | -9.146 | 1.00 33.23 |
| ATOM | 3196 | CB | THR | 621 | 37.505 | 8.351 | -9.182 | 1.00 34.83 |
| ATOM | 3197 | OG1 | THR | 621 | 37.348 | 7.801 | -7.865 | 1.00 34.63 |
| ATOM | 3198 | CG2 | THR | 621 | 38.853 | 7.918 | -9.741 | 1.00 34.93 |
| ATOM | 3199 | C | THR | 621 | 36.008 | 10.355 | -8.727 | 1.00 33.69 |
| ATOM | 3200 | O | THR | 621 | 35.089 | 10.387 | -9.539 | 1.00 32.60 |
| ATOM | 3201 | N | CYS | 622 | 35.860 | 10.705 | -7.449 | 1.00 35.29 |
| ATOM | 3202 | CA | CYS | 622 | 34.582 | 11.166 | -6.915 | 1.00 36.11 |
| ATOM | 3203 | CB | CYS | 622 | 34.584 | 11.148 | -5.379 | 1.00 34.25 |
| ATOM | 3204 | SG | CYS | 622 | 34.541 | 9.474 | -4.630 | 1.00 34.81 |
| ATOM | 3205 | C | CYS | 622 | 34.282 | 12.565 | -7.434 | 1.00 37.34 |
| ATOM | 3206 | O | CYS | 622 | 33.124 | 12.980 | -7.498 | 1.00 38.25 |
| ATOM | 3207 | N | MET | 623 | 35.329 | 13.284 | -7.823 | 1.00 38.28 |
| ATOM | 3208 | CA | MET | 623 | 35.161 | 14.626 | -8.352 | 1.00 40.10 |
| ATOM | 3209 | CB | MET | 623 | 36.477 | 15.399 | -8.297 | 1.00 38.66 |
| ATOM | 3210 | CG | MET | 623 | 37.160 | 15.447 | -6.952 | 1.00 38.37 |
| ATOM | 3211 | SD | MET | 623 | 36.295 | 16.417 | -5.730 | 1.00 38.37 |
| ATOM | 3212 | CE | MET | 623 | 36.561 | 15.423 | -4.310 | 1.00 38.68 |
| ATOM | 3213 | C | MET | 623 | 34.701 | 14.559 | -9.809 | 1.00 42.69 |
| ATOM | 3214 | O | MET | 623 | 33.953 | 15.425 | -10.263 | 1.00 44.25 |
| ATOM | 3215 | N | SER | 624 | 35.169 | 13.544 | -10.539 | 1.00 44.54 |
| ATOM | 3216 | CA | SER | 624 | 34.843 | 13.373 | -11.959 | 1.00 45.95 |
| ATOM | 3217 | CB | SER - | 624 | 35.862 | 12.432 | -12.624 | 1.00 46.09 |
| ATOM | 3218 | OG | SER | 624 | 36.043 | 11.237 | -11.879 | 1.00 45.68 |
| ATOM | 3219 | C | SER | 624 | 33.408 | 12.937 | -12.294 | 1.00 46.50 |
| ATOM | 3220 | O | SER | 624 | 32.901 | 11.984 | -11.658 | 1.00 48.12 |

SULFATE ION COORDINATES

| | | Atom Type | Resid | # | X | Y | Z | OCC | B |
|---|---|---|---|---|---|---|---|---|---|
| ATOM | 3221 | S | SO4 | 1001 | 8.646 | 28.709 | 22.190 | 1.00 | 32.01 |
| ATOM | 3222 | O1 | SO4 | 1001 | 9.006 | 27.263 | 22.094 | 1.00 | 35.92 |
| ATOM | 3223 | O2 | SO4 | 1001 | 8.328 | 28.982 | 23.610 | 1.00 | 33.43 |
| ATOM | 3224 | O3 | SO4 | 1001 | 9.821 | 29.520 | 21.744 | 1.00 | 33.54 |
| ATOM | 3225 | O4 | SO4 | 1001 | 7.429 | 28.930 | 21.367 | 1.00 | 32.87 |

DNA COORDINATES

| | | Atom Type | Resid | # | X | Y | Z | OCC | B |
|---|---|---|---|---|---|---|---|---|---|
| ATOM | 3226 | O3' | THY | 2 | 37.257 | 37.479 | 7.626 | 1.00 | 62.88 |
| ATOM | 3227 | P | THY | 3 | 38.537 | 37.587 | 8.598 | 1.00 | 64.59 |
| ATOM | 3228 | O1P | THY | 3 | 39.744 | 37.500 | 7.737 | 1.00 | 65.36 |
| ATOM | 3229 | O2P | THY | 3 | 38.349 | 38.772 | 9.478 | 1.00 | 64.52 |
| ATOM | 3230 | O5' | THY | 3 | 38.465 | 36.284 | 9.516 | 1.00 | 61.39 |
| ATOM | 3231 | C2' | THY | 3 | 39.582 | 33.841 | 11.157 | 1.00 | 57.22 |

FIGURE 1 (cont.)

| | | | | | | | | |
|---|---|---|---|---|---|---|---|---|
| ATOM | 3232 | C5' | THY | 3 | 37.215 | 35.787 | 9.985 | 1.00 58.94 |
| ATOM | 3233 | C4' | THY | 3 | 37.364 | 34.359 | 10.454 | 1.00 57.48 |
| ATOM | 3234 | O4' | THY | 3 | 38.030 | 33.610 | 9.411 | 1.00 57.98 |
| ATOM | 3235 | C1' | THY | 3 | 39.244 | 33.059 | 9.901 | 1.00 57.84 |
| ATOM | 3236 | C3' | THY | 3 | 38.209 | 34.160 | 11.712 | 1.00 55.51 |
| ATOM | 3237 | O3' | THY | 3 | 37.714 | 33.032 | 12.440 | 1.00 53.32 |
| ATOM | 3238 | P | THY | 4 | 37.453 | 33.144 | 14.024 | 1.00 51.06 |
| ATOM | 3239 | O1P | THY | 4 | 38.284 | 32.114 | 14.682 | 1.00 52.62 |
| ATOM | 3240 | O2P | THY | 4 | 37.572 | 34.555 | 14.460 | 1.00 52.47 |
| ATOM | 3241 | O5' | THY | 4 | 35.934 | 32.695 | 14.174 | 1.00 51.46 |
| ATOM | 3242 | N1 | THY | 4 | 33.007 | 29.972 | 13.415 | 1.00 46.84 |
| ATOM | 3243 | C6 | THY | 4 | 34.293 | 29.767 | 12.965 | 1.00 47.09 |
| ATOM | 3244 | C2 | THY | 4 | 31.944 | 29.300 | 12.868 | 1.00 45.86 |
| ATOM | 3245 | O2 | THY | 4 | 30.796 | 29.449 | 13.234 | 1.00 45.89 |
| ATOM | 3246 | N3 | THY | 4 | 32.280 | 28.434 | 11.866 | 1.00 46.41 |
| ATOM | 3247 | C4 | THY | 4 | 33.542 | 28.179 | 11.371 | 1.00 47.33 |
| ATOM | 3248 | O4 | THY | 4 | 33.690 | 27.380 | 10.465 | 1.00 49.11 |
| ATOM | 3249 | C5 | THY | 4 | 34.610 | 28.916 | 11.991 | 1.00 47.24 |
| ATOM | 3250 | C2' | THY | 4 | 33.891 | 30.788 | 15.545 | 1.00 50.03 |
| ATOM | 3251 | C5' | THY | 4 | 34.879 | 33.651 | 14.170 | 1.00 50.28 |
| ATOM | 3252 | C4' | THY | 4 | 33.674 | 33.079 | 14.873 | 1.00 49.97 |
| ATOM | 3253 | O4' | THY | 4 | 32.919 | 32.228 | 13.976 | 1.00 48.97 |
| ATOM | 3254 | C1' | THY | 4 | 32.790 | 30.920 | 14.512 | 1.00 47.73 |
| ATOM | 3255 | C3' | THY | 4 | 34.075 | 32.202 | 16.056 | 1.00 50.49 |
| ATOM | 3256 | O3' | THY | 4 | 33.236 | 32.403 | 17.179 | 1.00 50.67 |
| ATOM | 3257 | P | THY | 5 | 33.285 | 31.347 | 18.371 | 1.00 47.87 |
| ATOM | 3258 | O1P | THY | 5 | 34.541 | 30.575 | 18.215 | 1.00 48.85 |
| ATOM | 3259 | O2P | THY | 5 | 33.015 | 32.074 | 19.631 | 1.00 48.56 |
| ATOM | 3260 | O5' | THY | 5 | 32.072 | 30.374 | 18.051 | 1.00 49.19 |
| ATOM | 3261 | N1 | THY | 5 | 31.213 | 27.155 | 16.419 | 1.00 58.66 |
| ATOM | 3262 | C6 | THY | 5 | 32.482 | 27.691 | 16.481 | 1.00 59.82 |
| ATOM | 3263 | C2 | THY | 5 | 30.878 | 26.224 | 15.460 | 1.00 60.12 |
| ATOM | 3264 | O2 | THY | 5 | 29.775 | 25.706 | 15.384 | 1.00 61.69 |
| ATOM | 3265 | N3 | THY | 5 | 31.896 | 25.911 | 14.590 | 1.00 60.92 |
| ATOM | 3266 | C4 | THY | 5 | 33.180 | 26.422 | 14.589 | 1.00 60.86 |
| ATOM | 3267 | O4 | THY | 5 | 33.980 | 26.063 | 13.733 | 1.00 62.48 |
| ATOM | 3268 | C5 | THY | 5 | 33.467 | 27.375 | 15.633 | 1.00 60.58 |
| ATOM | 3269 | C2' | THY | 5 | 30.746 | 27.746 | 18.796 | 1.00 54.89 |
| ATOM | 3270 | C5' | THY | 5 | 30.759 | 30.895 | 17.870 | 1.00 52.14 |
| ATOM | 3271 | C4' | THY | 5 | 29.741 | 29.807 | 18.097 | 1.00 53.54 |
| ATOM | 3272 | O4' | THY | 5 | 29.757 | 28.886 | 16.980 | 1.00 54.95 |
| ATOM | 3273 | C1' | THY | 5 | 30.192 | 27.595 | 17.387 | 1.00 56.51 |
| ATOM | 3274 | C3' | THY | 5 | 30.042 | 28.976 | 19.338 | 1.00 53.67 |
| ATOM | 3275 | O3' | THY | 5 | 28.841 | 28.640 | 20.011 | 1.00 53.59 |
| ATOM | 3276 | P | THY | 6 | 28.902 | 27.677 | 21.286 | 1.00 55.49 |
| ATOM | 3277 | O1P | THY | 6 | 30.314 | 27.643 | 21.757 | 1.00 54.73 |
| ATOM | 3278 | O2P | THY | 6 | 27.825 | 28.072 | 22.235 | 1.00 56.13 |
| ATOM | 3279 | O5' | THY | 6 | 28.517 | 26.262 | 20.665 | 1.00 56.29 |
| ATOM | 3280 | N1 | THY | 6 | 29.855 | 23.122 | 18.173 | 1.00 60.63 |
| ATOM | 3281 | C6 | THY | 6 | 30.949 | 23.677 | 18.806 | 1.00 61.06 |
| ATOM | 3282 | C2 | THY | 6 | 29.949 | 22.610 | 16.902 | 1.00 61.67 |
| ATOM | 3283 | O2 | THY | 6 | 28.995 | 22.152 | 16.291 | 1.00 61.78 |
| ATOM | 3284 | N3 | THY | 6 | 31.212 | 22.658 | 16.363 | 1.00 63.46 |
| ATOM | 3285 | C4 | THY | 6 | 32.355 | 23.175 | 16.950 | 1.00 63.98 |
| ATOM | 3286 | O4 | THY | 6 | 33.427 | 23.132 | 16.348 | 1.00 66.37 |
| ATOM | 3287 | C5 | THY | 6 | 32.171 | 23.732 | 18.268 | 1.00 62.56 |
| ATOM | 3288 | C2' | THY | 6 | 28.701 | 23.043 | 20.380 | 1.00 58.18 |
| ATOM | 3289 | C5' | THY | 6 | 27.266 | 26.086 | 19.995 | 1.00 55.60 |

FIGURE 1 (cont.)

| | | | | | | | | |
|---|---|---|---|---|---|---|---|---|
| ATOM | 3290 | C4' | THY | 6 | 27.031 | 24.624 | 19.695 | 1.00 56.65 |
| ATOM | 3291 | O4' | THY | 6 | 27.827 | 24.224 | 18.554 | 1.00 57.17 |
| ATOM | 3292 | C1' | THY | 6 | 28.559 | 23.051 | 18.868 | 1.00 58.86 |
| ATOM | 3293 | C3' | THY | 6 | 27.402 | 23.677 | 20.838 | 1.00 57.43 |
| ATOM | 3294 | O3' | THY | 6 | 26.423 | 22.658 | 21.005 | 1.00 57.14 |
| ATOM | 3295 | P | THY | 7 | 26.118 | 22.092 | 22.476 | 1.00 55.41 |
| ATOM | 3296 | O1P | THY | 7 | 27.388 | 21.574 | 23.052 | 1.00 55.46 |
| ATOM | 3297 | O2P | THY | 7 | 25.341 | 23.126 | 23.212 | 1.00 55.42 |
| ATOM | 3298 | O5' | THY | 7 | 25.155 | 20.856 | 22.209 | 1.00 54.29 |
| ATOM | 3299 | N1 | THY | 7 | 28.804 | 18.991 | 19.952 | 1.00 50.01 |
| ATOM | 3300 | C6 | THY | 7 | 29.541 | 19.632 | 20.927 | 1.00 49.74 |
| ATOM | 3301 | C2 | THY | 7 | 29.235 | 18.962 | 18.632 | 1.00 49.72 |
| ATOM | 3302 | O2 | THY | 7 | 28.630 | 18.401 | 17.735 | 1.00 49.11 |
| ATOM | 3303 | N3 | THY | 7 | 30.418 | 19.620 | 18.403 | 1.00 49.95 |
| ATOM | 3304 | C4 | THY | 7 | 31.199 | 20.284 | 19.331 | 1.00 50.77 |
| ATOM | 3305 | O4 | THY | 7 | 32.238 | 20.836 | 18.973 | 1.00 52.95 |
| ATOM | 3306 | C5 | THY | 7 | 30.695 | 20.267 | 20.688 | 1.00 50.49 |
| ATOM | 3307 | C2' | THY | 7 | 27.275 | 18.299 | 21.813 | 1.00 49.16 |
| ATOM | 3308 | C5' | THY | 7 | 24.826 | 20.456 | 20.880 | 1.00 51.47 |
| ATOM | 3309 | C4' | THY | 7 | 25.318 | 19.048 | 20.636 | 1.00 49.37 |
| ATOM | 3310 | O4' | THY | 7 | 26.467 | 19.074 | 19.756 | 1.00 49.04 |
| ATOM | 3311 | C1' | THY | 7 | 27.533 | 18.322 | 20.317 | 1.00 49.64 |
| ATOM | 3312 | C3' | THY | 7 | 25.759 | 18.341 | 21.914 | 1.00 48.18 |
| ATOM | 3313 | O3' | THY | 7 | 25.208 | 17.033 | 22.016 | 1.00 45.69 |
| ATOM | 3314 | P | THY | 8 | 25.223 | 16.282 | 23.434 | 1.00 43.16 |
| ATOM | 3315 | O1P | THY | 8 | 26.128 | 17.012 | 24.351 | 1.00 44.74 |
| ATOM | 3316 | O2P | THY | 8 | 23.837 | 16.004 | 23.867 | 1.00 44.40 |
| ATOM | 3317 | O5' | THY | 8 | 25.923 | 14.895 | 23.096 | 1.00 45.67 |
| ATOM | 3318 | N1 | THY | 8 | 29.550 | 14.234 | 20.725 | 1.00 45.65 |
| ATOM | 3319 | C6 | THY | 8 | 30.514 | 14.642 | 21.618 | 1.00 44.74 |
| ATOM | 3320 | C2 | THY | 8 | 29.464 | 14.791 | 19.469 | 1.00 46.33 |
| ATOM | 3321 | O2 | THY | 8 | 28.611 | 14.482 | 18.661 | 1.00 48.73 |
| ATOM | 3322 | N3 | THY | 8 | 30.418 | 15.737 | 19.193 | 1.00 46.38 |
| ATOM | 3323 | C4 | THY | 8 | 31.416 | 16.183 | 20.035 | 1.00 45.35 |
| ATOM | 3324 | O4 | THY | 8 | 32.203 | 17.041 | 19.650 | 1.00 44.96 |
| ATOM | 3325 | C5 | THY | 8 | 31.435 | 15.573 | 21.343 | 1.00 45.22 |
| ATOM | 3326 | C2' | THY | 8 | 28.573 | 12.869 | 22.592 | 1.00 46.80 |
| ATOM | 3327 | C5' | THY | 8 | 25.331 | 13.994 | 22.171 | 1.00 46.20 |
| ATOM | 3328 | C4' | THY | 8 | 26.346 | 12.982 | 21.695 | 1.00 46.45 |
| ATOM | 3329 | O4' | THY | 8 | 27.289 | 13.613 | 20.792 | 1.00 45.83 |
| ATOM | 3330 | C1' | THY | 8 | 28.598 | 13.170 | 21.103 | 1.00 46.11 |
| ATOM | 3331 | C3' | THY | 8 | 27.170 | 12.324 | 22.806 | 1.00 46.52 |
| ATOM | 3332 | O3' | THY | 8 | 27.137 | 10.893 | 22.783 | 1.00 46.89 |

WATER MOLECULE COORDINATES

| | | Atom Type | Resid | # | X | Y | Z | OCC | B |
|---|---|---|---|---|---|---|---|---|---|
| ATOM | 3333 | OH2 | TIP3 | 1 | -0.245 | 23.385 | 32.975 | 1.00 | 19.18 |
| ATOM | 3334 | OH2 | TIP3 | 2 | 22.305 | 18.313 | 19.597 | 1.00 | 27.90 |
| ATOM | 3335 | OH2 | TIP3 | 3 | 16.363 | 43.283 | 27.772 | 1.00 | 24.59 |
| ATOM | 3336 | OH2 | TIP3 | 4 | 36.537 | 45.914 | 31.680 | 1.00 | 20.59 |
| ATOM | 3337 | OH2 | TIP3 | 5 | 17.542 | 27.937 | 8.465 | 1.00 | 18.37 |
| ATOM | 3338 | OH2 | TIP3 | 6 | 35.726 | 50.776 | 9.824 | 1.00 | 31.71 |
| ATOM | 3339 | OH2 | TIP3 | 7 | 20.453 | 38.335 | 27.173 | 1.00 | 47.06 |
| ATOM | 3340 | OH2 | TIP3 | 8 | 15.332 | 19.267 | 24.557 | 1.00 | 25.04 |
| ATOM | 3341 | OH2 | TIP3 | 9 | 31.258 | 50.983 | 30.493 | 1.00 | 29.38 |

FIGURE 1 (cont.)

| | | | | | | | | |
|---|---|---|---|---|---|---|---|---|
| ATOM | 3342 | OH2 | TIP3 | 10 | 28.501 | 7.997 | 7.807 | 1.00 21.94 |
| ATOM | 3343 | OH2 | TIP3 | 11 | 24.624 | 24.209 | 25.328 | 1.00 24.23 |
| ATOM | 3344 | OH2 | TIP3 | 12 | 14.538 | 39.417 | 17.207 | 1.00 26.71 |
| ATOM | 3345 | OH2 | TIP3 | 13 | 19.304 | 29.672 | 7.885 | 1.00 17.01 |
| ATOM | 3346 | OH2 | TIP3 | 14 | 9.539 | 36.215 | 8.250 | 1.00 19.38 |
| ATOM | 3347 | OH2 | TIP3 | 15 | 22.976 | 53.935 | 15.769 | 1.00 19.99 |
| ATOM | 3348 | OH2 | TIP3 | 16 | 11.332 | 38.883 | 13.163 | 1.00 41.21 |
| ATOM | 3349 | OH2 | TIP3 | 17 | 44.389 | 17.456 | 4.710 | 1.00 25.71 |
| ATOM | 3350 | OH2 | TIP3 | 18 | 18.217 | 51.026 | 25.327 | 1.00 21.08 |
| ATOM | 3351 | OH2 | TIP3 | 19 | 52.875 | 8.529 | 0.460 | 1.00 38.69 |
| ATOM | 3352 | OH2 | TIP3 | 20 | 49.464 | 5.589 | 3.749 | 1.00 29.49 |
| ATOM | 3353 | OH2 | TIP3 | 21 | 18.312 | 39.750 | 29.166 | 1.00 35.93 |
| ATOM | 3354 | OH2 | TIP3 | 22 | 45.019 | 20.106 | 5.017 | 1.00 21.12 |
| ATOM | 3355 | OH2 | TIP3 | 23 | 0.745 | 18.945 | 33.170 | 1.00 25.64 |
| ATOM | 3356 | OH2 | TIP3 | 24 | 43.077 | 1.470 | 3.086 | 1.00 41.57 |
| ATOM | 3357 | OH2 | TIP3 | 25 | 32.242 | 40.177 | 37.162 | 1.00 30.45 |
| ATOM | 3358 | OH2 | TIP3 | 26 | 22.005 | 19.740 | 17.116 | 1.00 23.05 |
| ATOM | 3359 | OH2 | TIP3 | 27 | 23.883 | 51.464 | 21.877 | 1.00 39.16 |
| ATOM | 3360 | OH2 | TIP3 | 28 | 23.231 | 34.878 | 17.602 | 1.00 27.32 |
| ATOM | 3361 | OH2 | TIP3 | 29 | 16.275 | 41.943 | 30.227 | 1.00 44.09 |
| ATOM | 3362 | OH2 | TIP3 | 31 | 24.393 | 23.198 | -0.349 | 1.00 34.79 |
| ATOM | 3363 | OH2 | TIP3 | 32 | 55.138 | 10.008 | 1.356 | 1.00 34.91 |
| ATOM | 3364 | OH2 | TIP3 | 33 | 8.529 | 32.844 | 5.639 | 1.00 48.78 |
| ATOM | 3365 | OH2 | TIP3 | 35 | 13.937 | 52.763 | 22.191 | 1.00 34.84 |
| ATOM | 3366 | OH2 | TIP3 | 36 | 17.459 | 5.667 | 9.998 | 1.00 37.45 |
| ATOM | 3367 | OH2 | TIP3 | 37 | 42.199 | 25.099 | -1.836 | 1.00 37.69 |
| ATOM | 3368 | OH2 | TIP3 | 38 | 7.460 | 11.207 | 37.359 | 1.00 41.26 |
| ATOM | 3369 | OH2 | TIP3 | 39 | 24.315 | 32.263 | 19.069 | 1.00 27.49 |
| ATOM | 3370 | OH2 | TIP3 | 40 | 17.157 | 21.378 | 10.360 | 1.00 29.71 |
| ATOM | 3371 | OH2 | TIP3 | 41 | 13.157 | 9.144 | 28.767 | 1.00 32.39 |
| ATOM | 3372 | OH2 | TIP3 | 42 | 12.931 | 38.890 | 19.337 | 1.00 35.82 |
| ATOM | 3373 | OH2 | TIP3 | 43 | 38.696 | 43.515 | 31.888 | 1.00 28.12 |
| ATOM | 3374 | OH2 | TIP3 | 44 | 29.294 | 19.356 | 13.799 | 1.00 43.11 |
| ATOM | 3375 | OH2 | TIP3 | 45 | 9.044 | 7.812 | 9.252 | 1.00 19.18 |
| ATOM | 3376 | OH2 | TIP3 | 46 | 21.324 | 52.606 | 27.604 | 1.00 54.59 |
| ATOM | 3377 | OH2 | TIP3 | 47 | 30.914 | 34.967 | 12.824 | 1.00 25.06 |
| ATOM | 3378 | OH2 | TIP3 | 48 | 13.454 | 2.315 | 10.562 | 1.00 34.40 |
| ATOM | 3379 | OH2 | TIP3 | 49 | 28.876 | 32.558 | 13.029 | 1.00 51.94 |
| ATOM | 3380 | OH2 | TIP3 | 50 | 1.840 | 14.917 | 35.047 | 1.00 25.56 |
| ATOM | 3381 | OH2 | TIP3 | 51 | 20.036 | 5.057 | 8.439 | 1.00 38.71 |
| ATOM | 3382 | OH2 | TIP3 | 52 | 21.989 | 31.348 | 10.718 | 1.00 34.34 |
| ATOM | 3383 | OH2 | TIP3 | 53 | 22.314 | 46.201 | 35.658 | 1.00 33.59 |
| ATOM | 3384 | OH2 | TIP3 | 54 | 26.721 | 19.845 | 14.781 | 1.00 29.32 |
| ATOM | 3385 | OH2 | TIP3 | 55 | 21.199 | 6.956 | 15.517 | 1.00 31.86 |
| ATOM | 3386 | OH2 | TIP3 | 56 | 24.460 | 56.129 | 15.361 | 1.00 47.79 |
| ATOM | 3387 | OH2 | TIP3 | 57 | 24.841 | 34.491 | 13.673 | 1.00 35.87 |
| ATOM | 3388 | OH2 | TIP3 | 58 | 34.366 | 27.984 | -0.318 | 1.00 26.26 |
| ATOM | 3389 | OH2 | TIP3 | 59 | 48.536 | 3.488 | 11.538 | 1.00 36.52 |
| ATOM | 3390 | OH2 | TIP3 | 60 | 2.038 | 28.386 | 33.590 | 1.00 32.11 |
| ATOM | 3391 | OH2 | TIP3 | 61 | 18.422 | 25.811 | 21.407 | 1.00 26.96 |
| ATOM | 3392 | OH2 | TIP3 | 62 | 12.957 | 44.530 | 11.249 | 1.00 28.06 |
| ATOM | 3393 | OH2 | TIP3 | 63 | 47.339 | 3.540 | 3.822 | 1.00 42.83 |
| ATOM | 3394 | OH2 | TIP3 | 64 | 11.061 | 26.825 | 19.834 | 1.00 26.76 |
| ATOM | 3395 | OH2 | TIP3 | 65 | 15.719 | 9.453 | 30.418 | 1.00 33.97 |
| ATOM | 3396 | OH2 | TIP3 | 66 | 45.394 | -0.086 | 3.586 | 1.00 37.65 |
| ATOM | 3397 | OH2 | TIP3 | 67 | 33.010 | 41.548 | 8.551 | 1.00 53.15 |
| ATOM | 3398 | OH2 | TIP3 | 68 | 5.850 | 48.967 | 10.652 | 1.00 54.79 |
| ATOM | 3399 | OH2 | TIP3 | 69 | 27.164 | 56.234 | 13.872 | 1.00 23.47 |

FIGURE 1 (cont.)

```
ATOM   3400  OH2  TIP3   70     30.776   23.190   13.426  1.00 35.94
ATOM   3401  OH2  TIP3   71     39.550    3.505   -0.797  1.00 44.89
ATOM   3402  OH2  TIP3   72     11.418   30.014   18.681  1.00 37.07
ATOM   3403  OH2  TIP3   73     12.592   28.999   20.880  1.00 37.53
ATOM   3404  OH2  TIP3   74     54.478    6.360   11.185  1.00 42.03
ATOM   3405  OH2  TIP3   75     12.086    2.791   12.915  1.00 29.59
ATOM   3406  OH2  TIP3   76     18.225   19.519   33.978  1.00 33.10
ATOM   3407  OH2  TIP3   77     11.677   36.171   12.007  1.00 56.16
ATOM   3408  OH2  TIP3   78     11.319   35.115   15.313  1.00 35.91
ATOM   3409  OH2  TIP3   79     49.775    4.145   -0.325  1.00 63.48
ATOM   3410  OH2  TIP3   80     46.373   21.363    6.807  1.00 26.12
ATOM   3411  OH2  TIP3   81     18.126   35.806   20.605  1.00 29.66
ATOM   3412  OH2  TIP3   82     28.293    3.447    0.583  1.00 21.79
ATOM   3413  OH2  TIP3   83     20.086    4.628   14.855  1.00 44.92
ATOM   3414  OH2  TIP3   85     19.694   33.413    0.806  1.00 34.26
ATOM   3415  OH2  TIP3   87     17.814    5.041   25.621  1.00 45.94
ATOM   3416  OH2  TIP3   88      9.151   35.189   12.200  1.00 50.30
ATOM   3417  OH2  TIP3   89     28.063   25.834    6.403  1.00 47.14
ATOM   3418  OH2  TIP3   90     23.930   54.835   27.010  1.00 36.48
ATOM   3419  OH2  TIP3   91      8.080   25.210    6.084  1.00 33.01
ATOM   3420  OH2  TIP3   92     25.675   26.853    5.755  1.00 39.86
ATOM   3421  OH2  TIP3   93     36.215   33.769    7.228  1.00 24.13
ATOM   3422  OH2  TIP3   94     44.576    4.479    5.203  1.00 49.35
ATOM   3423  OH2  TIP3   95      8.686   33.376    8.329  1.00 28.75
ATOM   3424  OH2  TIP3   96     16.567   43.764   11.647  1.00 37.52
ATOM   3425  OH2  TIP3   97     18.639   37.102   28.670  1.00 34.49
ATOM   3426  OH2  TIP3   98     11.850   38.492   15.839  1.00 58.36
ATOM   3427  OH2  TIP3   99      1.757   17.697   30.552  1.00 30.16
ATOM   3428  OH2  TIP3  100     38.062   41.239   27.946  1.00 17.16
ATOM   3429  OH2  TIP3  101     27.889   50.445   37.057  1.00 48.61
ATOM   3430  OH2  TIP3  102     47.875    2.606    1.215  1.00 45.89
ATOM   3431  OH2  TIP3  103     57.882   18.168    8.130  1.00 45.09
ATOM   3432  OH2  TIP3  104     21.556   43.776   35.255  1.00 33.42
ATOM   3433  OH2  TIP3  105     22.140   30.473    5.457  1.00 39.79
ATOM   3434  OH2  TIP3  106     32.336    8.468   23.760  1.00 73.89
ATOM   3435  OH2  TIP3  107     51.548    8.278   -1.912  1.00 28.27
ATOM   3436  OH2  TIP3  108      8.860   13.655   39.162  1.00 33.15
ATOM   3437  OH2  TIP3  109      6.700    4.449   19.242  1.00 51.28
ATOM   3438  OH2  TIP3  110     33.801   29.559   25.988  1.00 53.24
ATOM   3439  OH2  TIP3  111     42.999    2.893   -1.302  1.00 46.52
ATOM   3440  OH2  TIP3  112     31.945   15.930   15.358  1.00 47.42
ATOM   3441  OH2  TIP3  113     22.230   16.440   -7.612  1.00 56.68
ATOM   3442  OH2  TIP3  115     13.726   39.997   22.208  1.00 31.56
ATOM   3443  OH2  TIP3  116     23.251   37.041   24.987  1.00 53.40
ATOM   3444  OH2  TIP3  117     23.611   32.166   12.751  1.00 38.21
ATOM   3445  OH2  TIP3  118     30.487   26.338   -0.700  1.00 31.83
ATOM   3446  OH2  TIP3  119     19.447    2.060   15.121  1.00 39.28
ATOM   3447  OH2  TIP3  120     24.042   51.710    8.456  1.00 39.94
ATOM   3448  OH2  TIP3  121     47.391   -0.070    5.383  1.00 37.69
ATOM   3449  OH2  TIP3  122     59.581   21.821    1.048  1.00 54.95
ATOM   3450  OH2  TIP3  123      9.207   34.806   16.904  1.00 31.85
ATOM   3451  OH2  TIP3  124      3.401    4.534   13.008  1.00 53.38
ATOM   3452  OH2  TIP3  125     21.114   48.341   33.295  1.00 43.92
ATOM   3453  OH2  TIP3  126     20.174   32.741   20.466  1.00 66.24
ATOM   3454  OH2  TIP3  128     16.410   45.812   26.424  1.00 35.46
ATOM   3455  OH2  TIP3  129     32.863   61.435   29.648  1.00 66.85
ATOM   3456  OH2  TIP3  130     33.387   55.608    7.433  1.00 64.07
ATOM   3457  OH2  TIP3  131     28.167   51.328   29.584  1.00 27.99
```

FIGURE 1 (cont.)

| | | | | | | | | |
|---|---|---|---|---|---|---|---|---|
| ATOM | 3458 | OH2 | TIP3 | 132 | 16.147 | 45.753 | 6.715 | 1.00 54.98 |
| ATOM | 3459 | OH2 | TIP3 | 133 | 20.658 | 52.304 | 24.938 | 1.00 25.99 |
| ATOM | 3460 | OH2 | TIP3 | 134 | 44.627 | 9.499 | -13.307 | 1.00 44.79 |
| ATOM | 3461 | OH2 | TIP3 | 135 | 64.095 | 6.945 | 12.329 | 1.00 44.41 |
| ATOM | 3462 | OH2 | TIP3 | 136 | 18.514 | 41.737 | 27.310 | 1.00 19.89 |
| ATOM | 3463 | OH2 | TIP3 | 137 | 42.275 | 19.609 | -2.298 | 1.00 15.25 |
| ATOM | 3464 | OH2 | TIP3 | 139 | 14.970 | 49.971 | 28.272 | 1.00 35.15 |
| ATOM | 3465 | OH2 | TIP3 | 140 | 15.165 | 8.029 | 3.479 | 1.00 38.41 |
| ATOM | 3466 | OH2 | TIP3 | 141 | 17.347 | 7.548 | 21.016 | 1.00 36.09 |
| ATOM | 3467 | OH2 | TIP3 | 142 | 21.921 | 4.401 | 1.631 | 1.00 39.46 |
| ATOM | 3468 | OH2 | TIP3 | 143 | 23.711 | 49.091 | 33.933 | 1.00 39.80 |
| ATOM | 3469 | OH2 | TIP3 | 144 | 21.398 | 56.732 | 11.465 | 1.00 30.74 |
| ATOM | 3470 | OH2 | TIP3 | 145 | 15.424 | 25.910 | 28.153 | 1.00 28.23 |
| ATOM | 3471 | OH2 | TIP3 | 146 | 30.399 | 11.030 | -7.068 | 1.00 50.79 |
| ATOM | 3472 | OH2 | TIP3 | 147 | 12.734 | 29.004 | 16.438 | 1.00 22.08 |
| ATOM | 3473 | OH2 | TIP3 | 148 | 53.920 | 5.003 | 16.906 | 1.00 54.39 |
| ATOM | 3474 | OH2 | TIP3 | 149 | 7.523 | 36.343 | 15.403 | 1.00 44.62 |
| ATOM | 3475 | OH2 | TIP3 | 150 | 14.223 | 30.953 | 15.400 | 1.00 37.15 |
| ATOM | 3476 | OH2 | TIP3 | 151 | 28.644 | 2.628 | 3.023 | 1.00 31.14 |
| ATOM | 3477 | OH2 | TIP3 | 152 | 15.963 | 9.043 | 22.893 | 1.00 26.75 |
| ATOM | 3478 | OH2 | TIP3 | 153 | 17.823 | 10.746 | 23.731 | 1.00 20.71 |
| ATOM | 3479 | OH2 | TIP3 | 154 | 29.179 | 54.461 | 32.613 | 1.00 68.03 |
| ATOM | 3480 | OH2 | TIP3 | 155 | 35.993 | 37.805 | 29.152 | 1.00 20.17 |
| ATOM | 3481 | OH2 | TIP3 | 156 | 53.831 | 24.063 | 9.859 | 1.00 49.86 |
| ATOM | 3482 | OH2 | TIP3 | 157 | 20.267 | 46.970 | 30.983 | 1.00 34.93 |
| ATOM | 3483 | OH2 | TIP3 | 158 | 32.383 | 43.988 | 6.930 | 1.00 39.67 |
| ATOM | 3484 | OH2 | TIP3 | 159 | 2.201 | 6.263 | 18.618 | 1.00 35.49 |
| ATOM | 3485 | OH2 | TIP3 | 160 | 48.626 | 11.397 | -2.343 | 1.00 32.41 |
| ATOM | 3486 | OH2 | TIP3 | 161 | 21.594 | 8.868 | -2.657 | 1.00 47.49 |
| ATOM | 3487 | OH2 | TIP3 | 162 | 21.981 | 51.645 | 6.828 | 1.00 36.67 |
| ATOM | 3488 | OH2 | TIP3 | 163 | 41.875 | 36.089 | 18.851 | 1.00 38.83 |
| ATOM | 3489 | OH2 | TIP3 | 164 | 39.302 | 39.590 | 11.776 | 1.00 50.01 |
| ATOM | 3490 | OH2 | TIP3 | 165 | 40.112 | 35.572 | 14.944 | 1.00 47.69 |
| ATOM | 3491 | OH2 | TIP3 | 166 | 39.529 | 30.929 | 22.535 | 1.00 41.91 |

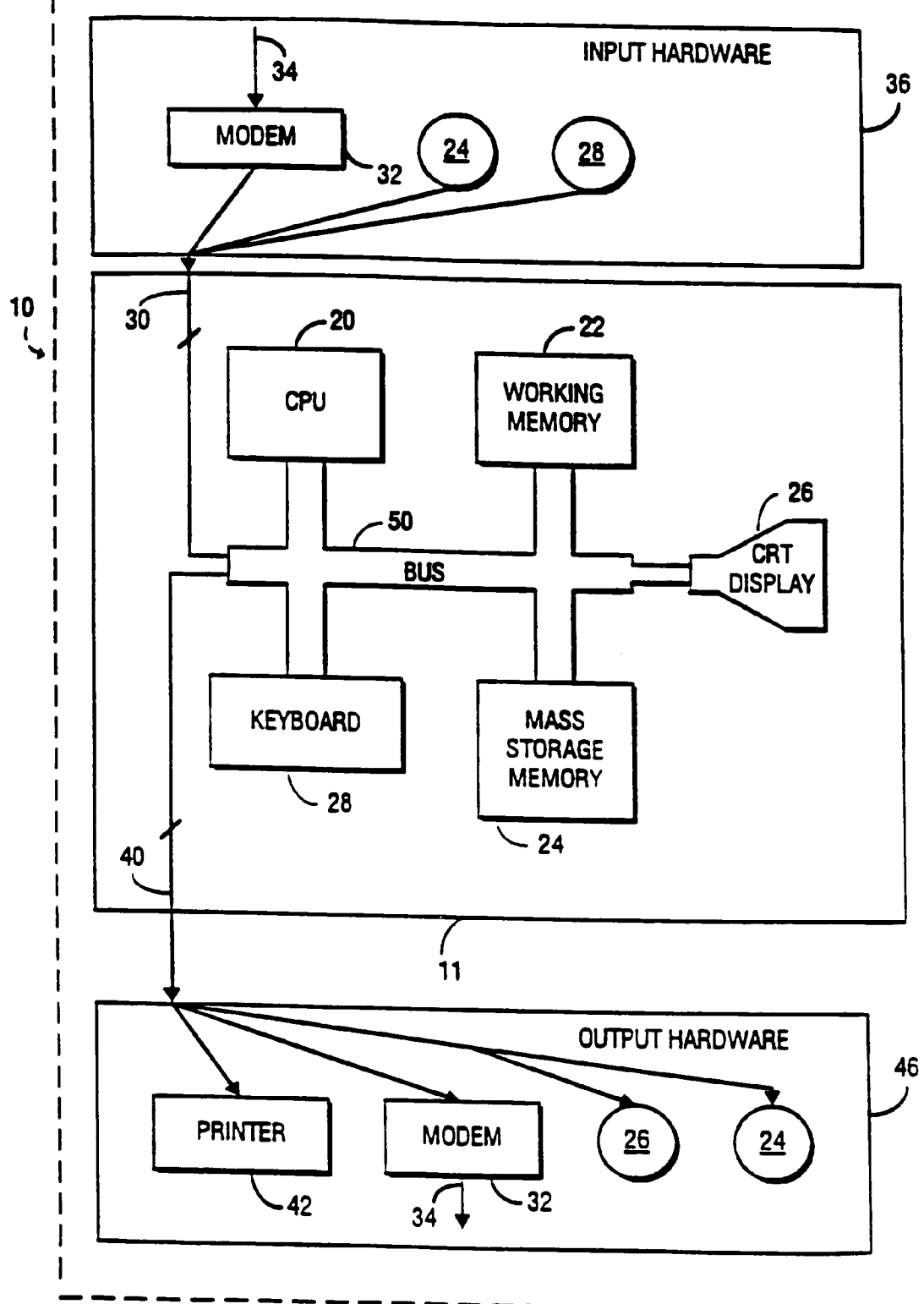

FIGURE 8

```
                                    β1            α1
                                |←——→|       |←————————→|
mVDFIPVENLETTMRSPVFTDNSSPPAVPQSFQVAHLHAPTGSGKSTKVPAAYAA      220

β2           α2             β3    β4    β5    α3
|←——→| |←———————————→|       |←→| |←——→| |←→| |←——→|
QGYKVLVLNPSVAATLGFGAYMSKAHGVDPNIRTGVRTITTGSPITYSTYGKFLADGGCS  280

β6              α4        α4A    β7                β1'
|←——→|     |←————————→|    ||↔|  |←——→|            |←——→|
GGAYDIIICDECHSTDATSILGIGTVLDQAETAGARLVVLATATPPGSVTVPHPNIEEVA  340

β1A' β1B'  α1'      β2'         α2'           β3'
|↔|  |↔|  |↔|   |←———→|   |←————————→|      |←—→|
LSTTGEIPFYGKAIPLEVIKGGRHLIFCHSKKKCDELAAKLVALGINAVAYYRGLDVSVI  400

β5'              β6'    β6A'       β6B'         α4'
   |←——→|             |←—→|   |←——→|     |←——→|      |←——
PTSGDVVVVATDALMTGFTGDFDSVIDCNTCVTQTVDFSLDPTFTIETTTLPQDAVSRTQ  460

—→|       β7'       β8       α5                α6
          |←—→|    |↔| |←————→|           |←————————→|
RRGRTGRGKPGIYRFVAPGERPSGMFDSSVLCECYDAGCAWYELTPAETTVRLRAYMNTP  520

β9        α7             α8              α9
|↔|    |←———————→|    |←————→|       |←————————→|
GLPVCQDHLEFWEGVFTGLTHIDAHFLSQTKQSENFPYLVAYQATVCARAQAPPPSWDQ   580

α10
                      |←————→|
MWKCLIRLKPTLHGPTPLLYRLGAVQNEVTLTHPITKYIMTCMSADLEVVTgsgshhhhhh  641
```

FIGURE 9A

|  |  | I |  | Ia |  | II |  | III |
|---|---|---|---|---|---|---|---|---|
| NS3 | 204 | APTGSGKSTK | (13) | VLNPSVAATLGF | (40) | DECHSTD | (25) | TATPPGSVTVPHPN |
| NPH-II | 185 | GGTGVGKTSQ | (28) | VILSLPRIALVR | (60) | DEVHEHD | (23) | TATLEDDRERLKVF |
| EIF-4A | 63 | ACSGTGKTGT | (19) | MLAPTRELALQI | (63) | DEADEML | (24) | SATMPNDVLEVTTK |
| PcrA | 31 | AGAGSGKTRV | (20) | AITFTNKAAREM | (150) | DEYQDTN | (19) | VGDADQSIYRWRGA |
| UvrD | 30 | AGAGSGKTRV | (20) | AVTFTNKAAREM | (150) | DEFQDTN | (19) | VGDDDQSIYGWRGA |
| Rep | 22 | AGAGSGKTRV | (20) | AVTFTNKAAAEM | (150) | DEYQDTN | (19) | VGDDDQSIYSWRGA |

|  |  | IV? |  | V |  | VI |
|---|---|---|---|---|---|---|
| NS3 | 365 | LIFCHSKKK | (36) | ATDALMTGFTGDFE | (32) | VSRTQRRGRTGRG |
| NPH-II | 397 | IVFVASVAQ | (43) | STPYLESSVTIRNV | (24) | SMRDQRKGRVGRV |
| EIF-4A | 263 | VIFCNTRRK | (43) | STDLLARGIDVQQV | (12) | EERRLAYVGITRA |
| PcrA | 280 | ILLEQNYRS | (273) | MTLHAAKGLEFPVV | (23) | EERRLAYVGITRA |
| UvrD | 278 | IRLEQNYRS | (271) | MTLHSAKGLEFPQV | (23) | EERRLAYVGVTRA |
| Rep | 272 | IKLEQNYRS | (275) | MTLHASKGLEFPYV | (22) | EERRLAYVGITRA |

SEQUENCE LISTING

```
<160> NUMBER OF SEQ ID NOS: 4

<210> SEQ ID NO 1
<211> LENGTH: 1932
<212> TYPE: DNA
<213> ORGANISM: Hepatitis C virus
<220> FEATURE:
<221> NAME/KEY: CDS
<222> LOCATION: (4)..(1896)
```

<223> OTHER INFORMATION: Full length HCV NS3 coding sequence
<220> FEATURE:
<221> NAME/KEY: misc_feature
<222> LOCATION: (504)..(1896)
<223> OTHER INFORMATION: Helicase domain

<400> SEQUENCE: 1

```
atg gcg ccc atc acg gcg tac gcc cag cag acg aga ggc aag ctt ggg        48
    Ala Pro Ile Thr Ala Tyr Ala Gln Gln Thr Arg Gly Lys Leu Gly
     1               5                  10                  15 tgt ata atc acc agc ctg act ggc cgg gac aaa aac caa gtg gag ggt        96
Cys Ile Ile Thr Ser Leu Thr Gly Arg Asp Lys Asn Gln Val Glu Gly
                 20                  25                  30 gag gtc cag atc gtg tca act gct acc caa acc ttc ctg gca acg tgc       144
Glu Val Gln Ile Val Ser Thr Ala Thr Gln Thr Phe Leu Ala Thr Cys
             35                  40                  45 atc aat ggg gta tgc tgg act gtc tac cac ggg gcc gga acg agg acc       192
Ile Asn Gly Val Cys Trp Thr Val Tyr His Gly Ala Gly Thr Arg Thr
         50                  55                  60 atc gca tca ccc aag ggt cct gtc atc cag atg tat acc aat gtg gac       240
Ile Ala Ser Pro Lys Gly Pro Val Ile Gln Met Tyr Thr Asn Val Asp
 65                  70                  75 caa gac ctt gtg ggc tgg ccc gct cct caa ggt tcc cgc tca ttg aca       288
Gln Asp Leu Val Gly Trp Pro Ala Pro Gln Gly Ser Arg Ser Leu Thr
 80                  85                  90                  95 ccc tgc acc tgc ggc tcc tcg gac ctt tac ctg gtt acg agg cac gcc       336
Pro Cys Thr Cys Gly Ser Ser Asp Leu Tyr Leu Val Thr Arg His Ala
                100                 105                 110 gac gtc atc ccg gtt cgc cgt cgc ggt gat agc cgt ggt agc ctg ctg       384
Asp Val Ile Pro Val Arg Arg Arg Gly Asp Ser Arg Gly Ser Leu Leu
            115                 120                 125 tct ccg cgt ccg att tcc tac ctg aaa ggc tcc tcg ggg ggt ccg ctg       432
Ser Pro Arg Pro Ile Ser Tyr Leu Lys Gly Ser Ser Gly Gly Pro Leu
        130                 135                 140 ttg tgc ccc gcg gga cac gcc gtg ggc cta ttc agg gcc gcg gtg tgc       480
Leu Cys Pro Ala Gly His Ala Val Gly Leu Phe Arg Ala Ala Val Cys
    145                 150                 155 acc cgt gga gtg gcc aag gcg gtg gac ttt atc cct gtg gag aac ctg       528
Thr Arg Gly Val Ala Lys Ala Val Asp Phe Ile Pro Val Glu Asn Leu
160                 165                 170                 175 gag acc acc atg cgt tcc ccg gtg ttc acg gac aac tcc tct cca cca       576
Glu Thr Thr Met Arg Ser Pro Val Phe Thr Asp Asn Ser Ser Pro Pro
                180                 185                 190 gct gtt ccc cag agc ttc cag gtg gcc cac ctg cat gct ccc acc ggc       624
Ala Val Pro Gln Ser Phe Gln Val Ala His Leu His Ala Pro Thr Gly
            195                 200                 205 agt ggt aag agc acc aag gtc ccg gct gcg tac gca gcc cag ggc tac       672
Ser Gly Lys Ser Thr Lys Val Pro Ala Ala Tyr Ala Ala Gln Gly Tyr
        210                 215                 220 aag gtg ttg gtg ctc aac ccc tct gtt gct gca acg ctg ggc ttt ggt       720
Lys Val Leu Val Leu Asn Pro Ser Val Ala Ala Thr Leu Gly Phe Gly
    225                 230                 235 gct tac atg tcc aag gcc cat ggg gtc gat cct aat atc cgc acc ggt       768
Ala Tyr Met Ser Lys Ala His Gly Val Asp Pro Asn Ile Arg Thr Gly
240                 245                 250                 255 gtg cgt aca att acc act ggc agc ccc atc acg tac tcc acc tac ggc       816
Val Arg Thr Ile Thr Thr Gly Ser Pro Ile Thr Tyr Ser Thr Tyr Gly
                260                 265                 270 aag ttc ctt gcc gac ggc ggg tgc tca ggt ggc gct tat gat atc atc       864
Lys Phe Leu Ala Asp Gly Gly Cys Ser Gly Gly Ala Tyr Asp Ile Ile
            275                 280                 285
```

```
att tgt gac gag tgc cac tcc acg gat gcc aca tcc atc ttg ggc atc      912
Ile Cys Asp Glu Cys His Ser Thr Asp Ala Thr Ser Ile Leu Gly Ile
        290                 295                 300 ggc act gtc ctt gac caa gca gag act gcg ggg gcg aga ttg gtt gtg      960
Gly Thr Val Leu Asp Gln Ala Glu Thr Ala Gly Ala Arg Leu Val Val
305                 310                 315 ctc gcc act gct acc cct ccg ggc tcc gtc acg gta ccg cat cct aac     1008
Leu Ala Thr Ala Thr Pro Pro Gly Ser Val Thr Val Pro His Pro Asn
320                 325                 330                 335 atc gag gag gtt gct ctg tcc acc acc gga gag atc cct ttc tac ggc     1056
Ile Glu Glu Val Ala Leu Ser Thr Thr Gly Glu Ile Pro Phe Tyr Gly
                340                 345                 350 aag gct atc ccc ctc gag gtg atc aag ggc ggc cgt cat ctc atc ttc     1104
Lys Ala Ile Pro Leu Glu Val Ile Lys Gly Gly Arg His Leu Ile Phe
            355                 360                 365 tgt cac tca aag aag aag tgc gac gag ctc gcc gcg aag ctg gtc gca     1152
Cys His Ser Lys Lys Lys Cys Asp Glu Leu Ala Ala Lys Leu Val Ala
        370                 375                 380 ttg ggc atc aat gcc gtg gcc tac tac cgc gga ctt gac gtg tct gtc     1200
Leu Gly Ile Asn Ala Val Ala Tyr Tyr Arg Gly Leu Asp Val Ser Val
385                 390                 395 atc ccg acc agc ggc gat gtt gtc gtc gtg gcg acc gat gct ctc atg     1248
Ile Pro Thr Ser Gly Asp Val Val Val Val Ala Thr Asp Ala Leu Met
400                 405                 410                 415 act ggc ttt acc ggc gac ttc gac tct gtg ata gac tgc aac acg tgt     1296
Thr Gly Phe Thr Gly Asp Phe Asp Ser Val Ile Asp Cys Asn Thr Cys
                420                 425                 430 gtc act cag aca gtc gat ttc agc ctt gac cct acc ttt acc att gag     1344
Val Thr Gln Thr Val Asp Phe Ser Leu Asp Pro Thr Phe Thr Ile Glu
            435                 440                 445 aca acc acg ctc ccc cag gat gct gtc tcc agg act cag cgc cgt ggt     1392
Thr Thr Thr Leu Pro Gln Asp Ala Val Ser Arg Thr Gln Arg Arg Gly
        450                 455                 460 cgt acc ggc cgt ggg aag cca ggc atc tac aga ttt gtg gca ccg ggg     1440
Arg Thr Gly Arg Gly Lys Pro Gly Ile Tyr Arg Phe Val Ala Pro Gly
465                 470                 475 gag cgc ccc tcc ggc atg ttc gac tcg tcc gtc ctc tgt gag tgc tat     1488
Glu Arg Pro Ser Gly Met Phe Asp Ser Ser Val Leu Cys Glu Cys Tyr
480                 485                 490                 495 gac gcg ggc tgt gct tgg tat gag ctc acg ccg gcg gag act aca gtt     1536
Asp Ala Gly Cys Ala Trp Tyr Glu Leu Thr Pro Ala Glu Thr Thr Val
                500                 505                 510 cgt ctg cgc gcg tac atg aac acc ccg ggg ctt ccc gtg tgc cag gac     1584
Arg Leu Arg Ala Tyr Met Asn Thr Pro Gly Leu Pro Val Cys Gln Asp
            515                 520                 525 cat ctt gaa ttt tgg gag ggc gtc ttt acg ggc ctc acc cat atc gat     1632
His Leu Glu Phe Trp Glu Gly Val Phe Thr Gly Leu Thr His Ile Asp
        530                 535                 540 gcc cac ttt ctg tcc cag aca aag cag agt ggg gag aac ttt cct tac     1680
Ala His Phe Leu Ser Gln Thr Lys Gln Ser Gly Glu Asn Phe Pro Tyr
545                 550                 555 ctg gta gcg tac caa gcc acc gtg tgc gct cgt gcg caa gcc cct ccg     1728
Leu Val Ala Tyr Gln Ala Thr Val Cys Ala Arg Ala Gln Ala Pro Pro
560                 565                 570                 575 cca tcg tgg gac cag atg tgg aag tgt ttg atc cgc ctt aaa ccc acc     1776
Pro Ser Trp Asp Gln Met Trp Lys Cys Leu Ile Arg Leu Lys Pro Thr
                580                 585                 590 ctc cat ggg cca aca ccg ctc ctg tac cgt ctg ggc gct gtt cag aat     1824
Leu His Gly Pro Thr Pro Leu Leu Tyr Arg Leu Gly Ala Val Gln Asn
```

-continued

```
                       595                 600                 605
gaa gtc acc ctg acg cac cca atc acc aaa tac atc atg aca tgc atg     1872
Glu Val Thr Leu Thr His Pro Ile Thr Lys Tyr Ile Met Thr Cys Met
        610                 615                 620 tcg gcc gac ctg gag gtc gtc acg ggatctggct cgcatcatca tcatcatcac    1926
Ser Ala Asp Leu Glu Val Val Thr
625                 630 taatag                                                              1932
```

<210> SEQ ID NO 2
<211> LENGTH: 631
<212> TYPE: PRT
<213> ORGANISM: Hepatitis C virus

<400> SEQUENCE: 2

```
Ala Pro Ile Thr Ala Tyr Ala Gln Gln Thr Arg Gly Lys Leu Gly Cys
  1               5                  10                  15

Ile Ile Thr Ser Leu Thr Gly Arg Asp Lys Asn Gln Val Glu Gly Glu
             20                  25                  30

Val Gln Ile Val Ser Thr Ala Thr Gln Thr Phe Leu Ala Thr Cys Ile
         35                  40                  45

Asn Gly Val Cys Trp Thr Val Tyr His Gly Ala Gly Thr Arg Thr Ile
     50                  55                  60

Ala Ser Pro Lys Gly Pro Val Ile Gln Met Tyr Thr Asn Val Asp Gln
 65                  70                  75                  80

Asp Leu Val Gly Trp Pro Ala Pro Gln Gly Ser Arg Ser Leu Thr Pro
                 85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Ile Ser Tyr Leu Lys Gly Ser Ser Gly Gly Pro Leu Leu
    130                 135                 140

Cys Pro Ala Gly His Ala Val Gly Leu Phe Arg Ala Ala Val Cys Thr
145                 150                 155                 160

Arg Gly Val Ala Lys Ala Val Asp Phe Ile Pro Val Glu Asn Leu Glu
                165                 170                 175

Thr Thr Met Arg Ser Pro Val Phe Thr Asp Asn Ser Ser Pro Pro Ala
            180                 185                 190

Val Pro Gln Ser Phe Gln Val Ala His Leu His Ala Pro Thr Gly Ser
        195                 200                 205

Gly Lys Ser Thr Lys Val Pro Ala Ala Tyr Ala Ala Gln Gly Tyr Lys
    210                 215                 220

Val Leu Val Leu Asn Pro Ser Val Ala Ala Thr Leu Gly Phe Gly Ala
225                 230                 235                 240

Tyr Met Ser Lys Ala His Gly Val Asp Pro Asn Ile Arg Thr Gly Val
                245                 250                 255

Arg Thr Ile Thr Thr Gly Ser Pro Ile Thr Tyr Ser Thr Tyr Gly Lys
            260                 265                 270

Phe Leu Ala Asp Gly Gly Cys Ser Gly Gly Ala Tyr Asp Ile Ile Ile
        275                 280                 285

Cys Asp Glu Cys His Ser Thr Asp Ala Thr Ser Ile Leu Gly Ile Gly
    290                 295                 300

Thr Val Leu Asp Gln Ala Glu Thr Ala Gly Ala Arg Leu Val Val Leu
305                 310                 315                 320
```

```
Ala Thr Ala Thr Pro Gly Ser Val Thr Val Pro His Pro Asn Ile
            325                 330                 335
Glu Glu Val Ala Leu Ser Thr Thr Gly Glu Ile Pro Phe Tyr Gly Lys
            340                 345                 350
Ala Ile Pro Leu Glu Val Ile Lys Gly Gly Arg His Leu Ile Phe Cys
            355                 360                 365
His Ser Lys Lys Lys Cys Asp Glu Leu Ala Ala Lys Leu Val Ala Leu
        370                 375                 380
Gly Ile Asn Ala Val Ala Tyr Tyr Arg Gly Leu Asp Val Ser Val Ile
385                 390                 395                 400
Pro Thr Ser Gly Asp Val Val Val Ala Thr Asp Ala Leu Met Thr
            405                 410                 415
Gly Phe Thr Gly Asp Phe Asp Ser Val Ile Asp Cys Asn Thr Cys Val
            420                 425                 430
Thr Gln Thr Val Asp Phe Ser Leu Asp Pro Thr Phe Thr Ile Glu Thr
            435                 440                 445
Thr Thr Leu Pro Gln Asp Ala Val Ser Arg Thr Gln Arg Arg Gly Arg
        450                 455                 460
Thr Gly Arg Gly Lys Pro Gly Ile Tyr Arg Phe Val Ala Pro Gly Glu
465                 470                 475                 480
Arg Pro Ser Gly Met Phe Asp Ser Ser Val Leu Cys Glu Cys Tyr Asp
                485                 490                 495
Ala Gly Cys Ala Trp Tyr Glu Leu Thr Pro Ala Glu Thr Thr Val Arg
            500                 505                 510
Leu Arg Ala Tyr Met Asn Thr Pro Gly Leu Pro Val Cys Gln Asp His
            515                 520                 525
Leu Glu Phe Trp Glu Gly Val Phe Thr Gly Leu Thr His Ile Asp Ala
        530                 535                 540
His Phe Leu Ser Gln Thr Lys Gln Ser Gly Glu Asn Phe Pro Tyr Leu
545                 550                 555                 560
Val Ala Tyr Gln Ala Thr Val Cys Ala Arg Ala Gln Ala Pro Pro
            565                 570                 575
Ser Trp Asp Gln Met Trp Lys Cys Leu Ile Arg Leu Lys Pro Thr Leu
            580                 585                 590
His Gly Pro Thr Pro Leu Leu Tyr Arg Leu Gly Ala Val Gln Asn Glu
        595                 600                 605
Val Thr Leu Thr His Pro Ile Thr Lys Tyr Ile Met Thr Cys Met Ser
            610                 615                 620
Ala Asp Leu Glu Val Val Thr
625                 630

<210> SEQ ID NO 3
<211> LENGTH: 8157
<212> TYPE: DNA
<213> ORGANISM: Artificial Sequence
<220> FEATURE:
<223> OTHER INFORMATION: Description of Artificial Sequence: Genetically
      engineered plasmid containing full-length HCV NS3 coding sequence

<400> SEQUENCE: 3
ttaatacgac tcactatagg ggaattgtga gcggataaca attcccctct agaataatt      60 ttgtttaact ttaagaagga gatataccat ggcgcccatc acggcgtacg cccagcagac     120
gagaggcaag cttgggtgta taatcaccag cctgactggc cgggacaaaa accaagtgga     180
gggtgaggtc cagatcgtgt caactgctac ccaaaccttc ctggcaacgt gcatcaatgg     240
```

-continued

```
ggtatgctgg actgtctacc acggggccgg aacgaggacc atcgcatcac ccaagggtcc      300
tgtcatccag atgtatacca atgtggacca agaccttgtg ggctggcccg ctcctcaagg      360
ttcccgctca ttgacaccct gcacctgcgg ctcctcggac ctttacctgg ttacgaggca      420
cgccgacgtc atcccggttc gccgtcgcgg tgatagccgt ggtagcctgc tgtctccgcg      480
tccgatttcc tacctgaaag gctcctcggg gggtccgctg ttgtgccccg cgggacacgc      540
cgtgggccta ttcagggccg cggtgtgcac ccgtggagtg gccaaggcgg tggactttat      600
ccctgtggag aacctggaga ccaccatgcg ttccccggtg ttcacggaca actcctctcc      660
accagctgtt ccccagagct tccaggtggc ccacctgcat gctcccaccg gcagtggtaa      720
gagcaccaag gtcccggctg cgtacgcagc ccagggctac aaggtgttgg tgctcaaccc      780
ctctgttgct gcaacgctgg gctttggtgc ttacatgtcc aaggcccatg ggtcgatcc       840
taatatccgc accggtgtgc gtacaattac cactggcagc cccatcacgt actccaccta      900
cggcaagttc cttgccgacg gcgggtgctc aggtggcgct tatgatatca tcatttgtga      960
cgagtgccac tccacggatg ccacatccat cttgggcatc ggcactgtcc ttgaccaagc      1020
agagactgcg ggggcgagat tggttgtgct cgccactgct acccctccgg gctccgtcac      1080
ggtaccgcat cctaacatcg aggaggttgc tctgtccacc accggagaga tcccttttcta    1140
cggcaaggct atccccctcg aggtgatcaa gggcggccgt catctcatct tctgtcactc      1200
aaagaagaag tgcgacgagc tcgccgcgaa gctggtcgca ttgggcatca atgccgtggc      1260
ctactaccgc ggacttgacg tgtctgtcat cccgaccagc ggcgatgttg tcgtcgtggc      1320
gaccgatgct ctcatgactg gctttaccgg cgacttcgac tctgtgatag actgcaacac      1380
gtgtgtcact cagacagtcg atttcagcct tgaccctacc tttaccattg agacaaccac      1440
gctcccccag gatgctgtct ccaggactca gcgccgtggt cgtaccggcc gtgggaagcc      1500
aggcatctac agatttgtgg caccgggggga gcgcccctcc ggcatgttcg actcgtccgt      1560
cctctgtgag tgctatgacg cgggctgtgc ttggtatgag ctcacgccgg cggagactac      1620
agttcgtctg cgcgcgtaca tgaacacccc ggggcttccc gtgtgccagg accatcttga      1680
attttgggag ggcgtcttta cgggcctcac ccatatcgat gcccactttc tgtcccagac      1740
aaagcagagt ggggagaact ttccttacct ggtagcgtac caagccaccg tgtgcgctcg      1800
tgcgcaagcc cctccgccat cgtgggacca gatgtggaag tgtttgatcc gccttaaacc      1860
cacccctccat gggccaacac cgctcctgta ccgtctgggc gctgttcaga atgaagtcac      1920
cctgacgcac ccaatcacca aatacatcat gacatgcatg tcggccgacc tggaggtcgt      1980
cacgggatct ggctcgcatc atcatcatca tcactaatag aattcggatc cggctgctaa      2040
caaagcccga aggaagctga gttggctgc tgccaccgct gagcaataac tagcataacc      2100
ccttggggcc tctaaacggg tcttgagggg ttttttgctg aaaggaggaa ctatatccgg      2160
atatcccgca agaggcccgg cagtaccggc ataaccaagc ctatgcctac agcatccagg      2220
gtgacggtgc cgaggatgac gatgagcgca ttgttagatt tcatacacgg tgcctgactg      2280
cgttagcaat ttaactgtga taaactaccg cattaaagct tatcgatacc gtcgacctcg      2340
aggggggggcc cggtacccaa ttcgccctat agtgagtcgt attacgcgcg ctcactggcc      2400
gtcgttttac aacgtcgtga ctgggaaaac cctggcgtta cccaacttaa tcgccttgca      2460
gcacatcccc ctttcgccag ctggcgtaat agcgaagagg cccgcaccga tcgcccttcc      2520
caacagttgc gcagcctgaa tggcgaatgg gacgcgccct gtagcggcgc attaagcgcg      2580
```

```
gcgggtgtgg tggttacgcg cagcgtgacc gctacacttg ccagcgccct agcgcccgct    2640
cctttcgctt tcttcccttc ctttctcgcc acgttcgccg gctttccccg tcaagctcta    2700 aatcggggc tccctttagg gttccgattt agtgctttac ggcacctcga ccccaaaaaa    2760
cttgattagg gtgatggttc acgtagtggg ccatcgccct gatagacggt ttttcgccct    2820
ttgacgttgg agtccacgtt ctttaatagt ggactcttgt tccaaactgg aacaacactc    2880
aaccctatct cggtctattc ttttgattta aagggatttt gccgatttc ggcctattgg    2940 ttaaaaatg agctgattta acaaaatttt aacgcgaatt ttaacaaaat attaacgctt    3000
acaatttagg tggcactttt cggggaaatg tgcgcggaac ccctatttgt ttatttttct    3060
aaatacattc aaatatgtat ccgctcatga caataaacc ctgataaatg cttcaataat    3120
attgaaaaag gaagagtatg agtattcaac atttccgtgt cgcccttatt cccttttttg    3180
cggcattttg ccttcctgtt tttgctcacc cagaaacgct ggtgaaagta aaagatgctg    3240
aagatcagtt gggtgcacga gtgggttaca tcgaactgga tctcaacagc ggtaagatcc    3300
ttgagagttt tcgccccgaa gaacgtttc caatgatgag cacttttaaa gttctgctat    3360
gtggcgcggt attatcccgt attgacgccg ggcaagagca actcggtcgc cgcatacact    3420
attctcagaa tgacttggtt gagtactcac cagtcacaga aaagcatctt acggatggca    3480
tgacagtaag agaattatgc agtgctgcca taaccatgag tgataacact gcggccaact    3540
tacttctgac aacgatcgga ggaccgaagg agctaaccgc ttttttgcac aacatggggg    3600
atcatgtaac tcgccttgat cgttgggaac cggagctgaa tgaagccata ccaaacgacg    3660
agcgtgacac cacgatgcct gcagcaatgg caacaacgtt gcgcaaacta ttaactggcg    3720
aactacttac tctagcttcc cggcaacaat taatagactg gatggaggcg gataaagttg    3780
caggaccact tctgcgctcg gcccttccgg ctggctggtt tattgctgat aaatctggag    3840
ccggtgagcg tgggtctcgc ggtatcattg cagcactggg gccagatggt aagccctccc    3900
gtatcgtagt tatctacacg acggggagtc aggcaactat ggatgaacga aatagacaga    3960
tcgctgagat aggtgcctca ctgattaagc attggtaact gtcagaccaa gtttactcat    4020
atatacttta gattgattta aaacttcatt tttaatttaa aaggatctag gtgaagatcc    4080 ttttgataa tctcatgacc aaaatccctt aacgtgagtt ttcgttccac tgagcgtcag    4140
accccgtaga aaagatcaaa ggatcttctt gagatccttt ttttctgcgc gtaatctgct    4200
gcttgcaaac aaaaaaacca ccgctaccag cggtggtttg tttgccggat caagagctac    4260
caactctttt tccgaaggta actggcttca gcagagcgca gataccaaat actgtccttc    4320
tagtgtagcc gtagttaggc caccacttca agaactctgt agcaccgcct acatacctcg    4380
ctctgctaat cctgttacca gtggctgctg ccagtggcga taagtcgtgt cttaccgggt    4440
tggactcaag acgatagtta ccggataagg cgcagcggtc gggctgaacg gggggttcgt    4500
gcacacagcc cagcttggag cgaacgacct acaccgaact gagatacta cagcgtgagc    4560 tatgagaaag cgccacgctt cccgaaggga gaaaggcgga caggtatccg gtaagcggca    4620
gggtcggaac aggagagcgc acgagggagc ttccaggggg aaacgcctgg tatctttata    4680
gtcctgtcgg gtttcgccac ctctgacttg agcgtcgatt tttgtgatgc tcgtcagggg    4740
ggcggagcct atgaaaaaac gccagcaacg cggccttttt acggttcctg gccttttgct    4800
ggccttttgc tcacatgttc tttcctgcgt tatcccctga ttctgtggat aaccgtatta    4860
ccgcctttga gtgagctgat accgctcgcc gcagccgaac gaccgagcgc agcgagtcag    4920
tgagcgagga agcggaagag cgcctgatgc ggtattttct ccttacgcat ctgtgcggta    4980
```

-continued

```
tttcacaccg catatatggt gcactctcag tacaatctgc tctgatgccg catagttaag    5040
ccagtataca ctccgctatc gctacgtgac tgggtcatgg ctgcgcccg acacccgcca    5100 acaccgctg acgcgccctg acgggcttgt ctgctcccgg catccgctta cagacaagct    5160
gtgaccgtct ccgggagctg catgtgtcag aggttttcac cgtcatcacc gaaacgcgcg    5220
aggcagctgc ggtaaagctc atcagcgtgg tcgtgaagcg attcacagat gtctgcctgt    5280
tcatccgcgt ccagctcgtt gagtttctcc agaagcgtta atgtctggct tctgataaag    5340
cgggccatgt taagggcggt ttttcctgt ttggtcactg atgcctccgt gtaaggggga    5400
tttctgttca tgggggtaat gataccgatg aaacgagaga ggatgctcac gatacgggtt    5460
actgatgatg aacatgcccg gttactggaa cgttgtgagg gtaaacaact ggcggtatgg    5520
atgcggcggg accagagaaa aatcactcag ggtcaatgcc agcgcttcgt taatacagat    5580
gtaggtgttc cacagggtag ccagcagcat cctgcgatgc agatccggaa cataatggtg    5640
cagggcgctg acttccgcgt ttccagactt tacgaaacac ggaaaccgaa gaccattcat    5700
gttgttgctc aggtcgcaga cgttttgcag cagcagtcgc ttcacgttcg ctcgcgtatc    5760
ggtgattcat tctgctaacc agtaaggcaa ccccgccagc ctagccgggt cctcaacgac    5820
aggagcacga tcatgcgcac ccgtggccag gacccaacgc tgcccgagat gcgccgcgtg    5880
cggctgctgg agatggcgga cgcgatggat atgttctgcc aagggttggt ttgcgcattc    5940
acagttctcc gcaagaattg attggctcca attcttggag tggtgaatcc gttagcgagg    6000
tgccgccggc ttccattcag gtcgaggtgg cccggctcca tgcaccgcga cgcaacgcgg    6060
ggaggcagac aaggtatagg gcggcgccta caatccatgc caacccgttc catgtgctcg    6120
ccgaggcggc ataaatcgcc gtgacgatca gcggtccagt gatcgaagtt aggctggtaa    6180
gagccgcgag cgatccttga agctgtccct gatggtcgtc atctacctgc ctggacagca    6240
tggcctgcaa cgcgggcatc ccgatgccgc cggaagcgag aagaatcata atggggaagg    6300
ccatccagcc tcgcgtcgcg aacgccagca agacgtagcc cagcgcgtcg gccgccatgc    6360
cggcgataat ggcctgcttc tcgccgaaac gtttggtggc gggaccagtg acgaaggctt    6420
gagcgagggc gtgcaagatt ccgaataccg caagcgacag gccgatcatc gtcgcgctcc    6480
agcgaaagcg gtcctcgccg aaaatgaccc agagcgctgc cggcacctgt cctacgagtt    6540
gcatgataaa gaagacagtc ataagtgcgg cgacgatagt catgccccgc gcccaccgga    6600
aggagctgac tgggttgaag gctctcaagg gcatcggtcg agatcccggt gcctaatgag    6660
tgagctaact tacattaatt gcgttgcgct cactgcccgc tttccagtcg ggaaacctgt    6720
cgtgccagct gcattaatga atcggccaac gcgcggggag aggcggtttg cgtattgggc    6780
gccagggtgg tttttctttt caccagtgag acgggcaaca gctgattgcc cttcaccgcc    6840
tggccctgag agagttgcag caagcggtcc acgctggttt gccccagcag gcgaaaatcc    6900
tgtttgatgg tggttaacgg cgggatataa catgagctgt cttcggtatc gtcgtatccc    6960
actaccgaga tatccgcacc aacgcgcagc ccggactcgg taatggcgcg cattgcgccc    7020
agcgccatct gatcgttggc aaccagcatc gcagtgggaa cgatgccctc attcagcatt    7080
tgcatggttt gttgaaaacc ggacatggca ctccagtcgc cttcccgttc cgctatcggc    7140
tgaatttgat tgcgagtgag atatttatgc cagccagcca gacgcagacg cgccgagaca    7200
gaacttaatg ggcccgctaa cagcgcgatt tgctggtgac ccaatgcgac cagatgctcc    7260
acgcccagtc gcgtaccgtc ttcatgggag aaaataatac tgttgatggg tgtctggtca    7320
```

```
gagacatcaa gaaataacgc cggaacatta gtgcaggcag cttccacagc aatggcatcc   7380
tggtcatcca gcggatagtt aatgatcagc ccactgacgc gttgcgcgag aagattgtgc   7440
accgccgctt tacaggcttc gacgccgctt cgttctacca tcgacaccac cacgctggca   7500
cccagttgat cggcgcgaga tttaatcgcc gcgacaattt gcgacggcgc gtgcagggcc   7560
agactggagg tggcaacgcc aatcagcaac gactgtttgc ccgccagttg ttgtgccacg   7620
cggttgggaa tgtaattcag ctccgccatc gccgcttcca cttttccccg cgttttcgca   7680
gaaacgtggc tggcctggtt caccacgcgg gaaacggtct gataagagac accggcatac   7740
tctgcgacat cgtataacgt tactggtttc acattcacca ccctgaattg actctcttcc   7800
gggcgctatc atgccatacc gcgaaaggtt ttgcgccatt cgatggtgtc cgggatctcg   7860
acgctctccc ttatgcgact cctgcattag gaagcagccc agtagtaggt tgaggccgtt   7920
gagcaccgcc gccgcaagga atggtgcatg caaggagatg gcgcccaaca gtcccccggc   7980
cacggggcct gccaccatac ccacgccgaa acaagcgctc atgagcccga agtggcgagc   8040
ccgatcttcc ccatcggtga tgtcggcgat ataggcgcca gcaaccgcac ctgtggcgcc   8100
ggtgatgccg gccacgatgc gtccggcgta gaggatcgag atctcgatcc cgcgaaa     8157

<210> SEQ ID NO 4
<211> LENGTH: 7659
<212> TYPE: DNA
<213> ORGANISM: Artificial Sequence
<220> FEATURE:
<223> OTHER INFORMATION: Description of Artificial Sequence: Genetically
      engineered plasmid containing helicase domain of HCV NS3

<400> SEQUENCE: 4
ttaatacgac tcactatagg ggaattgtga gcggataaca attcccctct agaaataatt     60
ttgtttaact ttaagaagga gatataccat ggtggacttt atccctgtgg agaacctgga   120
gaccaccatg cgttccccgg tgttcacgga caactcctct ccaccagctg ttccccagag   180
cttccaggtg gcccacctgc atgctcccac cggcagtggt aagagcacca aggtcccggc   240
tgcgtacgca gcccagggct acaaggtgtt ggtgctcaac ccctctgttg ctgcaacgct   300
gggctttggt gcttacatgt ccaaggccca tgggtcgat cctaatatcc gcaccggtgt   360
gcgtacaatt accactggca gccccatcac gtactccacc tacggcaagt ccttgccga   420 cggcgggtgc tcaggtggcg cttatgatat catcatttgt gacgagtgcc actccacgga   480
tgccacatcc atcttgggca tcggcactgt ccttgaccaa gcagagactg cggggcgag   540 attggttgtg ctcgccactg ctaccccctcc gggctccgtc acggtaccgc atcctaacat   600
cgaggaggtt gctctgtcca ccaccggaga gatcccttc tacggcaagg ctatccccct   660
cgaggtgatc aagggcggcc gtcatctcat cttctgtcac tcaaagaaga agtgcgacga   720
gctcgccgcg aagctggtcg cattgggcat caatgccgtg gcctactacc gcggacttga   780
cgtgtctgtc atcccgacca cggcgatgt tgtcgtcgtg gcgaccgatg ctctcatgac   840
tggctttacc ggcgacttcg actctgtgat agactgcaac acgtgtgtca ctcagacagt   900
cgatttcagc cttgacccta cctttaccat tgagacaacc acgctccccc aggatgctgt   960
ctccaggact cagcgccgtg gtcgtaccgg ccgtgggaag ccaggcatct acagatttgt   1020
ggcaccgggg gagcgcccct ccggcatgtt cgactcgtcc gtcctctgtg agtgctatga   1080
cgcgggctgt gcttggtatg agctcacgcc ggcggagact acagttcgtc tgcgcgcgta   1140
catgaacacc ccggggcttc ccgtgtgcca ggaccatctt gaattttggg agggcgtctt   1200
```

```
tacgggcctc acccatatcg atgcccactt tctgtcccag acaaagcaga gtggggagaa    1260
ctttccttac ctggtagcgt accaagccac cgtgtgcgct cgtgcgcaag cccctccgcc    1320
atcgtgggac cagatgtgga agtgtttgat ccgccttaaa cccaccctcc atgggccaac    1380
accgctcctg taccgtctgg gcgctgttca gaatgaagtc accctgacgc acccaatcac    1440
caaatacatc atgacatgca tgtcggccga cctggaggtc gtcacgggat ctggctcgca    1500
tcatcatcat catcactaat agaattcgga tccggctgct aacaaagccc gaaaggaagc    1560
tgagttggct gctgccaccg ctgagcaata actagcataa ccccttgggg cctctaaacg    1620
ggtcttgagg ggttttttgc tgaaaggagg aactatatcc ggatatcccg caagaggccc    1680
ggcagtaccg gcataaccaa gcctatgcct acagcatcca gggtgacggt gccgaggatg    1740
acgatgagcg cattgttaga tttcatacac ggtgcctgac tgcgttagca atttaactgt    1800
gataaactac cgcattaaag cttatcgata ccgtcgacct cgagggggg cccggtaccc    1860 aattcgccct atagtgagtc gtattacgcg cgctcactgg ccgtcgtttt acaacgtcgt    1920
gactgggaaa accctggcgt tacccaactt aatcgccttg cagcacatcc ccctttcgcc    1980
agctggcgta atagcgaaga ggcccgcacc gatcgccctt ccaacagtt gcgcagcctg    2040 aatggcgaat gggacgcgcc ctgtagcggc gcattaagcg cggcgggtgt ggtggttacg    2100
cgcagcgtga ccgctacact tgccagcgcc ctagcgcccg ctcctttcgc tttcttccct    2160
tcctttctcg ccacgttcgc cggctttccc cgtcaagctc taaatcgggg ctcccttta    2220 gggttccgat ttagtgcttt acggcacctc gaccccaaaa aacttgatta gggtgatggt    2280
tcacgtagtg ggccatcgcc ctgatagacg gttttcgcc ctttgacgtt ggagtccacg    2340
ttctttaata gtggactctt gttccaaact ggaacaacac tcaaccctat ctcggtctat    2400
tcttttgatt tataagggat tttgccgatt tcggcctatt ggttaaaaaa tgagctgatt    2460
taacaaaaat ttaacgcgaa ttttaacaaa atattaacgc ttacaattta ggtggcactt    2520
ttcggggaaa tgtgcgcgga acccctattt gtttatttt ctaaatacat tcaaatatgt    2580
atccgctcat gagacaataa ccctgataaa tgcttcaata atattgaaaa aggaagagta    2640
tgagtattca acatttccgt gtcgccctta ttccctttt tgcggcattt tgccttcctg    2700
tttttgctca cccagaaacg ctggtgaaag taaaagatgc tgaagatcag ttgggtgcac    2760
gagtgggtta catcgaactg gatctcaaca gcggtaagat ccttgagagt tttcgccccg    2820
aagaacgttt tccaatgatg agcactttta aagttctgct atgtggcgcg gtattatccc    2880
gtattgacgc cgggcaagag caactcggtc gccgcataca ctattctcag aatgacttgg    2940
ttgagtactc accagtcaca gaaaagcatc ttacggatgg catgacagta agagaattat    3000
gcagtgctgc cataaccatg agtgataaca ctgcggccaa cttacttctg acaacgatcg    3060
gaggaccgaa ggagctaacc gcttttttgc acaacatggg ggatcatgta actcgccttg    3120
atcgttggga accggagctg aatgaagcca taccaaacga cgagcgtgac caccgatgc    3180 ctgcagcaat ggcaacaacg ttgcgcaaac tattaactgg cgaactactt actctagctt    3240
cccggcaaca attaatagac tggatggagg cggataaagt tgcaggacca cttctgcgct    3300
cggcccttcc ggctggctgg tttattgctg ataaatctgg agccggtgag cgtgggtctc    3360
gcggtatcat tgcagcactg gggccagatg gtaagccctc ccgtatcgta gttatctaca    3420
cgacggggag tcaggcaact atggatgaac gaaatagaca gatcgctgag ataggtgcct    3480
cactgattaa gcattggtaa ctgtcagacc aagtttactc atatatactt tagattgatt    3540
taaaacttca ttttaattt aaaaggatct aggtgaagat cctttttgat aatctcatga    3600
```

```
ccaaaatccc ttaacgtgag ttttcgttcc actgagcgtc agaccccgta gaaaagatca   3660
aaggatcttc ttgagatcct ttttttctgc gcgtaatctg ctgcttgcaa acaaaaaaac   3720
caccgctacc agcggtggtt tgtttgccgg atcaagagct accaactctt tttccgaagg   3780
taactggctt cagcagagcg cagataccaa atactgtcct tctagtgtag ccgtagttag   3840
gccaccactt caagaactct gtagcaccgc ctacatacct cgctctgcta atcctgttac   3900
cagtggctgc tgccagtggc gataagtcgt gtcttaccgg gttggactca agacgatagt   3960
taccggataa ggcgcagcgg tcgggctgaa cggggggttc gtgcacacag cccagcttgg   4020
agcgaacgac ctacaccgaa ctgagatacc tacagcgtga gctatgagaa agcgccacgc   4080
ttcccgaagg gagaaaggcg gacaggtatc cggtaagcgg cagggtcgga acaggagagc   4140
gcacgaggga gcttccaggg ggaaacgcct ggtatcttta tagtcctgtc gggtttcgcc   4200
acctctgact tgagcgtcga ttttgtgat gctcgtcagg ggggcggagc ctatggaaaa   4260
acgccagcaa cgcggccttt ttacggttcc tggccttttg ctggcctttt gctcacatgt   4320
tctttcctgc gttatcccct gattctgtgg ataaccgtat taccgccttt gagtgagctg   4380
ataccgctcg ccgcagccga acgaccgagc gcagcgagtc agtgagcgag gaagcggaag   4440
agcgcctgat gcggtatttt ctccttacgc atctgtgcgg tatttcacac cgcatatatg   4500
gtgcactctc agtacaatct gctctgatgc cgcatagtta agccagtata cactccgcta   4560
tcgctacgtg actgggtcat ggctgcgccc cgacacccgc caacaccgc tgacgcgccc   4620 tgacgggctt gtctgctccc ggcatccgct tacagacaag ctgtgaccgt ctccgggagc   4680
tgcatgtgtc agaggttttc accgtcatca ccgaaacgcg cgaggcagct gcggtaaagc   4740
tcatcagcgt ggtcgtgaag cgattcacag atgtctgcct gttcatccgc gtccagctcg   4800
ttgagtttct ccagaagcgt taatgtctgg cttctgataa agcgggccat gttaagggcg   4860
gttttttcct gtttggtcac tgatgcctcc gtgtaagggg gatttctgtt catgggggta   4920
atgataccga tgaaacgaga ggatgctc acgatacggg ttactgatga tgaacatgcc   4980
cggttactgg aacgttgtga gggtaaacaa ctggcggtat ggatgcggcg ggaccagaga   5040
aaaatcactc agggtcaatg ccagcgcttc gttaatacag atgtaggtgt tccacagggt   5100
agccagcagc atcctgcgat gcagatccgg aacataatgg tgcagggcgc tgacttccgc   5160
gtttccagac tttacgaaac acggaaaccg aagaccattc atgttgttgc tcaggtcgca   5220
gacgttttgc agcagcagtc gcttcacgtt cgctcgcgta tcggtgattc attctgctaa   5280
ccagtaaggc aaccccgcca gcctagccgg gtcctcaacg acaggagcac gatcatgcgc   5340
acccgtggcc aggacccaac gctgcccgag atgcgccgcg tgcggctgct ggagatggcg   5400
gacgcgatgg atatgttctg ccaagggttg gtttgcgcat tcacagttct ccgcaagaat   5460
tgattggctc caattcttgg agtggtgaat ccgttagcga ggtgccgccg gcttccattc   5520
aggtcgaggt ggcccggctc catgcaccgc gacgcaacgc ggggaggcag acaaggtata   5580
gggcggcgcc tacaatccat gccaacccgt tccatgtgct cgccgaggcg cataaatcg   5640 ccgtgacgat cagcggtcca gtgatcgaag ttaggctggt aagagccgcg agcgatcctt   5700
gaagctgtcc ctgatggtcg tcatctacct gcctggacag catggcctgc aacgcgggca   5760
tcccgatgcc gccggaagcg agaagaatca taatgggaa ggccatccag cctcgcgtcg   5820
cgaacgccag caagacgtag cccagcgcgt cggccgccat gccggcgata atggcctgct   5880
tctcgccgaa acgtttggtg gcgggaccag tgacgaaggc ttgagcgagg gcgtgcaaga   5940
```

-continued

```
ttccgaatac cgcaagcgac aggccgatca tcgtcgcgct ccagcgaaag cggtcctcgc    6000
cgaaaatgac ccagagcgct gccggcacct gtcctacgag ttgcatgata aagaagacag    6060
tcataagtgc ggcgacgata gtcatgcccc gcgcccaccg gaaggagctg actgggttga    6120
aggctctcaa gggcatcggt cgagatcccg gtgcctaatg agtgagctaa cttacattaa    6180
ttgcgttgcg ctcactgccc gctttccagt cgggaaacct gtcgtgccag ctgcattaat    6240
gaatcggcca acgcgcgggg agaggcggtt tgcgtattgg gcgccagggt ggttttctt     6300
ttcaccagtg agacgggcaa cagctgattg cccttcaccg cctggccctg agagagttgc    6360
agcaagcggt ccacgctggt ttgccccagc aggcgaaaat cctgtttgat ggtggttaac    6420
ggcgggatat aacatgagct gtcttcggta tcgtcgtatc ccactaccga gatatccgca    6480
ccaacgcgca gcccggactc ggtaatggcg cgcattgcgc ccagcgccat ctgatcgttg    6540
gcaaccagca tcgcagtggg aacgatgccc tcattcagca tttgcatggt ttgttgaaaa    6600
ccggacatgg cactccagtc gccttccgt tccgctatcg gctgaatttg attgcgagtg     6660
agatatttat gccagccagc cagacgcaga cgcgccgaga cagaacttaa tgggcccgct    6720
aacagcgcga tttgctggtg acccaatgcg accagatgct ccacgcccag tcgcgtaccg    6780
tcttcatggg agaaaataat actgttgatg ggtgtctggt cagagacatc aagaaataac    6840
gccggaacat tagtgcaggc agcttccaca gcaatggcat cctggtcatc cagcggatag    6900
ttaatgatca gcccactgac gcgttgcgcg agaagattgt gcaccgccgc tttacaggct    6960
tcgacgccgc ttcgttctac catcgacacc accacgctgg cacccagttg atcggcgcga    7020
gatttaatcg ccgcgacaat ttgcgacggc gcgtgcaggg ccagactgga ggtggcaacg    7080
ccaatcagca acgactgttt gcccgccagt tgttgtgcca cgcggttggg aatgtaattc    7140
agctccgcca tcgccgcttc cactttttcc cgcgttttcg cagaaacgtg gctggcctgg    7200
ttcaccacgc gggaaacggt ctgataagag acaccggcat actctgcgac atcgtataac    7260
gttactggtt tcacattcac caccctgaat tgactctctt ccgggcgcta tcatgccata    7320
ccgcgaaagg ttttgcgcca ttcgatggtg tccgggatct cgacgctctc ccttatgcga    7380
ctcctgcatt aggaagcagc ccagtagtag gttgaggccg ttgagcaccg ccgccgcaag    7440
gaatggtgca tgcaaggaga tggcgcccaa cagtcccccg gccacggggc ctgccaccat    7500
acccacgccg aaacaagcgc tcatgagccc gaagtggcga gcccgatctt ccccatcggt    7560
gatgtcggcg atataggcgc cagcaaccgc acctgtggcg ccggtgatgc cggccacgat    7620
gcgtccggcg tagaggatcg agatctcgat cccgcgaaa                          7659
```

CRYSTALS OF HEPATITIS C VIRUS HELICASE OR FRAGMENTS THEREOF COMPRISING A HELICASE BINDING POCKET

CROSS-REFERENCE TO RELATED APPLICATIONS

This application is a continuing application of co-pending International Patent Application PCT/US98/16879, filed Aug. 13, 1998, which is a continuation-in-part of U.S. provisional patent application 60/055,772, filed Aug. 14, 1997.

TECHNICAL FIELD OF THE INVENTION

The invention relates to the X-ray crystal structure of the hepatitis C virus helicase domain. More specifically, the invention relates to crystallized complexes of HCV helicase and an oligonucleotide, to crystallizable compositions of HCV helicase and an oligonucleotide and to methods of crystallizing an HCV helicase-oligonucleotide complex. The invention further relates to a computer programmed with the structure coordinates of the HCV helicase oligonucleotide binding pocket or the HCV helicase nucleotide triphosphate pocket wherein said computer is capable of displaying a three-dimensional representation of that binding pocket.

BACKGROUND OF THE INVENTION

Infection by the hepatitis C virus (HCV) is responsible for most transfusion-associated cases of non-A, non-B hepatitis and also accounts for a significant proportion of community-acquired hepatitis cases worldwide. Relatively few HCV infected individuals experience acute hepatitis, but up to 85% appear to develop persistent infection that often leads to chronic hepatitis and liver cirrhosis, eventually predisposing them to hepatocellular carcinoma. At present, vaccines are unavailable and no broadly effective therapies exist for this viral disease. Consequently, much research has focused on the HCV replicative enzymes as targets for more effective therapies.

HCV contains an approximately 9.6 kb single-stranded positive sense RNA genome classified as its own genus in the Flaviviridae family of animal viruses, which also includes the flavivirus and pestivirus genera. Its genome consists of a conserved 5' nontranslated sequence that serves as an internal ribosome entry site, a single open reading frame that encodes a polyprotein of >3000 amino acids, and a 3' nontranslated region. The 3' nontranslated region contains tracts of poly $(U)_n$ and poly$(UC)_n$ followed by a novel conserved 98 nucleotide sequence.

Proteolytic processing of the HCV polyprotein by virally-encoded proteases generates several nonstructural (NS) proteins with enzymatic activities essential for the replicative cycle of the virus [P. Neddermann et al., Biol. Chem., 378, pp. 469-476 (1997)]. NS2 encodes a presumed metalloprotease, NS5B is a RNA-dependent RNA polymerase, and NS3 is a bifunctional enzyme with a serine protease localized to the N-terminal 181 residues of the protein and a RNA helicase in the C-terminal 465 amino acids. The NS3 protease performs an intramolecular cleavage at the NS3/NS4A junction to form a tight noncovalent NS3-NS4A complex necessary for efficient processing of the remaining polyprotein [C. Failla et al., J. Virol., 69, pp. 1769-1777 (1995); R. Bartenschlager et al., J. Virol., 69, pp. 7519-7528 (1995); Y. Tanji et al., J. Virol., 69, pp. 1575-1581 (1995)]. To date, no evidence exists to suggest that the serine protease and helicase domains are separated by proteolytic processing of NS3 in vivo. This may reflect economical packaging of these enzymatic components, or could imply a functional interdependence between the two domains.

Numerous studies have demonstrated that the serine protease [J. L. Kim et al., Cell, 87, pp. 343-355 (1996); W. Markland et al., J. Gen. Virol., 78, pp. 39-43 (1997).; C. Steinkuhler et al., J. Virol., 70, pp. 6694-6700 (1996)] and RNA helicase domains [J. A. Suzich et al., J. Virol., 67, pp. 6152-6158 (1993); C. L. Tai et al., J. Virol., 70, pp. 8477-8484 (1996); L. Jin et al., Arch. Biochem. Biophys., 323, pp. 47-53 (1995); and F. Preugschat et al., J. Biol. Chem., 271, pp. 24449-24457 (1996)] of NS3 can be expressed independently and isolated as catalytically active species. However, emerging evidence suggests that the NS3 protease and helicase domains may contact one another and modulate NS3 catalytic activities. Examples include apparent differences in pH optima of ATPase and RNA unwinding activities between a contiguous NS3 protein complexed with the NS4A cofactor [K. A. Morgenstern et al., J. Virol., 71, pp. 3767-3775 (1997); Z. Hong et al., J. Virol., 70, pp. 4261-4268 (1996)] and an isolated NS3 helicase domain [C. L. Tai et al., J. Virol., (1996), supra; L. Jin et al., Arch. Biochem. Biophys., (1995), supra; F. Preugschat et al., J. Biol. Chem., (1996), supra; and Y. Gwack et al., Biochem. Biophys. Res. Commun., 225, pp. 654-659 (1996)]. Similarly, the ATPase activities of both proteins differ in their sensitivity to polynucleotide stimulation. Contiguous NS3 appears to have a lower apparent dissociation constant for poly(U) than does the helicase domain [J. A. Suzich et al., J. Virol., (1993), supra; F. Preugschat et al., J. Biol. Chem., (1996), supra; K. A Morgenstern et al., J. Virol., (1997), supra; A. Kanai et al., FEBS Lett., 376, pp. 221-224 (1995)]. Aside from these differences, both proteins display nearly indistinguishable kinetic parameters for NTP hydrolysis when stimulated with saturating polynucleotide [J. A. Suzich et al., J. Virol., (1993), supra; K. A Morgenstern et al., J. Virol., (1997), supra], both display 3'-5' directionality for translocation along a polynucleotide substrate, and the helicases of both proteins effectively unwind duplex RNA: RNA substrates [C. L. Tai et al., J. Virol., (1996), supra; Z. Hong et al., J. Virol., (1996), supra].

In addition to HCV, all flavi- and pestiviruses sequenced to date contain conserved helicase sequence motifs in their homologous NS3 proteins, suggesting that this enzyme plays an important role in the HCV replicative cycle [R. H. Miller et al., Proc. Natl. Acad. Sci. USA, 87, pp. 2057-2061 (1990)]. Consistent with this possibility, helicase encoding sequences have been identified in other viruses and helicases are suggested to catalyze the separation of double-stranded nucleic acid structures during transcription and genome replication [G. Kadare et al., J. Virol., 71, pp. 2583-2590 (1997)]. Previous studies with poliovirus, a positive-stranded RNA virus of the Picornaviridae family, show that mutation of conserved sequence motifs in the 2C helicase inhibits virus replication and proliferation [C. Mirzayan et al., Virology, 189, pp. 547-555 (1992)]. Similar mutational studies on the helicases encoded by herpes simplex virus type 1 and bovine papilloma virus also show that these enzymes are critical for virus replication [P. MacPherson et al., Virology, 204, pp. 403-408 (1994); R. Martinez et al., J. Virol., 66, pp. 6735-6746 (1992)]. Thus, the ability to inhibit helicase activity in HCV may provide an avenue for the therapeutic treatment of HCV infection.

Unfortunately, little is known about the details of how ATP binding and hydrolysis leads to DNA or RNA strand unwinding by the helicase. Two structures of helicases crystallized in the absence of polynucleotide, but, unfortunately, they have not yielded the critical information needed to extrapolate to an enzyme mechanism [N. Yao et al., *Nat. Struct. Biol.,* 4, pp. 463-467 (1997); H. S. Subramanya et al., *Nature,* 384, pp. 379-383 (1996)].

Thus, there is a great need to solve the crystal structure of the helicase complexed with an oligonucleotide and, in particular, to delineate the oligonucleotide and nucleotide triphosphate (NTP) binding pockets of that enzyme. With this information, computer models of these binding sites can be created and potential inhibitors of HCV helicase can be rationally designed.

SUMMARY OF THE INVENTION

Applicants have solved this problem by providing a crystallized complex of the NS3 helicase domain of HCV and a single stranded oligonucleotide. That crystal has been solved by X-ray crystallography to a resolution of 2.2 Å. Based upon that crystal structure, applicants have identified the key amino acid residues that make up the oligonucleotide binding pocket of the helicase.

Thus, the invention relates to a crystallized complex comprising the NS3 helicase domain of hepatitis C virus or mutants thereof and an oligonucleotide.

The invention also relates to crystallizable compositions comprising the NS3 helicase domain, either as an isolated polypeptide or as part of the full length NS3 HCV protein, or single amino acid mutants thereof, and an oligonucleotide. And it relates to methods of using such compositions to produce the aforementioned crystals.

The invention also provides the X-ray structure coordinates of an NS3 helicase-oligonucleotide complex. Those coordinates, or at least the portion that define the oligonucleotide binding pocket or the NTP binding pocket are useful in methods for designing inhibitors of the NS3 helicase, which in turn may be useful in treating HCV infection. This is another aspect of the present invention.

In a related aspect, the invention provides a computer programmed with the coordinates of the NS3 helicase oligonucleotide binding pocket or the NTP binding pocket and with a program capable of converting those coordinates into a three-dimensional representation of the binding pocket on a display connected to the computer.

Finally, the invention provides a computer which, when programmed with at least a portion of the structural coordinates of HCV NS3 helicase and an X-ray diffraction data set of a different molecule or molecular complex, performs a Fourier transform of these structural coordinates of the helicase coordinates and then processes the X-ray diffraction data into structure coordinates of the different molecule or molecular complex via the process of molecular replacement.

BRIEF DESCRIPTION OF THE DRAWINGS

FIG. 1 lists the atomic structure coordinates for NS3 helicase in complex with $dU_8$ as derived by X-ray diffraction from a crystal of that complex. The following abbreviations are used in FIG. 1:

"Atom type" refers to the element whose coordinates are measured. The first letter in the column defines the element.

"X, Y, Z" crystallographically define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in all molecules of the crystal.

FIG. 2 shows a diagram of a computer used to generate a three-dimensional graphical representation of a molecule or molecular complex according to this invention.

Figure 3:
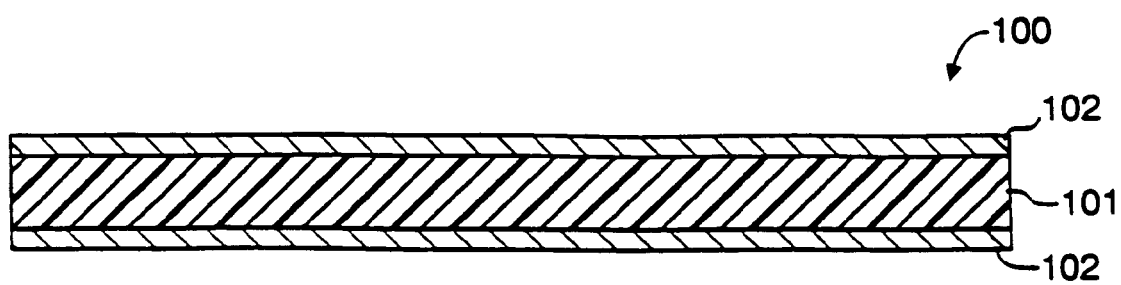

FIG. 3 shows a cross section of a magnetic storage medium.

Figure 4:
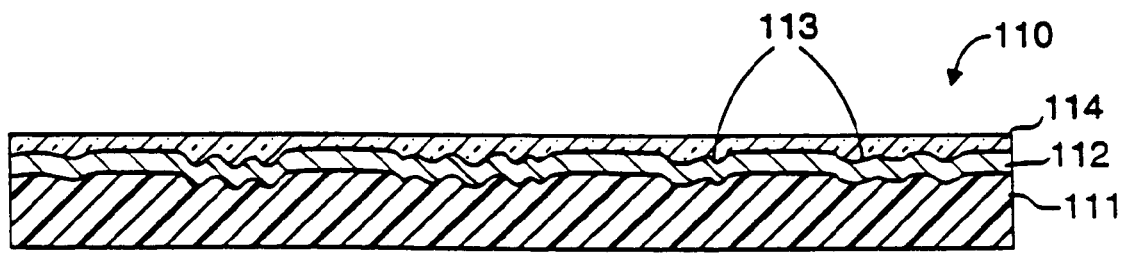

FIG. 4 shows a cross section of a optically-readable data storage medium.

Figure 5:

FIG. 5 depicts a stereo ribbon diagram of the overall fold of the NS3 helicase with bound $d(U)_8$. Domain 1 is located at the top left portion of the molecule containing a seventh N-strand running antiparallel to the rest of the sheet, domain 2 is located at the top right portion, domain 3 which is predominantly α-helical is situated at the bottom portion of the molecule. The DNA that is bound in the center of the molecule and the sulfate which is bound to domain 1 are also shown.

Figure 6:

FIG. 6 depicts a superposition of domains 1 and 2 of NS3 helicase based on conserved secondary structure motifs with a 2.0 Å C-alpha RMS deviation over 78 residues. Residues corresponding to binding to the 3' end of the oligonucleotide are depicted as thick lines. Also shown is the location of Trp-501.

FIG. 7, panel A, depicts the residues surrounding the bound sulfate superimposed on the phosphate binding loops of eight deoxynucleoside monophosphate kinases. Panel B depicts the electron density encompassing the bound DNA substrate. The bright and thick lines depict the difference Fourier ($F_O$-$F_C$) electron density map calculated before DNA or water molecules were built into the model. The faint and thin lines depict the final $2F_O$-$F_C$ electron density map calculated at 2.2 Å resolution using the refined model.

FIG. 8 depicts the secondary structure of HCV NS3 helicase (indicated above the sequence). The conserved sequence motifs are underscored. The non-HCV N-terminal and C-terminal residues which were added during cloning are depicted in lower case. No density was observed for residues in italics. The residues are numbered based on their location in the NS3 protein.

FIG. 9, panel A, depicts aligned sequences of conserved motifs from other helicases. The motifs are colored similar to what was previously reported for the PcrA helicase to aid in comparison of the structures of enzymes from superfamilies I and II. Panel B depicts the location of conserved motifs.

Figure 10:
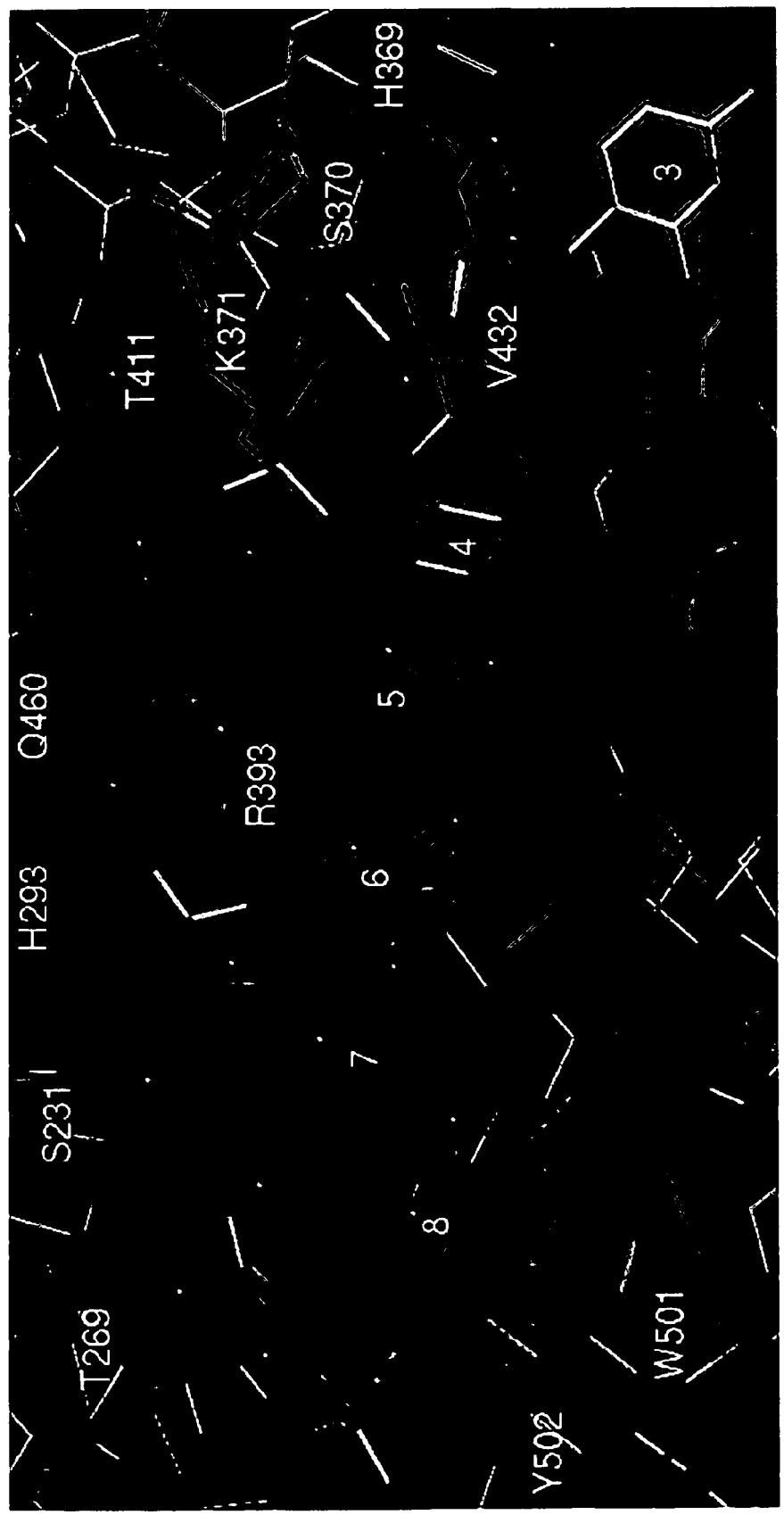

FIG. 10 depicts a view into the central binding cleft of the NS3 helicase domain.

FIG. 11, Panel A, depicts the effect of enzyme concentration and incubation time on HCV NS3 helicase. Panel B depicts the effect of incubation temperature on helicase activity. Panel C depicts the effect of pH on helicase activity. Panel D depicts the effect of monovalent cations on helicase activity. Panel E depicts the effect of ATP on helicase activity. Panel F depicts the effect of divalent cations on enzyme activity.

FIG. 12, Panel A depicts the effect of enzyme concentration on the binding of $[^{32}P]$-ssRNA substrate to HCV NS3 helicase. Panel B depicts the dissociation of pre-formed NS3 helicase/$[^{32}P]$-labeled ssRNA complex by $[^3H]$-labeled ssRNA over time. Panel C depicts the effect of pH on the binding of ssRNA to helicase. Panel D depicts the effect of monovalent cation on ssRNA binding to helicase. Panel E depicts the effect of divalent cations on ssRNA binding to helicase.

Figure 13A:
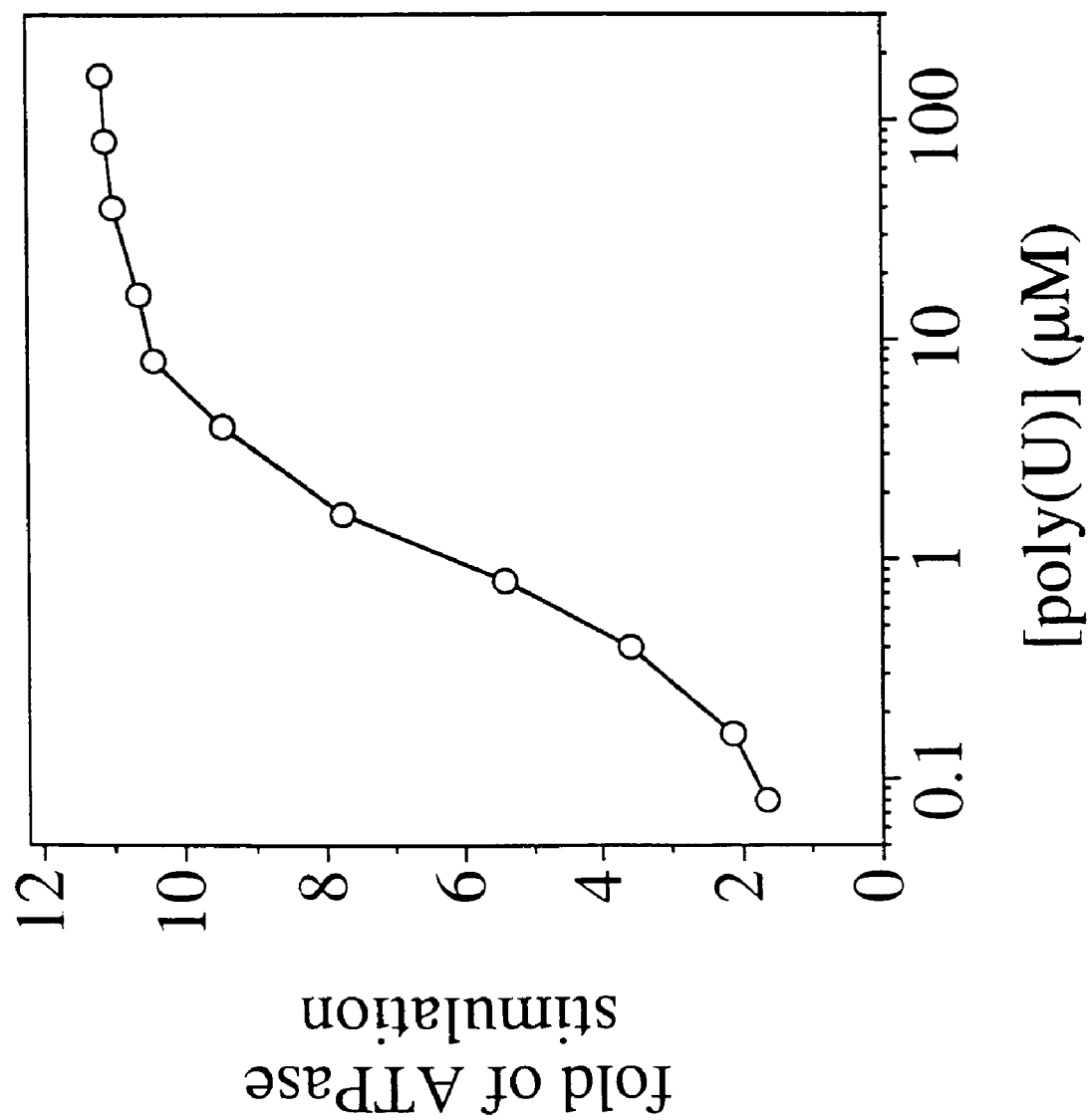
Figure 13B:
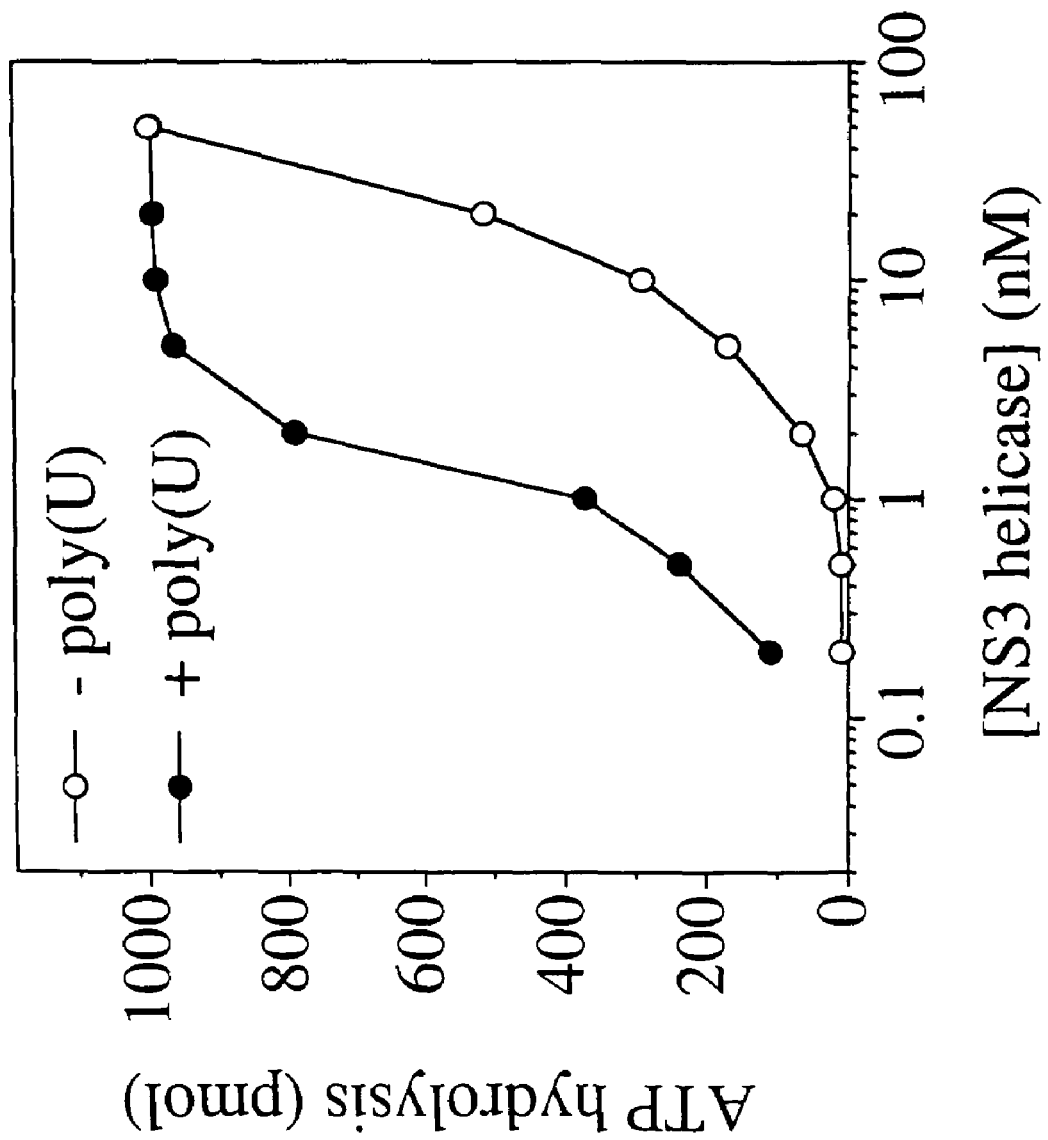

FIG. 13 Panel A depicts the effect of poly (U) on the ATPase activity of HCV NS3 helicase. Panel B depicts the effect of enzyme concentration on ATPase activity in the presence or absence of poly (U).

DETAILED DESCRIPTION OF THE INVENTION

In order that the invention described herein may be more fully understood, the following detailed description is set forth.

According to one embodiment, the invention provides a crystallizable composition comprising NS3 helicase and an oligonucleotide.

The NS3 helicase protein in the crystallizable complexes of this invention is selected from the isolated helicase domain from any strain or the consensus sequence of the HCV NS3 protein (e.g., amino acids 167-631 of SEQ ID NO:2); the entire NS3 protein from any strain of HCV or the consensus sequence of that protein (e.g., SEQ ID NO:2); any portion of the NS3 protein that contains a functional helicase domain, which has been indicated to be amino acids 183-582 by C. Hyun-Soo et al., *J. Biol. Chem.*, 273, pp. 15045-15052 (1998), from any strain of HCV or the consensus sequence of that protein (e.g., amino acids 183-582 of SEQ ID NO:2, amino acids 167-631 of SEQ ID NO:2, amino acids 183-631 of SEQ ID NO:2) and amino acid mutants of any of the above (including, but not limited to, SEQ ID NO:2 or any portion thereof that includes amino acids 183-582 of SEQ ID NO:2 and contains one or more of the following single amino acid replacements: Ser231-to-Ala, Thr269-to-Ala, Ser370-to-Ala, Thr411-to-Ala, Trp501-to-Phe, Trp501-to-Leu or Trp501-to-Ala, Gln460-to-Ala, Arg461-to-Ala, Arg462-to-Ala, Arg464-to-Ala, or Arg467-to-Ala).

The NS3 protein utilized in the crystallizable compositions of this invention may also contain additional amino acids at the N- and/or C-terminus which may be useful in purifying the protein when produced recombinantly. For example, we have found that a poly-histidine tag at the C-terminus is useful in purifying NS3 proteins produced in recombinant host cells through the use of appropriate resins, such as Q-Sepharose (Pharmacia, Piscataway, N.J.). Such tags may also be useful in increasing the solubility of the NS3 protein.

The second component in these compositions is an oligonucleotide. Preferably, the oligonucleotide is single-stranded, although double-stranded oligonucleotides may be used and subsequently dissociated prior to crystallization. Preferably, the oligonucleotide is a polynucleotide of between about 6 and 20 bases. More preferably, the oligonucleotide is between about 6 and 12 bases. Most preferably, the oligonucleotide is polyuracil 8 nucleotides long ($dU_8$).

The molar ratio of NS3 helicase to oligonucleotide should be about 1:1, although ranges between 1:5 and 5:1 are acceptable.

The buffers and other reagents present in the crystallizable compositions of this application may be any components that promote crystallization and/or are compatible with crystallization conditions. An example of such a buffer condition is 15 mM MES (pH 6.5), 2.5 mM β-mercaptoethanol.

The invention also relates to crystals of NS3 helicase complexed with an oligonucleotide. Both the NS3 helicase component and the oligonucleotide component are the same as those described above for crystallizable compositions. These crystals are obtained from the above described compositions by standard crystallization protocols, such as the protocol exemplified in the Example section below.

The invention also relates to a method of making NS3 helicase-containing crystals. Such methods comprise the steps of:

a) obtaining a crystallizable composition comprising an NS3 helicase protein and an oligonucleotide in a molar ratio of between 1:5 and 5:1; and b) subjecting said composition to conditions which promote crystallization.

Again, the choice for the NS3 helicase protein and the oligonucleotide utilized in the above crystallization method are the same as those set forth above for crystallizable compositions.

As mentioned above, applicants have solved the three-dimensional X-ray crystal structure of an NS3 helicase-$dU_8$ complex. The atomic coordinate data is presented in FIG. 1.

In order to use the structure coordinates generated for the NS3 helicase-$dU_8$ complex or its NTP or oligonucleotide binding pockets or portions or homologues thereof, it is often times necessary to convert them into a three-dimensional shape. This is achieved through the use of commercially available software that is capable of generating three-dimensional graphical representations of molecules or portions thereof from a set of structure coordinates.

Binding pockets, also referred to as binding sites in the present invention, are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or any parts of the binding pocket. An understanding of such associations will help lead to the design of drugs having more favorable associations with their target receptor or enzyme, and thus, improved biological effects. Therefore, this information is valuable in designing potential inhibitors of the binding sites of biologically important targets.

The term "binding pocket", as used herein, refers to a region of a molecule or molecular complex, that, as a result of its shape, favorably associates with another chemical entity or compound.

Applicants have identified three binding pockets which are good targets for designing inhibitors.

Two of these binding pockets reside in the region of the helicase where an oligonucleotide binds. These pockets are designated U4 and U8, based upon the nucleotide of $dU_8$ that lies in this pocket in an NS3 helicase-$dU_8$ complex. The third binding pocket is the NTP binding pocket. While this binding pocket has been partially described by others [T. Yao et al., *Nat. Struct. Biol.*, 4, pp. 463-467 (1997)], applicants have further defined this pocket in a way that was not derivable from what was known in the art.

The terms "U4-, U8- and NTP-like binding pocket", as used herein, refer to a portion of a molecule or molecular complex whose shape is sufficiently similar to the NS3 helicase U4, U8 and NTP binding pocket, so as to bind common ligands. These commonalties of shape are defined by a root mean square deviation from the structure coordinates of the backbone atoms of the amino acids that make up these binding pockets in the NS3 helicase structure (as set forth in FIG. 1) of not more than 1.5 Å. The method of performing this calculation is described below.

In resolving the crystal structure of NS3 helicase in complex with an oligonucleotide, applicants have determined that NS3 amino acids Val232, Thr254, Gly255, Thr269, Gly271, Lys272, Ala275, Trp501 and Tyr502 form close contacts (<4 Å) with $U8$ of $dU_8$ in the NS3 helicase-$dU_8$ complex. Thus, a binding pocket defined by the structural coordinates of those amino acids, as set forth in FIG. 1; or a binding pocket whose root mean square deviation from the structure coordinates of the backbone atoms of those amino acids of not more than 1.5 Å is considered a U8-like binding pocket of this invention.

Applicants have also determined that in addition to the NS3 amino acids set forth above, Pro230, Val256, Thr298, Ala497, Lys551, Gln552, Gly554, Glu555, Asn556 and Pro558 are within 8 Å of U8 of the bound oligonucleotide and therefore are also close enough to interact with that substrate. Thus, in a preferred embodiment, a binding pocket defined by the structural coordinates of the amino acids that are within 8 Å of U8 of the bound oligonucleotide, as set forth in FIG. 1; or a binding pocket whose root mean square deviation from the structure coordinates of the backbone atoms of those amino acids is not more than 1.5 Å is considered a preferred NS3 helicase U8-like binding pocket of this invention.

Applicants have further determined that the NS3 helicase amino acids that define the shape of the U4 oligonucleotide binding pocket are: His369, Ser370, Lys371, Tyr392, Arg393, Thr411, Asp412, Ala413, Cys431, Val432, Gln434, Ile446, Thr448, Arg461, Glu493, Glu555, Asn556 and Phe557. Thus, a binding pocket defined by the structural coordinates of these amino acids, as set forth in FIG. 1; or a binding pocket whose root mean square deviation from the structure coordinates of the backbone atoms of these amino acids is not more than 1.5 Å is considered a NS3 helicase U4-like binding pocket of this invention.

Applicants have also more completely determined, as compared to the prior art, the NS3 helicase amino acids that define the shape of the NTP binding pocket. Those amino acids are: Pro205, Thr206, Gly207, Ser208, Gly209, Lys210, Ser211, Thr212, Lys213, Asn229, Ala234, Gly237, Phe238, Tyr241, Asp290, Glu291, His 293, Thr322, Ala323, Thr324, Gln460, Gly463, Arg464 and Arg467. Thus, a binding pocket defined by the structural coordinates of these amino acids, as set forth in FIG. 1; or a binding pocket whose root mean square deviation from the structure coordinates of the backbone atoms of these amino acids is not more than 1.5 Å is considered a NS3 helicase NTP-like binding pocket of this invention.

It will be readily apparent to those of skill in the art that the numbering of amino acids in other isoforms of NS3 may be different than that set forth for herein. Corresponding amino acids in other isoforms of NS3 are easily identified by visual inspection of the amino acid sequences or by using commercially available homology software programs.

Each of those amino acids of NS3 helicase is defined by a set of structure coordinates set forth in FIG. 1. The term "structure coordinates" refers to Cartesian coordinates derived from mathematical equations related to the patterns obtained on diffraction of a monochromatic beam of X-rays by the atoms (scattering centers) of a protein or protein-ligand complex in crystal form. The diffraction data are used to calculate an electron density map of the repeating unit of the crystal. The electron density maps are then used to establish the positions of the individual atoms of the enzyme or enzyme complex.

Those of skill in the art understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

The term "associating with" refers to a condition of proximity between a chemical entity or compound, or portions thereof, and a binding pocket or binding site on a protein. The association may be non-covalent—wherein the juxtaposition is energetically favored by hydrogen bonding or van der Waals or electrostatic interactions—or it may be covalent.

The variations in coordinates discussed above may be generated because of mathematical manipulations of the NS3 helicase-oligonucleotide complex structure coordinates. For example, the structure coordinates set forth in FIG. 1 could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within an acceptable standard error as compared to the original coordinates, the resulting three-dimensional shape is considered to be the same. Thus, for example, a ligand that bound to the oligonucleotide binding pocket of NS3 helicase would also be expected to bind to another binding pocket whose structure coordinates defined a shape that fell within the acceptable error.

Various computational analyses are therefore necessary to determine whether a molecule or the binding pocket portion thereof is sufficiently similar to the NS3 helicase binding pockets described above. Such analyses may be carried out in well known software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: 1) load the structures to be compared; 2) define the atom equivalences in these structures; 3) perform a fitting operation; and 4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, C$\alpha$, C and O) for all conserved residues between the two structures being compared. We will also consider only rigid fitting operations.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any molecule or molecular complex or binding pocket thereof that has a root mean square deviation of Conserved residue backbone atoms (N, C$\alpha$, C, O) of less than 1.5 Å when superimposed on the relevant backbone atoms described by structure coordinates listed in FIG. 1 are considered identical. More preferably, the root mean square deviation is less than 1.0 Å.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the backbone of NS3 helicase or a binding pocket portion thereof, as defined by the structure coordinates of NS3 helicase described herein.

Therefore, according to another embodiment of this invention is provided a computer for producing:

a) a three-dimensional representation of a molecule or molecular complex, wherein said molecule or molecular complex comprises a binding pocket defined by structure coordinates of NS3 amino acids Val232, Thr254, Gly255, Thr269, Gly271, Lys272, Ala275, Trp501 and Tyr502 according to FIG. 1; or b) a three-dimensional representation of a homologue of said molecule or molecular complex, wherein said homologue comprises a binding pocket that has a root mean square deviation from the backbone atoms of said amino acids of not more than 1.5 Å, wherein said computer comprises:

(i) a machine-readable data storage medium comprising a data storage material encoded with machine-readable data, wherein said data comprises the structure coordinates of NS3 amino acids Val232, Thr254, Gly255, Thr269, Gly271, Lys272, Ala275, Trp501 and Tyr502 according to FIG. 1;

(ii) a working memory for storing instructions for processing said machine-readable data;

(iii) a central-processing unit coupled to said working memory and to said machine-readable data storage medium for processing said machine readable data into said three-dimensional representation; and (iv) a display coupled to said central-processing unit for displaying said three-dimensional representation.

According to a preferred embodiment, the computer produces a three-dimensional representation of:

a) a molecule or molecular complex comprising a binding pocket defined by the structure coordinates of NS3 helicase amino acids Val232, Thr254, Gly255, Thr269, Gly271, Lys272, Ala275, Trp501, Tyr502, Pro230, Val256, Thr298, Ala497, Lys551, Gln552, Gly554, Glu555, Asn556 and Pro558, according to FIG. 1; or b) a homologue of said molecule or molecular complex, wherein said homologue comprises a binding pocket that has a root mean square deviation from the backbone atoms of said amino acids of not more than 1.5 Å. In that preferred embodiment, the machine readable data comprises the structure coordinates of NS3 amino acids Val232, Thr254, Gly255, Thr269, Gly271, Lys272, Ala275, Trp501, Tyr502, Pro230, Val256, Thr298, Ala497, Lys551, Gln552, Gly554, Glu555, Asn556 and Pro558, according to FIG. 1.

In the above two embodiments, the computer is producing a three-dimensional graphical structure of a molecule or a molecular complex which comprises a NS3 helicase U8-like binding pocket.

In an alternate embodiment, the computer produces a three-dimensional representation of:

a) a molecule or molecular complex comprising a binding pocket defined by the structure coordinates of NS3 helicase amino acids His369, Ser370, Lys371, Tyr392, Arg393, Thr411, Asp412, Ala413, Cys431, Val432, Gln434, Ile446, Thr448, Arg461, Glu493, Glu555, Asn556 and Phe557, according to FIG. 1; or b) a homologue of said molecule or molecular complex, wherein said homologue comprises a binding pocket that =has a root mean square deviation from the backbone atoms of said amino acids of not more than 1.5 Å

In this alternate embodiment, the machine readable data comprises the structure coordinates of NS3 amino acids His369, Ser370, Lys371, Tyr392, Arg393, Thr411, Asp412, Ala413, Cys431, Val432, Gln434, Ile446, Thr448, Arg461, Glu493, Glu555, Asn556 and Phe557, according to FIG. 1.

In this embodiment, the computer is producing a three-dimensional graphical structure of a molecule or a molecular complex which comprises a NS3 helicase U4-like binding pocket.

In yet another alternate embodiment, the computer produces a three-dimensional representation of:

a) a molecule or molecular complex comprising a binding pocket defined by the structure coordinates of NS3 helicase amino acids Pro205, Thr206, Gly207, Ser208, Gly209, Lys210, Ser211, Thr212, Lys213, Asn229, Ala234, Gly237, Phe238, Tyr241, Asp290, Glu291, His 293, Thr322, Ala323, Thr324, Gln460, Gly463, Arg464 and Arg467, according to FIG. 1; or b) a homologue of said molecule or molecular complex, wherein said homologue comprises a binding pocket that has a root mean square deviation from the backbone atoms of said amino acids of not more than 1.5 Å

In this alternate embodiment, the machine readable data comprises the structure coordinates of NS3 amino acids Pro205, Thr206, Gly207, Ser208, Gly209, Lys210, Ser211, Thr212, Lys213, Asn229, Ala234, Gly237, Phe238, Tyr241, Asp290, Glu291, His293, Thr322, Ala323, Thr324, Gln460, Gly463, Arg464 and Arg467, according to FIG. 1.

In this embodiment, the computer is producing a three-dimensional graphical structure of a molecule or a molecular complex which comprises a NS3 helicase NTP-like binding pocket.

Even more preferred is a computer for producing a three-dimensional representation of a molecule or molecular complex defined by structure coordinates of all of the NS3 amino acids set forth in FIG. 1, or a three-dimensional representation of a homologue of said molecule or molecular complex, wherein said homologue comprises a binding pocket that has a root mean square deviation from the backbone atoms of said amino acids of not more than 1.5 Å. In this embodiment, the machined readable data contains the coordinates of all of the NS3

According to an alternate embodiment, the invention provides a computer for determining at least a portion of the structure coordinates corresponding to X-ray diffraction data obtained from a molecule or molecular complex, wherein said computer comprises:

(a) a machine-readable data storage medium comprising a data storage material encoded with machine-readable data, wherein said data comprises at least a portion of the structural coordinates of NS3 helicase according to FIG. 1;

(b) a machine-readable data storage medium comprising a data storage material encoded with machine-readable data, wherein said data comprises X-ray diffraction data from said molecule or molecular complex;

(c) a working memory for storing instructions for processing said machine-readable data of (a) and (b);

(d) a central-processing unit coupled to said working memory and to said machine-readable data storage medium of (a) and (b) for performing a Fourier transform of the machine readable data of (a) and for processing said machine readable data of (b) into structure coordinates; and (e) a display coupled to said central-processing unit for displaying said structure coordinates of said molecule or molecular complex.

For example, the Fourier transform of the structure coordinates set forth in FIG. 1 may be used to determine at least a portion of the structure coordinates of other helicases.

FIG. 2 demonstrates one version of these embodiments. System 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of a binding pocket of this invention using a program such as QUANTA as described herein. Output hardware might also include a printer 42, so that hard copy output may be produced, or a disk drive 24, to store system output for later use.

In operation, CPU 20 coordinates the use of the various input and output devices 36, 46, coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of the hardware system 10 are included as appropriate throughout the following description of the data storage medium.

FIG. 3 shows a cross section of a magnetic data storage medium 100 which can be encoded with a machine-readable data that can be carried out by a system such as system 10 of FIG. 2. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in manner which may be conventional, machine readable data such as that described herein, for execution by a system such as system 10 of FIG. 2.

FIG. 4 shows a cross section of an optically-readable data storage medium 110 which also can be encoded with such a machine-readable data, or set of instructions, which can be carried out by a system such as system 10 of FIG. 2. Medium 110 can be a conventional compact disk read only memory (CD-ROM) or a rewritable medium such as a magneto-optical disk which is optically readable and magneto-optically writable. Medium 100 preferably has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

Thus, in accordance with the present invention, X-ray coordinate data capable of being processed into a three dimensional graphical display of a molecule or molecular complex which comprises a NS3 helicase-like binding pocket is stored in a machine-readable storage medium.

The NS3 helicase X-ray coordinate data, when used in conjunction with a computer programmed with software to translate those coordinates into the 3-dimensional structure of a molecule or molecular complex comprising a NS3 helicase-like binding pocket may be used for a variety of purposes, such as drug discovery.

For example, the structure encoded by the data may be computationally evaluated for its ability to associate with chemical entities. Chemical entities that associate with NS3 helicase may inhibit that enzyme, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with a) a molecule or molecular complex comprising a binding pocket defined by structure coordinates of NS3 helicase amino acids Val232, Thr254, Gly255, Thr269, Gly271, Lys272, Ala275, Trp501 and Tyr502 according to FIG. 1, or b) a homologue of said molecule or molecular complex, wherein said homologue comprises a binding pocket that has a root mean square deviation from the backbone atoms of said amino acids of not more than 1.5 Å.

This method comprises the steps of:

i) employing computational means to perform a fitting operation between the chemical entity and a binding pocket of the molecule or molecular complex; and ii) analyzing the results of said fitting operation to quantify the association between the chemical entity and the binding pocket.

The term "chemical entity", as used herein, refers to chemical compounds, complexes of at least two chemical compounds, and fragments of such compounds or complexes.

Preferably, the method evaluates the potential of a chemical entity to associate with a) a molecule or molecular complex comprising a binding pocket defined by structure coordinates of NS3 helicase amino acids Val232, Thr254, Gly255, Thr269, Gly271, Lys272, Ala275, Trp501, Tyr502, Pro230, Val256, Thr298, Ala497, Lys551, Gln552, Gly554, Glu555, Asn556 and Pro558 according to FIG. 1, or b) a homologue of said molecule or molecular complex, wherein said homologue comprises a binding pocket that has a root mean square deviation from the backbone atoms of said amino acids of not more than 1.5 Å.

These embodiments relate to evaluating the potential of a chemical entity to associate with a NS3 helicase U8-like binding pocket.

In an alternate embodiment, the same steps indicated above are used in a method for evaluating the potential of a chemical entity to associate with
a) a molecule or molecular complex comprising a binding pocket defined by structure coordinates of NS3 helicase amino acids His369, Ser370, Lys371, Tyr392, Arg393, Thr411, Asp412, Ala413, Cys431, Val432, Gln434, Ile446, Thr448, Arg461, Glu493, Glu555, Asn556 and Phe557 according to FIG. 1, or
b) a homologue of said molecule or molecular complex, wherein said homologue comprises a binding pocket that has a root mean square deviation from the backbone atoms of said amino acids of not more than 1.5 Å.

These embodiments relate to evaluating the potential of a chemical entity to associate with a NS3 helicase U4-like binding pocket.

In yet another alternate embodiment, the same steps indicated above are used in a method for evaluating the potential of a chemical entity to associate with
a) a molecule or molecular complex comprising a binding pocket defined by structure coordinates of NS3 helicase amino acids Pro205, Thr206, Gly207, Ser208, Gly209, Lys210, Ser211, Thr212, Lys213, Asn229, Ala234, Gly237, Phe238, Tyr241, Asp290, Glu291, His 293, Thr322, Ala323, Thr324, Gln460, Gly463, Arg464 and Arg467 according to FIG. 1, or
b) a homologue of said molecule or molecular complex, wherein said homologue comprises a binding pocket that has a root mean square deviation from the backbone atoms of said amino acids of not more than 1.5 Å.

These embodiments relate to evaluating the potential of a chemical entity to associate with a NS3 helicase NTP-like binding pocket.

Even more preferably, the method evaluates the potential of a chemical entity to associate with a molecule or molecular complex defined by structure coordinates of all of the NS3 helicase amino acids, as set forth in FIG. 1, or a homologue of said molecule or molecular complex having a root mean square deviation from the backbone atoms of said amino acids of not more than 1.5 Å.

Alternatively, the structural coordinates of the NS3 helicase binding pocket can be utilized in a method for identifying a potential agonist or antagonist of a molecule comprising a NS3 helicase-like binding pocket. This method comprises the steps of:
   a. using the atomic coordinates of Val232, Thr254, Gly255, Thr269, Gly271, Lys272, Ala275, Trp501 and Tyr502 according to FIG. 1±a root mean square deviation from the backbone atoms of said amino acids of not more than 1.5 Å, to generate a three-dimensional structure of molecule comprising a NS3 helicase-like binding pocket;
   b. employing said three-dimensional structure to design or select said potential agonist or antagonist;
   c. synthesizing said agonist or antagonist; and
   d. contacting said agonist or antagonist with said molecule to determine the ability of said potential agonist or antagonist to interact with said molecule.

More preferred is when the atomic coordinates of Val232, Thr254, Gly255, Thr269, Gly271, Lys272, Ala275, Trp501, Tyr502, Pro230, Val256, Thr298, Ala497, Lys551, Gln552, Gly554, Glu555, Asn556 and Pro558 according to FIG. 1±a root mean square deviation from the backbone atoms of said amino acids of not more than 1.5 Å, are used to generate a three-dimensional structure of molecule comprising a NS3 helicase-like binding pocket.

These methods are designed to identify agonists and antagonists that associate with an NS3 helicase U8-like binding pocket.

Alternatively, the atomic coordinates of the NS3 helicase U4 binding pocket—His369, Ser370, Lys371, Tyr392, Arg393, Thr411, Asp412, Ala413, Cys431, Val432, Gln434, Ile446, Thr448, Arg461, Glu493, Glu555, Asn556 and Phe557 according to FIG. 1—±a root mean square deviation from the backbone atoms of said amino acids of not more than 1.5 Å, may be used in step a), above, to generate a three-dimensional structure of molecule comprising a NS3 helicase-like binding pocket.

In another alternative embodiment, the atomic coordinates of the NS3 helicase NTP binding site—Pro205, Thr206, Gly207, Ser208, Gly209, Lys210, Ser211, Thr212, Lys213, Asn229, Ala234, Gly237, Phe238, Tyr241, Asp290, Glu291, His293, Thr322, Ala323, Thr324, Gln460, Gly463, Arg464 and Arg467 according to FIG. 1—±a root mean square deviation from the backbone atoms of said amino acids of not more than 1.5 Å, may be used in step a), above, to generate a three-dimensional structure of molecule comprising a NS3 helicase-like binding pocket.

Most preferred is when the atomic coordinates of all the amino acids of NS3 helicase according to FIG. 1±a root mean square deviation from the backbone atoms of said amino acids of not more than 1.5 Å, are used to generate a three-dimensional structure of molecule comprising a NS3 helicase-like binding pocket.

For the first time, the present invention permits the use of molecular design techniques to identify, select and design chemical entities, including inhibitory compounds, capable of binding to NS3 helicase-like binding pockets—in particular, the oligonucleotide binding pocket of NS3 helicase.

Applicants' elucidation of the U4 and U8 binding pockets in the oligonucleotide binding site and an expanded elucidation of the NTP binding pocket on NS3 helicase provides the necessary information for designing new chemical entities and compounds that may interact with NS3 helicase-like binding pockets, in whole or in part.

Throughout this section, discussions about the ability of an entity to bind to, associate with or inhibit a NS3 helicase-like binding pocket refers to features of the entity alone. Assays to determine if a compound binds to NS3 helicase are well known in the art and are exemplified below.

The design of compounds that bind to or inhibit NS3 helicase-like binding pockets according to this invention generally involves consideration of two factors. First, the entity must be capable of physically and structurally associating with parts or all of the NS3 helicase-like binding pockets. Non-covalent molecular interactions important in this association include hydrogen bonding, van der Waals interactions, hydrophobic interactions and electrostatic interactions.

Second, the entity must be able to assume a conformation that allows it to associate with the NS3 helicase-like binding pocket directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the NS3 helicase-like binding pocket or homologues thereof.

The potential inhibitory or binding effect of a chemical entity on a NS3 helicase-like binding pocket may be analyzed prior to its actual synthesis and testing by the use of computer modeling techniques. If the theoretical structure of the given entity suggests insufficient interaction and association between it and the NS3 helicase-like binding pocket, testing of the entity is obviated. However, if computer modeling indicates a strong interaction, the molecule may then be synthesized and tested for its ability to bind to a NS3 helicase-like binding pocket. This may be achieved by testing the ability of the molecule to inhibit NS3 helicase using the assays described in Example 5. In this manner, synthesis of inoperative compounds may be avoided.

A potential inhibitor of a NS3 helicase-like binding pocket may be computationally evaluated by means of a series of steps in which chemical entities or fragments are screened and selected for their ability to associate with the NS3 helicase-like binding pockets.

One skilled in the art may use one of several methods to screen chemical entities or fragments for their ability to associate with a NS3 helicase-like binding pocket. This process may begin by visual inspection of, for example, a NS3 helicase-like binding pocket on the computer screen based on the NS3 helicase structure coordinates in FIG. 1 or other coordinates which define a similar shape generated from the machine-readable storage medium. Selected fragments or chemical entities may then be positioned in a variety of orientations, or docked, within that binding pocket as defined supra. Docking may be accomplished using software such as Quanta and Sybyl, followed by energy minimization and molecular dynamics with standard molecular mechanics force fields, such as CHARMM and AMBER.

Specialized computer programs may also assist in the process of selecting fragments or chemical entities. These include:

1. GRID (P. J. Goodford, "A Computational Procedure for Determining Energetically Favorable Binding Sites on Biologically Important Macromolecules", *J. Med. Chem.,* 28, pp. 849-857 (1985)). GRID is available from Oxford University, Oxford, UK.
2. MCSS (A. Miranker et al., "Functionality Maps of Binding Sites: A Multiple Copy Simultaneous Search Method." *Proteins: Structure, Function and Genetics,* 11, pp. 29-34 (1991)). MCSS is available from Molecular Simulations, San Diego, Calif.
3. AUTODOCK (D. S. Goodsell et al., "Automated Docking of Substrates to Proteins by Simulated Annealing", *Proteins: Structure, Function, and Genetics,* 8, pp. 195-202 (1990)). AUTODOCK is available from Scripps Research Institute, La Jolla, Calif.
4. DOCK (I. D. Kuntz et al., "A Geometric Approach to Macromolecule-Ligand Interactions", *J. Mol. Biol.,* 161, pp. 269-288 (1982)). DOCK is available from University of California, San Francisco, Calif.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of NS3 helicase. This would be followed by manual model building using software such as Quanta or Sybyl [Tripos Associates, St. Louis, Mo.].

Useful programs to aid one of skill in the art in connecting the individual chemical entities or fragments include:

1. CAVEAT (P. A. Bartlett et al, "CAVEAT: A Program to Facilitate the Structure-Derived Design of Biologically Active Molecules", in *Molecular Recognition in Chemical and Biological Problems*", Special Pub., Royal Chem. Soc., 78, pp. 182-196 (1989); G. Lauri and P. A. Bartlett, "CAVEAT: a Program to Facilitate the Design of Organic Molecules", *J. Comput. Aided Mol. Des.,* 8, pp. 51-66 (1994)). CAVEAT is available from the University of California, Berkeley, Calif.
2. 3D Database systems such as ISIS (MDL Information Systems, San Leandro, Calif.). This area is reviewed in Y. C. Martin, "3D Database Searching in Drug Design", *J. Med. Chem.,* 35, pp. 2145-2154 (1992).
3. HOOK (M. B. Eisen et al, "HOOK: A Program for Finding Novel Molecular Architectures that Satisfy the Chemical and Steric Requirements of a Macromolecule Binding Site", *Proteins: Struct., Funct., Genet.,* 19, pp. 199-221 (1994). HOOK is available from Molecular Simulations, San Diego, Calif.

Instead of proceeding to build an inhibitor of a NS3 helicase-like binding pocket in a step-wise fashion one fragment or chemical entity at a time as described above, inhibitory or other NS3 helicase binding compounds may be designed as a whole or "de novo" using either an empty binding site or optionally including some portion(s) of a known inhibitor(s). There are many de novo ligand design methods including:

1. LUDI (H.-J. Bohm, "The Computer Program LUDI: A New Method for the De Novo Design of Enzyme Inhibitors", *J. Comp. Aid. Molec. Design,* 6, pp. 61-78 (1992)). LUDI is available from Molecular Simulations Incorporated, San Diego, Calif.
2. LEGEND (Y. Nishibata et al., *Tetrahedron,* 47, p. 8985 (1991)). LEGEND is available from Molecular Simulations Incorporated, San Diego, Calif.
3. LeapFrog (available from Tripos Associates, St. Louis, Mo.).
4. SPROUT (V. Gillet et al, "SPROUT: A Program for Structure Generation)", *J. Comput. Aided Mol. Design,* 7, pp. 127-153 (1993)). SPROUT is available from the University of Leeds, UK.

Other molecular modeling techniques may also be employed in accordance with this invention [see, e.g., N. C. Cohen et al., "Molecular Modeling Software and Methods for Medicinal Chemistry, *J. Med. Chem.,* 33, pp. 883-894 (1990); see also, M. A. Navia and M. A. Murcko, "The Use of Structural Information in Drug Design", *Current Opinions in Structural Biology,* 2, pp. 202-210 (1992); L. M. Balbes et al., "A Perspective of Modern Methods in Computer-Aided Drug Design", in *Reviews in Computational Chemistry*, Vol. 5, K. B. Lipkowitz and D. B. Boyd, Eds., VCH, New York, pp. 337-380 (1994); see also, W. C. Guida, "Software For Structure-Based Drug Design", *Curr. Opin. Struct. Biology,* 4, pp. 777-781 (1994)].

Once a compound has been designed or selected by the above methods, the efficiency with which that entity may bind to an NS3 helicase binding pocket may be tested and optimized by computational evaluation. For example, an effective NS3 helicase binding pocket inhibitor must preferably demonstrate a relatively small difference in energy between its bound and free states (i.e., a small deformation energy of binding). Thus, the most efficient NS3 helicase binding pocket inhibitors should preferably be designed with a deformation energy of binding of not greater than about 10 kcal/mole, more preferably, not greater than 7 kcal/mole. NS3 helicase binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

An entity designed or selected as binding to an NS3 helicase binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. ©1995); AMBER, version 4.1 (P. A. Kollman, University of California at San Francisco, ©1995); QUANTA/CHARMM (Molecular Simulations, Inc., San Diego, Calif. ©1995); Insight II/Discover (Molecular Simulations, Inc., San Diego, Calif. ©1995); DelPhi (Molecular Simulations, Inc., San Diego, Calif. ©1995); and AMSOL (Quantum Chemistry Program Exchange, Indiana University). These programs may be implemented, for instance, using a Silicon Graphics workstation such as an Indigo$^2$ with "IMPACT" graphics. Other hardware systems and software packages will be known to those skilled in the art.

Another approach enabled by this invention, is the computational screening of small molecule databases for chemical entities or compounds that can bind in whole, or in part, to a NS3 helicase binding pocket. In this screening, the quality of fit of such entities to the binding site may be judged either by shape complementarity or by estimated interaction energy [E. C. Meng et al., *J. Comp. Chem.*, 13, pp. 505-524 (1992)].

According to another embodiment, the invention provides compounds which associate with a NS3 helicase-like binding pocket produced or identified by the method set forth above.

The structure coordinates set forth in FIG. 1 can also be used to aid in obtaining structural information about another crystallized molecule or molecular complex. This may be achieved by any of a number of well-known techniques, including molecular replacement.

Therefore, in another embodiment this invention provides a method of utilizing molecular replacement to obtain structural information about a molecule or molecular complex whose structure is unknown comprising the steps of:

a) crystallizing said molecule or molecular complex of unknown structure;

b) generating X-ray diffraction data from said crystallized molecule or molecular complex; and c) applying at least a portion of the structure coordinates set forth in FIG. 1 to the X-ray diffraction data to generate a three-dimensional electron density map of the molecule or molecular complex whose structure is unknown.

By using molecular replacement, all or part of the structure coordinates of the NS3 helicase/oligonucleotide complex as provided by this invention (and set forth in FIG. 1) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of the NS3 helicase/oligonucleotide complex according to FIG. 1 within the unit cell of the crystal of the unknown molecule or molecular complex so as best to account for the observed X-ray diffraction data of the crystal of the molecule or molecular complex whose structure is unknown. Phases can then be calculated from this model and combined with the observed X-ray diffraction data amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in *Meth. Enzymol.*, 115, pp. 55-77 (1985); M. G. Rossmann, ed., "The Molecular Replacement Method", *Int. Sci. Rev. Ser.*, No. 13, Gordon & Breach, New York (1972)].

The structure of any portion of any crystallized molecule or molecular complex that is sufficiently homologous to any portion of the NS3 helicase/oligonucleotide complex can be resolved by this method.

In a preferred embodiment, the method of molecular replacement is utilized to obtain structural information about another helicase. The structure coordinates of NS3 helicase as provided by this invention are particularly useful in solving the structure of other isoforms of NS3 helicase or other NS3 helicase-containing complexes.

Furthermore, the structure coordinates of NS3 helicase as provided by this invention are useful in solving the structure of NS3 helicase proteins that have amino acid substitutions, additions and/or deletions (referred to collectively as "NS3 helicase mutants", as compared to naturally occurring NS3 helicase isoforms. These NS3 helicase mutants may optionally be crystallized in co-complex with a chemical entity, such as a non-hydrolyzable NTP analogue or an oligonucleotide. The crystal structures of a series of such complexes may then be solved by molecular replacement and compared with that of wild-type NS3 helicase. Potential sites for modification within the various binding sites of the enzyme may thus be identified. This information provides an additional tool for determining the most efficient binding interactions, for example, increased hydrophobic interactions, between NS3 helicase and a chemical entity or compound.

The structure coordinates are also particularly useful to solve the structure of crystals of NS3 helicase or NS3 helicase homologues co-complexed with a variety of chemical entities. This approach enables the determination of the optimal sites for interaction between chemical entities, including between candidate NS3 helicase inhibitors and NS3 helicase. For example, high resolution X-ray diffraction data collected from crystals exposed to different types of solvent allows the determination of where each type of solvent molecule resides. Small molecules that bind tightly to those sites can then be designed and synthesized and tested for their NS3 helicase inhibition activity.

All of the complexes referred to above may be studied using well-known X-ray diffraction techniques and may be refined versus 1.5-3 Å resolution X-ray data to an R value of about 0.20 or less using computer software, such as X-PLOR [Yale University, ©1992, distributed by Molecular Simulations, Inc.; see, e.g., Blundell & Johnson, supra; *Meth. Enzymol.*, vol. 114 & 115, H. W. Wyckoff et al., eds., Academic Press (1985)]. This information may thus be used to optimize known NS3 helicase inhibitors, and more importantly, to design new NS3 helicase inhibitors.

In order that this invention be more fully understood, the following examples are set forth. These examples are for the purpose of illustration only and are not to be construed as limiting the scope of the invention in any way.

EXAMPLE 1

Cloning and Expression of NS3 Helicase

The HCV NS3 RNA helicase domain (encoded by nucleotides 502-1896 of SEQ ID NO:6) was subcloned from a cDNA of the HCV H strain [A. Grakoui et al., *J. Virol.*, 67, pp. 1385-95 (1993); C. Lin et al., *J. Virol.*, 68, pp. 8147-57 (1994), the disclosures of which are herein incorporated be reference] into a pET expression vector (Novagen, Madison, Wis.). The resulting plasmid, pET-BS(+)/HCV/NS3-C465-His (SEQ ID NO:4), also contained a methionine start codon, a linker encoded Gly-Ser-Gly-Ser sequence attached the C-terminal threonine of the NS3 helicase domain and a six-histidine tag fused to the C-terminus of the Gly-Ser-Gly-Ser sequence to facilitate protein purification. This plasmid was used as a template for single-stranded DNA-based site-directed mutagenesis essentially as described by (T. A. Kunkel, *Proc. Natl. Acad. Sci. USA*, 82, pp. 488-492 (1985) and C. Lin et al., *Virology*, 192, pp. 596-604 (1993), the disclosures of which are herein incorporated by reference) with the following modifications.

The single stranded phagemid DNA packaged in the presence of helper M13 phage corresponds to the HCV plus strand. A single colony of *E. coli* strain CJ 326, transformed with pET-BS(+)/HCV/NS3-C465-His, was grown in YT media containing 0.25 μg/ml of uridine and 50 μg/ml of carbenicillin. After three serial passages, M13 helper phage (Bio-Rad) was used to rescue uridylated phagemid single stranded DNA, which was then used as template for oligonucleotide-directed mutagenesis (T. A. Kunkel (1985), supra]. ABI automatic sequencing was used to identify mutations and ensure that there is no other unintended mutation within the HCV NS3 helicase domain sequences. Construct containing mutations were named according to the position of the substituted residue in the full-length HCV NS3 protein.

In this manner, we made NS3 helicase corresponding to the consensus sequence of the HCV genotype 1 (Pro at amino acid 332; Ser at amino acid 403; Ala at amino acid 410; and Thr at amino acid 505; hereinafter referred to as "wild type"); as well as NS3 helicase containing the following single amino acid mutations as compared to the consensus HCV genotype 1 NS3 helicase sequence: Ser231-to-Ala; Thr269-to-Ala; Ser370-to-Ala; Thr411-to-Ala; Trp501-to-Phe; Trp501-to-Leu; and Trp501-to-Ala.

*E. coli* BL21 (DE3) cells, freshly transformed with the pET-BS(+)/HCV/NS3-C465-His plasmid or similar plasmids encoding the single amino acid mutant NS3 helicases described above, were grown at 30° C. in LB media supplemented with 50 μg/ml of carbenicillin. When the density reached an $OD_{600}$ of 1.0, the cells were induced for 3 hr at 30° C. by the addition of IPTG to a final concentration of 0.8 mM. After induction, the cells were harvested and stored frozen at −70° C. until purification.

All the protein purification procedures were performed at 4° C. Typically, 10 g of cell paste was resuspended in 50 ml of buffer A [50 mM HEPES (pH 8), 300 mM NaCl, 10% glycerol, and 2.5 mM β-mercaptoethanol] containing 0.2 mM phenylmethylsulfonyl fluoride (PMSF), and lysed using a microfluidizer. The lysate was clarified by centrifugation at 100,000×g for 35 min. We then added 5 mM imidazole (pH 8) to the supernatant and the resulting solution was incubated for 2 hours with 2 ml of Ni-NTA-agarose (Qiagen, Chatsworth, Calif.).

The resin was packed into a column and washed with 10 bed volumes of buffer A containing 5 mM and 15 mM imidazole, and eluted with buffer A containing 100 mM imidazole. The eluant was desalted to buffer B [50 mM HEPES (pH 8), 10% glycerol, and 2.5 mM mercaptoethanol] containing 50 mM NaCl on a PD-10 column (Pharmacia). The desalted solution was loaded onto a Heparin-Sepharose column (Pharmacia). The flow-through was then applied onto a Q-Sepharose column (Pharmacia) and washed with 10 bed volumes of buffer B containing 50 mM NaCl. The column was then eluted with a NaCl gradient from 50 mM to 2M in buffer B.

The peak fraction containing the HCV NS3 helicase domain protein was shown by gel-filtration chromatography to be monomeric. The purified protein was judged to be greater than 90% pure by sodium dodecyl sulfate (SDS) polyacrylamide gel electrophoresis (PAGE) and Coomassie R-250 staining.

For crystallization studies, the protein was concentrated to 10 mg/ml by ultrafiltration and slowly diluted with 5 volumes of 15 mM MES (pH 6.5), 2.5 mM β-mercaptoethanol and again concentrated to 10 mg/ml. The dilution step was then repeated with 2 volumes of the MES buffer and concentrated to 13 mg/ml. We then added oligonucleotide ($dU_8$; Oligo Therapeutics, Inc., Wilsonville, Oreg.) to yield a 1:1 molar ration of protein to nucleic acid.

To produce recombinant full-length NS3 protein which was subsequently used for mutagenesis studies in the NTP binding pocket, we followed similar procedures as above. The full length NS3 coding sequence was also subcloned from the HCV H strain. It was placed in a pET expression vector to create the plasmid pET-BS(+)/HCV/FLNS3-His (SEQ ID NO:3). As with the helicase constructs previously described, the full-length NS3 coding sequence was preceded by a methionine start codon and had codons encoding Gly-Ser-Gly-Ser-His6 in frame at the C-terminus of the NS3 coding region. That plasmid was used as a template for single-stranded DNA-based site-directed mutagenesis as described above.

In this manner, we made NS3 containing the following single amino acid mutations as compared to the consensus HCV genotype 1 NS3 helicase sequence: Gln460→Ala, Arg461→Ala, Arg462→Ala, Arg464→Ala and Arg467→Ala.

Both the wild-type full-length NS3 and the single amino acid mutants were purified as described above.

EXAMPLE 2

Crystallization and Data Collection

Crystals of the NS3 helicase:$dU_8$ complex were grown by hanging-drop vapor diffusion over wells containing 0.1 M Tris pH 8.0, 0.2 M $Li_2SO_4$, 18% Polyethylene glycol 6000, and 8 mM β-mercaptoethanol. Drops were macroseeded within 12 hours after being set up. Crystals grew over the course of 2-3 weeks to dimensions of 0.4×0.4×0.1 $mm^3$. The crystals belong to space group $P2_12_12$ with unit cell dimensions a=73.1 Å b=117.5 Å, c=63.4 Å, and contain one helicase:$dU_8$ complex per asymmetric unit.

Heavy atom soaks were carried out by transferring crystals to a solution containing 0.1 M Tris pH 8.0, 0.2 M $Li_2SO_4$, 17% Polyethylene glycol 6000, 8 mM β-mercaptoethanol, in addition to the heavy atom in question. Heavy atom soaks with $K_2WO_4$ were performed in the absence of $Li_2SO_4$.

Crystals were transferred to a solution containing 0.08 M Tris pH 8.0, 0.2 M $Li_2SO_4$, 16% Polyethylene glycol 6000, 8 mM β-mercaptoethanol, and 15% glycerol and immediately frozen in a dry nitrogen gas stream at 100 K (Molecular Structure Corp., Houston, Tex.) for data collection.

Data was acquired by oscillation photography on a Rigaku R-AXIS IIC phosphor imaging area detector mounted on a Rigaku RU200 rotating anode generator (MSC), operating at 50 kV and 100 mA. Measured intensities were integrated, scaled, and merged using the HKL software package [Z. Otwinowski et al., *Meth. Enzymol.*, 276, pp. 307-326 (1997)].

EXAMPLE 3

Phasing, Model Building and Refinement

Heavy atom positions were located from difference Patterson and anomalous difference Patterson maps and confirmed with difference Fourier syntheses. Heavy atom parameters were refined and phases computed to 2.3 Å using the program PHASES [W. Furey et al., *Meth. Enzymol.*, 277, pp. 590-620, (1997) need full cite]. MIR phases were improved by cycles of solvent flattening [B. C. Wang, *Methods Enzymol.*, 115, pp. 90-112 (1985)] combined with histogram matching [K. Y. J. Zhang et al., *Acta Crystallogr.*, A46, pp. 377-381 (1990)] using the CCP4 crystallographic package [CCP4; C. C. Project, *Acta Crystallogr.*, D50, pp. 760-763 (1994)].

Model building was carried out using QUANTA96 (Molecular Simulations), and all refinement done in XPLOR [A. T. Brunger, "X-PLOR: A System for X-Ray Crystallography and NMR," Yale University Press, New Haven, Conn. (1993)], using the free R-value [A. T. Brunger, *Nature*, 355, pp. 472-475 (1992)] to monitor the course of refinement. The current model, refined using data from 6.0-2.2 Å, consists of NS3 helicase residues 190-414 and 418-626, residues 3-8 of $dU_8$, 1 bound sulfate ion, and 159 well-ordered water molecules.

EXAMPLE 4

Structural Features of the NS3 Helicase-$dU_8$ Complex

The structure of the resolved portion of HCV NS3 helicase (NS3 residues 189-626 of SEQ ID NO:1, corresponding to HCV polyprotein residues 1215-1652) complexed with a deoxyuridine octamer ($dU_8$) was determined by multiple isomorphous replacement combined with anomalous scattering. The protein consists of three domains separated by a series of clefts (FIG. 5).

Domains 1 and 3 share a more extensive interface than either share with domain 2. This interface is largely accounted for by packing of helices α5 and α6 from domain 3 on helix α4 from domain 1. As a result, the clefts between domains 1 and 2 and domains 2 and 3 are the largest. A published crystal structure of HCV NS3 helicase domain demonstrated that domain 2 could undergo rigid body movements relative to domains 1 and 3 based on a comparison of two crystallographically independent molecules (N. Yao et al., *Nat. Struct. Biol.*, 4, pp. 463-467 (1997)]. Preliminary structural studies on HCV helicase in a different crystal form also show a rotation of domain 2 relative to the first and third, confirming that this domain is flexibly linked to the other two.

Domains 1 and 2 of the HCV helicase, which contain all of the conserved helicase sequence motifs, have similar topologies (FIG. 6) and are also similar to domains 1A and 2A of the four domain PcrA and Rep DNA helicases [H. S. Subramanya et al., *Nature*, 384, pp. 379-383 (1996); S. Korolev et al., *Cell*, 90, pp. 635-647 (1997)]. The structurally homologous domains of PcrA, Rep, and HCV helicases each contain a parallel six-stranded β-sheet flanked by α-helices. In addition, domain 1 of HCV helicase contains a seventh β-strand running antiparallel to the rest of the sheet.

Superposition of domains 1 and 2 yields an rms deviation of 2.0 Å for 76 C-alpha atoms that form the core of each domain. Domain 3 is predominantly α-helical and is associated with domain 2 by a pair of anti-parallel β-strands (FIG. 5). An interesting component of domain 3 is a 40 amino acid region preceding the C-terminal α-helix that lacks secondary structure elements. This may represent a flexible region of the protein that allows the C-terminus of NS3 to reach the active site of its own serine protease domain to facilitate cleavage at the NS3/NS4A junction during HCV polyprotein processing. This cleavage is believed to occur in cis [R. Bartenschlager et al., *J. Virol.*, 68, pp. 5045-5055 (1994)].

Figure 7A:
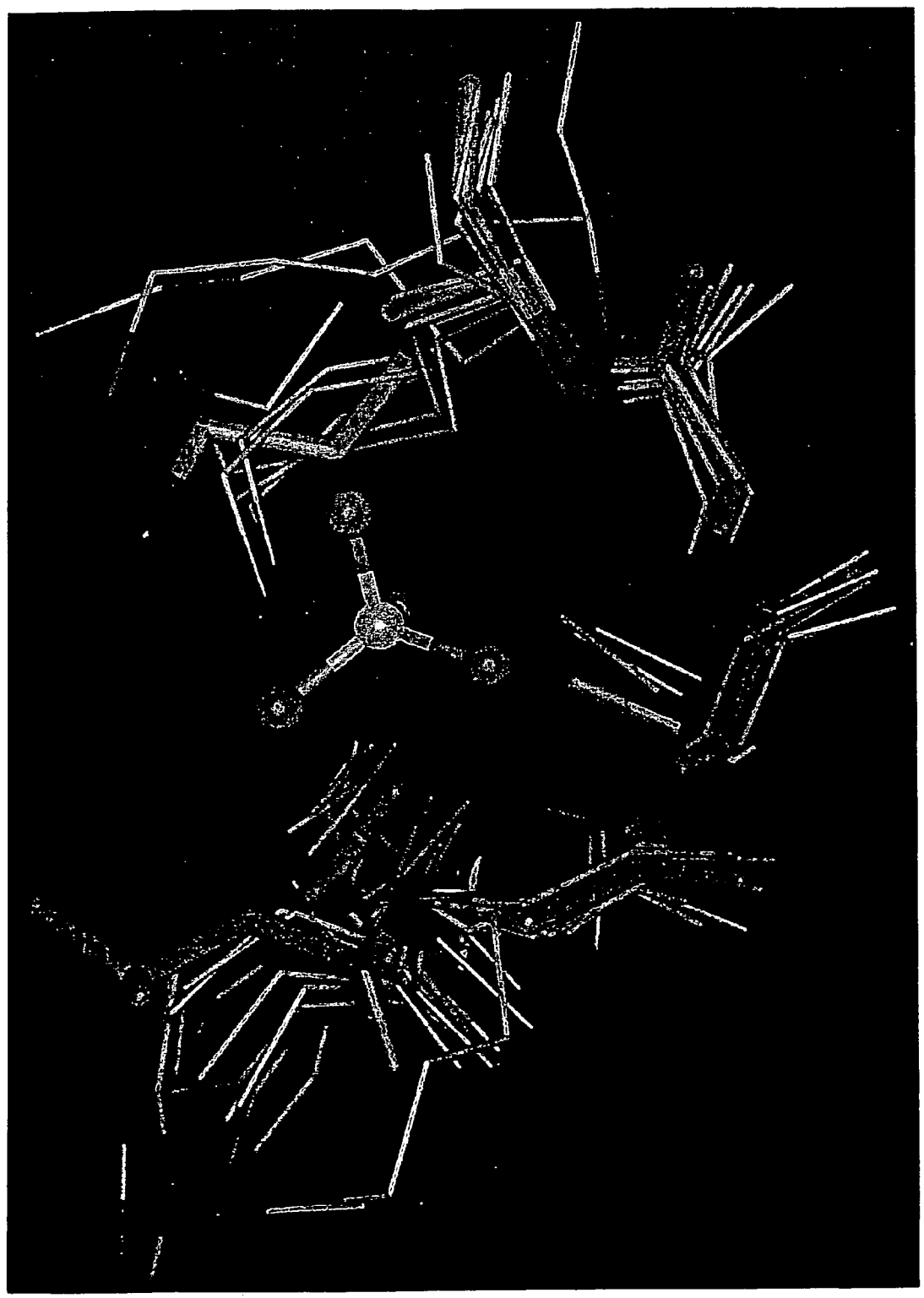
Figure 7B:
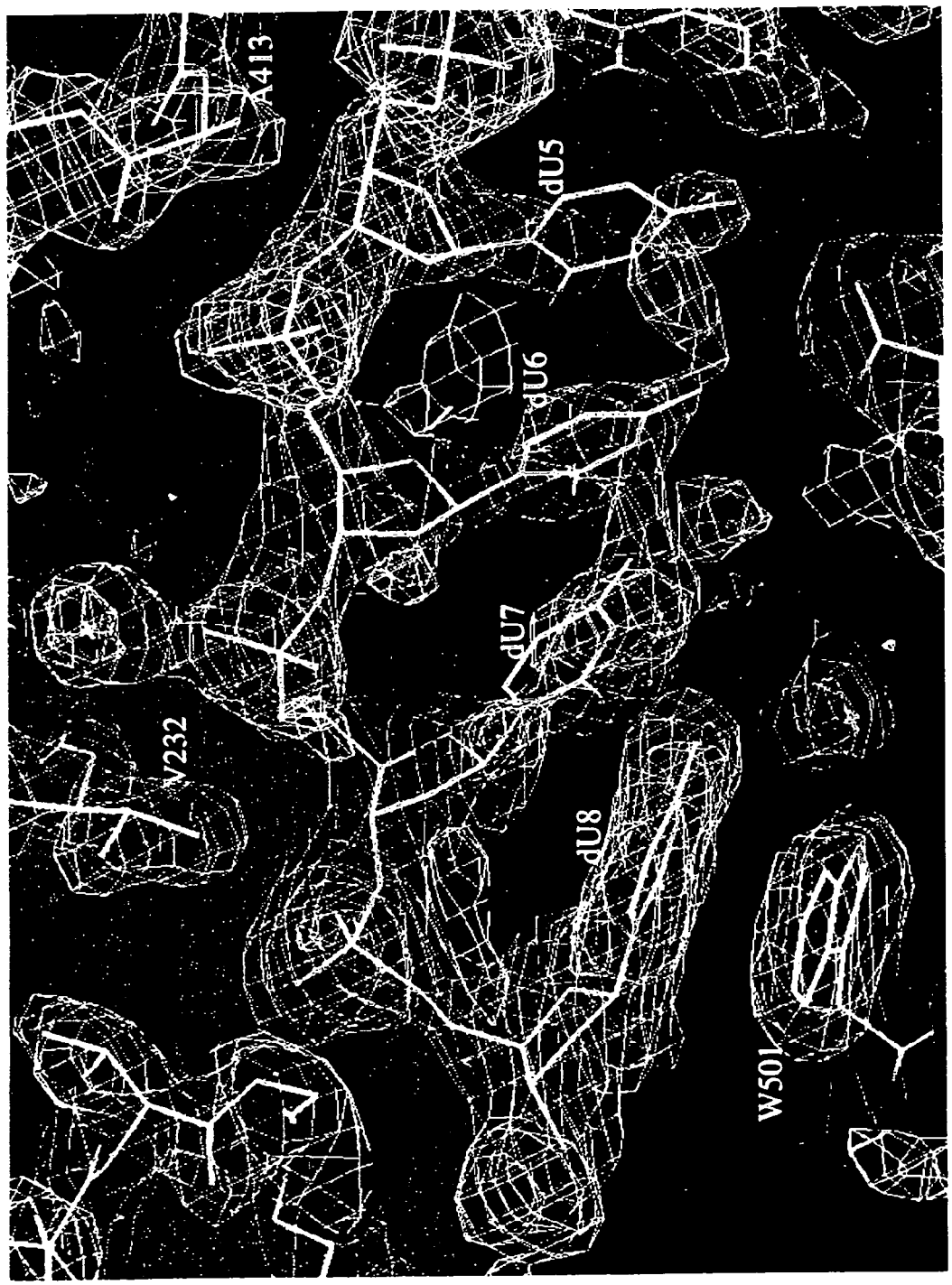

The N-terminal region of domain 1 contains a phosphate binding loop that is highly conserved among all helicases and commonly referred to as the Walker A box or motif I [J. E. Walker et al., *EMBO J.*, 1, pp. 945-951 (1982)]. In the structure presented here, this loop contains a bound sulfate ion (FIG. 7A). This phosphate binding loop is structurally similar to those found in a number of other ATPases [M. Saraste et al., *Trends Biochem. Sci.*, 15, 430-434 (1990)]. The sulfate ion is stabilized by hydrogen bonds from the amide nitrogens of Gly-207 and Gly-209, and the side chains of Ser-208, Lys-210, and Ser-211. Lys-210 makes an additional water-mediated contact to the conserved Asp-290 of the DECH motif (motif II or Walker motif B).

The side chains of Asp-290 and Glu-291, the most conserved residues in the DECH motif, point toward an open area beneath the phosphate binding loop that presumably is occupied by $Mg^{2+}$ and the γ-phosphate of the bound $Mg^{2+}$-NTP substrate. Cys-292 is buried in the protein interior while the His-293 side chain points into the cleft between domains 1 and 2. The position of the sulfate in this structure appears to be very similar to that of the β-phosphate of ADP in the PcrA helicase:ADP complex [H. S. Subramanya et al., *Nature*, (1996), supra]. It is therefore likely that this sulfate ion occupies the position of the β-phosphate when NTP or NDP is bound to the HCV helicase.

Highly conserved residues Gln-460, Arg-464, and Arg-467 from domain 2 are solvent exposed in the interdomain cleft, while Arg-461 and Arg-462 are buried in domain 2 and stabilized by internal salt bridges and hydrogen bonds. The position of Arg-461 contrasts that described in the structure of the apo HCV NS3 helicase, which reported this side chain as being solvent exposed and interacting with the phosphate backbone of single stranded nucleic acid modeled into this cleft [N. Yao et al., *Nat. Struct. Biol.*, (1997), supra].

Protein-Single Stranded DNA Interactions

Studies of HCV NS3 helicase single stranded nucleic acid binding have demonstrated that poly(dU) binds to the helicase with higher affinity than poly(rU) of the same length [F. Preugschat et al, *J. Biol. Chem.*, 271 (1996), supra]. Extrapolation of this data suggested that a deoxyoligonucleotide 8mer might be long enough to bind to the helicase with high affinity and not interfere with protein-protein contacts during crystallization. Therefore an oligo $dU_8$ was used for complex crystallization. In the structure presented here the first two residues of the oligonucleotide are disordered and have not been included in the model. The sugar-phosphate backbone of the third nucleotide is well represented in electron density maps (FIG. 7B) while density for the base is extremely weak. Electron density for residues 4-8 is very well defined for the sugar-phosphate backbone and slightly weaker for the bases.

Preliminary studies with $dU_{10}$ and $dU_{12}$ oligonucleotides show essentially the same electron density for the DNA.

The bound single stranded DNA ("ssDNA") lies in a channel approximately 16 angstroms in diameter that separates domain 3 from domains 1 and 2 (FIG. 10). The 5' end of the oligonucleotide resides at the interface of domains 2 and 3 and its 3' end at the interface of domains 1 and 3. This orientation of the DNA is roughly perpendicular to that of the ssRNA in a model derived from the apo HCV helicase structure, in which the ssRNA was placed in the cleft between domains 1 and 2 [N. Yao et al., *Nat. Struct. Biol.*, (1997), supra]. It is, however, consistent with the oligonucleotide binding site in the Rep helicase:DNA structure [S. Korolev et al., *Cell*, (1997), supra].

Interactions between the ssDNA and enzyme are mostly confined to the DNA backbone, as would be expected for a nonspecific protein-nucleic acid complex, and are concentrated at the two ends of the oligonucleotide. Protein contacts emanate mostly from loops between secondary structural elements in domains 1 and 2 (FIGS. 6A,B). Interestingly, these contacts arise from symmetrically equivalent residues in these two domains, so that protein contacts to the dU4 and dU5 backbone phosphates are nearly identical to those to the dU7 and dU8 phosphates.

At the 3' end of the DNA the dU8 phosphate is stabilized by a hydrogen bond with Thr-269 Oγ, which in turn accepts a hydrogen bond from the main chain NH of Lys-272, and by a hydrogen bond to the main chain NH of Gly-255. Equivalent contacts to the dU5 phosphate are made by the Arg-393 main chain NH and Thr-411 Oγ, which accepts a hydrogen bond from the Ala-413 NH. The dU7 phosphate accepts a hydrogen bond from the Val-232 NH and interacts with the Ala-233 NH and Ser-231 Oγ via a bridging water molecule. The direct and water mediated main chain interactions are duplicated by Lys-371 and Lys-372 from domain 2 to the dU4 phosphate. Ser-370, the equivalent residue in domain 2 to Ser-231, makes a water mediated contact to the dU3 phosphate rather than dU4. Superposition of domains 1 and 2 of HCV helicase reveals that the residues involved in phosphate contacts are structurally equivalent (FIG. 6). This was an unanticipated finding based on the poor sequence homology between these two domains. Additionally, the four residues interacting with the phosphate backbone, Ser-231, Thr-269, Ser-370, and Thr-411, are absolutely conserved in all HCV NS3 sequences known to date. These findings suggest that these two domains may have arisen from a gene duplication event.

Residues dU4-dU8 are capped by interactions at each end with hydrophobic side chains. Trp-501 stacks with the base of dU8 while Val-432 interacts with the dU4 base (FIG. 10). These two side chains act as a pair of bookends, defining a central binding cavity occupied by five nucleotides. Both Val-432 and Trp-501 are highly conserved among HCV NS3 sequences but neither have been implicated in nucleic acid binding nor duplex unwinding. The Val-432:dU4 base interaction induces significant rotation about the phosphate backbone between dU3 and dU4 such that the bases are completely unstacked (FIG. 10). Stacking of Trp-501 with the dU8 base should similarly necessitate a large rotation about the phosphate of the following nucleotide. The resulting conformation of the DNA could be stabilized by phosphate interactions with Arg-253 and Lys-272 from domain 1 and Lys-372 and Lys-373 from domain 2, which lie outside the central binding cavity.

Domain 2 contains a pair of extended anti-parallel strands encompassing residues 430-452, which are involved in binding the 5' end of the oligonucleotide (FIG. 5). Two other single-strand polynucleotide binding proteins, SSB and tRNA synthetase, contain anti-parallel strands extending from their protein core that are thought to make up the nucleic acid binding site [S. Raghunathan et al., *Proc. Natl. Acad. Sci. USA*, 94, pp. 6652-6657 (1997); M. Ruff et al., *Science*, 252, pp. 1682-1689 (1991)]. This region is termed the $L_{45}$ loop in this class of nucleic acid binding proteins. In the HCV helicase structure the oligonucleotide binds in a channel spanning two protein domains in a manner roughly similar to that seen for replication protein A (RPA) [A. Bochkarev et al., *Nature*, 385, pp. 176-181 (1997)]. In both structures, the oligonucleotide is most tightly bound at the 3' and 5' ends with few contacts with the central nucleotides. RPA also contains an $L_{45}$ loop, which binds to the 5' end of the oligonucleotide.

The five residues occupying the central binding cavity of HCV helicase adopt a conformation reminiscent of the central base pairs of DNA in the TBP-TATA box complex structures [Y. Kim et al., *Nature*, 365, pp. 512-520 (1993); J. L. Kim et al., *Nature*, 365, pp. 520-527 (1993)]. In both instances the DNA is underwound considerably and the backbone smoothly bent, compressing the edges of the bases. Comparison of the DNA structure here with the central pyrimidine stretch of the TATA box DNA reveals that this DNA is more underwound than that seen in the TBP-TATA box complex.

Our structure of the helicase:$dU_8$ complex does not offer a ready explanation as to why the enzyme binds to poly(dU) with higher affinity than to other homopolymer DNAs [F. Preugschat et al, *J. Biol. Chem.*, 271 (1996), supra]. Sequence specific interactions with the DNA bases are not observed within the central binding cavity of the helicase. Differences in DNA binding affinity between different sequences in this case may be a result of differences in energetics of DNA distortion and base stacking rather than base-specific hydrogen bonding patterns.

Location of Conserved Sequence Motifs

Figure 9B:

There is very high sequence conservation among various HCV strains in the NS3 RNA helicase domain with >80% sequence identity over the entire 456 amino acid polypeptide. The most highly conserved segments of these domains correspond to the canonical helicase sequence motifs (FIGS. 8, 9A) [A. Gorbalenya et al., *Curr. Opin. Struct. Biol.*, 3, pp. 419-429 (1993)]. In the three-dimensional structure residues from these motifs form the interface between the first two domains (FIG. 9B). Visual inspection of the structures of the PcrA DNA helicase from *Bacillus stearothermophilus* [H. S. Subramanya et al., *Nature*, (1996), supra] and *E. coli* Rep DNA helicase [S. Korolev et al., *Cell* (1997), supra; coordinates not available] suggests overall structural similarity between domains 1A and 2A of these DNA helicases and domains 1 and 2 of the HCV helicase. The locations of the conserved DNA helicase sequence motifs overlap with those of the HCV helicase allowing an unambiguous alignment of these motifs. Mutagenesis of individual residues within these motifs in HCV helicase or in other RNA helicases have demonstrated that they are essential for enzyme activity. The individual phenotypes of these mutants can now be more fully explained using the enzyme structure.

Domain 1 of the HCV helicase has a fold similar to that found in a number of adenosine triphosphate transphosphorylases, such as adenylate and thymidine kinases. In particular, the phosphate binding loop formed by motif I (GSGKT) is virtually identical to the corresponding loop in the kinases. In these kinases this loop is involved in binding the β phosphate of ATP. HCV helicase has a sulfate bound in this exact location (FIG. 7A). Mutation of residues corresponding to HCV helicase Lys-210 in other helicases invariably leads to inactivation [J. W. George et al., *J. Mol. Biol.*, 235, 424-435 (1994); T. W. Seeley et al., *J. Biol. Chem.*, 265, pp. 7158-7165 (1990)].

Motif II (DExH) is proximal to the GSGKT phosphate binding loop and is expected to be involved in binding the $Mg^{2+}$-ATP substrate. In adenylate and thymidine kinases, a conserved aspartate binds $Mg^{2+}$, which helps orient the ATP for nucleophilic attack [M. E. Black et al., *J. Biol. Chem.*, 267, pp. 6801-6806 (1992); H. G. Yan et al., *Biochemistry*, 30, pp. 5539-5546 (1991)]. Mutation of the equivalent aspartate residue in these kinases or in other helicases inactivates ATP hydrolysis [M. E. Black et al., *J. Biol. Chem.*, (1992), supra; C. H. Gross et al., *J. Virol.*, 69, pp. 4727-4736 (1995); R. M. Brosh Jr., et al., *J. Bacteriol.*, 177, pp. 5612-562 (1995); A. Pause et al., *EMBO J.*, 11, pp. 2643-2654 (1992)]. His-293 is located at the bottom of the interdomain cleft and approximately 4 Å away from Val-456 and Gln-460. This histidine appears to be essential for coupling the ATPase activity to polynucleotide binding; mutations of this histidine in HCV NS3 and vaccinia NPH-II helicases result in a functional ATPase with no helicase activity [C. H. Gross et al., *J. Virol.*, (1995), supra; G. M. Heilek et al. *J. Virol.*, 71, 6264-6266 (1997)]. Unfortunately, the structure presented here does not provide an obvious explanation as to how this residue couples the NTPase and unwinding activities.

Studies in several helicases have looked at the effects of mutations in motif VI (QRxGRxGR), yet a role for this motif has not been clearly defined. In the HCV helicase residues in this motif are located in the 1:2 interdomain cleft. Gln-460 lies at the bottom of the cleft opposite from His-293. Mutation of the corresponding glutamine in vaccinia virus helicase and in eIF-4A leads to significant decreases in ATPase activity [A. Pause et al., *EMBO J.*, (1992), supra; C. H. Gross et al., *J. Virol.*, 70, pp. 1706-1713 (1996)]. There are three conserved arginines in motif VI that were proposed by N. Yao et al., *Nat. Struct. Biol.* (1997), supra, to be involved in binding single-stranded RNA in the cleft between domains 1 and 2. Our structure of the helicase:$dU_8$ complex demonstrates that this interpretation is unlikely to be correct.

Here Arg-461 points away from the cleft and is hydrogen-bonded to Asp-412 and Asp-427. Mutation of this residue in a vaccinia virus helicase leads to decreases in RNA binding [C. H. Gross et al., *J. Virol.*, (1996), supra], possibly as a consequence of alterations in the conformation of Asp-412 which lines the polynucleotide binding channel. Arginines 464 and 467 extend into the interdomain cleft, directly across from the presumed locations of the γ and α phosphates of ATP. These residues appear to be poised to contact the ATP phosphates upon closure of this interdomain cleft. This would be similar to the function of conserved basic residues in the second domain of adenylate kinase.

Consistent with the possibility that Arg-464 and Arg-467 are directly involved in ATP binding, mutations of the corresponding residues to Ala or Gln in vaccinia NPH-II or eIF-4A reduce the ATPase activity to <20% of wild type levels [C. H. Gross et al., *J. Virol.*, (1996), supra; A. Pause et al., *Mol. Cell. Biol.*, 13, pp. 6789-6798 (1993)]. Arg-467 appears to be conserved among all three helicase superfamilies (FIG. 9A) [A. Gorbalenya et al., *Curr. Opin. Struct. Biol.* (1993), supra]

Motif III connects domains 1 and 2, and appears to be a flexible linker [N. Yao et al., *Nat. Struct. Biol.* (1997), supra]. Motif Ia forms part of the β sheet core of domain 1, but also extends to the oligonucleotide. Residues in motif V both contact the oligonucleotide and line the interface between the first two domains. In particular, Thr-411 makes a hydrogen bond to the phosphate of dU3 of the oligonucleotide.

The current structure lacks any region corresponding to motif IV in Rep and PcrA helicases [H. S. Subramanya et al., *Nature* (1996), supra; S. Korolev et al., *Cell*, (1997), supra], members of the superfamily I class of helicases. Previous sequence alignments that found similarities within motif IV between superfamily I and II helicases were done with rather weak criteria and may not have been significant. In the DNA helicases, motif IV is responsible for binding the adenine ring of ATP [H. S. Subramanya et al., *Nature* (1996), supra; S. Korolev et al., *Cell*, (1997), supra]. Mutation of a conserved arginine in this motif in UvrD increases the ATP Km by 37-fold [M. C. Hall et al., *J. Biol. Chem.*, 272, pp. 18614-18620 (1997)].

In HCV helicase either another protein segment which is not in the current structure substitutes for motif IV or the adenosine ring binds elsewhere. Residues from the putative motif IV in HCV helicase include Ser-370 and Lys-371, which contact the DNA via a water-mediated hydrogen bond and a backbone interaction, respectively. Therefore sequences corresponding to motif IV in superfamily I and superfamily II helicases occupy different regions and appear to have different functions. We suggest that a new motif, designated IVa, be used to describe residues corresponding to the putative HCV helicase motif IV. In *E. coli* UvrD, motif IVa may correspond to the sequence RSNAQSRVL (residues 355-363).

Proposed Domain Closure and Translocation

Conserved, basic residues from motif VI are positioned across the interdomain cleft from the expected location of the ATP γ phosphate in HCV helicase. A very similar situation is observed in the structures of the adenylate kinases, where basic residues lie across a cleft from the ATP binding site. Binding of ATP (or analogs) to these kinases leads to a conformational change in the enzyme, resulting in the burial of previously solvent-exposed phosphates [T. Bilderback et al., *Biochemistry*, 35, pp. 6100-6106 (1996)]. Mutation of these conserved basic residues in adenylate kinase results in an open structure with poor catalytic activity [G. E. Schulz, *Faraday Discuss.*, 93, pp. 85-93 (1992)].

We propose that an analogous closure occurs between domains 1 and 2 of HCV helicase upon ATP binding. This closure could be driven by interaction of basic residues in motif VI with the ATP phosphates. Sequence and structural conservation of these basic residues in motif VI among superfamily I and II helicases suggests that domain closure upon ATP binding is a general feature of these enzymes.

Gln-460 and His-293, from motifs VI and II respectively, lie on opposite sides of the interdomain cleft and possibly serve as gatekeepers, altering the equilibrium between the open and closed forms based on the binding of polynucleotide. Potential interaction of residues in these positions was predicted by the observation that helicases with the DExH motif II sequence usually contain a glutamine in motif VI, whereas those with a DEAD sequence contain a histidine [A. Gorbalenya et al., *Curr. Opin. Struct. Biol.* (1993), supra].

There is structural evidence that the linkage of the second domain in HCV helicase to the rest of the protein is flexible. In the HCV helicase structure reported by N. Yao et al., *Nat. Struct. Biol.* (1997), supra, the differences between the two molecules in the asymmetric unit can be attributed to a rotation of domain 2 by a few degrees. The relatively minor movement of domain 2 observed in their structures probably reflects changes in the local environment in the crystals. We propose a much more substantial conformational change would occur when the enzyme binds ATP or suitable analog. Our crystallographic results indicate that there are significant movements of this domain in different crystal forms. A conformational change could explain the observed two-stage kinetics of ATP binding to Rep where rapid initial binding is followed by a much slower step, leading to tighter binding [K. J. Moore et al., *Biochemistry*, 33, pp. 14550-14564 (1994)]. Evidence for conformational changes have been observed for Rep and helicase II based on alterations in protease sensitivity upon nucleotide binding [K. Chao et al., *J. Biol. Chem.*, 265, pp. 1067-1076 (1990)]. Binding of ATP to PcrA helicase has also been proposed to lead to a conformational change of the enzyme [H. S. Subramanya et al., *Nature* (1996), supra].

Large conformational changes in a DNA metabolizing enzyme are not unique, as they have been seen in the structures of mRNA capping enzyme in the presence of GTP [K. Hakansson et al., *Cell*, 89, pp. 545-553 (1997)]. In these structures the guanosine nucleotide is bound to the N-terminal domain with the phosphates located near the interface with the C-terminal domain. In the "open" conformation these domains are separated by a 10-13 Å cleft. Several residues which are highly conserved among mRNA capping enzymes are located in the C-terminal domain, including Arg-295 and Arg-298.

In the "closed" conformation, these residues are relocated by approximately 10 Å and are bound to the GTP β and γ phosphates. Closures of large interdomain clefts have also been proposed in the structurally homologous ATP-dependent DNA ligases, of which one structure has been solved in the open conformation [H. S. Subramanya et al., *Cell*, 85, pp. 607-615 (1996)].

The second domain of HCV helicase also interacts with the single-stranded polynucleotide. One could envision that movement of this domain results in concomitant movement of the nucleic acid substrate relative to the protein. Interactions between residues in domain 2 such as Val-432 and Thr-448 and the bases at the 5' end of the single stranded nucleic acid binding site would lead to translocation of the polynucleotide in the 5' to 3' direction as domain 2 closes.

Trp-501 in domain 3 stacks with a base near the 3' end of the single stranded oligonucleotide and disrupts stacking with neighboring bases. Closure of the interdomain cleft would force several bases to slip past Trp-501. Hydrolysis of ATP would then result in opening of the cleft and release of ADP. The orientation of Trp-501 favors movement of the polynucleotide in only the 5' to 3' direction such that opening of the cleft results in net movement of domain 2 in a 3' to 5' direction. By this mechanism the translocation reaction of the helicase resembles a ratchet. A general ratchet-like mechanism has been proposed for the RecB helicase based on conformational changes observed by protease mapping [R. J. Phillips et al., *Mol. Gen. Genet.*, 254, pp. 319-329 (1997)].

Such a model suggests that a single ATP hydrolysis event can result in protein translocation of several bases along a polynucleotide. Studies with the UvrD DNA helicase have demonstrated that the enzyme is capable of translocating more than one base per reaction cycle [J. A. Ali et al., *Science*, 275, pp. 377-380 (1997)], although the number of ATP hydrolysis events per observed reaction cycle was unknown in this experiment. Our model is consistent with predictions that helicases need not actively unwind the double-stranded substrate, but can function by capturing the single-stranded regions which arise due to thermal fluctuations at the fork [Y. Z. Chen et al., *J. Biomol. Struct. Dyn.*, 10, pp. 415-427 (1992)]. The translocation process proposed here would thus be considered an active process while the melting of double stranded structure at the fork would be passive.

The mechanism which we propose is substantially different from one described for the Rep helicase by Wong and Lohman [I. Wong et al., *Science*, 256, pp. 350-355 (1992)] and recently advanced in a paper describing the 3.0 and 3.2 Å structures of Rep bound to single-stranded DNA [S. Korolev et al., *Cell* (1997), supra]. As we previously noted there is overall structural similarity between domains 1 and 2 of HCV helicase and domains 1A and 2A of Rep. Important to our proposed mechanism, these two domains contain all the motifs conserved among DNA/RNA helicase sequences listed in FIG. 9A. In HCV helicase, there is no structural equivalent of Rep domain 2B which has been proposed to have a critical role in the active rolling mechanism [S. Korolev et al., *Cell* (1997), supra].

EXAMPLE 5

Assays

A. Helicase Assay

The standard 3'-tailed double-stranded RNA/DNA hybrid was prepared as described as follows. The long 98-nucleotide ("nt") RNA template was transcribed from a BsrBI-digested plasmid pSP65 (Promega, Madison, Wis.) in the presence of [α-$^{32}$P-GTP] (New England Nuclear, Boston, Mass.). The short 34-nt DNA release strand corresponds to a SP6 RNA transcript from a BamHI-digested pSP64 (Promega).

Standard helicase reactions (20 μl) were carried out as follows. HCV NS3 helicase (0.3 or 1 nM) was added to a mixture of 25 mM morpholinepropanesulfonic acid (MOPS)-NaOH (pH 6.5), 1 mM ATP, 0.5 mM MnCl$_2$, 2 mM dithiothreitol (DTT), 0.1 mg of bovine serum albumin (BSA) per ml, 4 units of RNasin (Promega), and 5 nM of 3'-tailed double-stranded RNA/DNA hybrid substrate. Mixtures were incubated for 20 min at 37° C. and stopped by the addition of 5 liters of 5× loading buffer [100 mM Tris-Cl (pH7.5), 20 mM EDTA, 50% glycerol, 0.5% SDS, 0.1% NP-40, 0.1% bromophenol blue, and 0.1% xylene cyanole). The reactions were then electrophoresed on 10% PAGE with 0.5×TBE and 0.1% SDS. Gels were dried and exposed using Fuji 1500 phosphorimager (Fuji, Stamford, Conn.). Helicase activity was determined by radioactivity of the double-stranded substrate and single-stranded template.

First, we characterized unwinding activity of the purified wild type NS3 helicase domain protein with regarding to the following parameters: protein concentration, incubation time course, incubation temperature, ATP concentration, pH, monovalent cation (Na$^+$), and divalent cation (Mn$^{2+}$ and Mg$^{2+}$) (FIG. 11).

Figure 11A:
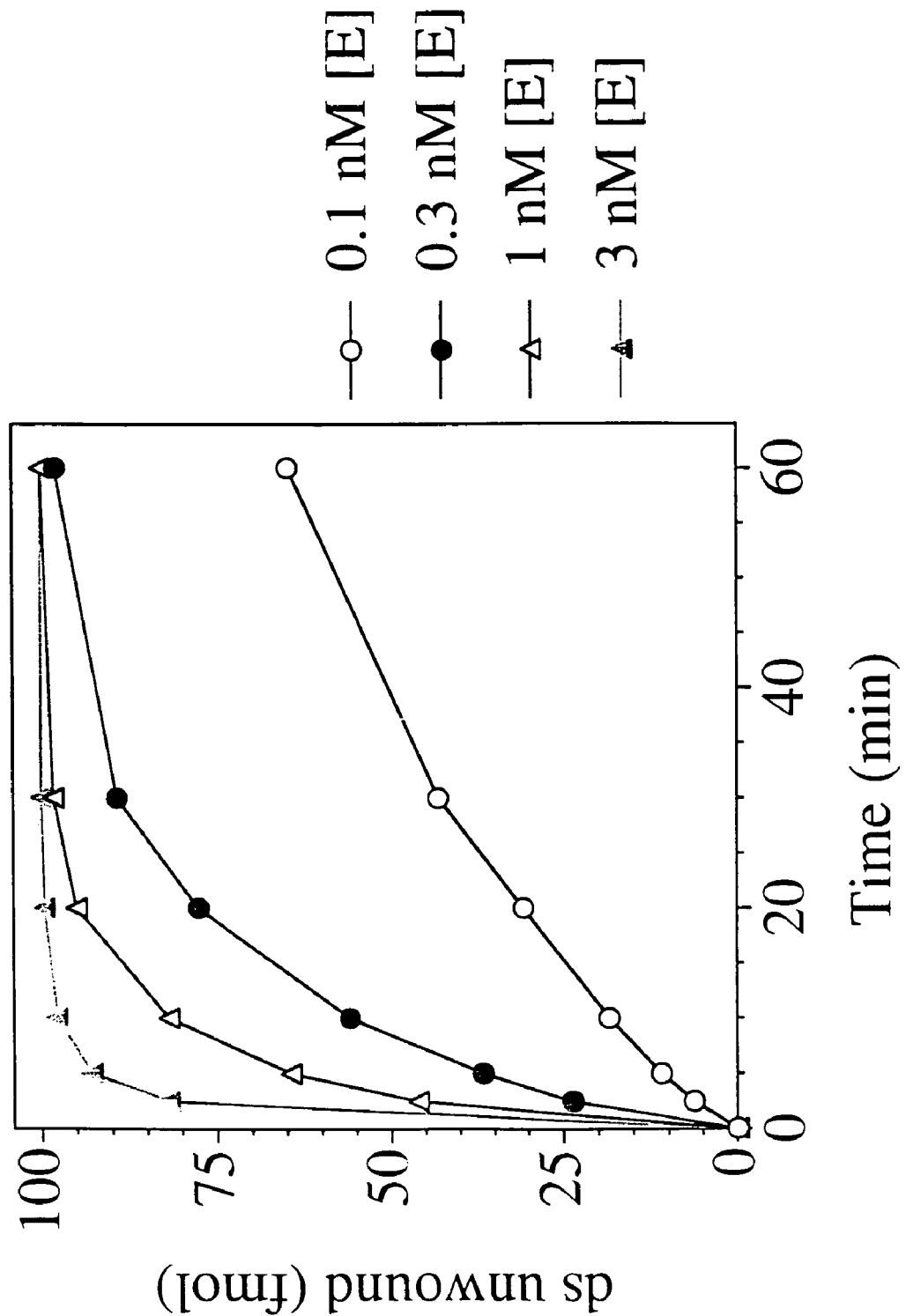
Figure 11B:
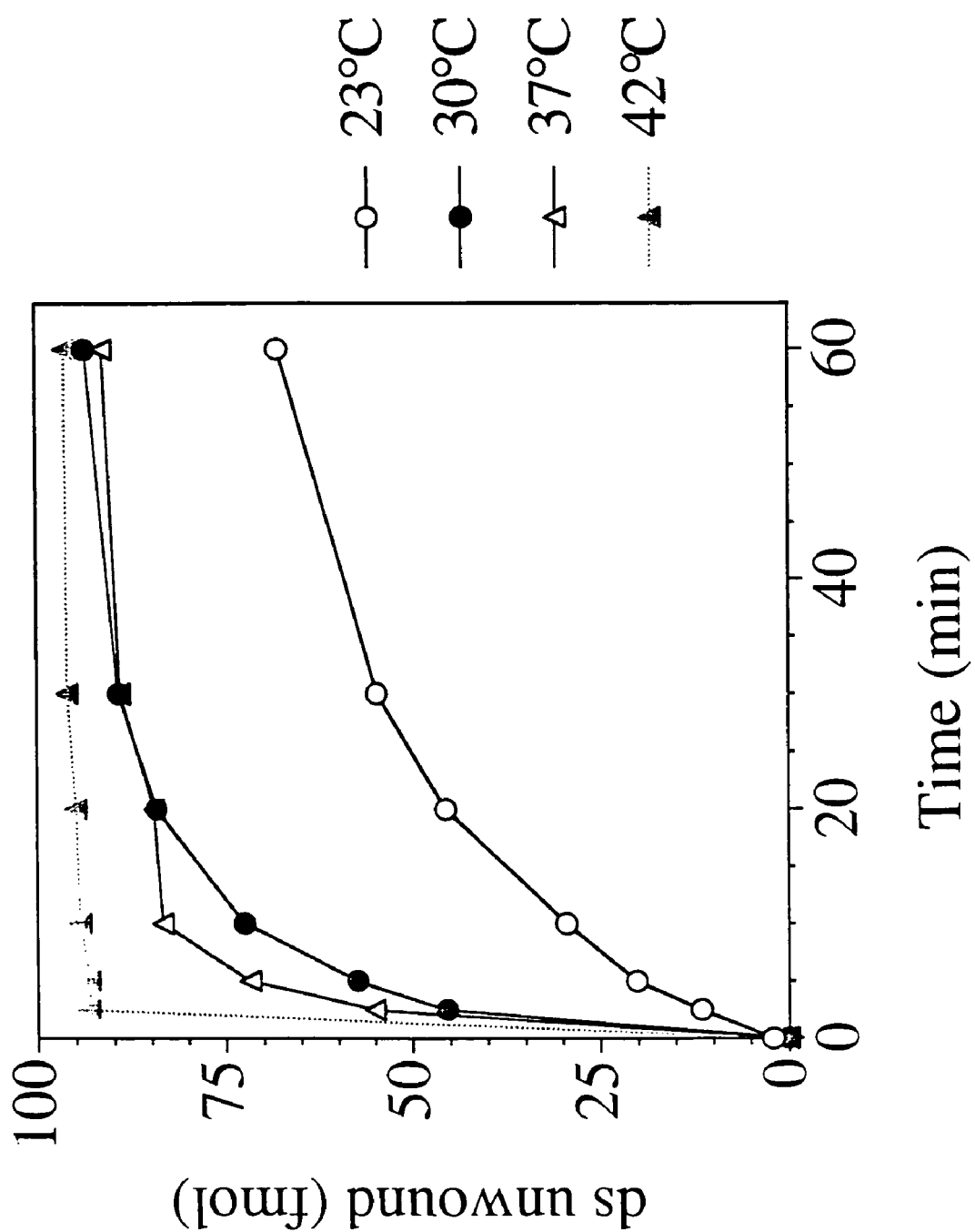

The helicase unwinding activity increased as the protein concentration or incubation time increased (FIG. 11A). At 0.1 nM of the NS3 helicase, the reaction was almost linear with regard to the incubation time up to 30 min (FIG. 11A). Several NS3 helicase mutants purified by the same chromatograph method did not show any unwinding activity (see Table 1 and Example 6, below), indicating that the unwinding activity shown here is due to the purified HCV NS3 helicase, not containment proteins from *E. coli*.

Figure 11C:
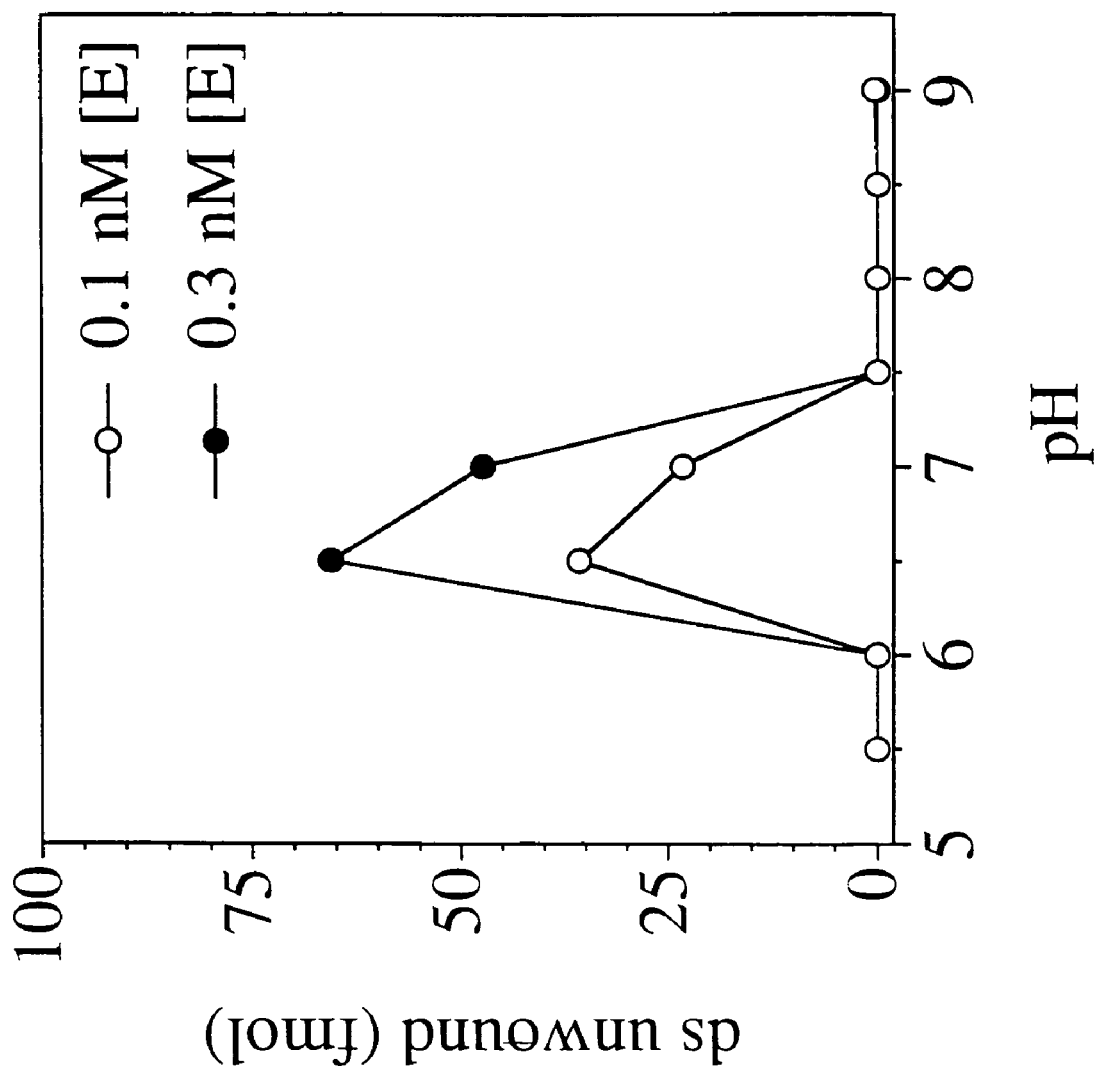

Higher incubation temperature also led to more rapid unwinding of substrate (FIG. 11B), presumably due to lower energy required for break-down of hydrogen bonds between two strands at higher temperature. The unwinding activity of this NS3 helicase domain was optimal at pH 6.5, with a very narrow pH window of being active (FIG. 11C).

Figure 11D:
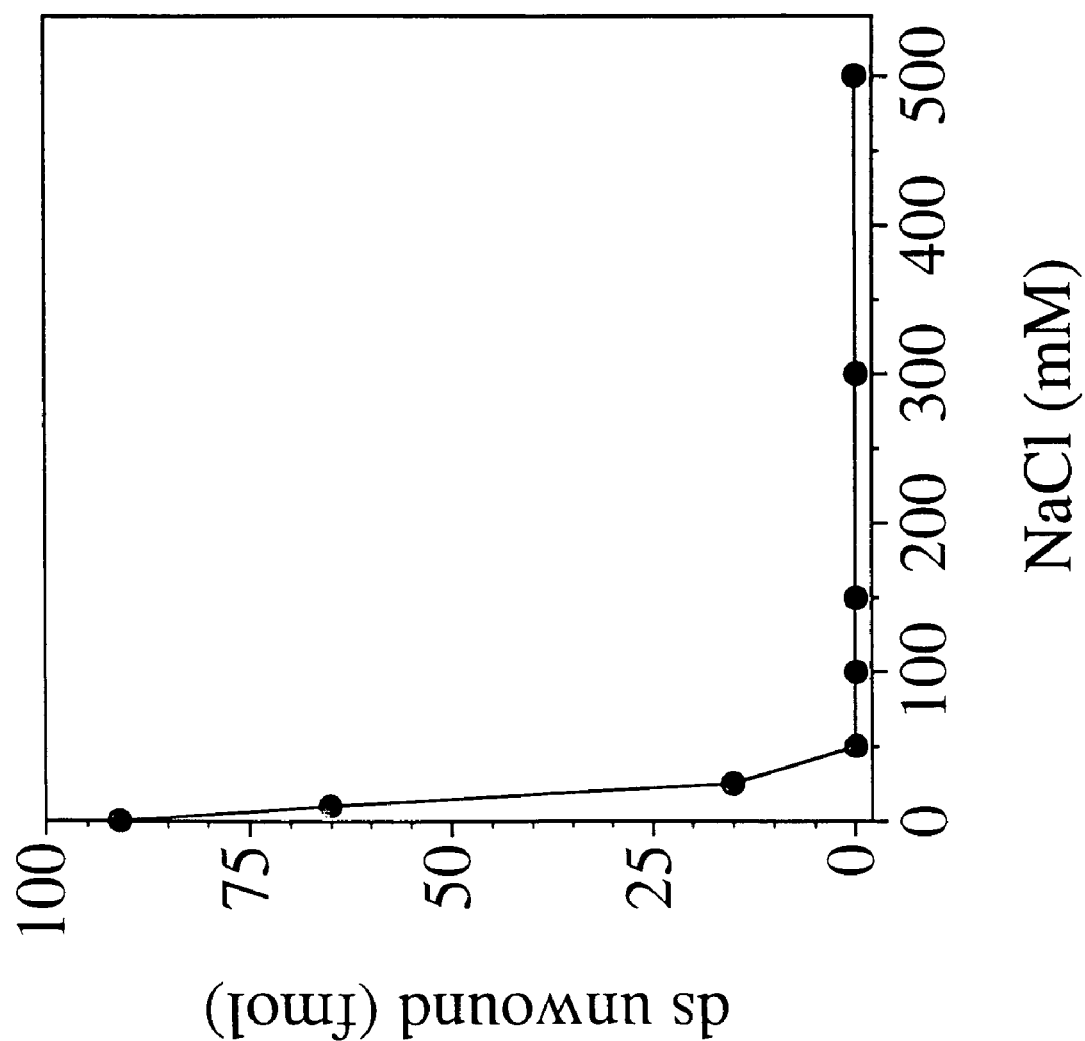

In addition, the unwinding reaction was very sensitive to the monovalent cation, such as Na$^+$ (FIG. 11D). Addition of 25 mM NaCl decreased the unwinding activity to about 15% of that in the absence of extra NaCl.

Figure 11E:
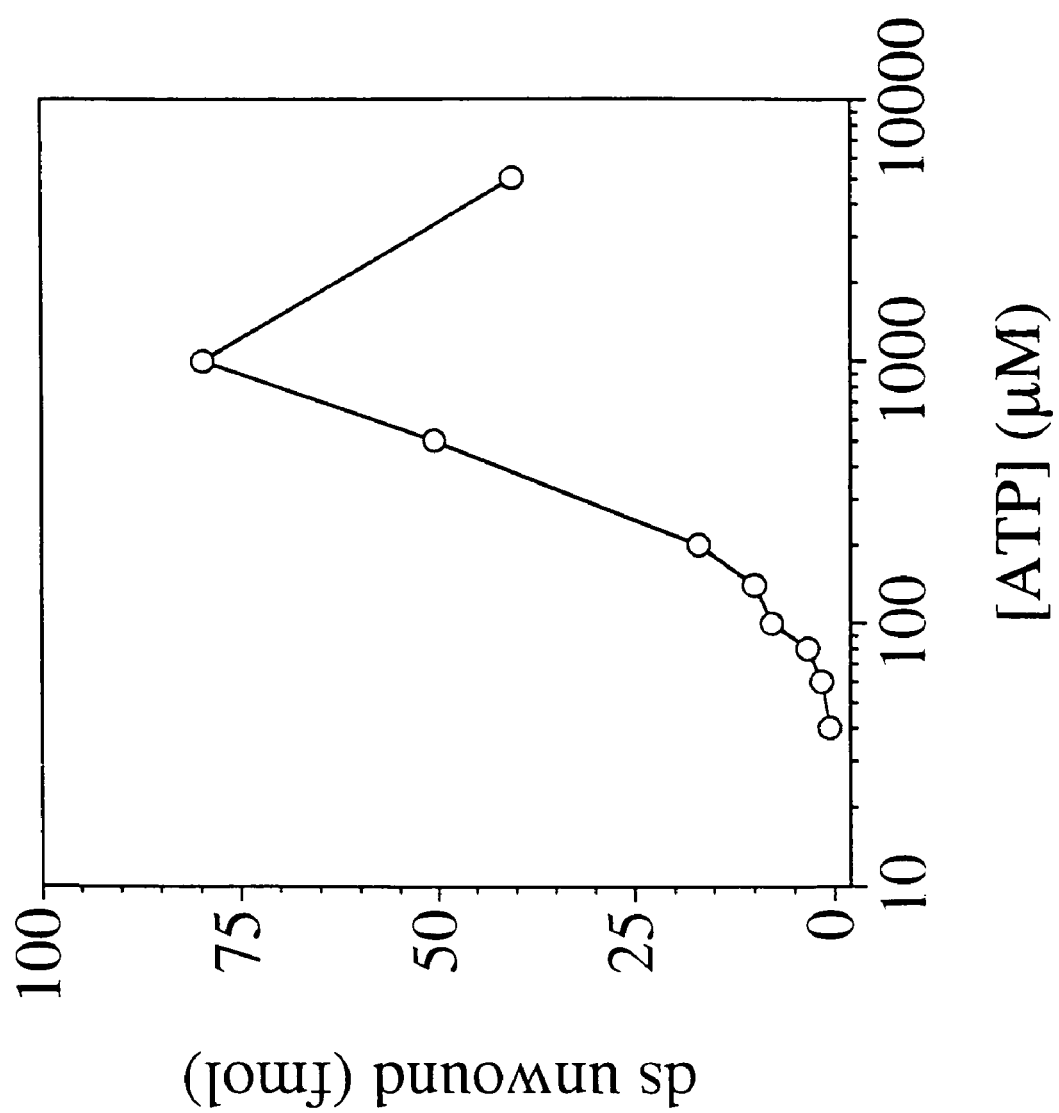

This helicase activity was absolutely dependent on the presence of ATP (FIG. 11E) or any other type of nucleotide triphosphate (NTP) (data not shown). The unwinding activity increased almost linearly as the concentration of ATP increased up to 1 mM (FIG. 11E). However, at 5 mM of ATP, the unwinding activity is lower than that at 1 mM of ATP, probably due to inhibition of extra $Na^+$ brought in with the ATP.

Figure 11F:
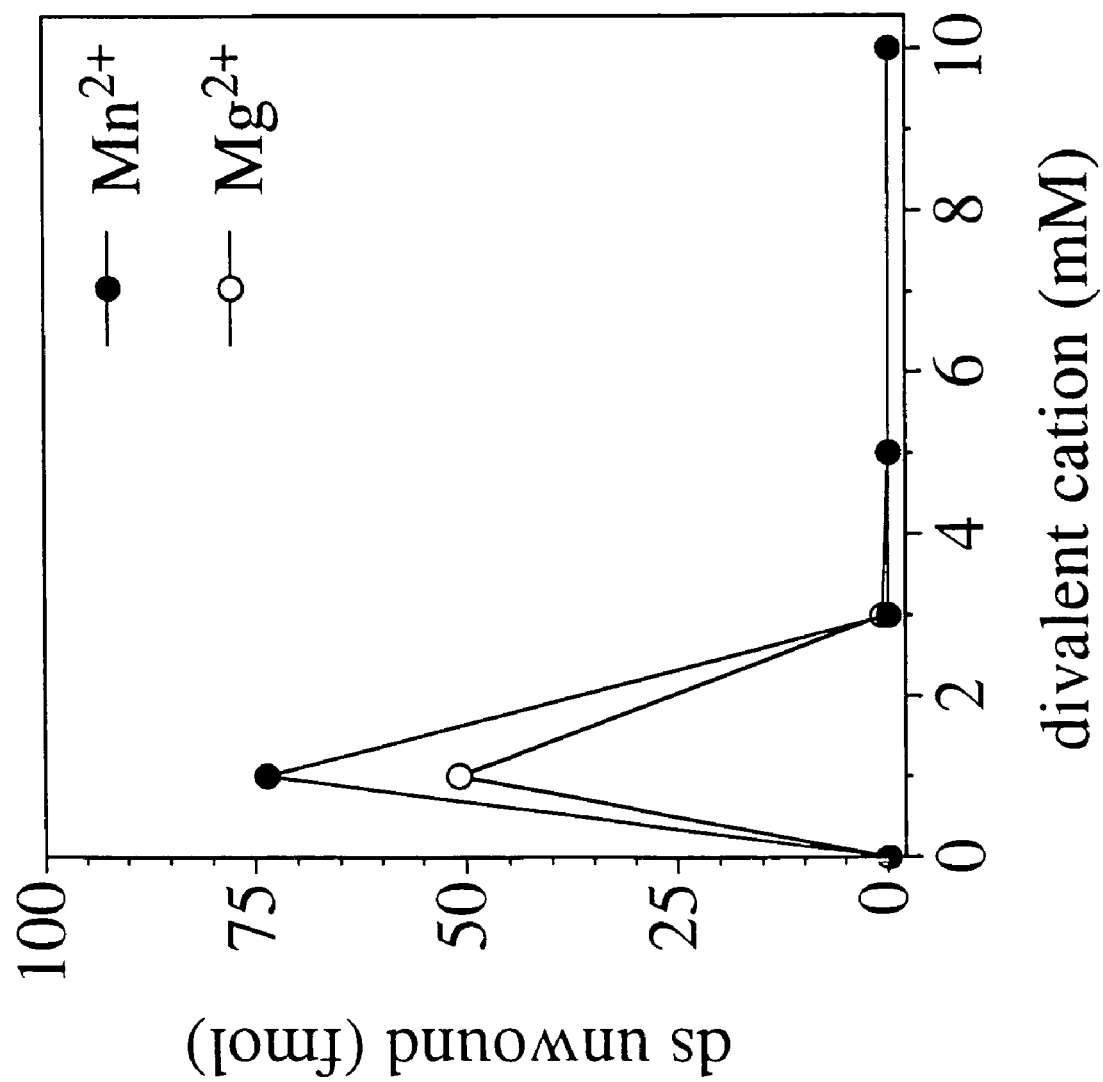

The helicase activity also absolutely require the presence of divalent cations, such as $Mn^{2+}$ or $Mg^{2+}$ (FIG. 11F). However, if the concentration of divalent cation was higher than that of ATP, inhibition of the helicase activity was observed. At equal concentration of ATP and divalent cation (1 mM or 5 mM), $Mn^{2+}$ showed higher unwinding activity than $Mg^{2+}$ (FIG. 11F).

B. Single Stranded RNA Binding Assay

The binding of single stranded RNA ("ssRNA") to the HCV NS3 helicase was measured by a nitrocellulose filter binding assay. A 34-nt RNA transcript was generated from BamHI-digested pSP64 plasmid using SP6 RNA polymerase in the presence of [$\alpha$-$^{32}$P-GTP]. Standard ssRNA binding reactions (40 μl) were carried out as follows.

HCV NS3 helicase domain protein (6.25 nM) was added to a mixture of 25 mM morpholinepropanesulfonic acid (MOPS)-NaOH (pH 7.0), 2 mM dithiothreitol (DTT), 0.1 mg of bovine serum albumin (BSA) per ml, 4 units of RNasin (Promega), and 5 nM of [$^{32}$P]-ssRNA substrate. Mixtures were incubated for 15 min at 30° C. and filtered through a pre-wet nitrocellulose membrane. The filter were washed twice with washing buffer [50 mM MOPS-NaOH (pH 7.0) and 1 mM EDTA], dried and quantified in scintillation counter.

Next, we determine several parameters in the ssRNA binding to the purified NS3 helicase using a filter binding assay (FIG. 12). The association of $^{32}$P-labeled ssRNA to the NS3 helicase was very quick, usually close to completion within a couple minutes of incubation (data not shown). As shown in FIG. 12A, binding of ssRNA to the NS3 helicase is protein concentration-dependent. Under 8 nM of the NS3 helicase, the amount of ssRNA bound is a linear function of protein concentration (FIG. 12A, insert), and there is 0.445 molecule of ssRNA bound for every molecule of the NS3 helicase being present in the reaction. The maximal amount of ssRNA binding achieved in this reaction is about 94%. The $K_d$ of the ssRNA-NS3 helicase complex is calculated to be 5.18 nM, at which the 50% of maximal binding of ssRNA to the NS3 helicase domain was observed.

Figure 12A:
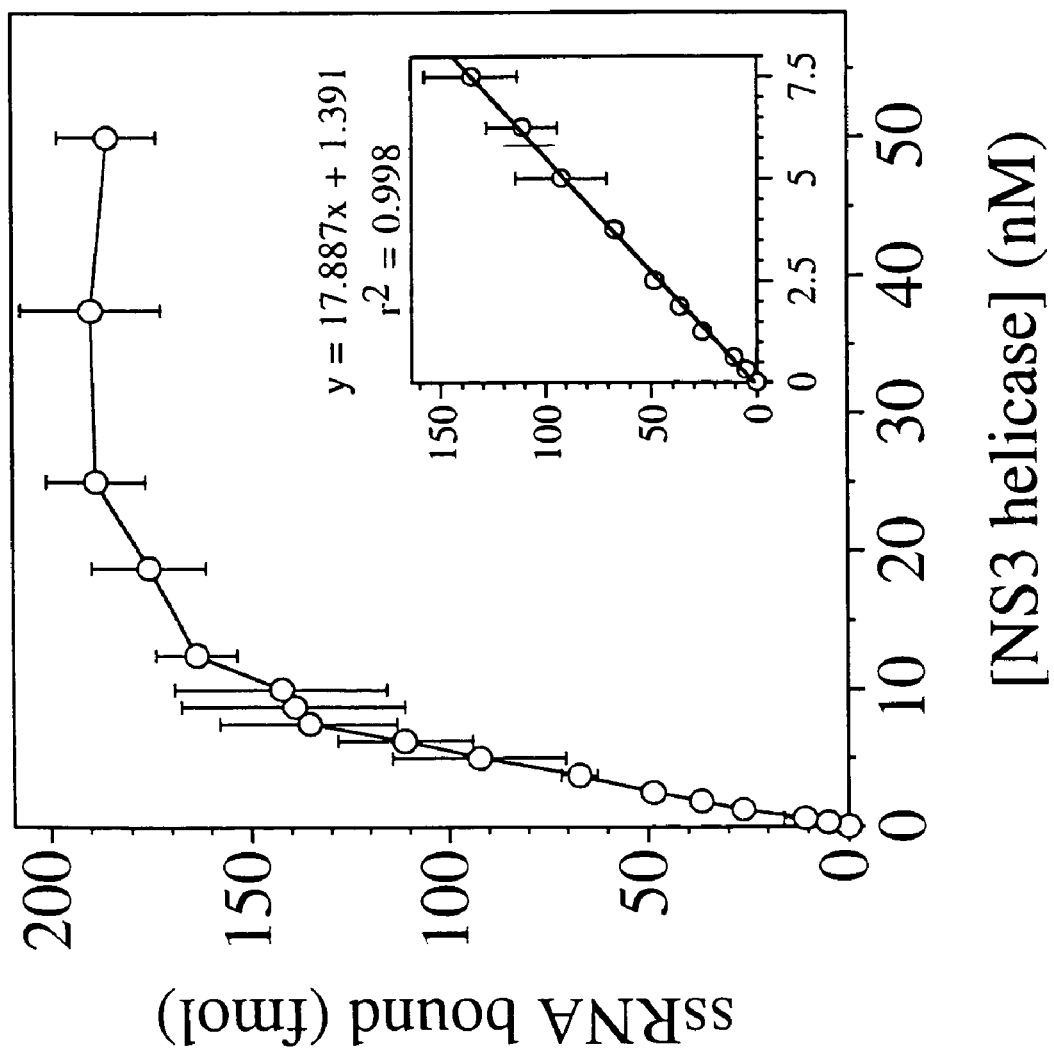
Figure 12B:
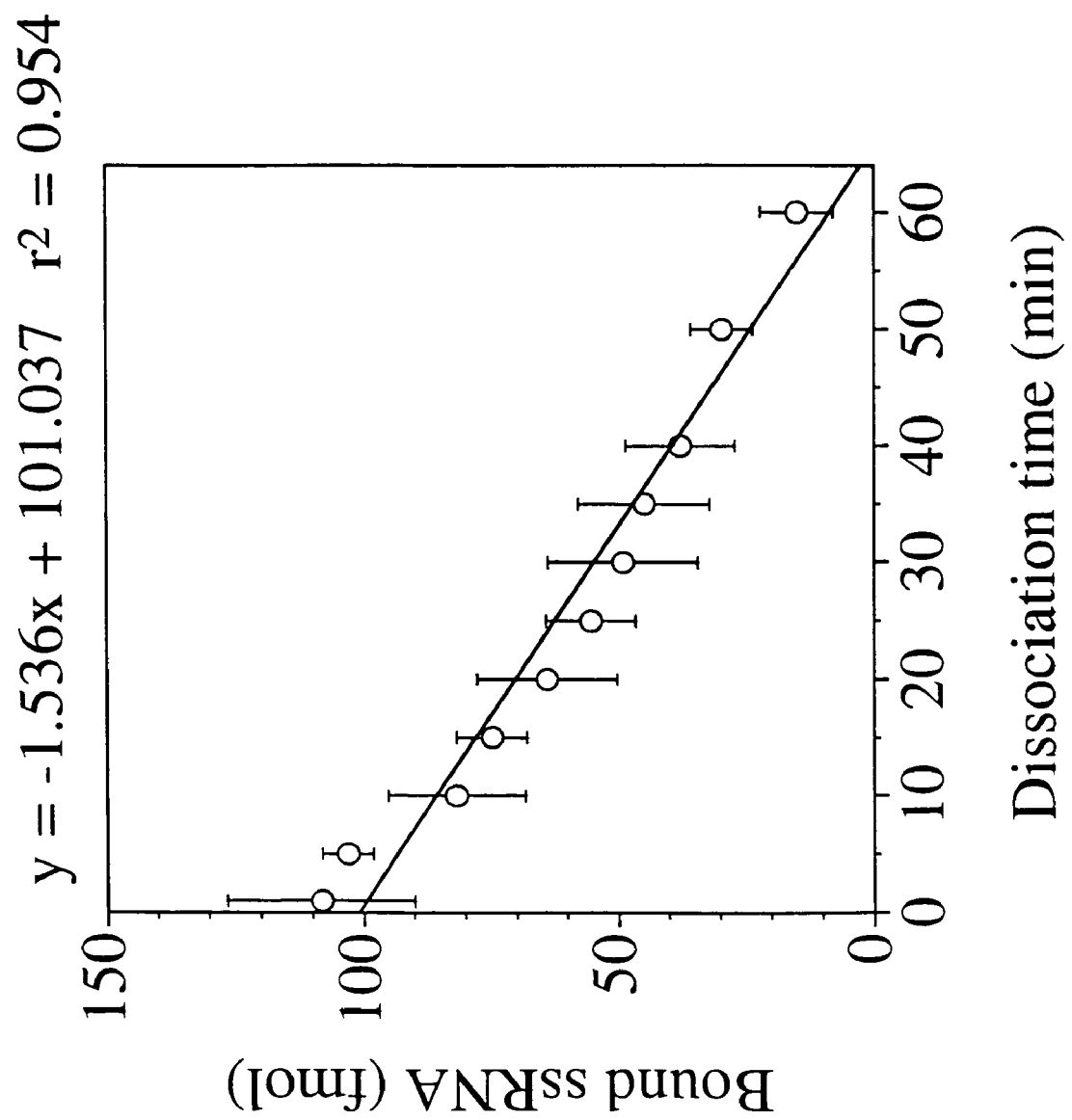

We also measured the off rate constant of pre-formed ssRNA-NS3 helicase complex (FIG. 12B). In this case, $^{32}$P-labeled ssRNA was incubated with the NS3 helicase protein was incubated together for 15 minutes to allow the formation of $^{32}$P-ssRNA-NS3 helicase complex. Then 50-fold excess of $^{3}$H-labeled ssRNA with the same sequence was added to the reaction so that any $^{32}$P-labeled ssRNA dissociated from the complex with the NS3 helicase would have very little chance to re-associate with the NS3 protein again. The dissociation rate was determined to be $1.52 \times 10^{-2}$ min−1.

Figure 12C:
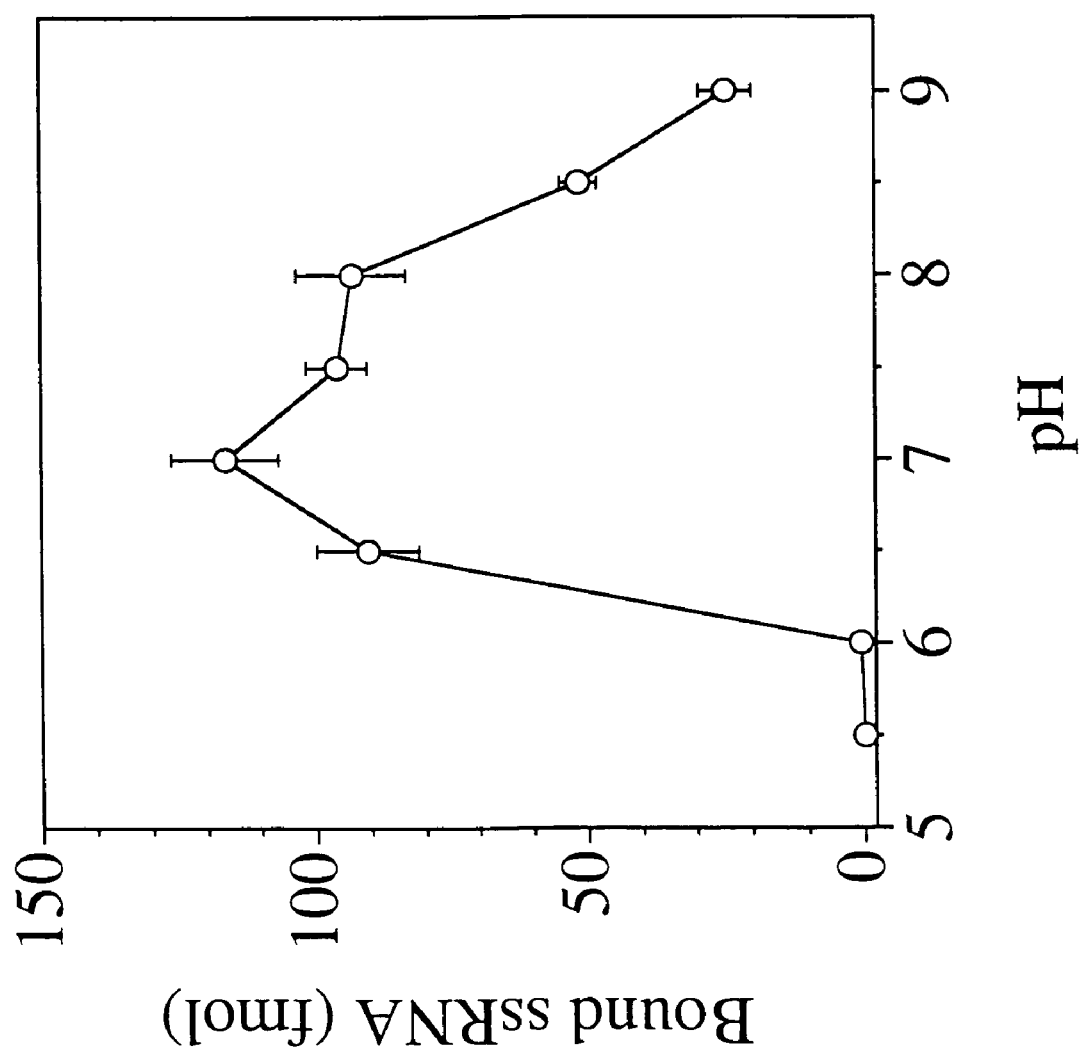
Figure 12D:
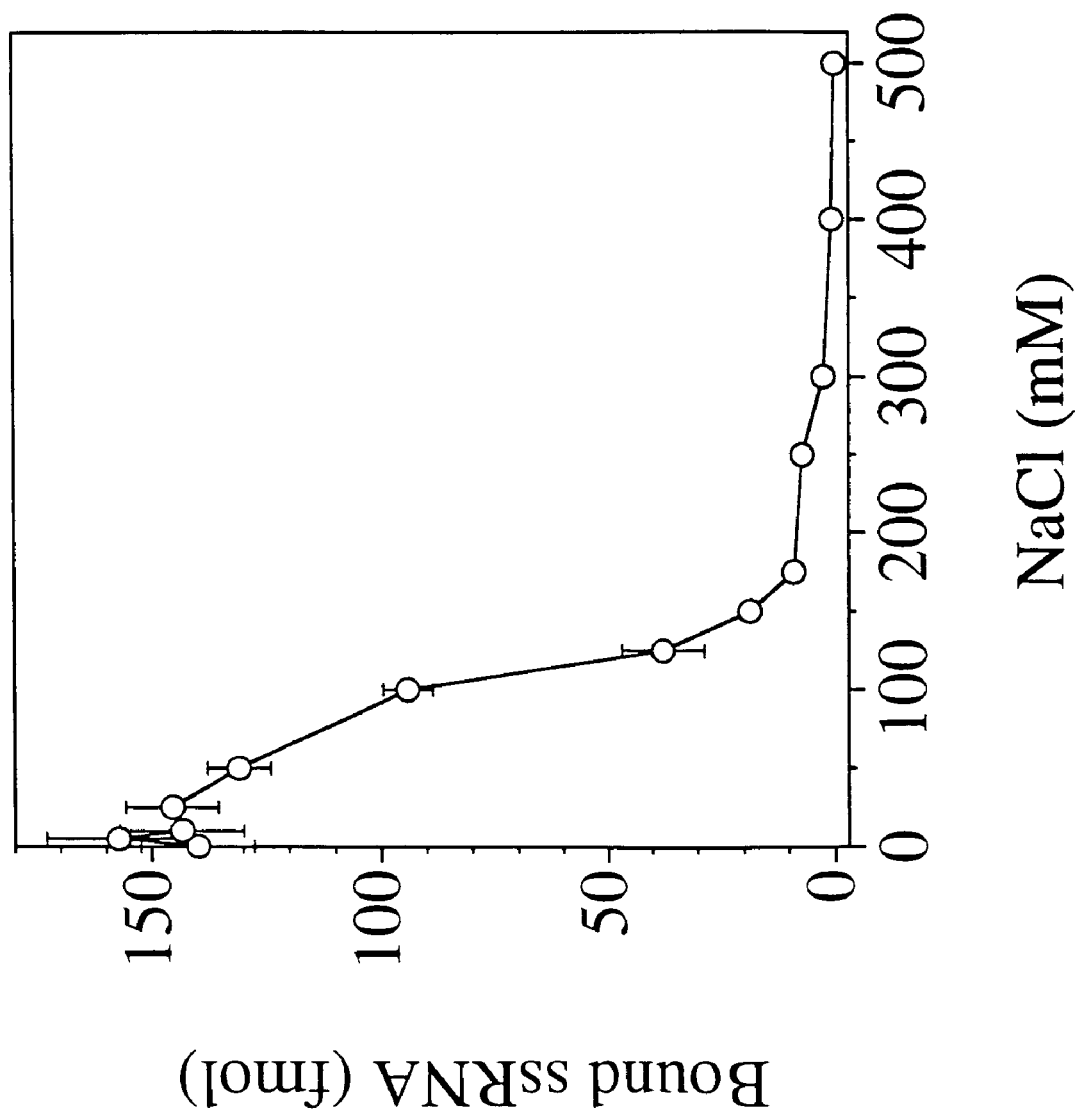
Figure 12E:
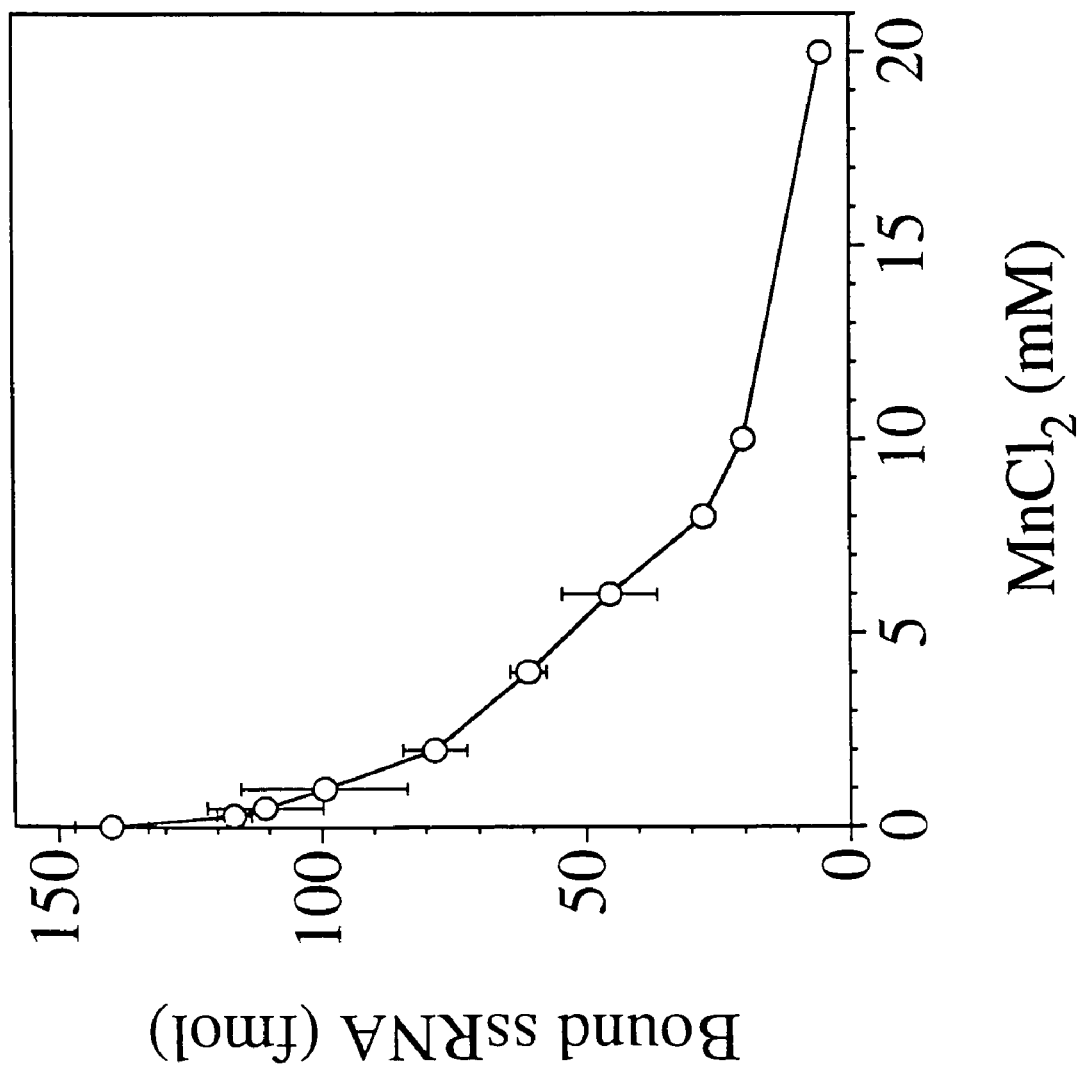

We also examined effect of pH, monovalent ($Na^+$) and divalent ($Mn^{2+}$) cations on the ssRNA binding to the NS3 helicase. In contrast to the unwinding activity, ssRNA binding of the NS3 helicase was less sensitive to the pH change (FIG. 12C). The optimal binding was observed at pH 7.0, although ssRNA binding did not change significantly between pH 6.5 to 8.0. NaCl (FIG. 12D) and $MgCl_2$ (FIG. 12E) has an inhibitory effect on the ssRNA binding, although this inhibition curve as a function of salt concentration is not as sharp as that on unwinding activity.

C. ATPase Assay

ATPase was measured by hydrolysis of ATP to ADP using a thin layer chromatography method [J. K. Tamura et. al., *Virology*, 193, pp. 1-10 (1993)]. Standard ssRNA binding reactions (10 μl) were carried out as follows. HCV NS3 helicase domain protein (2 nM) was added to a mixture of 50 mM morpholinepropanesulfonic acid (MOPS)-NaOH (pH 7.0), 0.1 mM ATP, 2.5 μCi of [$\alpha$-$^{32}$P-ATP] (NEN), 0.5 mM $MgCl_2$, 1 mM dithiothreitol (DTT), 0.1 mg of bovine serum albumin (BSA) per ml, and in the presence or absence of 5 μM poly U (Uridine concentration) (Pharmacia). Mixtures were incubated for 30 min at 37° C. and terminated by addition of EDTA to a final concentration of 20 mM. 0.5 μl of the reaction was spotted on a polyethyleneimine-cellulose plate, ATP and ADP were separated in 375 mM potassium phosphate (pH 3.5) and quantified by Fuji phosphorimager.

ATPase activity of the purified NS3 helicase was examined using this method. As shown in FIG. 13, this NS3 helicase domain has a basal ATPase activity in the absence of any polynucleotide, and the ATPase activity was stimulated up to 11-fold in the presence of poly(U). The order of ATPase stimulation by polynucleotides is poly(U)>poly(C)>poly(A)>poly(G) (data not shown).

EXAMPLE 6

Structure-Based Mutagenesis Study of RNA-Binding Residues of the NS3 Helicase

Mutagenesis experiments were performed to examine the roles of several residues predicted to be important in the NS3 helicase:oligonucleotide interaction based upon the crystal structure of that complex.

Ser231, Thr269, Ser370 and Thr411 formed direct water-mediated hydrogen bonds with the phosphate groups of the bound oligonucleotide. We replaced each one of these amino acids individually with alanine (see Example 1) and observed the effect of that mutation on various helicase activities. Alanine substitution at Ser231 or Ser370 had no observable effect on basal or polyU-stimulated ATPase activity, unwinding activity or ssRNA binding activity as compared to wild type helicase (see Table 1, below). Thus, it was concluded that those amino acids were not essential to define the oligonucleotide binding pocket in NS3 helicase.

In contrast, alanine substitution at Thr269 or Thr411 decreased the ssRNA binding to 20% of wild type level and completely abolished both polyU-stimulated ATPase activity and unwinding activity. Interestingly, basal ATPase activity was unaffected by either of these mutations.

The crystal structure also suggested that the side chain of Trp501 interacts with the bound oligonucleotide. Substitution of this Trp with either Ala or Leu resulted in decreased ssRNA binding and abolished polyU-stimulated ATPase activity and unwinding activity, although basal ATPase activity was unaffected. In contrast a Trp501-to-Phe mutation did not affect basal ATPase, unwinding and ssRNA binding activities. This mutant was, however, less sensitive to polyU-stimulation of ATPase activity as compared to the wild type helicase. Surprisingly, the ATPase activity of this mutant when stimulated by other polynucleotides, such as polyC, was similar to that of the wild type.

TABLE 1

Mutational Study of Amino Acids in the RNA Binding Site of HCV NS3 Helicase

| Amino Acid Mutation | Basal ATPase Activity (% of basal WT level) | Poly-U Stimulated ATPase Activity (% of basal WT level) | ssRNA Binding Activity (% of WT level) | ds RNA/DNA Unwinding Activity (% of WT level) |
|---|---|---|---|---|
| None (WT) | 100 | 823 | 100 | 100 |
| S231->A | 260 | 709 | 121 | 99.8 |
| T269->A | 60 | 47 | 21 | 1 |
| S370->A | 104 | 694 | 124 | 109 |
| T411->A | 274 | 205 | 24 | 0.25 |
| W501->F | 99 | 197 | 100 | 112 |
| W501->L | 114 | 47 | 21 | 0.07 |
| W501->A | 101 | 49 | 40 | 0.36 |

Based upon these studies, it is apparent that Thr269, Thr411 and Trp501 are key residues for oligonucleotide binding. As indicated above, Thr269 and Trp501 make direct contacts with dU8. The minimal helicase amino acids which define the pocket in which dU8 lies are Val232, Thr254, Gly255, Thr269, Gly271, Lys272, Ala275, Trp501 and Tyr502. Thus, any compound which fits into a pocket comprising the structural coordinates ±a root mean square of 1.5 Å or less from the backbone atoms of these amino acids is a potential inhibitor of the NS3 helicase.

Additional amino acids that are located within 4 Å to 8 Å from the dU8 pocket are Pro230, Val256, Thr298, Ala497, Lys551, Gln552, Gly554, Glu555, Asn556 and Pro558. Thus, the combination of these amino acids with those above further define the dU8 pocket.

Based upon the crystal structure and these mutagenesis experiments, it is clear that Thr411 makes direct contact with dU4 and is a key residue in the U4 binding pocket. Other amino acids that are close enough to that U4 pocket to define its shape are His369, Ser370, Lys371, Tyr392, Arg393, Asp412, Ala413, Cys431, Val432, Gln434, Ile446, Thr448, Arg461, Glu493, Glu555, Asn556 and Phe557.

EXAMPLE 7

Structure-Based Mutagenesis Study of ATP-Binding Residues of the NS3 Helicase

Mutagenesis experiments were performed to examine the roles of several residues predicted to be important in the NS3 helicase:ATP interaction based upon the crystal structure of that complex.

The mutations were achieved by the methods described in Example 1.

TABLE 2

Mutational Study of Amino Acids in the ATP Binding Site of HCV NS3 Helicase

| Mutation | Basal ATPase Activity (% of basal WT level) | Poly U-Stimulated ATPase Activity (% of basal WT level) | ssRNA Binding Activity (% of WT level) | ds RNA/DNA Unwinding Activity (% of WT level) |
|---|---|---|---|---|
| wild-type | 100 | 581 | 100 | 100 |
| Q460->A | 23 | 32 | 97 | 3 |
| R461->A | 140 | 193 | 57 | 2 |
| R462->A | 247 | 337 | 99 | 81 |
| R464->A | 33 | 21 | 105 | <0.01 |
| R467->A | 7 | 14 | 116 | <0.05 |

In our model, R464 and R467 were predicted to bind to the γ- and α-phosphate groups of NTP, respectively. This is in contrast to what has previously been reported in the art, wherein these residues were predicted to be involved in RNA binding (T. Yao et al., *Nat. Struct. Biol.*, 4, pp. 463-467 (1997); C. Hyun-Soo et al., *J. Biol. Chem.*, 273, pp. 15045-15052 (1998)].

Two individual mutations, R464→A and R467→A, showed very low basal and polyU-stimulated ATPase activities. Although they had normal RNA binding ability, which suggested that the mutated protein has a proper fold, helicase unwinding activity was almost non-existent in these two mutant proteins, presumably due to the loss of NTPase activity. These results indicated that these two Arg residues are critical for NTPase activity.

The Q460→A mutation had a similar effect as two abovementioned Arg-to-Ala mutations. This Gln was predicted to interact with and maintain the proper conformation of the imidazole ring of His-293 of the DECH motif.

The R461→A mutation led to lower RNA binding and less polyU stimulation of ATPase activity, which resulted in a very low helicase unwinding activity.

The R462→A mutation had no major effect on any of these four activities as predicted.

While we have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

We claim:

1. A crystallizable composition capable of producing crystals for use in X-ray crystallography comprising:
   a. an HCV NS3 helicase protein selected from SEQ ID NO:2; fragments of SEQ ID NO:2 comprising at least amino acids 183 to 582; mutants of SEQ ID NO:2 containing one or more of the following amino acid substitutions: Ser231-to-Ala, Thr269-to-Ala, Ser370-to-Ala, Thr411-to-Ala, Trp501-to-Phe, Trp501-to-Leu or Trp501-to-Ala, Gln460-to-Ala, Arg461-to-Ala, Arg462-to-Ala, Arg464-to-Ala, or Arg467-to-Ala; or fragments of SEQ ID NO:2 comprising at least amino acids 183 to 582 and containing one or more, of the following amino acid substitutions: Ser231-to-Ala, Thr269-to-Ala, Ser370-to-Ala, Thr411-to-Ala, Trp501-to-Phe, Trp501-to-Leu or Trp501-to-Ala, Gln460-to-Ala, Arg461-to-Ala, Arg462-to-Ala, Arg464-to-Ala, or Arg467-to-Ala; and
   b. a single stranded dU oligonucleotide consisting of between 6 and 12 nucleotides.

2. The composition according to claim 1, wherein said HCV NS3 helicase protein comprises amino acids 167-631 of SEQ ID NO:2.

3. A crystallized complex for use in X-ray crystallography comprising:
   a. an HCV NS3 helicase protein selected from SEQ ID NO:2; fragments of SEQ ID NO:2 comprising at least amino acids 183 to 582; mutants of SEQ ID NO:2 containing one or more of the following amino acid substitutions; Ser231-to-Ala, Thr269-to-Ala, Ser370-to-Ala, Thr411-to-Ala, Trp501-to-Phe, Trp501-to-Leu or Trp501-to-Ala, Gln460-to-Ala, Arg461-to-Ala, Arg462-to-Ala, Arg464-to-Ala, or Arg467-to-Ala; or fragments of SEQ ID NO:2 comprising at least amino acids 183 to 582 and containing one or more of the following amino acid substitutions: Ser231-to-Ala, Thr269-to-Ala, Ser370-to-Ala, Thr411-to-Ala, Trp501- to-Phe, Trp501-to-Leu or Trp501-to-Ala, Gln460-to-Ala, Arg461-to-Ala, Arg462-to-Ala, Arg464-to-Ala, or Arg467-to-Ala; and b. a single-stranded dU oligonucleotide consisting of between 6 and 12 nucleotides.

* * * * *

UNITED STATES PATENT AND TRADEMARK OFFICE
CERTIFICATE OF CORRECTION

| | | |
|---|---|---|
| PATENT NO. | : 7,438,920 B1 | Page 1 of 1 |
| APPLICATION NO. | : 09/303216 | |
| DATED | : October 21, 2008 | |
| INVENTOR(S) | : Kim et al. | |

It is certified that error appears in the above-identified patent and that said Letters Patent is hereby corrected as shown below:

On the title page, item (56) References Cited

The following references cited by applicants are omitted. They should be printed on cover page of patent.

U. S. Patent Documents

4,833,233 05/23/89   Carter.......530/363
5,353,236 10/04/94   Subbiah....364/499

Foreign Patent Documents

WO 92/14211 20/08/92
WO 94/25860 10/11/94
WO 97/15588 05/01/97

Column 53, line 65: Delete "," after the word "more"

Signed and Sealed this

Twenty-fifth Day of October, 2011

David J. Kappos
*Director of the United States Patent and Trademark Office*